(12) United States Patent
Pedersen et al.

(10) Patent No.: US 12,129,289 B2
(45) Date of Patent: *Oct. 29, 2024

(54) ANTIBODIES SPECIFIC FOR HYPERPHOSPHORYLATED TAU AND METHODS OF USE THEREOF

(71) Applicant: H. Lundbeck A/S, Valby (DK)

(72) Inventors: Jan Torleif Pedersen, Valby (DK); Kristian Kjaergaard, Valby (DK); Lars Østergaard Pedersen, Valby (DK); Ayodeji Abdur-Rasheed Asuni, Valby (DK); Nina Helen Rosenqvist, Valby (DK); Justus Claus Alfred Daechsel, Valby (DK); Karsten Juhl, Greve (DK); Lena Tagmose, Lyngby (DK); Mauro Marigo, Skovlunde (DK); Thomas Jensen, Copenhagen (DK); Søren Christensen, Valby (DK); Laurent David, Valby (DK); Christiane Volbracht, Valby (DK); Lone Helboe, Valby (DK)

(73) Assignee: H. Lundbeck A/S, Valby (DK)

( * ) Notice: Subject to any disclaimer, the term of this patent is extended or adjusted under 35 U.S.C. 154(b) by 291 days.

This patent is subject to a terminal disclaimer.

(21) Appl. No.: 17/399,205

(22) Filed: Aug. 11, 2021

(65) Prior Publication Data

US 2022/0177557 A1 Jun. 9, 2022

Related U.S. Application Data

(63) Continuation of application No. 16/585,207, filed on Sep. 27, 2019, now Pat. No. 11,111,290, which is a continuation of application No. 15/645,442, filed on Jul. 10, 2017, now Pat. No. 10,472,415.

(30) Foreign Application Priority Data

| Jul. 12, 2016 | (DK) | ............................... PA201600416 |
| Jan. 4, 2017 | (DK) | ............................... PA201700005 |
| Jan. 4, 2017 | (DK) | ............................... PA201700008 |
| Mar. 14, 2017 | (DK) | ............................... PA201700179 |

(51) Int. Cl.
| *C07K 16/18* | (2006.01) |
| *A61K 39/395* | (2006.01) |
| *A61K 49/00* | (2006.01) |
| *G01N 33/68* | (2006.01) |
| *A61K 39/00* | (2006.01) |

(52) U.S. Cl.
CPC ............ *C07K 16/18* (2013.01); *A61K 39/395* (2013.01); *A61K 49/00* (2013.01); *G01N 33/6896* (2013.01); *A61K 2039/505* (2013.01); *C07K 2317/24* (2013.01); *C07K 2317/30* (2013.01); *C07K 2317/33* (2013.01); *C07K 2317/34* (2013.01); *C07K 2317/51* (2013.01); *C07K 2317/515* (2013.01); *C07K 2317/565* (2013.01); *C07K 2317/75* (2013.01); *C07K 2317/76* (2013.01); *C07K 2317/92* (2013.01); *C07K 2317/94* (2013.01); *G01N 2800/2814* (2013.01); *G01N 2800/2821* (2013.01)

(58) Field of Classification Search
CPC ................ C07K 16/18; C07K 2317/24; C07K 2317/30; C07K 2317/33; C07K 2317/34; C07K 2317/51; C07K 2317/515; C07K 2317/56; C07K 2317/565; C07K 2317/76; C07K 2317/92; C07K 2317/94; A61K 39/395; A61K 2039/505; A61K 49/00; G01N 33/6896; G01N 2800/2814; G01N 2800/2821

See application file for complete search history.

(56) References Cited

U.S. PATENT DOCUMENTS

| 4,179,337 A | 12/1979 | Davis et al. |
| 4,495,285 A | 1/1985 | Shimizu et al. |
| 4,609,546 A | 9/1986 | Hiratani |
| 4,735,210 A | 4/1988 | Goldenberg |
| 4,766,106 A | 8/1988 | Katre et al. |
| 4,861,581 A | 8/1989 | Epstein et al. |
| 4,946,778 A | 8/1990 | Ladner et al. |
| 5,101,827 A | 4/1992 | Goldenberg |
| 5,102,990 A | 4/1992 | Rhodes |
| 5,225,539 A | 7/1993 | Winter |
| 5,530,101 A | 6/1996 | Queen et al. |
| 5,545,806 A | 8/1996 | Lonberg et al. |
| 5,545,807 A | 8/1996 | Surani et al. |
| 5,569,825 A | 10/1996 | Lonberg et al. |

(Continued)

FOREIGN PATENT DOCUMENTS

| EP | 2009104 A1 | 12/2008 |
| WO | WO 1992/003918 A1 | 3/1992 |

(Continued)

OTHER PUBLICATIONS

International Search Report and Written Opinion for Application No. PCT/EP2016/066470 mailed Mar. 6, 2017.
International Search Report and Written Opinion for Application No. PCT/EP2017/067067 mailed Oct. 18, 2017.
International Search Report and Written Opinion for Application No. PCT/EP2018/050149 mailed May 4, 2018.

(Continued)

*Primary Examiner* — Kimberly Ballard
(74) *Attorney, Agent, or Firm* — Wolf, Greenfield & Sacks, P.C.

(57) ABSTRACT

The present invention relates to a class of monoclonal antibody that specifically binds the phosphorylated serine 396 residue on pathological hyperphosphorylated (PHF) tau (pS396) with improved affinity, as well as to methods of using these molecules and their tau binding fragments in the treatment of Alzheimer's disease and other tauopathies.

15 Claims, 26 Drawing Sheets

Specification includes a Sequence Listing.

(56) References Cited

U.S. PATENT DOCUMENTS

| | | | |
|---|---|---|---|
| 5,585,089 | A | 12/1996 | Queen et al. |
| 5,589,466 | A | 12/1996 | Felgner et al. |
| 5,625,126 | A | 4/1997 | Lonberg et al. |
| RE35,500 | E | 5/1997 | Rhodes |
| 5,633,425 | A | 5/1997 | Lonberg et al. |
| 5,648,471 | A | 7/1997 | Buttram et al. |
| 5,661,016 | A | 8/1997 | Lonberg et al. |
| 5,697,902 | A | 12/1997 | Goldenberg |
| 5,741,957 | A | 4/1998 | Deboer et al. |
| 5,750,172 | A | 5/1998 | Meade et al. |
| 5,756,687 | A | 5/1998 | Denman et al. |
| 5,770,429 | A | 6/1998 | Lonberg et al. |
| 5,789,650 | A | 8/1998 | Lonberg et al. |
| 5,814,318 | A | 9/1998 | Lonberg et al. |
| 5,827,690 | A | 10/1998 | Meade et al. |
| 5,859,205 | A | 1/1999 | Adair et al. |
| 5,874,299 | A | 2/1999 | Lonberg et al. |
| 5,877,397 | A | 3/1999 | Lonberg et al. |
| 5,973,972 | A | 10/1999 | Kwon et al. |
| 6,077,835 | A | 6/2000 | Hanson et al. |
| 6,407,213 | B1 | 6/2002 | Carter et al. |
| 6,881,557 | B2 | 4/2005 | Foote |
| 8,609,097 | B2 | 12/2013 | Bormann et al. |
| 8,926,974 | B2 | 1/2015 | Griswold-Prenner et al. |
| 8,940,272 | B2 | 1/2015 | Nitsch et al. |
| 10,196,439 | B2 | 2/2019 | Pedersen et al. |
| 10,364,286 | B2 | 7/2019 | Fog et al. |
| 10,472,415 | B2 | 11/2019 | Pedersen et al. |
| 10,487,142 | B2 | 11/2019 | Pedersen et al. |
| 10,562,962 | B2 | 2/2020 | Pedersen et al. |
| 10,647,762 | B2 | 5/2020 | Pedersen et al. |
| 10,934,348 | B2 | 3/2021 | Pedersen et al. |
| 10,934,438 | B2 | 3/2021 | Pedersen et al. |
| 10,995,137 | B2 | 5/2021 | Pedersen et al. |
| 11,111,290 | B2 | 9/2021 | Pedersen et al. |
| 11,739,140 | B2 | 8/2023 | Pedersen et al. |
| 2010/0316564 | A1 | 12/2010 | Sigurdsson |
| 2012/0087861 | A1 | 4/2012 | Nitsch et al. |
| 2012/0276009 | A1 | 11/2012 | Pfeifer et al. |
| 2014/0086921 | A1 | 3/2014 | Griswold-Prenner et al. |
| 2014/0248666 | A1 | 9/2014 | Paszty et al. |
| 2014/0302046 | A1 | 10/2014 | Sigurdsson |
| 2016/0031976 | A1 | 2/2016 | Seubert et al. |
| 2017/0015738 | A1 | 1/2017 | Pedersen et al. |
| 2018/0016330 | A1 | 1/2018 | Pedersen et al. |
| 2019/0177401 | A1 | 6/2019 | Pedersen et al. |
| 2019/0284265 | A1 | 9/2019 | Pedersen et al. |
| 2019/0284266 | A1 | 9/2019 | Pedersen et al. |
| 2019/0330320 | A1 | 10/2019 | Pedersen et al. |
| 2020/0109192 | A1 | 4/2020 | Pedersen et al. |
| 2020/0190178 | A1 | 6/2020 | Pedersen et al. |
| 2021/0206843 | A1 | 7/2021 | Pedersen et al. |

FOREIGN PATENT DOCUMENTS

| | | |
|---|---|---|
| WO | WO 1992/022645 A1 | 12/1992 |
| WO | WO 1993/001227 A1 | 1/1993 |
| WO | WO 1993/012227 A1 | 6/1993 |
| WO | WO 1994/025585 A1 | 11/1994 |
| WO | WO 1998/024884 A1 | 6/1998 |
| WO | WO 2000/046147 A2 | 8/2000 |
| WO | WO 2000/070087 A1 | 11/2000 |
| WO | WO 2001/009187 A2 | 2/2001 |
| WO | WO 2001/014424 A2 | 3/2001 |
| WO | WO 2002/027017 A2 | 4/2002 |
| WO | WO 2002/043478 A2 | 6/2002 |
| WO | WO 2007/019273 A2 | 2/2007 |
| WO | WO 2007/059782 A1 | 5/2007 |
| WO | WO 2009/033743 A1 | 3/2009 |
| WO | WO 2009/097006 A2 | 8/2009 |
| WO | WO 2012/045882 A2 | 4/2012 |
| WO | WO 2012/049570 A1 | 4/2012 |
| WO | WO 2013/050567 A1 | 4/2013 |
| WO | WO 2013/151762 A1 | 10/2013 |
| WO | WO 2014/008404 A1 | 1/2014 |
| WO | WO 2014/028777 A2 | 2/2014 |
| WO | WO 2014/165271 A2 | 10/2014 |
| WO | WO 2014/170549 A1 | 10/2014 |
| WO | WO 2016/007414 A1 | 1/2016 |
| WO | WO 2017/009308 A2 | 1/2017 |
| WO | WO 2018/011073 A1 | 1/2018 |

OTHER PUBLICATIONS

Aboelnour et al., Amyloid beta deposition and phosphorylated tau accumulation are key features in aged choroidal vessels in the complement factor H knock out model of retinal degeneration. Exp Eye Res. Jun. 2016;147:138-143. doi: 10.1016/j.exer.2016.05.015. Epub May 12, 2016.

Ahmed Z. et al., A Novel In Vivo Model Of Tau Propagation With Rapid And Progressive Neurofibrillary Tangle Pathology: The Pattern Of Spread Is Determined By Connectivity, Not Proximity, Acta Neuropathol. 2014;127:667-683.

Allen, B. et al. (2002) "Abundant Tau Filaments and Nonapoptotic Neurodegeneration in Transgenic Mice Expressing Human P301S Tau Protein," J. Neurosci. 22(21): 9340-9351.

Altschul S.F., Amino Acid Substitution Matrices From An Information Theoretic Perspective. J. Mol. Biol. 1991;219:555-565.

Anonymous (2006) Anti-phospho-Tau (pSer199/202), Data sheet; Sigma Aldrich, Cat. No. T6819 (2 pages).

Anonymous (2008) "Mouse anti-Phospho-Tau 396," Invitrogen Catalogue, Catalog No. 35-5300 (2 pages).

Anonymous (2010) "Tau Phosphorylation Site-Specific Antibody Sampler (Containing Tau pS199, pT205, pT231, pS262, pS356, pS396, pS404, pS409, pS422 Rabbit Polyclonal & tau [Tau-5] Monoclonal Antibodies, Unconjugated)," Product Analysis Sheet Invitrogen (2 pages).

Anonymous (2011) "Tau [pS199] Abfinity TM Recombinant Rabbit Monoclonal Antibody—Purified; Cat. No. 701054," Product Analysis Sheet, Novex (2 pages).

Anonymous (2014) "Anti-Tau (phospho S199) antibody [EPR2401Y] (ab81268)," Product Datasheet; retrieved on Feb. 3, 2017; Abcam (4 pages).

Anonymous (2014) "Anti-Tau (Phospho S396) Antibody [EPR2731] ab109390," Product Data Sheet, Abcam Product Catalogue (6 pages).

Barderas R., et al. (2008) "Affinity Maturation of Antibodies Assisted by In Silico Modeling," Proc. Natl. Acad. Sci. (USA) 105(26):9029-9034.

Benvenisty N., et al. (1986) "Direct Introduction Of Genes Into Rats And Expression Of The Genes," Proc. Natl. Acad. Sci. U.S.A. 83: 9551-9555.

Bird R.E., et al. (1988) "Single-Chain Antigen-Binding Proteins," Science 242: 423-426.

Bitter G.A. et al. (1987) "Expression and Secretion Vectors for Yeast," Methods Enzymol. 153: 516-544.

Boer E. et al. (2007) "Yeast Expression Platforms," Appl. Microbial. Biotechnol. 77(3): 513-523.

Bondareff et al. (1990) "Molecular Analysis Of Neurofibrillary Degeneration In Alzheimer's Disease: An Immunohistochemical Study," Am. J. Pathol. 137(3): 711-723.

Bostrom J., et al. (2009) "Improving Antibody Binding Affinity And Specificity For Therapeutic Development," Methods Mol. Biol. 525: 353-376.

Boutajangout, A. et al. (2011) "Passive Immunization Targeting Pathological Phospho-tau Protein in a Mouse Model Reduces Functional Decline and Cleans Tau Aggregates from the Brain," J. Neurochem. 118:658-667.

Boutajangout, A. et al. (2011) "Targeting Hypeiphosphorylated Tau Protein with a Monoclonal Antibody at an Advances Stage of Tau Pathology Improves Cognition in a Mouse Model," AAIC 7(4) Suppl. Ed.: s480-s481.

Braak, E. et al. (1999) "Neuropathology of Alzheimer's Disease: What is New Since A. Alzheimer?" Eur. Arch. Psychiatry. Clin. Neurosci. 249(Suppl. 3): III/14-III/22.

Braak, H. et al. (1996) "Evolution of the Neuropathology of Alzheimer's Disease," Acta Neurol. Scand. Suppl. 165:3-12.

(56) References Cited

OTHER PUBLICATIONS

Breteler M.M. et al. (1992) "A Community-Based Study Of Dementia: The Rotterdam Elderly Study," Neuroepidemiology 11 (Suppl 1): 23-28.
Bright, J. et al. (2015) "Human Secreted Tau Increases Amyloid-Beta Production," Neurobiol. Aging, 36: 693-709.
Brister M.A. et al. (2014) "OG1cNAcylation and Phosphorylation Have Opposing Structural Effects In Tau: Phosphothreonine Induces Particular Conformational Order," J. Am. Chem. Soc. 136:3803-3816.
Brister, M.A. et al. (2014) "OG1cNAcylation and Phosphorylation Have Opposing Structural Effects in Tau: Phosphothreonine nduces Particular Conformational Order," J. Am. Chem. Soc. 136:3803-3816.
Carter P. et al. (1992) "Humanization Of An Anti-p185her2 Antibody For Human Cancer Therapy," Proc. Natl. Acad. Sci. (U.S.A.) 89:4285-4289.
Celik E. et al. (2012) "Production Of Recombinant Proteins By Yeast Cells," Biotechnol. Adv. 30(5): 1108-1118.
Chai, X. et al. (2011) "Passive Immunization with Anti-Tau Antibodies in Two Transgenic Models," J. Biol. Chem. 286(39):34457-34467.
Chen J. et al. (1993) "Immunoglobulin Gene Rearrangement In B Cell Deficient Mice Generated By Targeted Deletion Of The JH Locus," Int. Immunol. 5( 6) :647-656.
Chiasseu et al., Tau Accumulation, Altered Phosphorylation, and Missorting Promote Neurodegeneration in Glaucoma. J Neurosci. May 25, 2016;36(21):5785-98. doi: 10.1523/JNEUROSCI.3986-15.2016.
Chothia C. et al. (1987) "Canonical Structures For The Hypervariable Regions Of Immunoglobulins," J. Mol. Biol. 196:901-917.
Clackson T. et al. (1991) "Making Antibody Fragments Using Phage Display Libraries," Nature 352:624-628.
Clavaguera F. et al. (2014) "Peripheral Administration Of Tau Aggregates Triggers Intracerebral Tauopathy In Transgenic Mice," Acta Neuropathol. 127: 299-301.
Clavaguera, F. et al. (2009) "Transmission and Spreading of Tauopathy in Transgenic Mouse Brain," Nat. Cell Biol. 11(7):909-913.
Clavaguera, F. et al. (2013) "Brain Homogenates from Human Tauopathies Induce Tau Inclusions in Mouse Brain," PNAS 110(23):9535-9540.
Co M.S. et al. (1991) "Humanized Antibodies For Antiviral Therapy," Proc. Natl. Acad. Sci. U.S.A. 88:2869-2873.
Co M.S. et al. (1992) "Chimeric And Humanized Antibodies With Specificity For The CD33 Antigen," J. Immunol. 148:1149-1154.
Cohen T.J. et al. (2011) "The Acetylation Of Tau Inhibits Its Function And Promotes Pathological Tau Aggregation," Nat. Commun. 2:252 (9 pages).
Congdon, E.E. et al. (2013) "Antibody Uptake into Neurons Occurs Primarily via Cathrin-dependent Fey Receptor Endocytosis and is a Prerequisite for Acute Tau Protein Clearance," J. Biol. Chem. 288(49):35452-35465.
Corsaro C.M. et al. (1981) "Enhancing The Efficiency Of DNA-Mediated Gene Transfer In Mammalian Cells," Somatic Cell Genetics (2):603-616.
Crary J.F. et al. (2014) "Primary Age-Related Tauopahty (Part): A Common Pathology Associated with Human Aging," Acta Neuropathol. 128:755-766.
D'Abramo, C. et al. (2013) "Tau Passive Immunotherapy in Mutant P301L Mice: Antibody Affinity versus Specificity," PLoS One 8(4): e62402:1-10.
De Calignon A. et al. (2010) "Caspase Activation Precedes And Leads To Tangles," Nature 464: 1201-1204.
Delobel P. et al. (2008) "Analysis Of Tau Phosphrylation And Truncation In A Mouse Model Of Human Tauopathy," Am. J. Pathol. 172:123-131.
Eddy S.R. (2004) "Where Did The BLOSUM62 Alignment Score Matrix Come From?," Nature Biotech. 22(8): 1035-1036.

Edwards et al., The remarkable flexibility of the human antibody repertoire; isolation of over one thousand different antibodies to a single protein, BLyS. J Mol Biol. Nov. 14, 2003;334(1):103-18. doi: 10.1016/j.jmb.2003.09.054.
Evans M.J. et al. (1995) "Rapid Expression of an Anti-Human C5 Chimeric Fab Utilizing A Vector That Replicates In COS and 293 Cells," J. Immunol. Meth. 184: 123-138.
Ferreira A. et al. (2011) "Calpain-Mediated Tau Cleavage: A Mechanism Leading to Neurodegeneration Shared by Multiple Tauopathies," Mol. Med. 17:676-685.
Finlay W.J. et al. (2009) "Affinity Maturation Of A Humanized Rat Antibody For Anti-RAGE Therapy: Comprehensive Mutagenesis Reveals A High Level Of Mutational Plasticity Both Inside And Outside The Complementarity-Determining Regions," J. Mol. Biol. 388(3):541-558.
Fishwild D.M. et al. (1996) "High Avidity Human IgGkMonoclonal Antibodies From A Novel Strain Of Minilocus Transgenic Mice," Nat. Biotechnol. 14:845-851.
Gamblin T.C. et al. (2003) "Caspase Cleavage Of Tau: Linking Amyloid And Neurofibrillary Tangles In Alzheimer's Disease," Proc. Natl. Acad. Sci. U.S.A. 100:10032-10037.
Glaser S.M. et al. (1992) "Antibody Engineering By Codon-Based Mutagenesis In A Filamentous Phage Vector System," J. Immunol. 149:3903-3913.
Goedert M. et al. (2010) "The Propagation Of Prion-Like Protein Inclusions In Neurodegenerative Diseases," Trends Neurosci. 33:317-325.
Gonzales N.R. et al. (2004) "SDR Grafting Of A Murine Antibody Using Multiple Human Germline Templates To Minimize Its Immunogenicity," Mol. Immunol. 41:863-872.
Gorman S.D. et al. (1991) "Reshaping A Therapeutic CD4 Antibody," Proc. Natl. Acad. Sci. U.S.A. 88:4181-4185.
Greenberg, S.G. et al. (1990) "A Preparation of Alzheimer Paired Helical Filaments That Displays Distinct T Proteins by Polyacrylamide Gel Electrophoresis," PNAS USA 87:5827-5831.
Gu, J. et al. (2013) "Two Novel Tau Antibodies Targeting the 396/404 Region are Primarily Taken Up by Neurons and Reduce Tau Protein Pathology," J. Biol. Chem. 288(46):33081-33095.
Gunasekaran K. et al. (2010) "Enhancing Antibody Fc Heterodimer Formation Through Electrostatic Steering Effects," J. Biol. Chem. 285:19637-19646.
Gupta et al., Retinal tau pathology in human glaucomas. Can J Ophthalmol. Feb. 2008;43(1):53-60. doi: 10.3129/i07-185.
Gustchina E. et al. (2009) "Affinity maturation by targeted diversification of the CDR-H2 loop of a monoclonal Fab derived from a synthetic naïve human antibody library and directed against the internal trimeric coiled-coil of gp41 yields a set of Fabs with improved HIV-1 neutralization potency and breadth," Virology 393(1):112-119.
Hackel B.J. et al. (2010) "Stability And CDR Composition Biases Enrich Binder Functionality Landscapes," J. Mol. Biol. 401(1)84-96.
Hanger D.P. et al. (2009) "Tau Phosphorylation: The Therapeutic Challenge For Neurodegenerative Disease," Trends Mol. Med. 15(3):112-119.
Harding F.A. et al. (1995) "Class Switching In Human Immunoglobulin Transgenic Mice," Ann. N. Y. Acad. Sci. 764:536-546.
Hasegawa M. et al. (1992) "Protein Sequence And Mass Spectrometric Analyses of Tau In The Alzheimer's Disease Brain," J. Biol. Chem. 267:17047-17054.
Henikoff J.G. (1992) "Amino Acid Substitution Matrices From Protein Blocks," Proc. Natl. Acad. Sci. U.S.A. 89:10915-10919.
Hoffmann, R. et al. (1997) "Unique Alzheimer's Disease Paired Helical Filament Specific Epitopes Involve Double Phosphorylation at Specific Sites," Biochemistry 36:8114-8124.
Holliger P. et al. (1993) "'Diabodies': Small Bivalent And Bispecific Antibody Fragments," Proc. Natl. Acad. Sci. 90(14):6444-6448.
Holliger, P. (2002) "Expression Of Antibody Fragments In Pichia Pastoris," Methods Mol. Biol. 178, 349-357.
Holt L.J. et al. (2003) "Domain Antibodies: Proteins For Therapy," Trends Biotechnol. 21(11):484-90.

(56) References Cited

OTHER PUBLICATIONS

Hu et al., Levels of nonphosphorylated and phosphorylated tau in cerebrospinal fluid of Alzheimer's disease patients : an ultrasensitive bienzyme-substrate-recycle enzyme-linked immunosorbent assay. Am J Pathol. Apr. 2002;160(4):1269-78.
Huston et al. (1988) "Protein Engineering Of Antibody Binding Sites: Recovery Of Specific Activity In An Anti-Digoxin Single-Chain Fv Analogue Produced In *Escherichia coli*," Proc. Natl. Acad. Sci. (U.S.A.) 85:5879-5883.
Jack, C.R. et al. (2013) "Update on Hypothetical Model of Alzheimer's Disease Biomarkers," Lancet Neurol. 12(2):207-216.
Jackson, J.R. et al. (1994) "In Vitro Antibody Maturation," J Immunol. Apr. 1, 1995;154(7):3310-9.
Jicha, G.A. et al. (1997) "Alz-50 And MC-1, A New Monoclonal Antibody Raised To Paired Helical Filaments, Recognize Conformational Epitopes On Recombinant Tau," J. Neurosci. Res. 48, 128-132.
Karlin, S. et al. (1990) "Methods For Assessing The Statistical Significance Of Molecular Sequence Features By Using General Scoring Schemes," Proc. Natl. Acad. Sci. (USA) 87:2264-2268.
Kettleborough, C. A. et al. (1991) "Humanization Of A Mouse Monoclonal Antibody By CDR-Grafting: The Importance Of Framework Residues On Loop Conformation," Protein Engineering 4:773-783.
Kfoury, N. et al. (2012) "Trans-cellular Propagation of Tau Aggregation by Fibrillar Species," J. Biol. Chem. 287(23):19440-19451.
Kohler G. et al., (1975) "Continuous Cultures Of Fused Cells Secreting Antibody Of Predefined Specificity," Nature 256, 495-497 (1975).
Kolarova, M. et al. (2012) "Structure And Pathology Of Tau Protein In Alzheimer Disease," Int. J. Alzheimers. Dis. 2012, 731526 (13 pages).
Kosik K.S. et al. (1986) "Microtubule-Associated Protein Tau(t) Is A Major Antigenic Component Of Paired Helical Filaments In Alzheimer Disease," Proc. Natl. Acad. Sci. U.S.A. 86, 4044-4048.
Krause, J.C. et al. (2011) "An Insertion Mutation That Distorts Antibody Binding Site Architecture Enhances Function Of A Human Antibody," MBio. 2(1): e00345-10. (8 pages).
Kuan, C.T. et al. (2011) "Affinity-Matured Anti-Glycoprotein NMB Recombinant Immunotoxins Targeting Malignant Gliomas And Melanomas," Int. J. Cancer 129:111-121.
Kurth, M. et al. (1993) "Site-specific conjugation of a radioiodinated phenethylamine derivative to a monoclonal antibody results in increased radioactivity localization in tumor," J. Med. Chem. 36(9):1255-1261.
Labrijn A.F. et al. (2013) "Efficient Generation Of Stable Bispecific IgG1 By Controlled Fab-Arm Exchange," Proc. Natl. Acad. Sc. U.S.A. 100(113):5145-5150.
Lambert J.C. et al. (2013) "Meta-Analysis Of 74,046 Individuals Identifies 11 New Susceptibility Loci For Alzheimer's Disease," Nat. Genet. 45:1452-1460.
Launer L.J. (1992) "Overview Of Incidence Studies Of Dementia Conducted in Europe," Neuroepidemiology 11 (Suppl 1):2-13.
Li P. et al. (2007) "Expression Of Recombinant Proteins In Pichia Pastoris," Appl. Biochem. Biotechnol. 142(2):105-124.
Lindegren, S. et al. (1998) "Chloramine-T In High-Specific-Activity Radioiodination Of Antibodies Using N-Succinimidyl-3-(Trimethylstannyl)Benzoate As An Intermediate," Nucl. Med. Biol. 25(7):659-665.
LoBuglio, A.F. et al. (1989) "Mouse/Human Chimeric Monoclonal Antibody In Man: Kinetics And Immune Response," Proc. Natl. Acad. Sci. (U.S.A.) 86:4220-4224.
Lonberg N. et al. (1994) "Antigen-specific human antibodies from mice comprising four distinct genetic modifications," Nature 368:856-859.
Lonberg N. et al. (1995) "Human Antibodies From Transgenic Mice," Intern. Rev. Immunol. 13:65-93.
Mabry R. et al. (2010) "Engineering Of Stable Bispecific Antibodies Targeting IL-17A And IL-23," Protein Eng. Des. Sel. 23(3):115-127.

Maeda, H. et al. (1991) "Construction Of Reshaped Human Antibodies With HIV-Neutralizing Activity," Human Antibodies Hybridoma 2:124-134.
Marks et al. (1991) "By-Passing Immunization—Human Antibodies From V-Gene Libraries Displayed On Page," J. Mol. Biol. 222, 581-597.
McCafferty J. et al. (1990) "Phage Antibodies: Filamentous Phage Displaying Antibody Variable Domains," Nature 348, 552-554.
Metz S. et al. (2012) "Bispecific Antibody Derivatives With Restricted Binding Functionalities That Are Activated By Proteolytic Processing," Protein Eng. Des. Sel. 25(10):571-580.
Min S.W. et al. (2010) "Acetylation Of Tau Inhibits Its Degradation And Contributes To Tauopathy," Neuron 67:953-966.
Montgomery, D.L. et al. (2009) "Affinity Maturation And Characterization Of A Human Monoclonal Antibody Against HIV-1 gp41," MAbs 1(5):462-474.
Moore G.L. et al. (2011) "A Novel Bispecific Antibody Format Enables Simultaneous Bivalent And Monovalent Co-Engagement Of Distinct Target Antigens," MAbs 3(6):546-557.
Mukrasch, M.D. et al. (2009) "Structural Polymorphism of 441-Residue Tau at Single Residue Resolution," PLoS Biol. 7(2): e1000034: 0399-0414.
Nelson, P.T. et al. (2012) "Correlation of Alzheimer Disease Neuropathologic Changes with Cognitive Status: A Review of the Literature," J. Neuropathol. Exp. Neurol. 71(5):362-381.
Ohgushi M. et al. (1983) "'Molten-Globule State': A Compact Form Of Globular Proteins With Mobile Side Chains," FEBS Lett. 164:21-24.
Paul, Chapter 9: Structure and Function of Immunoglobulins. Fundamental Immunology, 3rd Edition. 1993:292-295.
Petry et al., Specificity of anti-tau antibodies when analyzing mice models of Alzheimer's disease: problems and solutions. PLoS One. May 2, 2014;9(5):e94251. doi: 10.1371/journal.pone.0094251.
Probst, A. et al. (2000) "Axonopathy and Amyotrophy in Mice Transgenic for Human Four-Repeat Tau Protein," Acta Neuropathol. 99:469-481.
Rafii et al., Recent developments in Alzheimer's disease therapeutics. BMC Med. Feb. 19, 2009;7:7. doi: 10.1186/1741-7015-7-7.
Rea, D.W. et al. (1990) "Site-specifically radioiodinated antibody for targeting tumors," Cancer Res. 50(3 Suppl):857s-861s.
Reinecke, J.B. et al. (2011) "Implicating Calpain In Tau-Mediated Toxicity In Vivo," PLoS One. 6:e23865 (9 pages).
Revets H. et al. (2005) "Nanobodies As Novel Agents For Cancer Therapy," Expert Opin. Biol. Ther. 5(1):111-124.
Ridgway J.B.B. et al. (1996) "'Knobs-Into-holes' Engineering Of Antibody CH3 Domains For Heavy Chain Heterodimerization," Protein Eng 9(7):617-621.
Riechmann, L. et al. (1988) "Reshaping Human Antibodies for Therapy," Nature 332:323-327.
Rosseels, J. et al. (2015) "Tau Monoclonal Antibody Generation Based on Humanized Yeast Models," J. Biol. Chem. 290(7):4059-4074.
Rudikoff, S. et al. (1982) "Single Amino Acid Substitution Altering Antigen-Binding Specificity," Proc. Nat'l. Acad. Sci. USA 79:1979-1983.
Sahara, N. et al. (2013) "Characteristics of TBS-extractable Hyperphosphorylated Tau Species: Aggregation Intermediates in rTg4510 Mouse Brain," J. Alzheimer's Dis. 33:249-263.
Sanders, D.W. et al. (2014) "Distinct Tau Prion Strains Propagate in Cells and Mice and Define Different Tauopathies," Neuron 82: 1271-1288.
Sankaranarayanan, S. et al. (2015) "Passive Immunization with Phospho-Tau Antibodies Reduces Tau Pathology and Functional Deficits in Two Distinct Mouse Tauopathy Models," PLoS One 10(5): e0125614:1-28.
Sato K. et al. (1993) "Reshaping A Human Antibody To Inhibit The Interleukin 6-Dependent Tumor Cell Growth," Cancer Res 53:851-856.
Schakowski F. et al. (2001) "A Novel Minimal-Size Vector (MIDGE) Improves Transgene Expression In Colon Carcinoma Cells And Avoids Transfection Of Undesired DNA," Mol. Ther. 3:793-800.

(56) References Cited

OTHER PUBLICATIONS

Schier R. et al. (1996) "Isolation of picomolar affinity anti-c-erbB-2 single-chain Fv by molecular evolution of the complementarity determining regions in the center of the antibody binding site," J. Mol. Biol. 263:551-567.

Schraen-Maschke et al., Tau as a biomarker of neurodegenerative diseases. Biomark Med. Aug. 2008;2(4):363-84. doi: 10.2217/17520363.2.4.363.

Sigurdsson E.M. et al. (2002) "Infectivity Of Amyloid Diseases," Trends Mol. Med. 8:411-413.

Singer, D. et al. (2005) "Characterization of Phosphorylation Dependent Antibodies to Study the Phosphorylation Status of the Tau Protein," nt'l J. Peptide Res. and Therapeutics 11(4):279-289.

Steidl, S. et al. (2008) "In Vitro Affinity Maturation Of Human GM-CSF Antibodies By Targeted CDR-Diversification," Mol. Immunol. 46(1):135-144.

Strop P. et al. (2012) Generating Bispecific Human IgG1 And IgG2 Antibodies From Any Antibody Pair, J. Mol. Biol. 420:204-219.

Sykes K.F. et al. (1997) "Linear Expression Elements: A Rapid, In Vivo, Method To Screen For Gene Functions," Nat Biotech 12:355-359.

Taylor L. D. et al. (1992) "A Transgenic Mouse That Expresses A Diversity Of Human Sequence Heavy and Light Chain Immunoglobulins," Nucleic Acids Res. 20:6287-6295.

Taylor L. D. et al. (1994) "Human Immunoglobulin Transgenes Undergo Rearrangement, Somatic Mutation And Class Switching In Mice That Lack Endogenous IgM," Int Immunol 6(4):579-591.

Tempest, P.R. et al. (1991) "Reshaping A Human Monoclonal Antibody To Inhibit Human Respiratory Syncytial Virus Infection in vivo," Bio/Technology 9:266-271.

Tuaillon N. et al. (1994) "Biased Utilization Of DHQ52 and JH4 Gene Segments In A Human Ig Transgenic Minilocus Is Independent Of Antigenic Selection," J. Immunol. 152:2912-2920.

Van der Vaart J.M. (2002) "Expression of VHH antibody fragments in *Saccharomyces cerevisiae*," Methods Mol. Biol. 178:359-366.

Van Heeke G. et al. (1989) "Expression Of Human Asparagine Synthetase in *Escherichia coli*," J. Biol. Chem. 264:5503-5509.

Verhoeyen, M. et al. (1988) "Reshaping Human Antibodies: Grafting An Antilysozyme Activity," Science 239:1534-1536.

Von Kreudenstein T.S. et al. (2013) "Improving Biophysical Properties Of A Biospecific Antibody Scaffold To Aid Developability," MAbs 5(5):646-654.

Walker, L.C. et al. (2013) "Mechanism Of Protein Seeding In Neurodegenerative Diseases," JAMA Neurol. 70:304-310.

Ward E.S. et al. (1989) "Binding Activities Of A Repertoire Of Single Immunoglobulin Variable Domains Secreted From *Escherichia coli*," Nature 341:544-546.

Weiner, M.W. et al. (2015) "Impact of the Alzheimer's Disease neuroimaging Initiative, 2004-2014," Alzheimers Dement. 11(7):865-884.

Wigler M. et al. (1978) "Biochemical Transfer Of Single-Copy Eucaryotic Genes Using Total Cellular DNA As Donor," Cell 14:725-731.

Wong, Y.W. et al. (1998) "Structural Requirements for a Specificity Switch and for Maintenance of Affinity Using Mutational Analysis of a Phage-Displayed Anti-Arsonate Antibody of Fab Heavy Chain First Complementarity-Determining Region," J. Immunol. 160:5990-5997.

Wostyn et al., Alzheimer's disease: cerebral glaucoma? Med Hypotheses. Jun. 2010;74(6):973-7. doi: 10.1016/j.mehy.2009.12.019. Epub Jan. 6, 2010.

Wu H. et al. (1998) "Stepwise In Vitro Affinity Maturation Of Vitaxin, An avb3-Specific Humanized mAb," Proc. Natl. Acad. Sci. U.S.A. 95:6037-6042.

Yanamandra et al., Anti-tau antibodies that block tau aggregate seeding in vitro markedly decrease pathology and improve cognition in vivo. Neuron. Oct. 16, 2013;80(2):402-414. doi: 10.1016/j.neuron.2013.07.046. Epub Sep. 26, 2013.

Yelton D.E. et al. (1995) "Affinity Maturation Of The BR96 Anti-Carcinoma Antibody By Codon-Based Mutagenesis," J. Immunol. 155:1994-2004.

Zhu Y. et al. (2014) "The Emerging Link Between O-GlcNAc And Alzheimer Disease," J. Biol. Chem. 289:50:34472-34481.

Zou Y.R. et al. (1993) "Gene Targeting In The IgK Locus: Efficient Generation Of ? Chain-Expressing B Cells, Independent Of Gene Rearrangement In IgK," EMBO J. 12(3):811-820.

[No Author Listed] PDB Accession No. 4CNI_B. Nov. 6, 2022. 4 pages. www.ncbi.nlm.nih.gov/protein/4CNI_B?report=genbank&log$=smartblast.

[No Author Listed], Genbank Accession No. AIC63043.1. Mar. 19, 2015. 4 pages. www.ncbi.nlm.nih.gov/protein/AIC63043.1?report=genbank&log$=smartblast.

[No Author Listed], Genbank Accession No. EGW13193.1. Mar. 14, 2015. 1 page. www.ncbi.nlm.nih.gov/protein/EGW13193.1.

▲ 2.10.3 immuno-depletion
◆ hC10-2 immuno-depletion

Figure 20

| Variant | % Deamidated LC:T2 peptide (28 Days at 40°C) |
|---|---|
| D55E N32Q | 0 |
| wt | 50 |
| D55E N32S | 0 |
| D55E | 40 |
| N32Q | 0 |
| N32S | 0 |
| A101T N32Q | 0 |
| A101T N32S | 0 |
| A101T | 93 |

SEQUENCE LISTING

<160> NUMBER OF SEQ ID NOS: 63

<210> SEQ ID NO 1
<211> LENGTH: 441
<212> TYPE: PRT
<213> ORGANISM: Artificial
<220> FEATURE:
<223> OTHER INFORMATION: Human Tau

<400> SEQUENCE: 1

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His

```
                20                  25                  30
Gln Asp Gln Glu Gly Asp Thr Asp Ala Gly Leu Lys Glu Ser Pro Leu
            35                  40                  45
Gln Thr Pro Thr Glu Asp Gly Ser Glu Glu Pro Gly Ser Glu Thr Ser
        50                  55                  60
Asp Ala Lys Ser Thr Pro Thr Ala Glu Asp Val Thr Ala Pro Leu Val
 65                  70                  75                  80
Asp Glu Gly Ala Pro Gly Lys Gln Ala Ala Gln Pro His Thr Glu
                85                  90                  95
Ile Pro Glu Gly Thr Thr Ala Glu Glu Ala Gly Ile Gly Asp Thr Pro
            100                 105                 110
Ser Leu Glu Asp Glu Ala Ala Gly His Val Thr Gln Ala Arg Met Val
        115                 120                 125
Ser Lys Ser Lys Asp Gly Thr Gly Ser Asp Asp Lys Lys Ala Lys Gly
    130                 135                 140
Ala Asp Gly Lys Thr Lys Ile Ala Thr Pro Arg Gly Ala Ala Pro Pro
145                 150                 155                 160
Gly Gln Lys Gly Gln Ala Asn Ala Thr Arg Ile Pro Ala Lys Thr Pro
                165                 170                 175
Pro Ala Pro Lys Thr Pro Ser Ser Gly Glu Pro Pro Lys Ser Gly
            180                 185                 190
Asp Arg Ser Gly Tyr Ser Ser Pro Gly Ser Pro Gly Thr Pro Gly Ser
        195                 200                 205
Arg Ser Arg Thr Pro Ser Leu Pro Thr Pro Pro Thr Arg Glu Pro Lys
    210                 215                 220
Lys Val Ala Val Val Arg Thr Pro Pro Lys Ser Pro Ser Ser Ala Lys
225                 230                 235                 240
Ser Arg Leu Gln Thr Ala Pro Val Pro Met Pro Asp Leu Lys Asn Val
                245                 250                 255
Lys Ser Lys Ile Gly Ser Thr Glu Asn Leu Lys His Gln Pro Gly Gly
            260                 265                 270
Gly Lys Val Gln Ile Ile Asn Lys Lys Leu Asp Leu Ser Asn Val Gln
        275                 280                 285
Ser Lys Cys Gly Ser Lys Asp Asn Ile Lys His Val Pro Gly Gly Gly
    290                 295                 300
Ser Val Gln Ile Val Tyr Lys Pro Val Asp Leu Ser Lys Val Thr Ser
305                 310                 315                 320
Lys Cys Gly Ser Leu Gly Asn Ile His His Lys Pro Gly Gly Gly Gln
                325                 330                 335
Val Glu Val Lys Ser Glu Lys Leu Asp Phe Lys Asp Arg Val Gln Ser
            340                 345                 350
Lys Ile Gly Ser Leu Asp Asn Ile Thr His Val Pro Gly Gly Gly Asn
        355                 360                 365
Lys Lys Ile Glu Thr His Lys Leu Thr Phe Arg Glu Asn Ala Lys Ala
    370                 375                 380
Lys Thr Asp His Gly Ala Glu Ile Val Tyr Lys Ser Pro Val Val Ser
385                 390                 395                 400
Gly Asp Thr Ser Pro Arg His Leu Ser Asn Val Ser Ser Thr Gly Ser
                405                 410                 415
Ile Asp Met Val Asp Ser Pro Gln Leu Ala Thr Leu Ala Asp Glu Val
            420                 425                 430
Ser Ala Ser Leu Ala Lys Gln Gly Leu
        435                 440
```

<210> SEQ ID NO 2
<211> LENGTH: 23
<212> TYPE: PRT
<213> ORGANISM: Artificial
<220> FEATURE:
<223> OTHER INFORMATION: tau residues 386-408 (pS396, pS404)

<400> SEQUENCE: 2

Thr Asp His Gly Ala Glu Ile Val Tyr Lys Ser Pro Val Val Ser Gly
1               5                   10                  15

Asp Thr Ser Pro Arg His Leu
            20

<210> SEQ ID NO 3
<211> LENGTH: 11
<212> TYPE: PRT
<213> ORGANISM: Artificial
<220> FEATURE:
<223> OTHER INFORMATION: C10-2 Light Chain CDR1

<400> SEQUENCE: 3

Gln Ala Ser Gln Asp Thr Ser Ile Asn Leu Asn
1               5                   10

<210> SEQ ID NO 4
<211> LENGTH: 7
<212> TYPE: PRT
<213> ORGANISM: Artificial
<220> FEATURE:
<223> OTHER INFORMATION: C10-2 Light Chain CDR2

<400> SEQUENCE: 4

Gly Ala Ser Asn Leu Glu Thr
1               5

<210> SEQ ID NO 5
<211> LENGTH: 9
<212> TYPE: PRT
<213> ORGANISM: Artificial
<220> FEATURE:
<223> OTHER INFORMATION: C10-2 Light Chain CDR3

<400> SEQUENCE: 5

Leu Gln His Thr Tyr Leu Pro Phe Thr
1               5

<210> SEQ ID NO 6
<211> LENGTH: 5
<212> TYPE: PRT
<213> ORGANISM: Artificial
<220> FEATURE:
<223> OTHER INFORMATION: C10-2 Heavy Chain CDR1

<400> SEQUENCE: 6

Asp Arg Thr Ile His
1               5

<210> SEQ ID NO 7
<211> LENGTH: 17
<212> TYPE: PRT
<213> ORGANISM: Artificial
<220> FEATURE:
<223> OTHER INFORMATION: C10-2 Heavy Chain CDR2

<400> SEQUENCE: 7

Tyr Ile Tyr Pro Gly Asp Gly Ser Thr Lys Tyr Ser Gln Lys Phe Gln
1               5                   10                  15

Gly

<210> SEQ ID NO 8
<211> LENGTH: 6
<212> TYPE: PRT
<213> ORGANISM: Artificial
<220> FEATURE:
<223> OTHER INFORMATION: C10-2 Heavy Chain CDR3

<400> SEQUENCE: 8

Arg Gly Ala Met Asp Tyr
1               5

<210> SEQ ID NO 9
<211> LENGTH: 214
<212> TYPE: PRT
<213> ORGANISM: Mus musculus
<220> FEATURE:
<221> NAME/KEY: misc_feature
<222> LOCATION: (1)..(214)
<223> OTHER INFORMATION: C10-2 Light Chain

<400> SEQUENCE: 9

Asp Val Gln Met Ile Gln Ser Pro Ser Ser Leu Ser Ala Ser Leu Gly
1               5                   10                  15

Asp Ile Val Thr Met Thr Cys Gln Ala Ser Gln Gly Thr Ser Ile Asn
            20                  25                  30

Leu Asn Trp Phe Gln Lys Pro Gly Lys Ala Pro Lys Leu Leu Ile
        35                  40                  45

Tyr Gly Ala Ser Asn Leu Glu Asp Gly Val Pro Ser Arg Phe Ser Gly
    50                  55                  60

Ser Arg Tyr Gly Thr Asp Phe Thr Leu Thr Ile Ser Ser Leu Glu Asp
65                  70                  75                  80

Glu Asp Met Ala Thr Tyr Phe Cys Leu Gln His Thr Tyr Leu Pro Phe
                85                  90                  95

Thr Phe Gly Ser Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 10
<211> LENGTH: 439
<212> TYPE: PRT
<213> ORGANISM: Mus musculus
<220> FEATURE:
<221> NAME/KEY: misc_feature
<222> LOCATION: (1)..(439)
<223> OTHER INFORMATION: C10-2 HeavyChain

<400> SEQUENCE: 10

```
Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp Arg
            20                  25                  30

Thr Ile His Trp Val Lys Gln Arg Pro Glu Gln Gly Leu Glu Trp Ile
        35                  40                  45

Gly Tyr Ile Tyr Pro Gly Asp Gly Ser Thr Lys Tyr Asn Glu Asn Phe
    50                  55                  60

Lys Gly Lys Ala Thr Leu Thr Ala Asp Lys Ser Ser Thr Ala Tyr
65                  70                  75                  80

Met Gln Leu Asn Ser Leu Thr Ser Glu Asp Ser Ala Val Tyr Phe Cys
                85                  90                  95

Ala Arg Arg Gly Ala Met Asp Tyr Trp Gly Gln Gly Thr Ser Val Thr
            100                 105                 110

Val Ser Ser Ala Lys Thr Thr Pro Pro Ser Val Tyr Pro Leu Ala Pro
        115                 120                 125

Gly Ser Ala Ala Gln Thr Asn Ser Met Val Thr Leu Gly Cys Leu Val
    130                 135                 140

Lys Gly Tyr Phe Pro Glu Pro Val Thr Val Thr Trp Asn Ser Gly Ser
145                 150                 155                 160

Leu Ser Ser Gly Val His Thr Phe Pro Ala Val Leu Gln Ser Asp Leu
                165                 170                 175

Tyr Thr Leu Ser Ser Ser Val Thr Val Pro Ser Ser Thr Trp Pro Ser
            180                 185                 190

Glu Thr Val Thr Cys Asn Val Ala His Pro Ala Ser Ser Thr Lys Val
        195                 200                 205

Asp Lys Lys Ile Val Pro Arg Asp Cys Gly Cys Lys Pro Cys Ile Cys
    210                 215                 220

Thr Val Pro Glu Val Ser Ser Val Phe Ile Phe Pro Pro Lys Pro Lys
225                 230                 235                 240

Asp Val Leu Thr Ile Thr Leu Thr Pro Lys Val Thr Cys Val Val Val
                245                 250                 255

Asp Ile Ser Lys Asp Asp Pro Glu Val Gln Phe Ser Trp Phe Val Asp
            260                 265                 270

Asp Val Glu Val His Thr Ala Gln Thr Gln Pro Arg Glu Glu Gln Phe
        275                 280                 285

Asn Ser Thr Phe Arg Ser Val Ser Glu Leu Pro Ile Met His Gln Asp
    290                 295                 300

Trp Leu Asn Gly Lys Glu Phe Lys Cys Arg Val Asn Ser Ala Ala Phe
305                 310                 315                 320

Pro Ala Pro Ile Glu Lys Thr Ile Ser Lys Thr Lys Gly Arg Pro Lys
                325                 330                 335

Ala Pro Gln Val Tyr Thr Ile Pro Pro Pro Lys Glu Gln Met Ala Lys
            340                 345                 350

Asp Lys Val Ser Leu Thr Cys Met Ile Thr Asp Phe Phe Pro Glu Asp
        355                 360                 365

Ile Thr Val Glu Trp Gln Trp Asn Gly Gln Pro Ala Glu Asn Tyr Lys
    370                 375                 380

Asn Thr Gln Pro Ile Met Asp Thr Asp Gly Ser Tyr Phe Val Tyr Ser
385                 390                 395                 400
```

```
Lys Leu Asn Val Gln Lys Ser Asn Trp Glu Ala Gly Asn Thr Phe Thr
                405                 410                 415

Cys Ser Val Leu His Glu Gly Leu His Asn His His Thr Glu Lys Ser
            420                 425                 430

Leu Ser His Ser Pro Gly Lys
            435

<210> SEQ ID NO 11
<211> LENGTH: 445
<212> TYPE: PRT
<213> ORGANISM: Artificial
<220> FEATURE:
<223> OTHER INFORMATION: humanized C10-2 Heavy Chain

<400> SEQUENCE: 11

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Asp Arg
            20                  25                  30

Thr Ile His Trp Val Arg Gln Ala Pro Gly Gln Gly Leu Glu Trp Ile
        35                  40                  45

Gly Tyr Ile Tyr Pro Gly Asp Gly Ser Thr Lys Tyr Ser Gln Lys Phe
    50                  55                  60

Gln Gly Arg Ala Thr Leu Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Ala Met Asp Tyr Trp Gly Gln Gly Thr Ser Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320
```

```
Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 12
<211> LENGTH: 214
<212> TYPE: PRT
<213> ORGANISM: Artificial
<220> FEATURE:
<223> OTHER INFORMATION: humanized C10-2 Light Chain

<400> SEQUENCE: 12

Asp Val Gln Met Thr Gln Ser Pro Ser Ser Leu Ser Ala Ser Val Gly
1               5                   10                  15

Asp Arg Val Thr Met Thr Cys Gln Ala Ser Gln Asp Thr Ser Ile Asn
            20                  25                  30

Leu Asn Trp Phe Gln Gln Lys Pro Gly Lys Ala Pro Lys Leu Leu Ile
        35                  40                  45

Tyr Gly Ala Ser Asn Leu Glu Thr Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Met Ala Thr Tyr Tyr Cys Leu Gln His Thr Tyr Leu Pro Phe
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 13
```

<211> LENGTH: 444
<212> TYPE: PRT
<213> ORGANISM: Artificial
<220> FEATURE:
<223> OTHER INFORMATION: humanized C10-2 Heavy Chain Variant D55E

<400> SEQUENCE: 13

```
Gln Val Gln Leu Val Gln Ser Gly Ala Glu Val Lys Pro Gly Ala
1               5                   10                  15

Ser Val Lys Ile Ser Cys Lys Ala Ser Gly Tyr Thr Phe Thr Asp Arg
            20                  25                  30

Thr Ile His Trp Val Arg Gln Ala Pro Gly Gln Gly Leu Glu Trp Ile
        35                  40                  45

Gly Tyr Ile Tyr Pro Gly Glu Gly Ser Thr Lys Tyr Ser Gln Lys Phe
    50                  55                  60

Gln Gly Arg Ala Thr Leu Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Ala Met Asp Tyr Trp Gly Gln Gly Thr Ser Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380
```

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
        420                 425                 430

His Tyr Thr Gln Lys Ser Leu Ser Leu Ser Pro Gly
    435                 440

<210> SEQ ID NO 14
<211> LENGTH: 444
<212> TYPE: PRT
<213> ORGANISM: Artificial
<220> FEATURE:
<223> OTHER INFORMATION: humanized C10-2 Heavy Chain Variant D55Q

<400> SEQUENCE: 14

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Asp Arg
            20                  25                  30

Thr Ile His Trp Val Arg Gln Ala Pro Gly Gln Gly Leu Glu Trp Ile
        35                  40                  45

Gly Tyr Ile Tyr Pro Gly Gln Gly Ser Thr Lys Tyr Ser Gln Lys Phe
    50                  55                  60

Gln Gly Arg Ala Thr Leu Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Ala Met Asp Tyr Trp Gly Gln Gly Thr Ser Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

```
Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
        340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
            435                 440

<210> SEQ ID NO 15
<211> LENGTH: 444
<212> TYPE: PRT
<213> ORGANISM: Artificial
<220> FEATURE:
<223> OTHER INFORMATION: humanized C10-2 Heavy Chain Variant D55S

<400> SEQUENCE: 15

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Asp Arg
            20                  25                  30

Thr Ile His Trp Val Arg Gln Ala Pro Gly Gln Gly Leu Glu Trp Ile
        35                  40                  45

Gly Tyr Ile Tyr Pro Gly Ser Gly Ser Thr Lys Tyr Ser Gln Lys Phe
    50                  55                  60

Gln Gly Arg Ala Thr Leu Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Ala Met Asp Tyr Trp Gly Gln Gly Thr Ser Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220
```

```
Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
        260                 265                 270

Phe Asn Trp Tyr Val Asp Gly Val Glu Val His Asn Ala Lys Thr Lys
    275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
            435                 440

<210> SEQ ID NO 16
<211> LENGTH: 214
<212> TYPE: PRT
<213> ORGANISM: Artificial
<220> FEATURE:
<223> OTHER INFORMATION: humanized C10-2 Light Chain Variant N32S

<400> SEQUENCE: 16

Asp Val Gln Met Thr Gln Ser Pro Ser Ser Leu Ser Ala Ser Val Gly
1               5                   10                  15

Asp Arg Val Thr Met Thr Cys Gln Ala Ser Gln Asp Thr Ser Ile Ser
            20                  25                  30

Leu Asn Trp Phe Gln Gln Lys Pro Gly Lys Ala Pro Lys Leu Leu Ile
        35                  40                  45

Tyr Gly Ala Ser Asn Leu Glu Thr Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Met Ala Thr Tyr Tyr Cys Leu Gln His Thr Tyr Leu Pro Phe
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 17
<211> LENGTH: 214
<212> TYPE: PRT
<213> ORGANISM: Artificial
<220> FEATURE:
<223> OTHER INFORMATION: humanized C10-2 Light Chain Variant N32Q

<400> SEQUENCE: 17

Asp Val Gln Met Thr Gln Ser Pro Ser Ser Leu Ser Ala Ser Val Gly
1               5                   10                  15

Asp Arg Val Thr Met Thr Cys Gln Ala Ser Gln Asp Thr Ser Ile Gln
                20                  25                  30

Leu Asn Trp Phe Gln Lys Pro Gly Lys Ala Pro Lys Leu Leu Ile
            35                  40                  45

Tyr Gly Ala Ser Asn Leu Glu Thr Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Met Ala Thr Tyr Tyr Cys Leu Gln His Thr Tyr Leu Pro Phe
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 18
<211> LENGTH: 214
<212> TYPE: PRT
<213> ORGANISM: Artificial
<220> FEATURE:
<223> OTHER INFORMATION: humanized C10-2 Light Chain Variant N34S

<400> SEQUENCE: 18

Asp Val Gln Met Thr Gln Ser Pro Ser Ser Leu Ser Ala Ser Val Gly
```

```
            1               5                  10                 15
          Asp Arg Val Thr Met Thr Cys Gln Ala Ser Gln Asp Thr Ser Ile Asn
                          20                  25                  30

Leu Ser Trp Phe Gln Gln Lys Pro Gly Lys Ala Pro Lys Leu Leu Ile
                          35                  40                  45

Tyr Gly Ala Ser Asn Leu Glu Thr Gly Val Pro Ser Arg Phe Ser Gly
                          50                  55                  60

Ser Arg Ser Gly Thr Asp Phe Thr Leu Thr Ile Ser Ser Leu Gln Pro
           65                  70                  75                  80

Glu Asp Met Ala Thr Tyr Tyr Cys Leu Gln His Thr Tyr Leu Pro Phe
                          85                  90                  95

Thr Phe Gly Ser Gly Thr Lys Leu Glu Ile Lys Arg Thr Val Ala Ala
                         100                 105                 110

Pro Ser Val Phe Ile Phe Pro Pro Ser Asp Glu Gln Leu Lys Ser Gly
                         115                 120                 125

Thr Ala Ser Val Val Cys Leu Leu Asn Asn Phe Tyr Pro Arg Glu Ala
                         130                 135                 140

Lys Val Gln Trp Lys Val Asp Asn Ala Leu Gln Ser Gly Asn Ser Gln
          145                 150                 155                 160

Glu Ser Val Thr Glu Gln Asp Ser Lys Asp Ser Thr Tyr Ser Leu Ser
                         165                 170                 175

Ser Thr Leu Thr Leu Ser Lys Ala Asp Tyr Glu Lys His Lys Val Tyr
                         180                 185                 190

Ala Cys Glu Val Thr His Gln Gly Leu Ser Ser Pro Val Thr Lys Ser
                         195                 200                 205

Phe Asn Arg Gly Glu Cys
                         210

<210> SEQ ID NO 19
<211> LENGTH: 214
<212> TYPE: PRT
<213> ORGANISM: Artificial
<220> FEATURE:
<223> OTHER INFORMATION: humanized C10-2 Light Chain Variant N34Q

<400> SEQUENCE: 19

Asp Val Gln Met Thr Gln Ser Pro Ser Ser Leu Ser Ala Ser Val Gly
           1               5                  10                  15

Asp Arg Val Thr Met Thr Cys Gln Ala Ser Gln Asp Thr Ser Ile Asn
                          20                  25                  30

Leu Gln Trp Phe Gln Gln Lys Pro Gly Lys Ala Pro Lys Leu Leu Ile
                          35                  40                  45

Tyr Gly Ala Ser Asn Leu Glu Thr Gly Val Pro Ser Arg Phe Ser Gly
                          50                  55                  60

Ser Arg Ser Gly Thr Asp Phe Thr Leu Thr Ile Ser Ser Leu Gln Pro
           65                  70                  75                  80

Glu Asp Met Ala Thr Tyr Tyr Cys Leu Gln His Thr Tyr Leu Pro Phe
                          85                  90                  95

Thr Phe Gly Ser Gly Thr Lys Leu Glu Ile Lys Arg Thr Val Ala Ala
                         100                 105                 110

Pro Ser Val Phe Ile Phe Pro Pro Ser Asp Glu Gln Leu Lys Ser Gly
                         115                 120                 125

Thr Ala Ser Val Val Cys Leu Leu Asn Asn Phe Tyr Pro Arg Glu Ala
                         130                 135                 140

Lys Val Gln Trp Lys Val Asp Asn Ala Leu Gln Ser Gly Asn Ser Gln
```

```
                145                 150                 155                 160
Glu Ser Val Thr Glu Gln Asp Ser Lys Asp Ser Thr Tyr Ser Leu Ser
                    165                 170                 175

Ser Thr Leu Thr Leu Ser Lys Ala Asp Tyr Glu Lys His Lys Val Tyr
                    180                 185                 190

Ala Cys Glu Val Thr His Gln Gly Leu Ser Ser Pro Val Thr Lys Ser
                    195                 200                 205

Phe Asn Arg Gly Glu Cys
                    210

<210> SEQ ID NO 20
<211> LENGTH: 214
<212> TYPE: PRT
<213> ORGANISM: Artificial
<220> FEATURE:
<223> OTHER INFORMATION: humanized C10-2 Light Chain Variant N32S, N34S

<400> SEQUENCE: 20

Asp Val Gln Met Thr Gln Ser Pro Ser Ser Leu Ser Ala Ser Val Gly
1               5                   10                  15

Asp Arg Val Thr Met Thr Cys Gln Ala Ser Gln Asp Thr Ser Ile Ser
                20                  25                  30

Leu Ser Trp Phe Gln Gln Lys Pro Gly Lys Ala Pro Lys Leu Leu Ile
            35                  40                  45

Tyr Gly Ala Ser Asn Leu Glu Thr Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Met Ala Thr Tyr Tyr Cys Leu Gln His Thr Tyr Leu Pro Phe
                    85                  90                  95

Thr Phe Gly Ser Gly Thr Lys Leu Glu Ile Lys Arg Thr Val Ala Ala
                    100                 105                 110

Pro Ser Val Phe Ile Phe Pro Pro Ser Asp Glu Gln Leu Lys Ser Gly
                    115                 120                 125

Thr Ala Ser Val Val Cys Leu Leu Asn Asn Phe Tyr Pro Arg Glu Ala
                130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                    165                 170                 175

Ser Thr Leu Thr Leu Ser Lys Ala Asp Tyr Glu Lys His Lys Val Tyr
                    180                 185                 190

Ala Cys Glu Val Thr His Gln Gly Leu Ser Ser Pro Val Thr Lys Ser
                    195                 200                 205

Phe Asn Arg Gly Glu Cys
                    210

<210> SEQ ID NO 21
<211> LENGTH: 214
<212> TYPE: PRT
<213> ORGANISM: Artificial
<220> FEATURE:
<223> OTHER INFORMATION: humanized C10-2 Light Chain Variant N32Q, N34S

<400> SEQUENCE: 21

Asp Val Gln Met Thr Gln Ser Pro Ser Ser Leu Ser Ala Ser Val Gly
1               5                   10                  15
```

```
Asp Arg Val Thr Met Thr Cys Gln Ala Ser Gln Asp Thr Ser Ile Gln
             20                  25                  30

Leu Ser Trp Phe Gln Gln Lys Pro Gly Lys Ala Pro Lys Leu Leu Ile
         35                  40                  45

Tyr Gly Ala Ser Asn Leu Glu Thr Gly Val Pro Ser Arg Phe Ser Gly
     50                  55                  60

Ser Arg Ser Gly Thr Asp Phe Thr Leu Thr Ile Ser Ser Leu Gln Pro
 65                  70                  75                  80

Glu Asp Met Ala Thr Tyr Tyr Cys Leu Gln His Thr Tyr Leu Pro Phe
                 85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 22
<211> LENGTH: 214
<212> TYPE: PRT
<213> ORGANISM: Artificial
<220> FEATURE:
<223> OTHER INFORMATION: humanized C10-2 Light Chain Variant N32Q, N34Q

<400> SEQUENCE: 22

Asp Val Gln Met Thr Gln Ser Pro Ser Ser Leu Ser Ala Ser Val Gly
 1               5                  10                  15

Asp Arg Val Thr Met Thr Cys Gln Ala Ser Gln Asp Thr Ser Ile Gln
             20                  25                  30

Leu Gln Trp Phe Gln Gln Lys Pro Gly Lys Ala Pro Lys Leu Leu Ile
         35                  40                  45

Tyr Gly Ala Ser Asn Leu Glu Thr Gly Val Pro Ser Arg Phe Ser Gly
     50                  55                  60

Ser Arg Ser Gly Thr Asp Phe Thr Leu Thr Ile Ser Ser Leu Gln Pro
 65                  70                  75                  80

Glu Asp Met Ala Thr Tyr Tyr Cys Leu Gln His Thr Tyr Leu Pro Phe
                 85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

-continued

```
Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
    195                 200                 205

Phe Asn Arg Gly Glu Cys
    210

<210> SEQ ID NO 23
<211> LENGTH: 214
<212> TYPE: PRT
<213> ORGANISM: Artificial
<220> FEATURE:
<223> OTHER INFORMATION: humanized C10-2 Light Chain Variant N32S, N34Q

<400> SEQUENCE: 23

Asp Val Gln Met Thr Gln Ser Pro Ser Ser Leu Ser Ala Ser Val Gly
1               5                   10                  15

Asp Arg Val Thr Met Thr Cys Gln Ala Ser Gln Asp Thr Ser Ile Ser
            20                  25                  30

Leu Gln Trp Phe Gln Gln Lys Pro Gly Lys Ala Pro Lys Leu Leu Ile
        35                  40                  45

Tyr Gly Ala Ser Asn Leu Glu Thr Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Met Ala Thr Tyr Tyr Cys Leu Gln His Thr Tyr Leu Pro Phe
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 24
<211> LENGTH: 444
<212> TYPE: PRT
<213> ORGANISM: Artificial
<220> FEATURE:
<223> OTHER INFORMATION: humanized C10-2 Heavy Chain Variant A101T

<400> SEQUENCE: 24

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Asp Arg
            20                  25                  30
```

```
Thr Ile His Trp Val Arg Gln Ala Pro Gly Gln Gly Leu Glu Trp Ile
         35                  40                  45
Gly Tyr Ile Tyr Pro Gly Asp Gly Ser Thr Lys Tyr Ser Gln Lys Phe
         50                  55                  60
Gln Gly Arg Ala Thr Leu Thr Ala Asp Thr Ser Ala Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Arg Gly Thr Met Asp Tyr Trp Gly Gln Gly Thr Ser Val Thr
                100                 105                 110
Val Ser Ser Ala Ser Thr Lys Gly Pro Ser Val Phe Pro Leu Ala Pro
                115                 120                 125
Ser Ser Lys Ser Thr Ser Gly Gly Thr Ala Ala Leu Gly Cys Leu Val
        130                 135                 140
Lys Asp Tyr Phe Pro Glu Pro Val Thr Val Ser Trp Asn Ser Gly Ala
145                 150                 155                 160
Leu Thr Ser Gly Val His Thr Phe Pro Ala Val Leu Gln Ser Ser Gly
                165                 170                 175
Leu Tyr Ser Leu Ser Ser Val Val Thr Val Pro Ser Ser Ser Leu Gly
            180                 185                 190
Thr Gln Thr Tyr Ile Cys Asn Val Asn His Lys Pro Ser Asn Thr Lys
        195                 200                 205
Val Asp Lys Arg Val Glu Pro Lys Ser Cys Asp Lys Thr His Thr Cys
    210                 215                 220
Pro Pro Cys Pro Ala Pro Glu Leu Leu Gly Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser His Glu Asp Pro Glu Val Lys
            260                 265                 270
Phe Asn Trp Tyr Val Asp Gly Val Glu Val His Asn Ala Lys Thr Lys
        275                 280                 285
Pro Arg Glu Glu Gln Tyr Asn Ser Thr Tyr Arg Val Val Ser Val Leu
    290                 295                 300
Thr Val Leu His Gln Asp Trp Leu Asn Gly Lys Glu Tyr Lys Cys Lys
305                 310                 315                 320
Val Ser Asn Lys Ala Leu Pro Ala Pro Ile Glu Lys Thr Ile Ser Lys
                325                 330                 335
Ala Lys Gly Gln Pro Arg Glu Pro Gln Val Tyr Thr Leu Pro Pro Ser
            340                 345                 350
Arg Glu Glu Met Thr Lys Asn Gln Val Ser Leu Thr Cys Leu Val Lys
        355                 360                 365
Gly Phe Tyr Pro Ser Asp Ile Ala Val Glu Trp Glu Ser Asn Gly Gln
    370                 375                 380
Pro Glu Asn Asn Tyr Lys Thr Thr Pro Pro Val Leu Asp Ser Asp Gly
385                 390                 395                 400
Ser Phe Phe Leu Tyr Ser Lys Leu Thr Val Asp Lys Ser Arg Trp Gln
                405                 410                 415
Gln Gly Asn Val Phe Ser Cys Ser Val Met His Glu Ala Leu His Asn
            420                 425                 430
His Tyr Thr Gln Lys Ser Leu Ser Leu Ser Pro Gly
        435                 440
```

```
<210> SEQ ID NO 25
<211> LENGTH: 444
<212> TYPE: PRT
<213> ORGANISM: Artificial
<220> FEATURE:
<223> OTHER INFORMATION: humanized C10-2 Heavy Chain Variant D55E, A101T

<400> SEQUENCE: 25

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Asp Arg
            20                  25                  30

Thr Ile His Trp Val Arg Gln Ala Pro Gly Gln Gly Leu Glu Trp Ile
        35                  40                  45

Gly Tyr Ile Tyr Pro Gly Glu Gly Ser Thr Lys Tyr Ser Gln Lys Phe
50                  55                  60

Gln Gly Arg Ala Thr Leu Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Thr Met Asp Tyr Trp Gly Gln Gly Thr Ser Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365
```

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
            435                 440

<210> SEQ ID NO 26
<211> LENGTH: 444
<212> TYPE: PRT
<213> ORGANISM: Artificial
<220> FEATURE:
<223> OTHER INFORMATION: humanized C10-2 Heavy Chain Variant D55Q, A101T

<400> SEQUENCE: 26

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Asp Arg
            20                  25                  30

Thr Ile His Trp Val Arg Gln Ala Pro Gly Gln Gly Leu Glu Trp Ile
        35                  40                  45

Gly Tyr Ile Tyr Pro Gly Gln Gly Ser Thr Lys Tyr Ser Gln Lys Phe
    50                  55                  60

Gln Gly Arg Ala Thr Leu Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Thr Met Asp Tyr Trp Gly Gln Gly Thr Ser Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

-continued

```
Pro Arg Glu Glu Gln Tyr Asn Ser Thr Tyr Arg Val Ser Val Leu
    290                 295                 300
Thr Val Leu His Gln Asp Trp Leu Asn Gly Lys Glu Tyr Lys Cys Lys
305                 310                 315                 320
Val Ser Asn Lys Ala Leu Pro Ala Pro Ile Glu Lys Thr Ile Ser Lys
                325                 330                 335
Ala Lys Gly Gln Pro Arg Glu Pro Gln Val Tyr Thr Leu Pro Pro Ser
                340                 345                 350
Arg Glu Glu Met Thr Lys Asn Gln Val Ser Leu Thr Cys Leu Val Lys
                355                 360                 365
Gly Phe Tyr Pro Ser Asp Ile Ala Val Glu Trp Glu Ser Asn Gly Gln
370                 375                 380
Pro Glu Asn Asn Tyr Lys Thr Thr Pro Pro Val Leu Asp Ser Asp Gly
385                 390                 395                 400
Ser Phe Phe Leu Tyr Ser Lys Leu Thr Val Asp Lys Ser Arg Trp Gln
                405                 410                 415
Gln Gly Asn Val Phe Ser Cys Ser Val Met His Glu Ala Leu His Asn
                420                 425                 430
His Tyr Thr Gln Lys Ser Leu Ser Leu Ser Pro Gly
                435                 440

<210> SEQ ID NO 27
<211> LENGTH: 444
<212> TYPE: PRT
<213> ORGANISM: Artificial
<220> FEATURE:
<223> OTHER INFORMATION: humanized C10-2 Heavy Chain Variant D55S, A101T

<400> SEQUENCE: 27

Gln Val Gln Leu Val Gln Ser Gly Ala Glu Val Val Lys Pro Gly Ala
1               5                   10                  15
Ser Val Lys Ile Ser Cys Lys Ala Ser Gly Tyr Thr Phe Thr Asp Arg
                20                  25                  30
Thr Ile His Trp Val Arg Gln Ala Pro Gly Gln Gly Leu Glu Trp Ile
            35                  40                  45
Gly Tyr Ile Tyr Pro Gly Ser Gly Ser Thr Lys Tyr Ser Gln Lys Phe
50                  55                  60
Gln Gly Arg Ala Thr Leu Thr Ala Asp Thr Ser Ala Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Arg Gly Thr Met Asp Tyr Trp Gly Gln Gly Thr Ser Val Thr
                100                 105                 110
Val Ser Ser Ala Ser Thr Lys Gly Pro Ser Val Phe Pro Leu Ala Pro
            115                 120                 125
Ser Ser Lys Ser Thr Ser Gly Gly Thr Ala Ala Leu Gly Cys Leu Val
130                 135                 140
Lys Asp Tyr Phe Pro Glu Pro Val Thr Val Ser Trp Asn Ser Gly Ala
145                 150                 155                 160
Leu Thr Ser Gly Val His Thr Phe Pro Ala Val Leu Gln Ser Ser Gly
                165                 170                 175
Leu Tyr Ser Leu Ser Ser Val Val Thr Val Pro Ser Ser Ser Leu Gly
                180                 185                 190
Thr Gln Thr Tyr Ile Cys Asn Val Asn His Lys Pro Ser Asn Thr Lys
                195                 200                 205
```

-continued

```
Val Asp Lys Arg Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440

<210> SEQ ID NO 28
<211> LENGTH: 18
<212> TYPE: PRT
<213> ORGANISM: Artificial
<220> FEATURE:
<223> OTHER INFORMATION: humanized C10-2 Heavy Chain CDR2 Variant D55E

<400> SEQUENCE: 28

Tyr Ile Tyr Pro Gly Glu Gly Ser Thr Lys Tyr Ser Gln Lys Phe Gln
1               5                   10                  15

Gly Arg

<210> SEQ ID NO 29
<211> LENGTH: 18
<212> TYPE: PRT
<213> ORGANISM: Artificial
<220> FEATURE:
<223> OTHER INFORMATION: humanized C10-2 Heavy Chain CDR2 Variant D55Q

<400> SEQUENCE: 29

Tyr Ile Tyr Pro Gly Gln Gly Ser Thr Lys Tyr Ser Gln Lys Phe Gln
1               5                   10                  15

Gly Arg

<210> SEQ ID NO 30
<211> LENGTH: 18
<212> TYPE: PRT
```

```
<213> ORGANISM: Artificial
<220> FEATURE:
<223> OTHER INFORMATION: humanized C10-2 Heavy Chain CDR2 Variant D55S

<400> SEQUENCE: 30

Tyr Ile Tyr Pro Gly Ser Gly Ser Thr Lys Tyr Ser Gln Lys Phe Gln
1               5                   10                  15

Gly Arg

<210> SEQ ID NO 31
<211> LENGTH: 11
<212> TYPE: PRT
<213> ORGANISM: Artificial
<220> FEATURE:
<223> OTHER INFORMATION: humanized C10-2 Light Chain CDR1 Variant N32S

<400> SEQUENCE: 31

Gln Ala Ser Gln Asp Thr Ser Ile Ser Leu Asn
1               5                   10

<210> SEQ ID NO 32
<211> LENGTH: 11
<212> TYPE: PRT
<213> ORGANISM: Artificial
<220> FEATURE:
<223> OTHER INFORMATION: humanized C10-2 Light Chain CDR1 Variant N32Q

<400> SEQUENCE: 32

Gln Ala Ser Gln Asp Thr Ser Ile Gln Leu Gln
1               5                   10

<210> SEQ ID NO 33
<211> LENGTH: 11
<212> TYPE: PRT
<213> ORGANISM: Artificial
<220> FEATURE:
<223> OTHER INFORMATION: humanized C10-2 Light Chain CDR1 Variant N34S

<400> SEQUENCE: 33

Gln Ala Ser Gln Asp Thr Ser Ile Asn Leu Ser
1               5                   10

<210> SEQ ID NO 34
<211> LENGTH: 11
<212> TYPE: PRT
<213> ORGANISM: Artificial
<220> FEATURE:
<223> OTHER INFORMATION: humanized C10-2 Light Chain CDR1 Variant N34Q

<400> SEQUENCE: 34

Gln Ala Ser Gln Asp Thr Ser Ile Asn Leu Gln
1               5                   10

<210> SEQ ID NO 35
<211> LENGTH: 11
<212> TYPE: PRT
<213> ORGANISM: Artificial
<220> FEATURE:
<223> OTHER INFORMATION: humanized C10-2 Light Chain CDR1 Variant N32S,
      N34S

<400> SEQUENCE: 35

Gln Ala Ser Gln Asp Thr Ser Ile Ser Leu Ser
1               5                   10

<210> SEQ ID NO 36
```

```
<211> LENGTH: 11
<212> TYPE: PRT
<213> ORGANISM: Artificial
<220> FEATURE:
<223> OTHER INFORMATION: humanized C10-2 Light Chain CDR1 Variant N32Q,
      N34S

<400> SEQUENCE: 36

Gln Ala Ser Gln Asp Thr Ser Ile Gln Leu Ser
1               5                   10

<210> SEQ ID NO 37
<211> LENGTH: 11
<212> TYPE: PRT
<213> ORGANISM: Artificial
<220> FEATURE:
<223> OTHER INFORMATION: humanized C10-2 Light Chain CDR1 Variant N32Q,
      N34Q

<400> SEQUENCE: 37

Gln Ala Ser Gln Asp Thr Ser Ile Gln Leu Gln
1               5                   10

<210> SEQ ID NO 38
<211> LENGTH: 11
<212> TYPE: PRT
<213> ORGANISM: Artificial
<220> FEATURE:
<223> OTHER INFORMATION: humanized C10-2 Light Chain CDR1 Variant N32S,
      N34Q

<400> SEQUENCE: 38

Gln Ala Ser Gln Asp Thr Ser Ile Ser Leu Gln
1               5                   10

<210> SEQ ID NO 39
<211> LENGTH: 6
<212> TYPE: PRT
<213> ORGANISM: Artificial
<220> FEATURE:
<223> OTHER INFORMATION: humanized C10-2 Heavy Chain CDR3 Variant A101T

<400> SEQUENCE: 39

Arg Gly Thr Met Asp Tyr
1               5

<210> SEQ ID NO 40
<211> LENGTH: 6
<212> TYPE: PRT
<213> ORGANISM: Artificial
<220> FEATURE:
<223> OTHER INFORMATION: IMGT C10.2 LC CDR1

<400> SEQUENCE: 40

Gln Asp Thr Ser Ile Asn
1               5

<210> SEQ ID NO 41
<211> LENGTH: 3
<212> TYPE: PRT
<213> ORGANISM: Artificial
<220> FEATURE:
<223> OTHER INFORMATION: IMGT C10.2 LC CDR2

<400> SEQUENCE: 41

Gly Ala Ser
1
```

```
<210> SEQ ID NO 42
<211> LENGTH: 9
<212> TYPE: PRT
<213> ORGANISM: Artificial
<220> FEATURE:
<223> OTHER INFORMATION: IMGT C10.2 LC CDR3

<400> SEQUENCE: 42

Leu Gln His Thr Tyr Leu Pro Phe Thr
1               5

<210> SEQ ID NO 43
<211> LENGTH: 8
<212> TYPE: PRT
<213> ORGANISM: Artificial
<220> FEATURE:
<223> OTHER INFORMATION: IMGT C10.2 HC CDR1

<400> SEQUENCE: 43

Gly Tyr Thr Phe Thr Asp Arg Thr
1               5

<210> SEQ ID NO 44
<211> LENGTH: 8
<212> TYPE: PRT
<213> ORGANISM: Artificial
<220> FEATURE:
<223> OTHER INFORMATION: IMGT C10.2 HC CDR2

<400> SEQUENCE: 44

Ile Tyr Pro Gly Asp Gly Ser Thr
1               5

<210> SEQ ID NO 45
<211> LENGTH: 8
<212> TYPE: PRT
<213> ORGANISM: Artificial
<220> FEATURE:
<223> OTHER INFORMATION: IMGT C10.2 HC CDR3

<400> SEQUENCE: 45

Ala Arg Arg Gly Ala Met Asp Tyr
1               5

<210> SEQ ID NO 46
<211> LENGTH: 6
<212> TYPE: PRT
<213> ORGANISM: Artificial
<220> FEATURE:
<223> OTHER INFORMATION: IMGT N32S/ N32S,A101T LC CDR1

<400> SEQUENCE: 46

Gln Asp Thr Ser Ile Ser
1               5

<210> SEQ ID NO 47
<211> LENGTH: 3
<212> TYPE: PRT
<213> ORGANISM: Artificial
<220> FEATURE:
<223> OTHER INFORMATION: IMGT N32S/N32S,A101T LC CDR2

<400> SEQUENCE: 47

Gly Ala Ser
1
```

```
<210> SEQ ID NO 48
<211> LENGTH: 9
<212> TYPE: PRT
<213> ORGANISM: Artificial
<220> FEATURE:
<223> OTHER INFORMATION: IMGT N32S/N32S,A101T LC CDR3

<400> SEQUENCE: 48

Leu Gln His Thr Tyr Leu Pro Phe Thr
1               5

<210> SEQ ID NO 49
<211> LENGTH: 8
<212> TYPE: PRT
<213> ORGANISM: Artificial
<220> FEATURE:
<223> OTHER INFORMATION: IMGT A101T/N32S,A101T HC CDR1

<400> SEQUENCE: 49

Gly Tyr Thr Phe Thr Asp Arg Thr
1               5

<210> SEQ ID NO 50
<211> LENGTH: 8
<212> TYPE: PRT
<213> ORGANISM: Artificial
<220> FEATURE:
<223> OTHER INFORMATION: IMGT A101T/N32S,A101T HC CDR2

<400> SEQUENCE: 50

Ile Tyr Pro Gly Asp Gly Ser Thr
1               5

<210> SEQ ID NO 51
<211> LENGTH: 8
<212> TYPE: PRT
<213> ORGANISM: Artificial
<220> FEATURE:
<223> OTHER INFORMATION: IMGT A101T/N32S,A101T HC CDR3

<400> SEQUENCE: 51

Ala Arg Arg Gly Thr Met Asp Tyr
1               5

<210> SEQ ID NO 52
<211> LENGTH: 7
<212> TYPE: PRT
<213> ORGANISM: Artificial
<220> FEATURE:
<223> OTHER INFORMATION: Chotia C10.2 /N32S HC CDR1

<400> SEQUENCE: 52

Gly Tyr Thr Phe Thr Asp Arg
1               5

<210> SEQ ID NO 53
<211> LENGTH: 6
<212> TYPE: PRT
<213> ORGANISM: Artificial
<220> FEATURE:
<223> OTHER INFORMATION: Chotia C10.2/N32S HC CDR2

<400> SEQUENCE: 53

Tyr Pro Gly Asp Gly Ser
1               5

<210> SEQ ID NO 54
```

```
<211> LENGTH: 6
<212> TYPE: PRT
<213> ORGANISM: Artificial
<220> FEATURE:
<223> OTHER INFORMATION: Chotia C10.2/N32S HC CDR3

<400> SEQUENCE: 54

Arg Gly Ala Met Asp Tyr
1               5

<210> SEQ ID NO 55
<211> LENGTH: 7
<212> TYPE: PRT
<213> ORGANISM: Artificial
<220> FEATURE:
<223> OTHER INFORMATION: Chotia A101T/N32S,A101T HC CDR1

<400> SEQUENCE: 55

Gly Tyr Thr Phe Thr Asp Arg
1               5

<210> SEQ ID NO 56
<211> LENGTH: 6
<212> TYPE: PRT
<213> ORGANISM: Artificial
<220> FEATURE:
<223> OTHER INFORMATION: Chotia A101T/N32S,A101T HC CDR2

<400> SEQUENCE: 56

Tyr Pro Gly Asp Gly Ser
1               5

<210> SEQ ID NO 57
<211> LENGTH: 6
<212> TYPE: PRT
<213> ORGANISM: Artificial
<220> FEATURE:
<223> OTHER INFORMATION: Chotia A101T/N32S,A101T HC CDR3

<400> SEQUENCE: 57

Arg Gly Thr Met Asp Tyr
1               5

<210> SEQ ID NO 58
<211> LENGTH: 5
<212> TYPE: PRT
<213> ORGANISM: Artificial Sequence
<220> FEATURE:
<223> OTHER INFORMATION: 5--Residue Motif of HC CDR1

<400> SEQUENCE: 58

Thr Phe Thr Asp Arg
1               5

<210> SEQ ID NO 59
<211> LENGTH: 8
<212> TYPE: PRT
<213> ORGANISM: Artificial Sequence
<220> FEATURE:
<223> OTHER INFORMATION: 8--Residue Motif of HC CDR1

<400> SEQUENCE: 59

Thr Phe Thr Asp Arg Thr Ile His
1               5

<210> SEQ ID NO 60
<211> LENGTH: 22
```

```
<212> TYPE: DNA
<213> ORGANISM: Artificial Sequence
<220> FEATURE:
<223> OTHER INFORMATION: First Primer for tTA Activator Transgene

<400> SEQUENCE: 60
gattaacagc gcattagagc tg                                          22

<210> SEQ ID NO 61
<211> LENGTH: 27
<212> TYPE: DNA
<213> ORGANISM: Artificial Sequence
<220> FEATURE:
<223> OTHER INFORMATION: Second Primer for tTA Activator Transgene

<400> SEQUENCE: 61
gcatatgatc aattcaaggc cgataag                                     27

<210> SEQ ID NO 62
<211> LENGTH: 20
<212> TYPE: DNA
<213> ORGANISM: Artificial Sequence
<220> FEATURE:
<223> OTHER INFORMATION: First Primer for Mutant Tau Responder Transgene

<400> SEQUENCE: 62
tgaaccagga tggctgagcc                                             20

<210> SEQ ID NO 63
<211> LENGTH: 22
<212> TYPE: DNA
<213> ORGANISM: Artificial Sequence
<220> FEATURE:
<223> OTHER INFORMATION: Second Primer for Mutant Tau Responder
      Transgene

<400> SEQUENCE: 63
ttgtcatcgc ttccagtccc cg                                          22
```

ANTIBODIES SPECIFIC FOR HYPERPHOSPHORYLATED TAU AND METHODS OF USE THEREOF

CROSS REFERENCE TO RELATED APPLICATIONS

This Application is a continuation application of U.S. application Ser. No. 16/585,207, filed Sep. 27, 2019, which is a continuation application of U.S. application Ser. No. 15/645,442, filed Jul. 10, 2017, which claims priority to Danish application number PA201700179, filed Mar. 14, 2017, Danish application number PA201700008, filed Jan. 4, 2017, Danish application number PA201700005, filed Jan. 4, 2017, and Danish application number PA201600416, filed Jul. 12, 2016, the entire contents of each of which are incorporated herein by reference in their entirety.

FIELD OF THE INVENTION

The present invention relates to a novel class of monoclonal antibodies that specifically binds the phosphorylated serine 396 residue on pathological hyperphosphorylated (PHF) tau (pS396), as well as to methods of using these molecules and their tau binding fragments in the treatment of Alzheimer's disease and tauopathies.

REFERENCE TO SEQUENCE LISTING

This application includes one or more Sequence Listings pursuant to 37 C.F.R. 1.821 et seq., which are disclosed in computer-readable media (file name: H0952.70048US04-SEQ.txt, created on Aug. 2, 2021, and having a size of 67,745 bytes), which file is herein incorporated by reference in its entirety.

BACKGROUND OF THE INVENTION

Age-related neurodegenerative diseases such as Alzheimer's disease (AD) and dementia are one of the largest societal challenges today. The World Health Organization estimates that costs for care of the elderly will continue to increase and that the number of diagnosed dementia cases will triple by 2050 (World Health Organization and Alzheimer's Disease International—Status Report (2012) DEMENTIA: A public health priority, WHO). The first treatments for AD were neurotransmitter modulators such as acetylcholine esterase inhibitors and NMDA modulators. These therapies became available at the turn of the millennium and still form the cornerstone for symptomatic relief of memory deficits related to dementia and AD. However, these drugs do not target the underlying causes of AD: accumulation of amyloid-β (Aβ) peptide and tau protein aggregates and associated loss of neuronal synapses and eventually neurons.

Longitudinal, community-wide studies of the elderly (Weiner, M. W. et al. (2014) ADNI online: adni-info.org/; Breteler, M. M. et al. (1992) Neuroepidemiology 11 Suppl 1, 23-28; Launer, L. J. (1992) Neuroepidemiology 11 Suppl 1, 2-13) together with large genome-wide association studies (Lambert, J. C. et al. (2013) Nat. Genet. 45, 1452-1458) have shown that AD is a heterogeneous mix of dementias where up to 10 percent of the advanced AD patients lack amyloid pathology (Crary, J. F. et al. (2014) Acta Neuropathol. 128, 755-766). Furthermore, seminal pathological studies by Braak & Braak (Braak, H. and Braak, E. (1996) Acta Neurol. Scand. Suppl 165, 3-12) demonstrated a clear correlation between the degree of neurofibrillary tangle pathology and cognitive state prior to autopsy. These observations have been reinforced by several investigators (Nelson, P. T. et al. (2012) J. Neuropathol. Exp. Neurol. 71, 362-381), and in recent longitudinal biomarker studies, which indicate that cerebrospinal fluid (CSF) levels of tau and hyperphosphorylated tau increase throughout early and late stages of the disease (Jack, C. R., Jr. et al. (2013) Lancet Neurol. 12, 207-216).

As indicated above, the microtubule-associated protein, tau, and its hyper-phosphorylated version, form the main constituent of intracellular neurofibrillary tangles, which are one of the main hallmarks of AD. Furthermore, specific genetic variants of tau are associated with familial forms of fronto-temporal dementia (FTD). Appearance of tau pathology in AD occurs in a distinct spatial pattern, starting in the entorhinal cortex, followed by hippocampal and cortical areas (Braak, H. and Braak, E. (1996) Acta Neurol. Scand. Suppl 165, 3-12). The specific stage of tau pathology also correlates well with cognitive abilities (Nelson, P. T. et al. (2012) J. Neuropathol. Exp. Neurol. 71, 362-381; Braak, E. et al. (1999) Eur. Arch. Psychiatry Clin. Neurosci. 249 Suppl 3, 14-22). Taken together, this evidence forms the basis of a tau-based hypothesis for AD. It entails that the intracellular accumulation of tau leads to microtubule degeneration and spinal collapse. As a result, communication between neurons malfunctions and cell death follows. Recently, it has also been shown that tau itself may form an endo-pathogenic species that can transmit neurodegeneration from one cell to the next (Clavaguera, F. et al. (2009) Nat. Cell Biol. 11, 909-913).

I. Tau As An Endo-Pathogen

Clavaguera and colleagues have demonstrated that tau itself may act as an endo-pathogen (Clavaguera, F. et al. (2009) Nat. Cell Biol. 11, 909-913). Low spin brain extracts were isolated from P301S tau transgenic mice (Allen, B. et al. (2002) J. Neurosci. 22, 9340-9351), diluted and injected into the hippocampus and cortical areas of young ALZ17 mice. The ALZ17 mouse is a tau transgenic mouse line which only develops late pathology (Probst, A. et al. (2000) Acta Neuropathol. 99, 469-481). The injected ALZ17 mice quickly developed solid filamentous pathology, and administration of tau immuno-depleted brain extracts from P301S mice or extracts from wild type mice did not induce tau pathology. Fractionation of the brain extracts in soluble (S1) and sarcosyl-insoluble tau (P3) (Sahara, N. et al. (2013) J. Alzheimer's. Dis. 33, 249-263) and injection of these into ALZ17 mice demonstrated that the P3 fraction is most competent in inducing pathology. It contains most of the intracellular hyper-phosphorylated filamentous tau. The majority of pathology could also be induced when injecting P301S extracts into the brains of wild type mice, but no NFTs were formed. In subsequent studies, Clavaguera et al. have shown that human tau extracted from post-mortem brain tissue of other tauopathies (Argyrophilic Grain Disease (AGD), Progressive Supranuclear Palsy (PSP), and Corticobasal Degeneration (CBD)) may also induce tau pathology in the ALZ17 model (Clavaguera, F. et al. (2013) Proc. Natl. Acad. Sci. U.S.A. 110, 9535-9540). Since the presentation of these data, several other tau seeding and spreading models have been reported (Ahmed, Z. et al. (2014) Acta Neuropathol. 127, 667-683; Walker, L. C. et al. (2013) JAMA Neurol. 70, 304-310). The main conclusion from these studies indicates a mechanism by which pathogenic tau in intracellular inclusions is secreted from the cell into the periplasmic space. The pathological tau material is then transported along the vesicular sheath in both anterograde and retrograde direction and subsequently taken up by neighboring cells by means of bulk endocytosis. This mechanism explains why the spread of pathology observed in human disease follows a distinct anatomical pattern. Intriguingly, peripheral administration of pathological tau may accelerate the formation of tau pathology in ALZ17 mice (Clavaguera, F. et al. (2014) Acta Neuropathol. 127, 299-301). This spreading mechanism may explain disease propagation in other proteinopathies (Goedert, M. et al. (2010) Trends Neurosci. 33, 317-325; Sigurdsson, E. M. et al. (2002) Trends Mol. Med. 8, 411-413).

II. Tau Species

The discovery that the tau protein may act as an endopathogen has spawned a search for "The Pathogenic Species" that could be targeted in potential interventive therapies.

The microtubule-associated protein tau gene (MAPT) is located on chromosome 17 of the human genome and expresses six isoforms of the tau protein in adult human brain. These isoforms arise from the alternative splicing of exons 2, 3 and 10 of the 16 exons within the MAPT gene. Exons 2 and 3 express a 29-amino acid repeat and exon 10 expresses an additional microtubule binding domain. As a result, tau isoforms will contain 0, 1 or 2 N-terminal repeats and 3 or 4 C-terminal microtubule binding domains (3R or 4R tau). Commonly six isoforms of tau are expressed. The longest (2N4R) and shortest (0N3R) isoforms consist of 441 and 352 amino acids, respectively (Kolarova, M. et al. (2012) Int. J. Alzheimers. Dis. 2012, 731526). The N-terminal projection domain of tau (2N4R) consists of a 44-amino acid glycine-rich tail and residues 45-102 encompass two highly acidic regions (N1, N2-domains). Two proline-rich regions are found at residues 151-243 (P1, P2 domains). The remainder of the protein is constituted by four microtubule binding domains (R1-R4), followed by a short C-terminal region.

Tau is soluble and highly phosphorylation-labile protein. Approximately 20 percent or 85 amino acid residues in the longest isoform of tau are potential (Ser, Thr or Tyr) phosphorylation sites. Approximately half of these have been observed to be phosphorylated experimentally (Hanger, D. P. et al. (2009) Trends Mol. Med. 15, 112-119; Hasegawa, M. et al. (1992) J. Biol. Chem. 267, 17047-17054), and the phosphorylation sites are clustered around the terminal residues of the microtubule binding domains. Tau is dynamically phosphorylated and de-phosphorylated during the cell cycle. It must dissociate from microtubules to allow for mitosis to occur. Its main role in post mitotic cells (the differentiated neuron) is to act as a microtubule stabilizer, allowing for optimal axonal transport. It can only associate with microtubules in its mostly de-phosphorylated form, thus phosphorylation acts as a direct microtubule association/dissociation switch within the neuron. Under normal conditions, cytosolic tau contains on average two phosphorylated sites. In paired helical filamentous material, at least 7-8 sites are phosphorylated (Hanger, D. P. et al. (2009) Trends Mol. Med. 15, 112-119; Hasegawa, M. et al. (1992) J. Biol. Chem. 267, 17047-17054). Hyperphosphorylated, paired helical filamentous tau is a key hallmark of Alzheimer's disease (Kosik et. al. (1986) PNAS, 86, 4044-4048), a distinct mobility shift of hyperphosphorylated tau is observed in immune-cytochemical analysis of human AD brain material.

It has been difficult to study the tau protein with traditional structural techniques like x-ray crystallography or NMR spectroscopy, reflecting its meta-stable nature. Such studies have mainly been conducted on domain fragments of the un-phosphorylated tau protein. The only structural study to date on full-length tau (2N4R), using NMR spectroscopy, reveals that the protein contains only sparse stretches of stable secondary structure (Mukrasch, M. D. et al. (2009) PLoS. Biol. 7, e34). This analysis indicates that the secondary structure of the peptide backbone has a large propensity for adapting a β-sheet structure. The backbone's first 200 residues are considerably more ordered than the C-terminus encompassing the microtubule binding domains. The presence of many specific long-range interactions within the protein in solution indicates that it exists in a largely disordered molten globular state (Ohgushi, M. and Wada, A. (1983) FEBS Lett. 164, 21-24).

Protease products of tau generated in particular by caspase and calpain (Asp13, Glu391 and Asp421) have been identified in tangle material (Gamblin, T. C. et al. (2003) Proc. Natl. Acad. Sci. U.S.A. 100, 10032-10037). In particular, the truncation at Asp421 has been studied in detail using the tau C3 antibody, which binds to the free Asp421 terminus. This truncation has been postulated as an early event in AD pathogenesis associated with induction of apoptosis (deCalignon A. et al. (2010) Nature 464, 1201-1204). The N-terminal cleavage at Asp13 and the C-terminal cleavage at Glu391 are considered late events in the pathogenesis (deCalignon A. et al. (2010) Nature 464, 1201-1204; Delobel, P. et al. (2008) Am. J. Pathol. 172, 123-131). Recently, an additional N-terminal fragment (residues 1-224) was identified in CSF from AD and PSP patients, and has been hypothesized to be an early marker of disease and particularly pathogenic (U.S. Ser. No. 14/092,539; Bright, J. et al. (2014) Neurobiol. Ageing, 1-17). A similar calpain cleaved fragment was reported by other groups (Ferreira, A. and Bigio, E. H. (2011) Mol. Med. 17, 676-685; Reinecke, J. B. et al. (2011) PLoS. One. 6, e23865).

Apart from hyper-phosphorylation and tau fragmentation, post-translational acetylation (Cohen, T. J. et al. (2011) Nat. Commun. 2, 252; Min, S. W. et al. (2010) Neuron 67, 953-966) and O-GlcNAcylation (Zhu, Y. et al. (2014) J. Biol. Chem.) have been proposed to be pathology defining processes in the formation of tangle pathology associated with AD.

III. Tau Immunotherapies

Immunotherapies are traditionally separated into passive and active vaccine approaches. In an active vaccine approach, a pathogenic agent or an inactivated pathogenic form thereof, is injected into the patient and the immune system elicits an immune response. This triggers the maturation of B-cells generating high affinity antibodies or cellular response against the administered antigen. In a passive vaccine approach, the triggering of the immune system is circumvented by infusing a specific antibody against the antigen. The inherent clearance system then removes antibody-bound ligand.

AC Immune is pursuing a mouse monoclonal antibody against phospho-serine 409 of tau. Antibodies were profiled against human AD and control brain tissue and were selected based on their ability to recognize tangle pathology. The humanized version of two antibodies, hACI-36-2B6-Ab1 and hACI-36-3A8-Ab1, both bind to a tau epitope within amino acids 401-418 (WO 2013/151762).

The group of Roger Nitsch has isolated tau auto-antibodies from elderly healthy individuals with no sign of degenerative tauopathy. A number of antibodies have been isolated using full length recombinant human tau (2N4R) to find tau specific antibodies. These were then screened for their ability to discriminate tau isolates from diseases and healthy individuals. Three lead antibodies, 4E4, 4A3 and 24B2, have been described in the patent literature (WO2012049570; US2012087861). Their epitope mapping indicates that all recognize amino acids within and C-terminal to the microtubule binding region, from position V339 to K369. These antibodies do not exhibit any phospho-specificity.

C2N Diagnostics focuses mainly on developing diagnostic tools for early detection of neurodegenerative disease. Antibodies were generated against full length human and mouse tau protein. Eight and five antibodies were identified, recognizing human and mouse tau, respectively (Yanamandra, K. et al. (2013) Neuron 80, 402-414). Three antibodies with different binding kinetics were selected for in vivo evaluation. Namely, HJ9.3, HJ9.4 and HJ8.5, recognizing tau residues 306-320, 7-13 and 25-30, respectively, with the last one (HJ8.5) being specific for human tau. The antibodies were also selected based on their ability to prevent transfer of pathology in an ingenious mechanistic reporter assay of trans-cellular propagation of tau (Sanders, D. W. et al. (2014) Neuron 82, 1271-1288; Kfoury, N. et al. (2012) J. Biol. Chem. 287, 19440-19451). Their evaluation in chronic i.e.v. injection studies in P301S transgenic mice demonstrated their ability to reduce levels of hyper-phosphorylated tau protein as determined in immuno-histochemical analysis of the treated mice.

The antibodies of Peter Davies were developed originally as diagnostic tools that could differentiate between pathological and normal tau in AD and control brain material (Greenberg, S. G. and Davies, P. (1990) Proc. Natl. Acad. Sci. U.S.A. 87, 5827-5831). Evaluation of the therapeutic utility of the PHF1 and MC1 antibodies was demonstrated in P301 S and JPNL3 (P301L) (Boutajangout, A. et al. (2011) J. Neurochem. 118, 658-667; Chai, X. et al. (2011) J. Biol. Chem. 286, 34457-34467; D'Abramo, C. et al. (2013) PLoS. One. 8, e62402 mice). PHF1 recognizes a linear phospho-tau epitope (pS396, pS404) whereas MC1 is a conformation-dependent antibody that recognizes a structural tau epitope requiring two distinct parts of the linear sequence, an epitope within residues 46-202 and a C-terminal epitope between residues 312-342 (Jicha, G. A. et al. (1997) J. Neurosci. Res. 48, 128-132). Injection of these two antibodies in chronic 12-13-week immunization studies resulted in substantial reduction of spinal cord and brainstem pathology among other brain regions, which translated to an attenuation of the motor deficit observed in these mice. (D'Abramo, C. et al. (2013) PLoS. One. 8, e62402).

iPerian/Bristol Meyers Squibb has developed tau antibodies against a postulated pathological tau species, composed of an N-terminal fragment of tau (etau: residues 1-224), which promoted hyperactivity in induced pluripotent stem cell based neuronal cultures. A portfolio of antibodies has been developed, but characterization has focused on antibodies IPN001 and IPN002 that recognize an N-terminal epitope within residues 9-18. Accordingly, these antibodies detect elevated tau levels in CSF from staged AD and PSP patients that may be an early sign of disease. In vivo injections of the antibodies in JPNL3 (P301L) mice led to partial reversal of progressive motor deficits (U.S. Ser. No. 14/092,539).

Einar Sigurdsson reported the first program to demonstrate the efficacy of tau-based immunotherapy. An active vaccine consisting of tau peptide 379-408[pS396, pS404] together with Adju-Phos adjuvant was used to immunize JPNL3 (P301L) mice. In this study a prominent reduction of tau pathology was observed in the vaccine treated mice when compared to control animals. An attenuation of tauopathy-related motor phenotype was detected as well. Its efficacy was confirmed in a different mouse model (htau/PS1) not driven by mutant tau (Boutajangout, A. et al. (2011) AAIC 2011 (7, issue 4, Supplement edn) p. s480-s431; Congdon, E. E. et al. (2013) J. Biol. Chem. 288, 35452-35465; Gu, J. et al. (2013) J. Biol. Chem. 288, 33081-33095).

Prothena has evaluated three tau antibodies in the K3691 (K3) transgenic tau mouse and in a P301L mouse model. Antibodies with varying properties were selected for in-vivo evaluation. Two pS404-specific antibodies with different isotype (IgG1/k and IgG2a/k) or a total (pan) anti-tau antibody (IgG1/k) were injected in a chronic paradigm. K3691 mice were treated with weekly injections for 21 weeks starting at 3 weeks of age, and P301L mice were treated for 7 months with weekly injections starting at 4 months of age. A reduction in tau-positive neurofibrillary inclusions was observed in the K3 mice with the IgG2a/k pS404 antibody. Both of the pS404-specific antibodies were able to reduce the level of pS422-positive tau, whereas no reduction was observed in the pan tau antibody treated mice. These studies suggest that: 1) tau clearance may be antibody isotype-dependent, and; 2) It may be important to target a tau species that is relevant to disease, as the total-anti-tau antibody was unable to reduce hyper-phosphorylated tau (PCT/US2014/025044).

The inventors of the present invention have surprisingly found antibodies specific for the phosphorylated tau serine residue 396 (pS396) to be effective in disease models; this is in contrast to the prior art antibodies which recognize primarily the tau proteins phosphorylated at both 396 and 404 residues, phosphorylated at the 404 residue only or at other residues on tau.

The inventors have developed antibodies which furthermore have a remarkable specificity and selectivity to human pathological tau. The antibodies of the present invention show a much higher degree of specificity and selectivity towards human pathological tau over non-pathological tau compared to the antibodies of WO2013/050567 (see FIG. 1 of WO2013/050567). The antibodies of WO2012/045882 reported to have a specific binding, were elicited from 6 to 9 residue amino acid sequences of Tau amino acids 393-401, 396-401, 394-400 and 393-400. This contrasts from the antibodies of the present invention which were elicited against pathogenic hyperphosphorylated tau comprising a longer amino acid sequence as described herein.

Furthermore, the antibodies and epitope-binding fragments thereof, of the present invention show many advantageous features such as the ability to discriminate between pathological and non-pathological human tau protein, and in particular to bind tau associated with Alzheimer's (AD) pathology. In electrophysiological studies, the antibodies, and epitope-binding fragments thereof, of the invention were additionally able to reverse reduced paired pulse facilitation and spontaneous miniature excitatory synaptic current (mEPSC).

SUMMARY OF THE INVENTION

The present invention relates to monoclonal antibodies, and epitope-binding fragments thereof, capable of specifically binding to the phosphorylated residue serine 396 of human (2N4R isoform) tau (SEQ ID NO:1). The antibodies are further characterized by their ability to discriminate between phosphorylated residues 396 and 404 such that they substantially do not bind the phosphorylated 404 residue.

The antibodies of the present invention are selective for pathological tau in the presence of non-pathological—yet phosphorylated—tau. The antibodies of the present invention are able to selectively deplete tau tangles of pathological tau in the presence of normal tau. Without being bound to a particular theory, it is believed that depleting tangles of tau comprising tau protein that has been phosphorylated at tau position 396 prevents seeding of pathological tau into tau tangles. Accordingly, one aspect of the invention relates to an antibody that is capable of selectively binding to 396-phosphorylated tau even when such molecules are in the presence of tau protein that has been phosphorylated at tau position 404. A related aspect of the invention relates to an antibody that is capable of selectively binding to 396-phosphorylated tau even when such molecules are in the presence of non-pathogenic tau. Further defined, the invention relates to an antibody selective for pathological tau said pathological tau being hyperphosphorylated tau appearing as 64 kDa band (by Western Blot analysis) in transgenic mice overexpressing the human 2N4R isoform of tau.

One aspect of the invention is directed to an anti-tau antibody that, when used with immune-depleted rTg4510 extracts from transgenic mice, specifically reduces the hyperphosphorylated tau 64 kDa and 70 kDa bands by at least 90%, while reducing the 55 kDa tau band by no more than 10%. A further aspect of the invention is directed to an anti-tau antibody that specifically reduces the hyperphosphorylated tau 64 and 70 kDa bands by at least 90%, while reducing the 55 kDa tau band by no more than 10%; or the capability, when used as described herein with extracts from human AD post-mortem brains, to specifically reduce the pS396 hyperphosphorylated tau bands by at least 90%, while not reducing the non-hyperphosphorylated tau bands by more than 10%.

Another aspect of the invention is directed to a method of treating a patient with a taupathy, such as Alzheimer's Disease, comprising depleting a tangle or attenuating the progression of said tangle, said tangle comprising hyperphosphorylated Tau, said method comprising contacting hyperphosphorylated Tau with an antibody of the invention such that the tangle is depleted, reduced in its content of hyperphosphorylated tau or progression of tangle formation is attenuated.

Alternatively defined, the invention relates to a method of treating a patient with a taupathy, such as Alzheimer's Disease, said method comprising contacting tangles with an antibody selective for tau having residue 396 phosphorylated such that the tangle is depleted of hyperphosphorylated Tau.

One aspect of the invention is directed to a monoclonal antibody to hyperphosphorylated human tau, or epitope-binding fragment thereof, comprising:
(a) a Light Chain CDR1 comprising the amino acid sequence selected from the group consisting of SEQ ID NO:3, SEQ ID NO:31; SEQ ID NO:32; SEQ ID NO:33; SEQ ID NO:34; SEQ ID NO:35; SEQ ID NO:36; SEQ ID NO:37; SEQ ID NO:38; SEQ ID NO:40; and SEQ ID NO:46;
(b) a Light Chain CDR2 comprising the amino acid sequence of SEQ ID NO:4; SEQ ID NO:41; and SEQ ID NO:47;
(c) a Light Chain CDR3 comprising the amino acid sequence of SEQ ID NO:5; SEQ ID NO:42; and SEQ ID NO:48;
(d) a Heavy Chain CDR1 comprising the amino acid sequence of SEQ ID NO:6; SEQ ID NO:43; SEQ ID NO:49; SEQ ID NO:52; and SEQ ID NO:55;
(e) a Heavy Chain CDR2 comprising the amino acid sequence selected from the group consisting of SEQ ID NO:7; SEQ ID NO:28; SEQ ID NO:29; SEQ ID NO:30; SEQ ID NO:44; SEQ ID NO:50; SEQ ID NO:53; and SEQ ID NO:56; and
(f) a Heavy Chain CDR3 comprising the amino acid sequence selected from the group consisting of SEQ ID NO:8, SEQ ID NO:39; SEQ ID NO:45; SEQ ID NO:51; SEQ ID NO:54; and SEQ ID NO:57.

One aspect of the invention is directed to a monoclonal antibody to hyperphosphorylated human tau, or an epitope-binding fragment thereof, comprising:
(a) a Light Chain selected from the group consisting of SEQ ID NO:12; SEQ ID NO:16; SEQ ID NO:17; SEQ ID NO:18; SEQ ID NO:19; SEQ ID NO:20; SEQ ID NO:21; SEQ ID NO:22 and SEQ ID NO:23; and
(b) a Heavy Chain selected from the group consisting of SEQ ID NO:11; SEQ ID NO:13; SEQ ID NO:14; SEQ ID NO:15; SEQ ID NO:24; SEQ ID NO:25; SEQ ID NO:26; and SEQ ID NO:27.

A further aspect of the invention is directed to a monoclonal antibody to hyperphosphorylated human tau, or epitope binding fragment thereof, comprising
(a) a Light Chain CDR1 having the amino acid sequence of SEQ ID NO:3;
(b) a Light Chain CDR2 having the amino acid sequence of SEQ ID NO:4;
(c) a Light Chain CDR3 having the amino acid sequence of SEQ ID NO:5;
(d) a Heavy Chain CDR1 having the amino acid sequence of SEQ ID NO:6;
(e) a Heavy Chain CDR2 having the amino acid sequence of SEQ ID NO:7; and
(f) a Heavy Chain CDR3 having the amino acid sequence of SEQ ID NO:8.

An interesting aspect of the invention is directed to a monoclonal antibody to hyperphosphorylated human tau, or epitope binding fragment thereof, comprising:
(a) a Light Chain CDR1 having the amino acid sequence of SEQ ID NO:31;
(b) a Light Chain CDR2 having the amino acid sequence of SEQ ID NO:4; and
(c) a Light Chain CDR3 having the amino acid sequence of SEQ ID NO:5;
and further comprising at least one of
(d) a Heavy Chain CDR1 having the amino acid sequence of SEQ ID NO:6;
(e) a Heavy Chain CDR2 having the amino acid sequence of SEQ ID NO:7; and
(f) a Heavy Chain CDR3 having the amino acid sequence of SEQ ID NO:8.

An interesting aspect of the invention is directed to a monoclonal antibody to hyperphosphorylated human tau, or epitope binding fragment thereof, comprising:
(a) a Light Chain CDR1 having the amino acid sequence of SEQ ID NO:31; and
(f) a Heavy Chain CDR3 having the amino acid sequence of SEQ ID NO:39;
and further comprising at least one of
(b) a Light Chain CDR2 having the amino acid sequence of SEQ ID NO:4; and
(c) a Light Chain CDR3 having the amino acid sequence of SEQ ID NO:5;
and further comprising at least one of
(d) a Heavy Chain CDR1 having the amino acid sequence of SEQ ID NO:6; and
(e) a Heavy Chain CDR2 having the amino acid sequence of SEQ ID NO:7.

The antibodies, and epitope-binding fragments thereof, of the invention can be used in treating tauopathies such as Alzheimer's disease (AD), Argyrophilic Grain Disease (AGD), Progressive Supranuclear Palsy (PSP), Corticobasal Degeneration (CBD), TBI (traumatic brain injury, mild, acute or chronic), and chronic traumatic encephalopathy (CTE).

The antibodies and epitope-binding fragments thereof of the invention are furthermore intended for use in treating Psychosis, particularly Psychosis due to AD or Psychosis in patients with AD, and apathy due to AD or apathy in patients with AD.

The IC50 of the hC10-2_N32S (black circles) and hC10-2_N332_A101T (open circles) antibodies are calculated to be 44 nM and 14 nM, respectively. This is a notable improvement over hC10-2, as can be seen when comparing the curves of FIG. 1. Accordingly, in one aspect of the invention, the antibodies inhibit AD-P3 in the fluid phase inhibition assay described herein, such that the signal is reduced by 50% at a concentration of 100 nM or less of the antibody based on fluid phase inhibition assay for AD-P3 capture.

Figure 2:
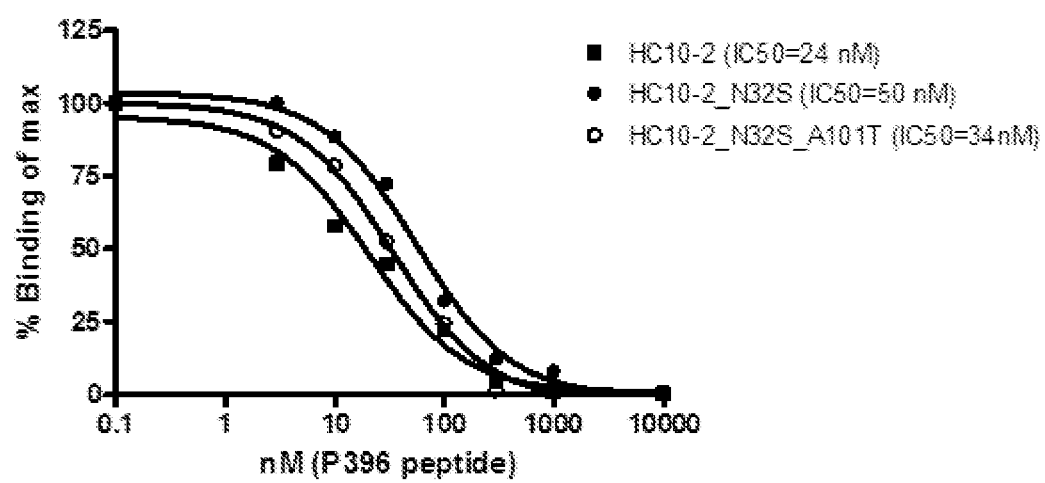

FIG. 2. Peptide inhibition assay illustrating apparent affinity hC10-2 and related variants. As described in Example 3B, concentration dependent inhibition of antibody binding in fluid phase solution to Ptau 386-408 (pS396) peptide was investigated with antibodies hC10-2 (squares), hC10-2_N32S (black circles) and hC10-2_N32_A101T (open circles). The antibodies were pre-incubated at 1 ng/ml for 60 min. at r/t with increasing concentrations (0-10000 nM) of Ptau 386-408 (pS396) prior to incubation in wells coated with 100 ng/ml Ptau 386-408 (pS396/pS404). Well-bound antibody was detected with sulfo-tagged anti-human IgG antibody (MSD).

As can be seen from FIG. 2, Antibody hC-10.2 (IC50=24 nM), Antibody hC10.2_N32S (IC50=50 nM) and Antibody hC10.2_N32S, A101T (IC50=34 nM) have IC50s of less than 100 nM, and even less than 60 nM, based on apparent affinity studies using fluid phased solution with Ptau (P396) 386-408.

Figure 3:
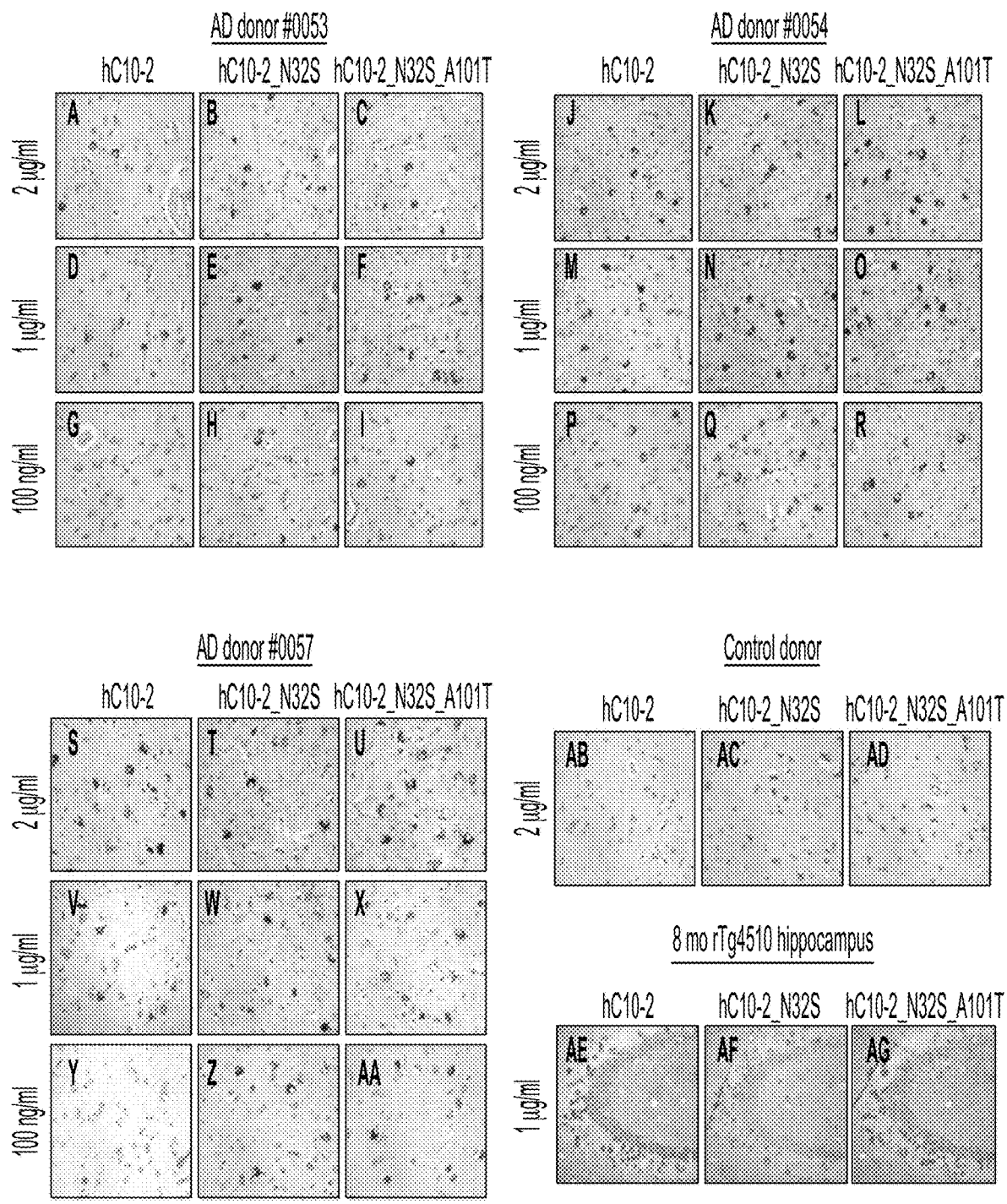

FIG. 3 (Panels A-Z and AA-AG). Immunohistochemical detection of pathological tau in post mortem brains from donors with AD and in rTg4510 mouse brain. As described in Example 4, in the prefrontal cortex from 3 different AD donors, hC10-2, hC10-2_N32S and hC10-2_N32S_A101T labelled neurofibrillary tangles, neuropil threads and dystrophic neurites. The strongest staining intensities were detected with the highest concentrations of antibody. Control brain sections are devoid of immunoreactivity. All 3 antibodies labelled phosphorylated tau in rTg4510 brain with advanced pathology.

Staining increased from hC10-2 to hC10-2_N32S and to hC10-2_N32S_A101T. The strongest staining intensities were detected with hC10-2_N32S_A101T, then hC10-2_N32S, then hC10-2. At concentrations as low as 100 ng/mL hC10-2_N32S_A101T and hC10-2_N32S, there was immunohistochemical detection of pathological tau in Alzheimer's brains.

Figure 4:
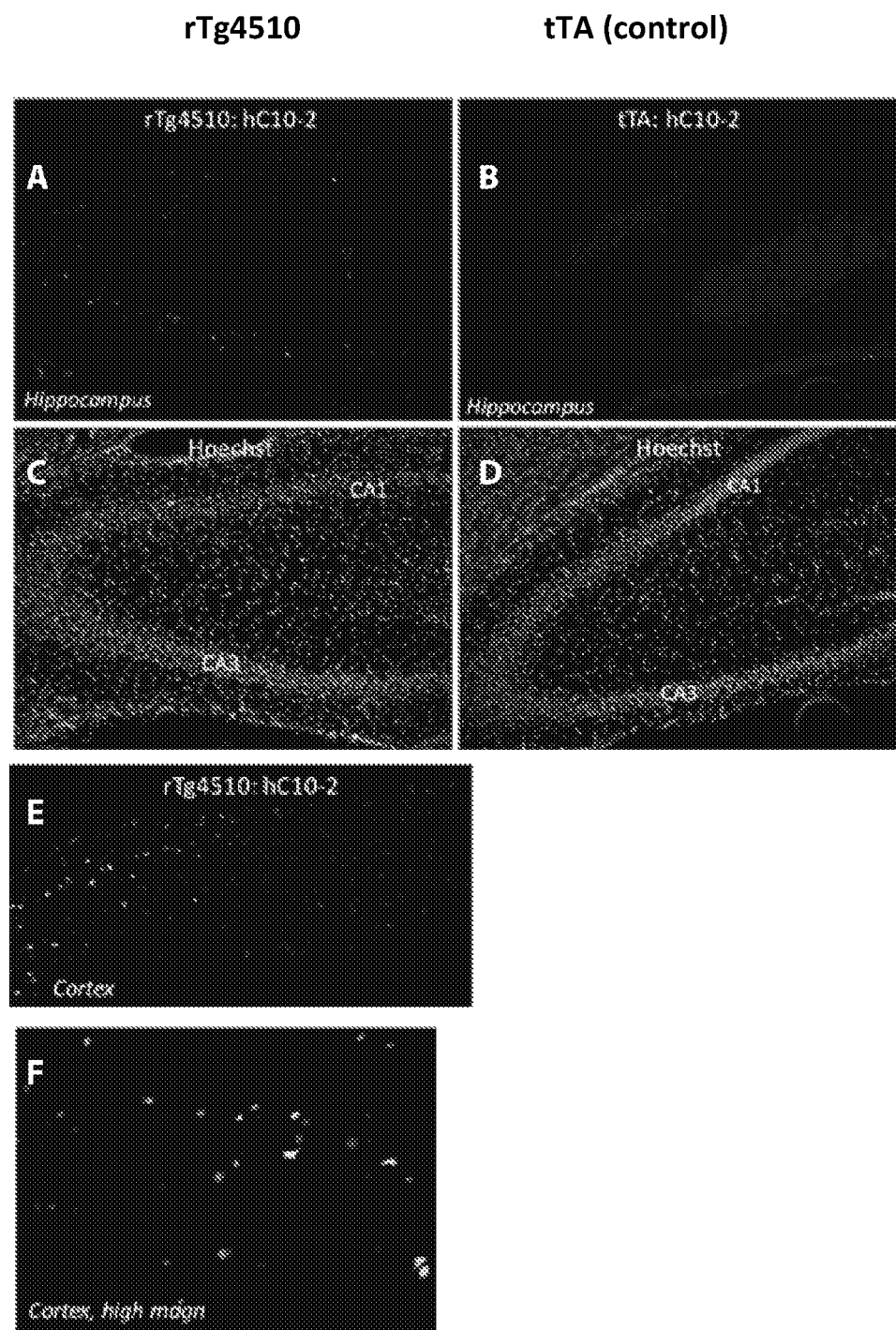

FIG. 4 (Panels A-F). Decoration of tau structures in rTg4510 mice treated with hC10-2. hC10.2 was administrated i.v. (Panels A, C, E and F represent rTg4510; Panels B and D represent tTA). The mice received a single injection of a volume of 150 µL of hC10-2 antibodies at a concentration of 80 mg/kg. Brain slices were taken after 3 days according to the process described in Example 5. hC10-2 specifically labels target structures in vivo in hippocampus and cortex in rTg4510 brains, but not in control tTA brains. Paired images for AlexaFluor488 and Hoechst signal are shown in hippocampal sections.

Figure 5:
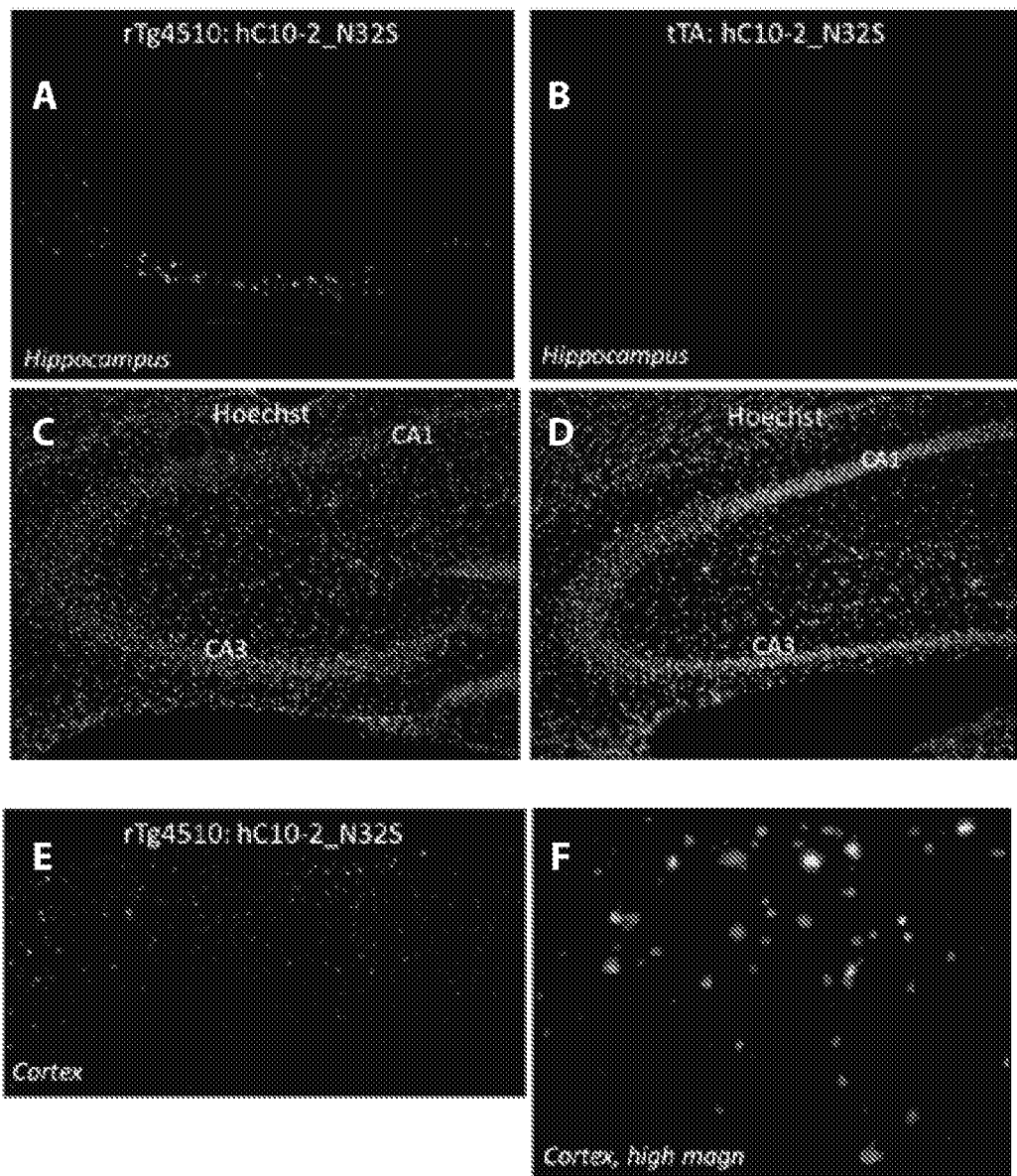

FIG. 5 (Panels A-F). Decoration of tau structures in rTg4510 mice treated with hC10-2_N32S. (Panels A, C and E represent rTg4510; Panels B, D and F represent tTA). The mice received a single injection of a volume of 150 µL of hC10-2_N32S antibodies at a concentration of 80 mg/kg. Brain slices were taken after 3 days according to the process described in Example 5. hC10-2_N32S specifically labels target structures in vivo in hippocampus and cortex in rTg4510 brains, but not in control tTA brains. Paired images for AlexaFluor488 and Hoechst signal are shown in hippocampal sections.

Figure 6:
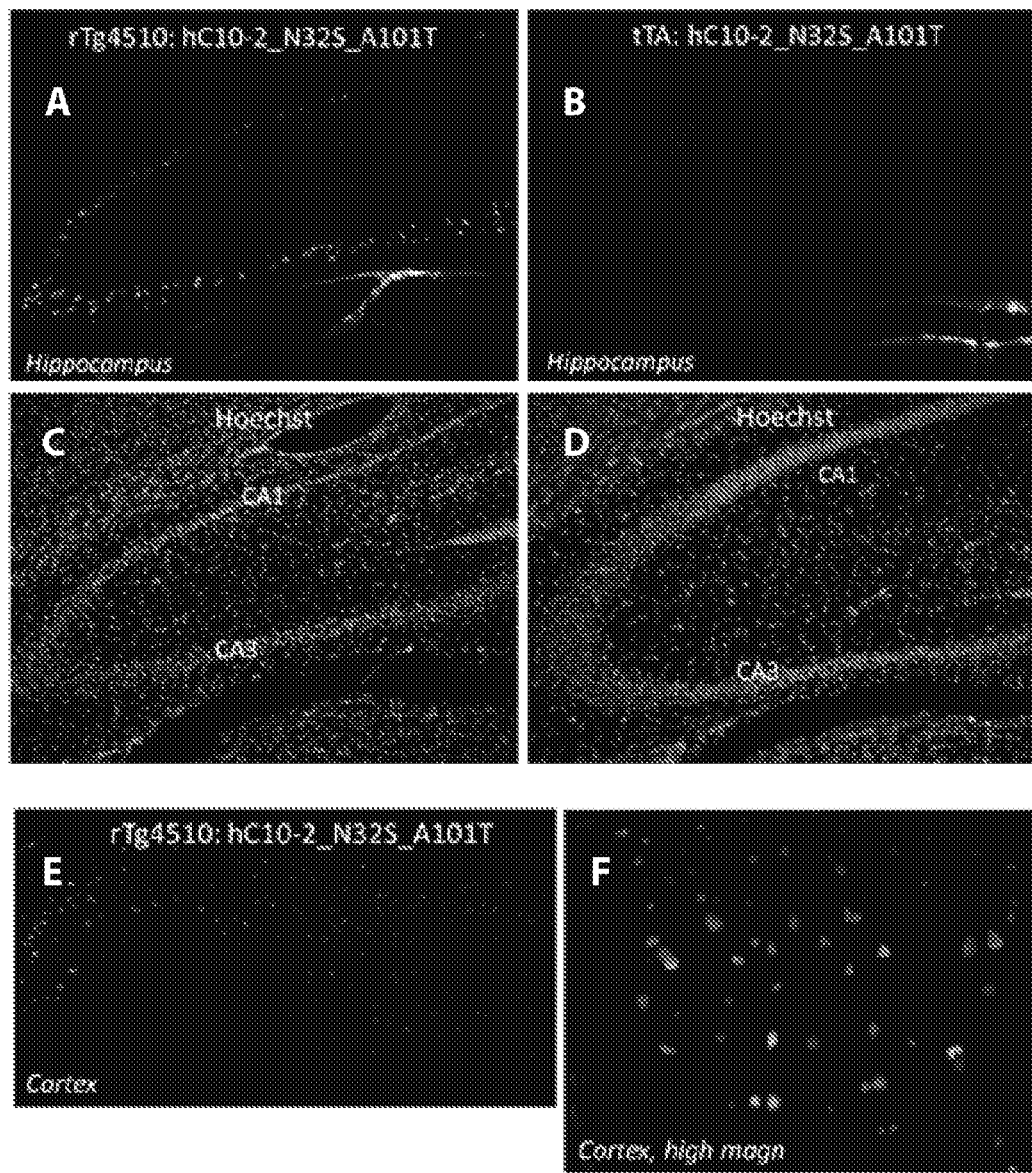

FIG. 6 (Panels A-F). Decoration of tau structures in rTg4510 mice following i.v. injection of hC10-2_N32S_A101T (Panles A, C and E represent rTg4510; Panels B, D and F represent tTA). The mice received a single injection of a volume of 150 µL of hC10-2_N32S_A101T antibodies at a concentration of 80 mg/kg. Brain slices were taken after 3 days according to the process described in Example 5. hC10-2_N32S_A101T specifically labels target structures in vivo in hippocampus and cortex in rTg4510 brains, but not in control tTA brains. Paired images for AlexaFluor488 and Hoechst signal are shown in hippocampal sections.

Comparing FIGS. 4-6 indicates that hC10.2, hC10-2_N32S and hC10-2_N32S_A101T cross the blood brain barrier upon intravenous injection. The Figures further indicate that hC10-2_N32S and hC10-2_N32S_A101T labels tau structures (immunoreactive to tau tangles) the hippocampus and cortex with improved results compared to hC10-2.

Figure 7:
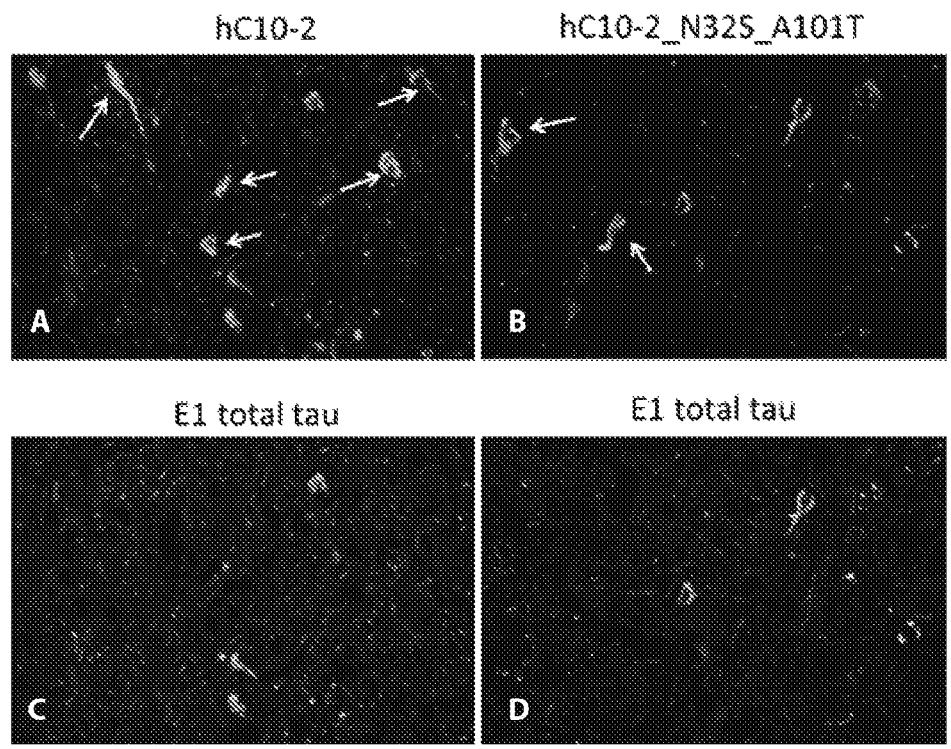

FIG. 7 (Panels A-D). Tau species recognized by pS396 specific antibodies in Alzheimer's diseased (AD) brain. As described in Example 6, in sections of AD brain, tau tangles were either co-labelled by E1 and p396 antibodies or positive for pS396 antibodies alone (arrows). The sections were analyzed by fluorescent microscopy. A number of tau tangles were only labelled by either hC10-2 and hC10-2_N32S_A101T antibodies (arrows). Given ghost tangles are not stained by N-terminal tau antibodies, the tau species labelled by hC10-2 or hC10-2_N32S_A101T antibodies alone likely represent extracellular ghost tangles.

Figure 8A:
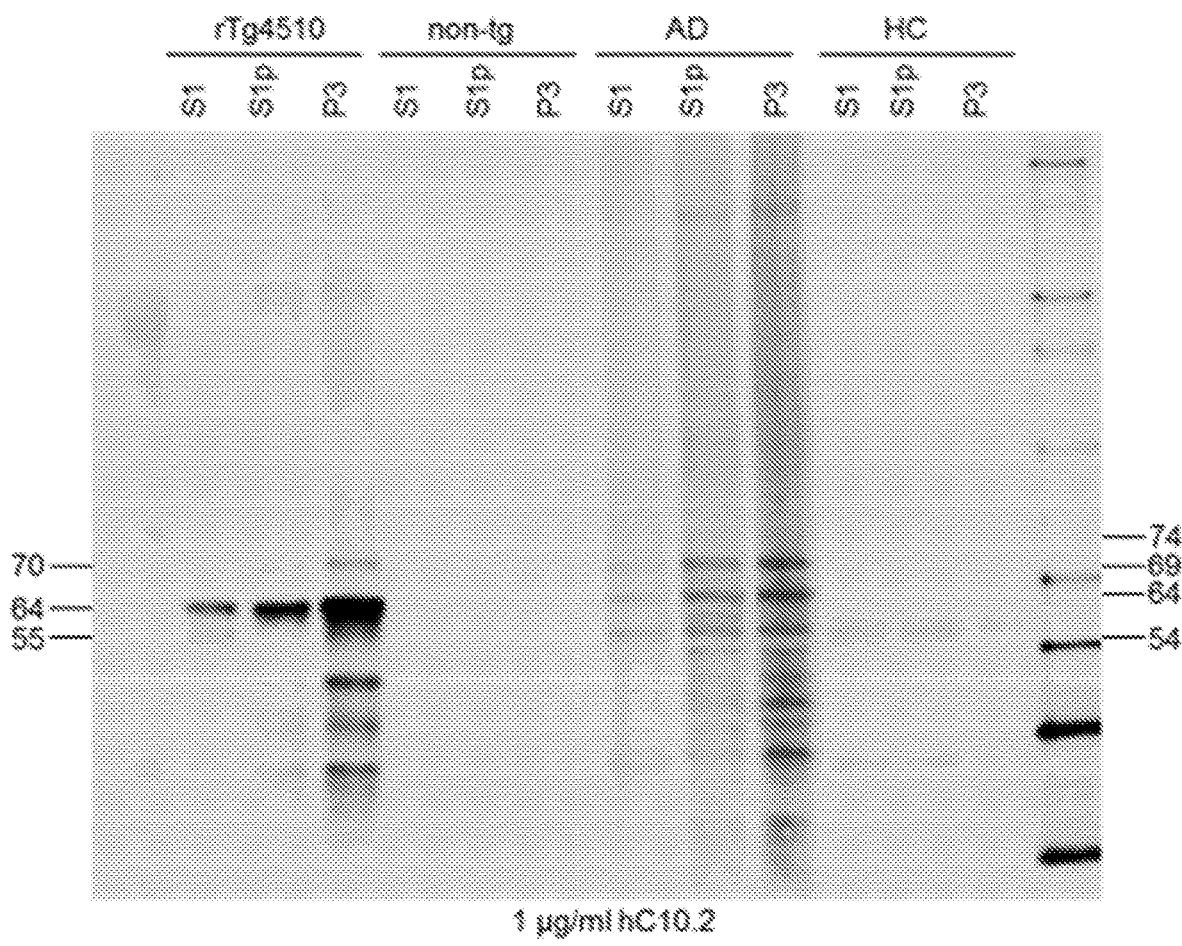
Figure 8B:
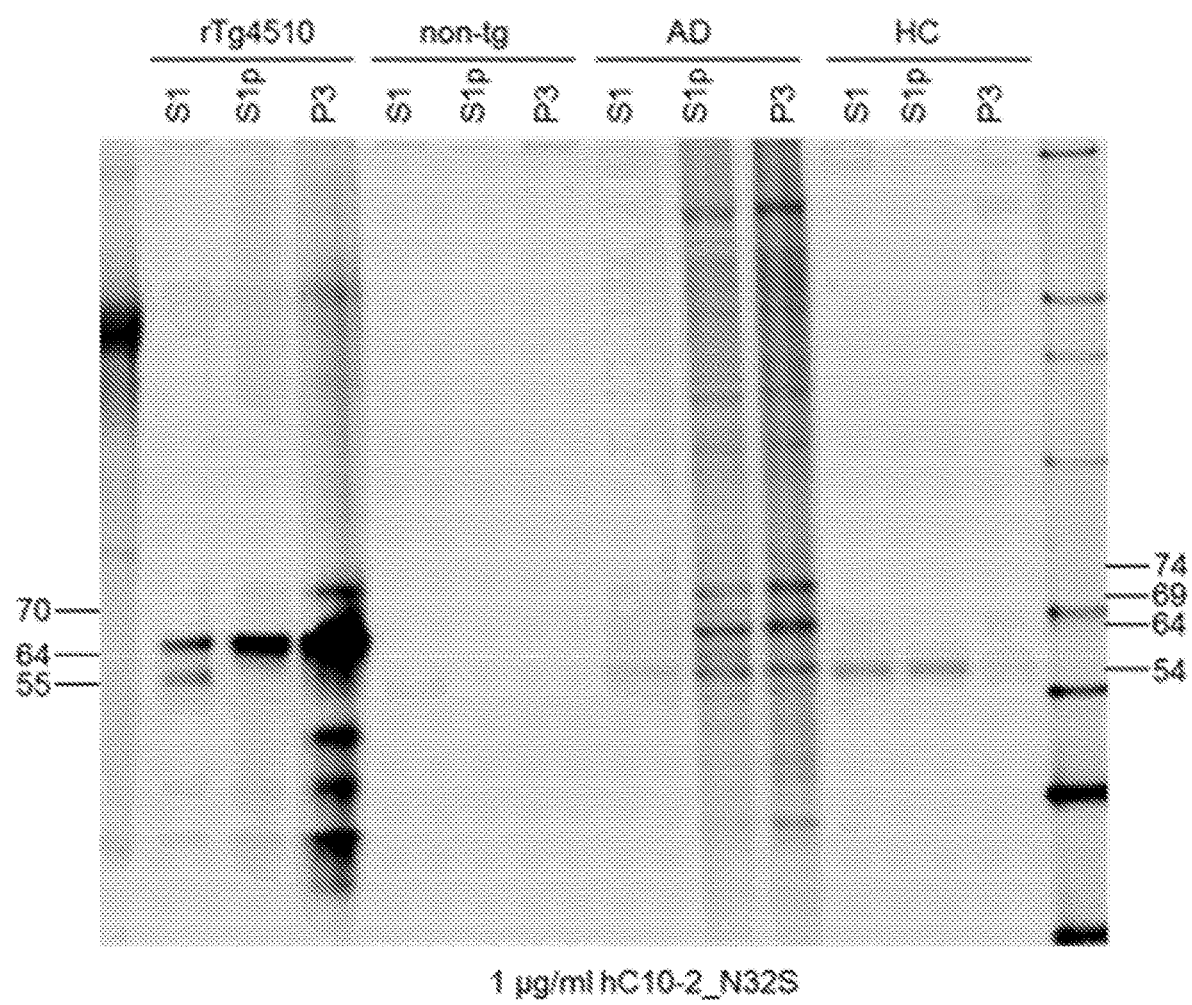
Figure 8C:
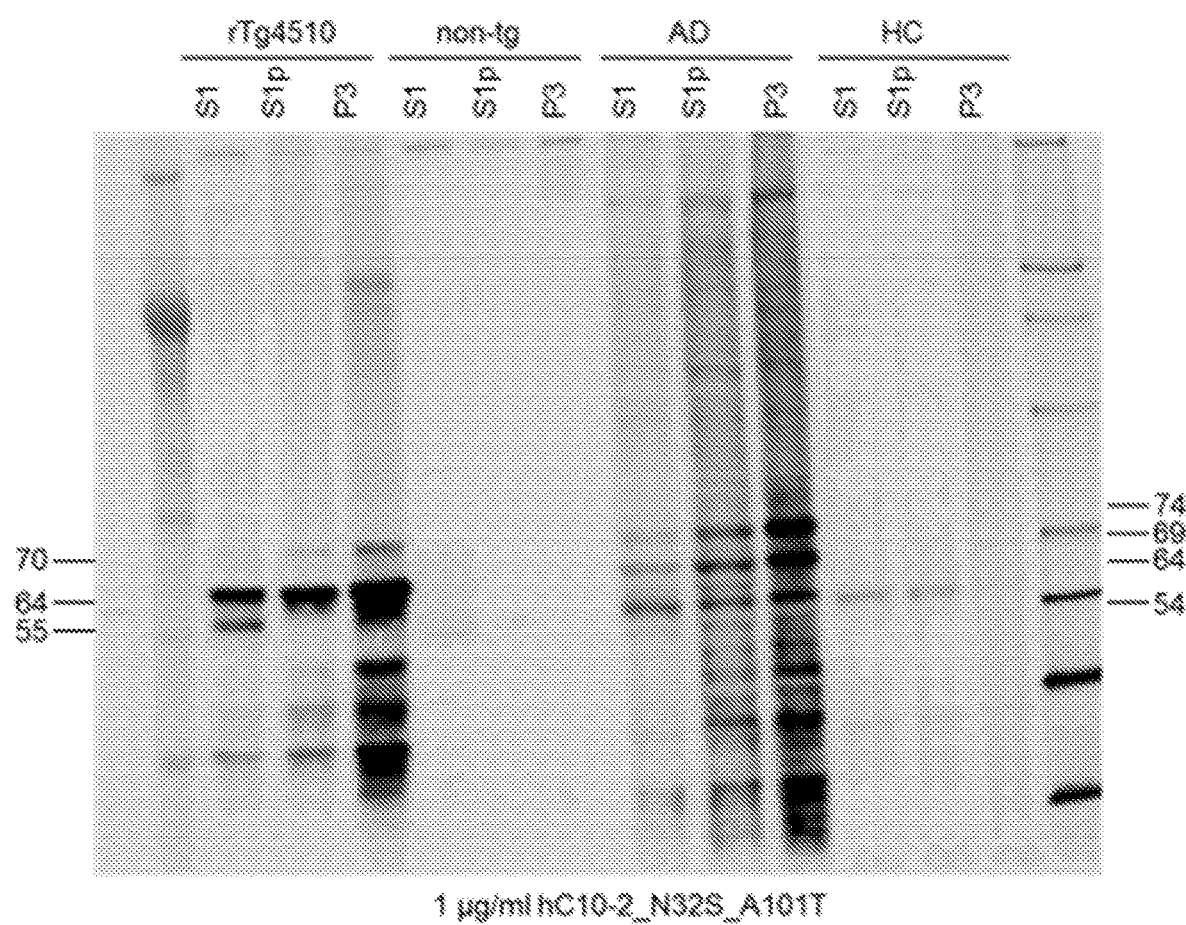

FIGS. 8A-8C. Detection of pathological tau by Western blot. As described in Example 6 section "Detection of pathological tau by Western blot", pathological tau with hC10.2, hC10-2_N32S, hC10-2_N32S_A101T by detected by Western blot. Forebrain pooled from three rTg4510 mice and non-transgenic (non-tg) control littermates euthanized at 32 weeks of age and pooled cortical specimen from four AD mice and four healthy control (HC) donors, respectively were fractioned into soluble (S1), TBS-soluble pellet (S1p) and sarkosyl-insoluble (P3) fractions and analyzed by western blot for phosphorylated tau at pS396 epitope with 1 µg/ml hC10.2 (A), hC10-2_N32S (B), hC10-

2_N32S_A101T (C). In rTg4510, normal human 4RON tau is displayed at 55 kDa, while hyperphosphorylated tau species are displayed at 64 kDa and 70 kDa. In AD, hyperphosphorylated tau species are displayed as four bands of 54, 64, 69 kDa, and 74 kDa, with a variable amount of AD typical smear.

Each of hC10-2, hC10-2_N32S and hC10-2_N32S_A101T are selective for tau proteins of rTg4510 mice over non-transgenic mice and for AD donors over healthy control donors. Moreover, in soluble (S1), TBS-soluble pellet (S1p) and sarkosyl-insoluble (P3) fractions, each of hC10-2, hC10-2_N32S and hC10-2_N32S_A101T are selective to the pathogenic tau 64 kDa protein of rTg4510 mice over the normal tau 55 kDa protein of rTg4510 mice.

Figure 9:
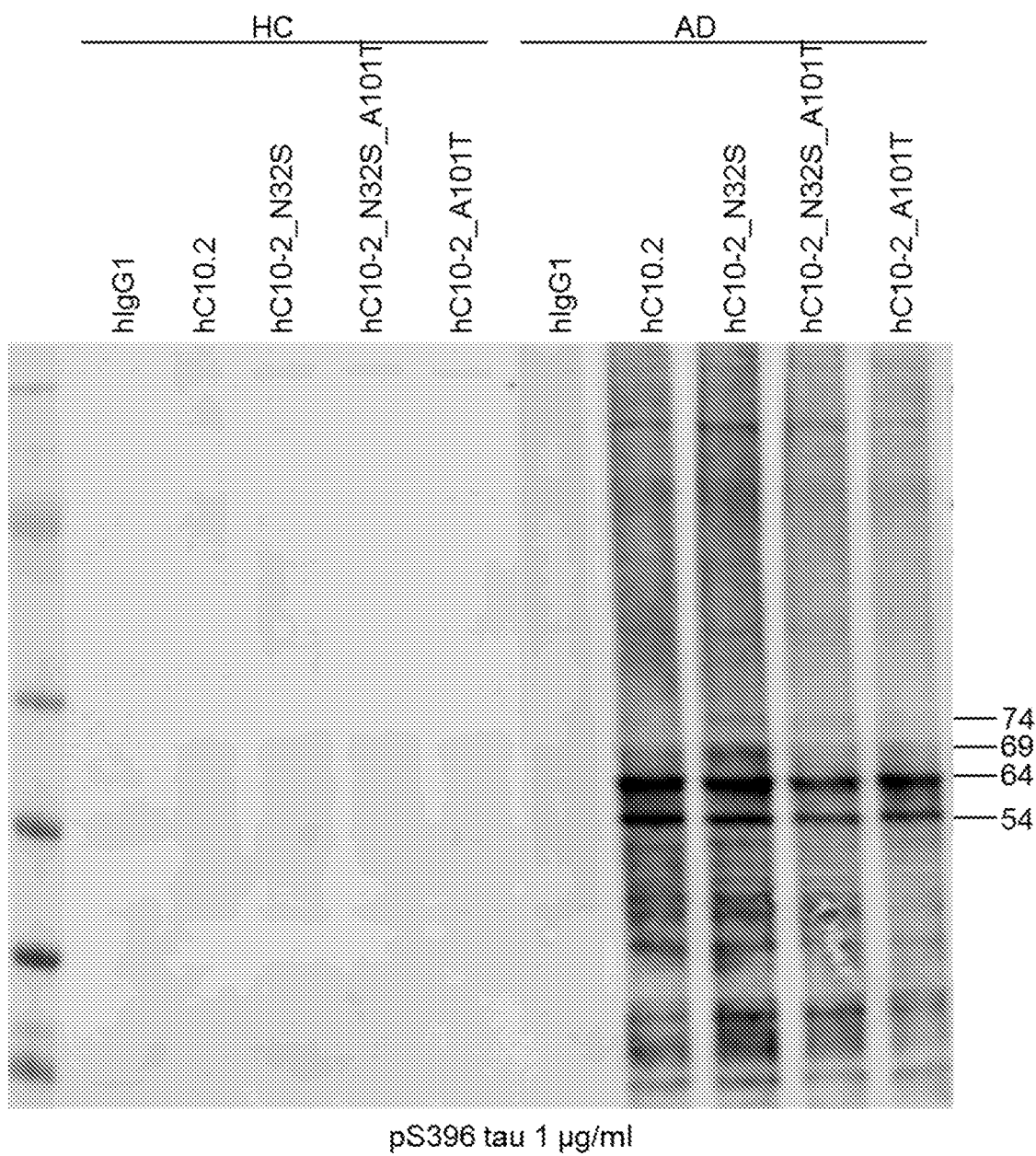

FIG. 9. Immunoprecipitation of tau from AD brains. As described in the Example 6 section "Immunoprecipitation of pathological tau" immunoprecipitation of tau with 10 µg hC10.2, hC10-2_N32S, hC10-2_N32S_A101T, using human IgG1 control (hIgG1) from 500 µg pre-cleared lysates of cortical brain homogenates pooled from four AD and health control (HC) donors was analyzed by western blot with polyclonal rabbit anti-pS396 tau (pS396 tau) antibody. In AD, hyperphosphorylated tau species are displayed as four bands of 54, 64, 69 kDa, and 74 kDa, with a variable amount of AD typical smear.

Figure 10A:
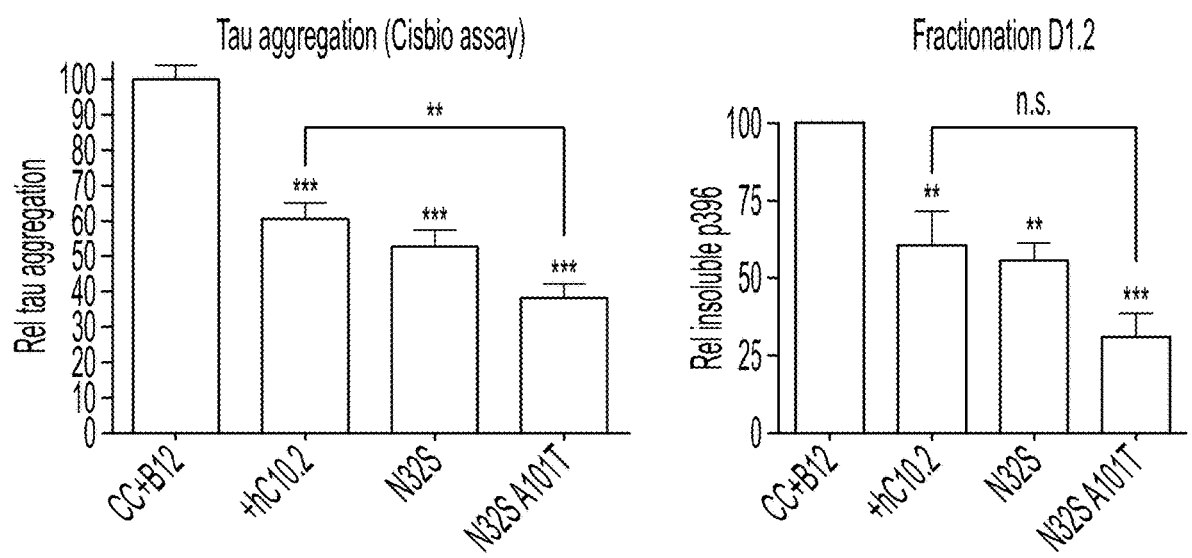
Figure 10B:
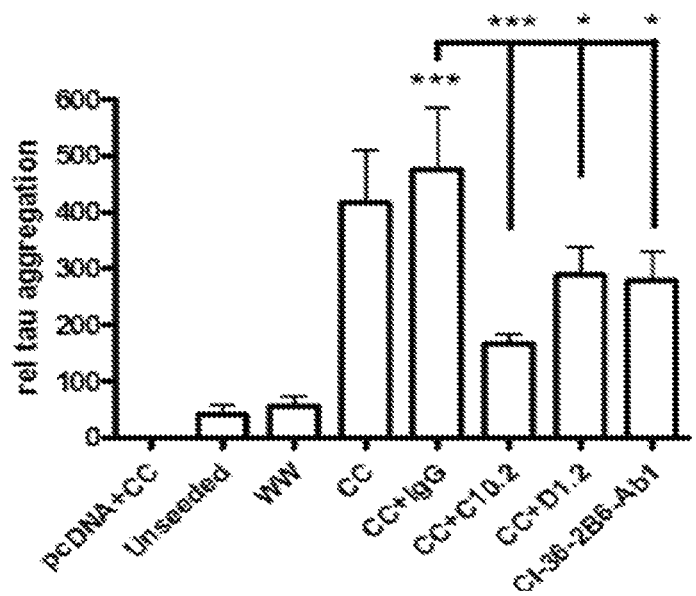
Figure 10C:
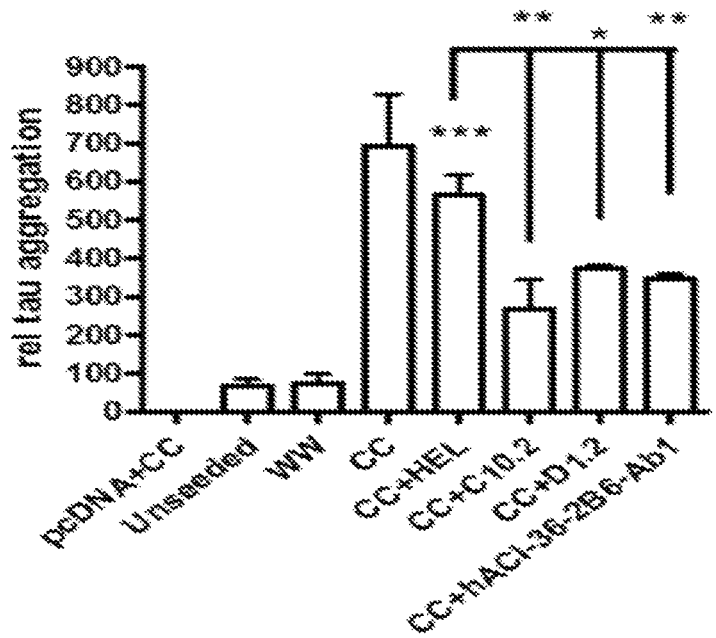

FIGS. 10A-10C Quantification of tau aggregation by Cisbio assay. Wild type (Wt) seeding material (WW) showed no seeding and background signal was subtracted from all seeded samples. Tg4510 homogenates seeded efficiently and the seeding effect was not affected by treatment with B12, but was effected to various degree by treatment in seeding studies performed at a concentration of 20 µg/mL with tau antibodies of the invention (hC10-2_N32S_A101T>hC10-2_N32S>hC10-2). Graphs represent results of four independent sets of experiments and are plotted as relative tau aggregation (fold signal over background normalized to total protein) and relative insoluble p396 tau was quantified by densitometry of western blots of the triton-X insoluble fraction (fold signal over background normalized). All samples were normalized to isotype control antibody B12. FIG. 10 B-C presents a quantification of tau aggregation by Cisbio assay. Seeded pcDNA HEK293 cells showed no signal, confirming the absence of detection for input seeding material. Wt (wild type) seeding material (WW) showed no seeding, but in contrast rTg4510 homogenates (CC) seeded efficiently, compared to unseeded. This seeding effect was not affected by treatment with HEL, but was partially reversed by treatment with tau antibodies (C10-2>D1.2>hACl36-2B6-Ab1). Graphs represent three independent sets of samples and are plotted as relative tau aggregation (fold signal over background normalized to total protein). Example 6, the section "Cell and Aggregation assay", describes the protocol followed.

Figure 11:
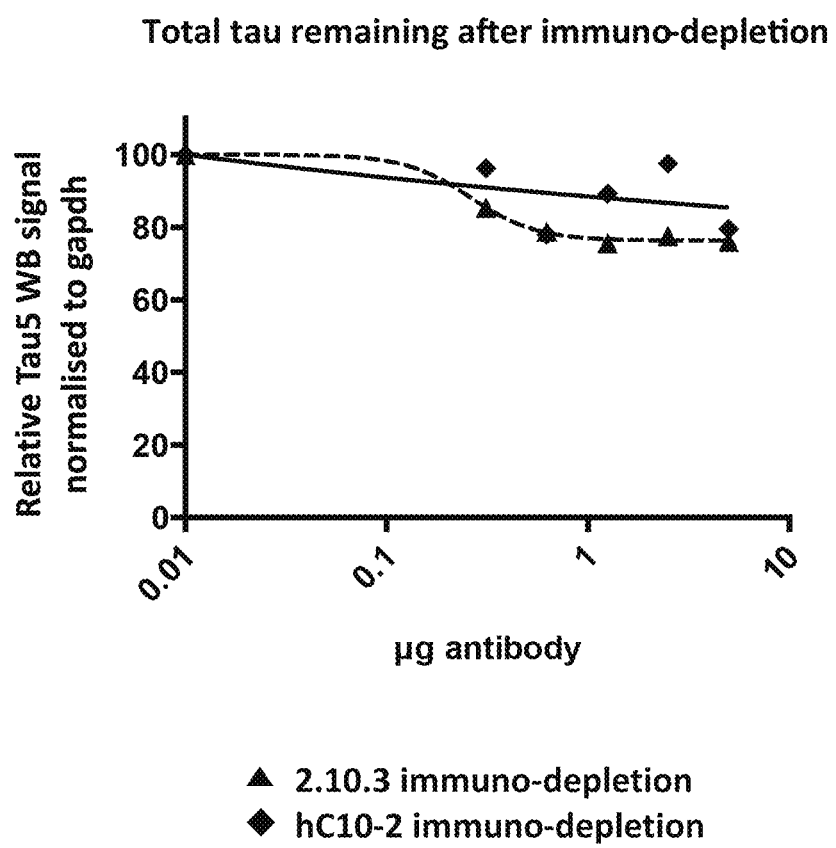

FIG. 11. Quantification of Tau5 western blot signal after immunodepletion of AD brain extracts using different amounts of hC10-2 and 2.10.3 antibody. As described in Example 7, both antibodies did remove a small fraction of total tau from Alzheimer brain extracts.

Figure 12:
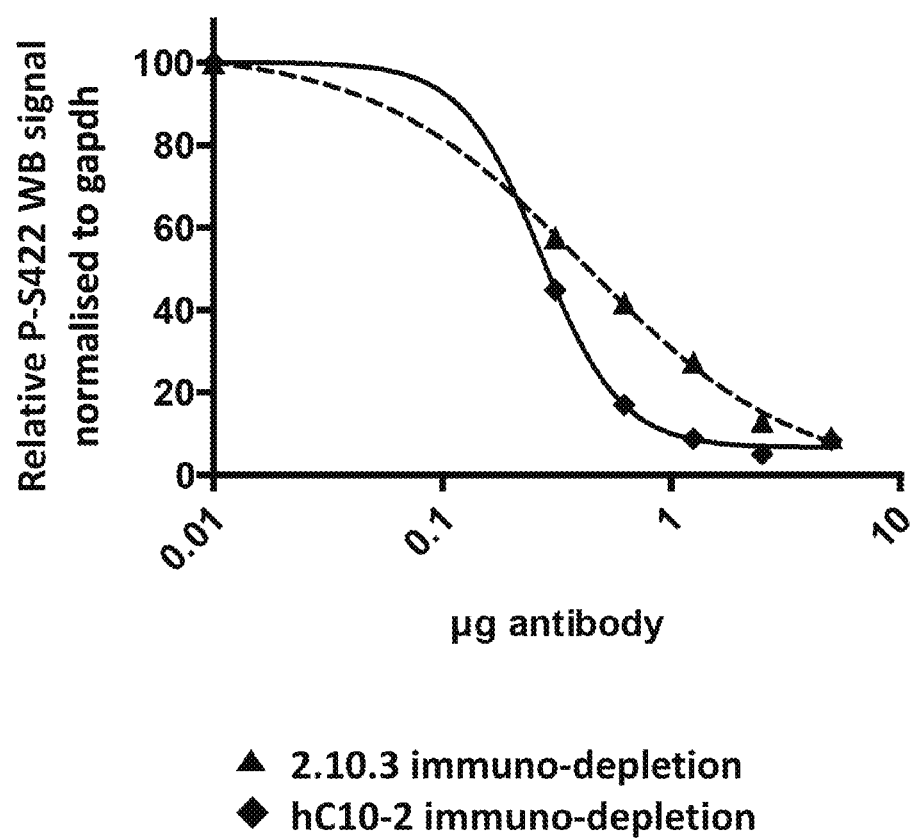

FIG. 12. Quantification of P-S422 Tau western blot signal after immunodepletion AD brain extracts using different amounts of hC10-2 (diamonds) and 2.10.3 (triangles) antibody. The figure shows results from Example 7. Tau phosphorylated at Serine 422 can be efficiently removed from AD brain extracts by immune depletion using either hC10-2 or 2.10.3. Both antibodies did remove more than 90% P-S422 Tau, although more of the 2.10.3 antibody was needed to reach the same effect.

Figure 13:
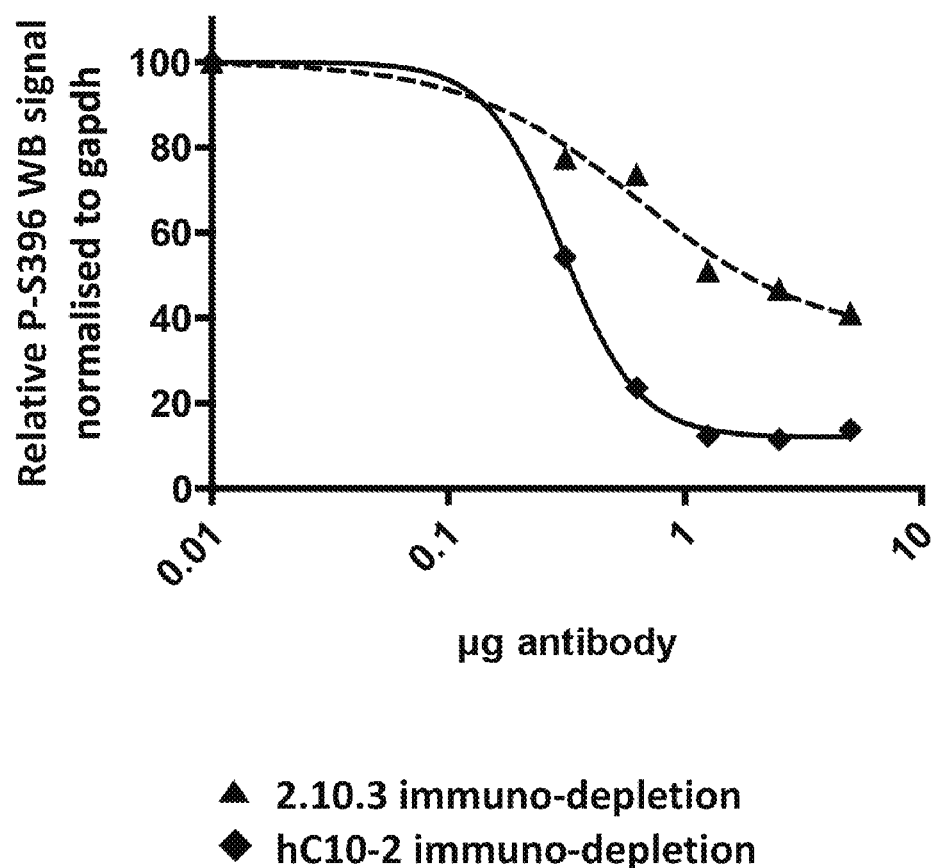

FIG. 13. Quantification of pS396 Tau western blot signal after immunodepletion AD brain extracts using different amounts of hC10-2 and 2.10.3 antibody. The figure shows results from Example 7. hC10-2 immunodepletion removed 88% of tau phosphorylated at Serine 396, whereas 2.10.3 only removed 55% of pS396 Tau from AD brain extracts.

Figure 14:
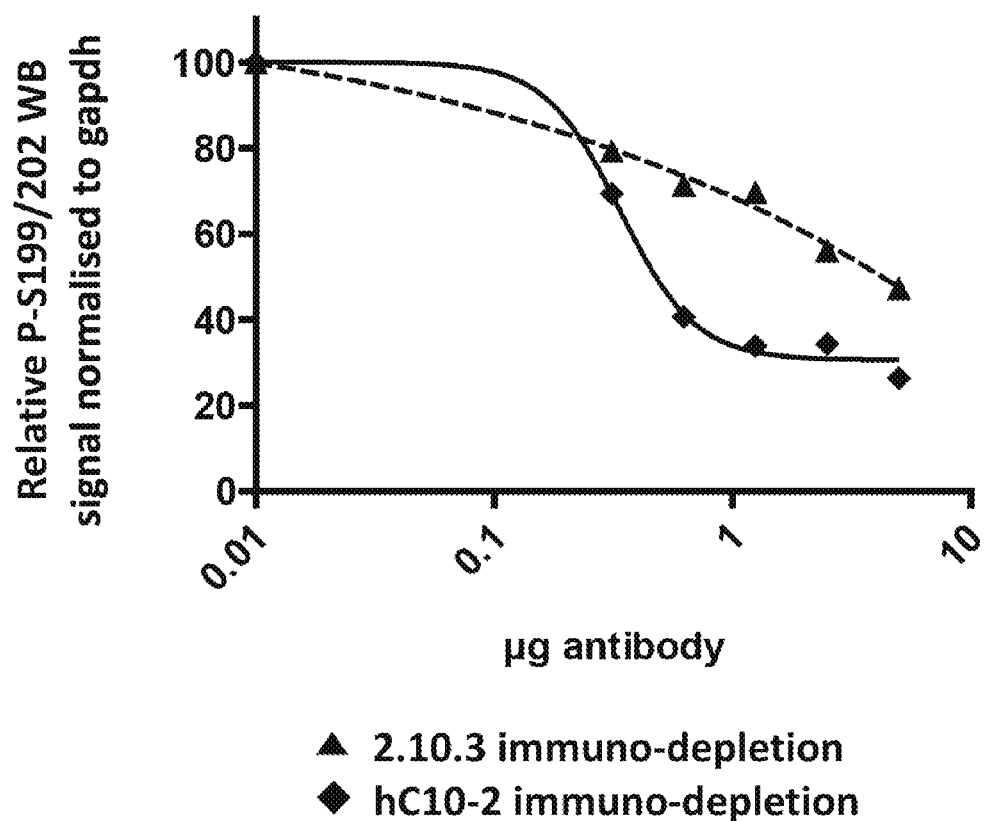

FIG. 14. Quantification of P-S199/202 Tau western blot signal after immunodepletion of AD brain extracts using different amounts of hC10-2 and 2.10.3 antibody. The figure shows results from Example 7. The hC10-2 immunodepletion cleared 69% of tau being phosphorylated at Serine 199/202. The 2.10.3 antibody did not give the same dose dependent reduction.

Figure 15:
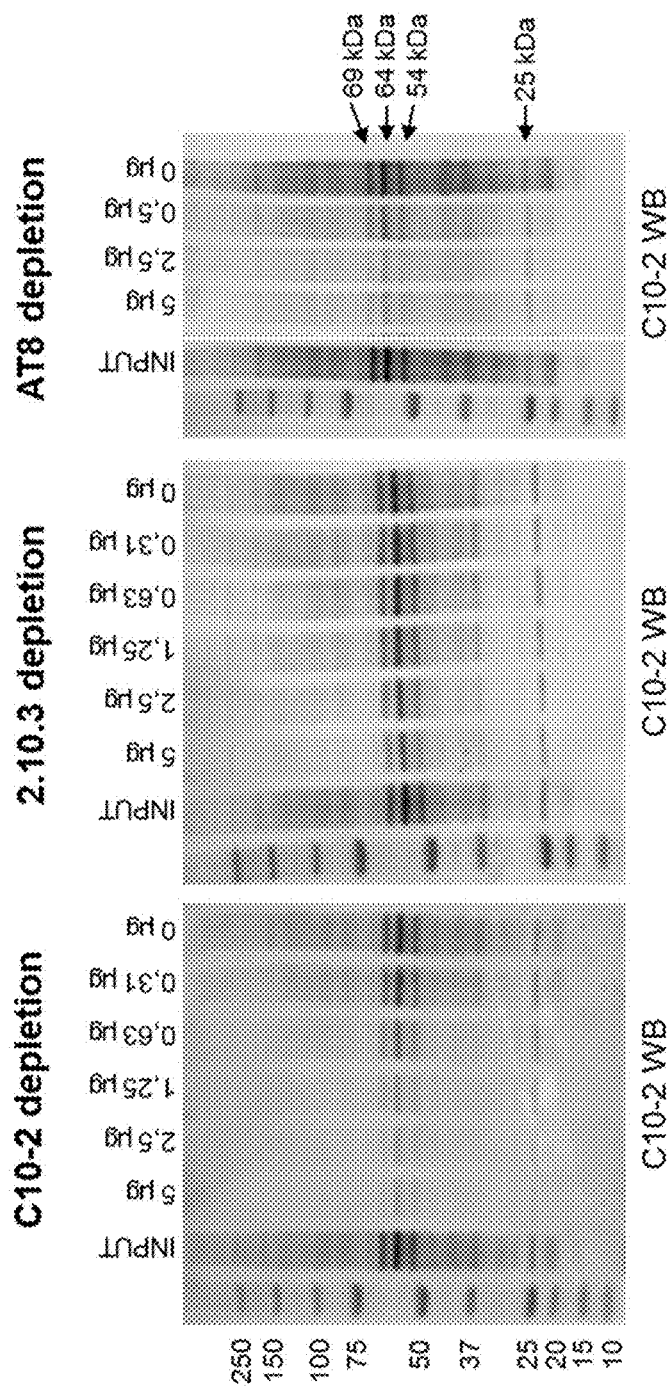

FIG. 15. Alzheimers diseased brain extracts on a western blot before and after immune depletion. The figure shows results from Example 7. There is a 25 kDa Tau fragment phosphorylated at serine 396. Immunodepletion using hC10-2 resulted in a reduction of the 25 kDa Tau band. The 2 other phospho-specific antibodies 2.10.3 and AT8 did not remove this 25 kDa species.

Figure 16:
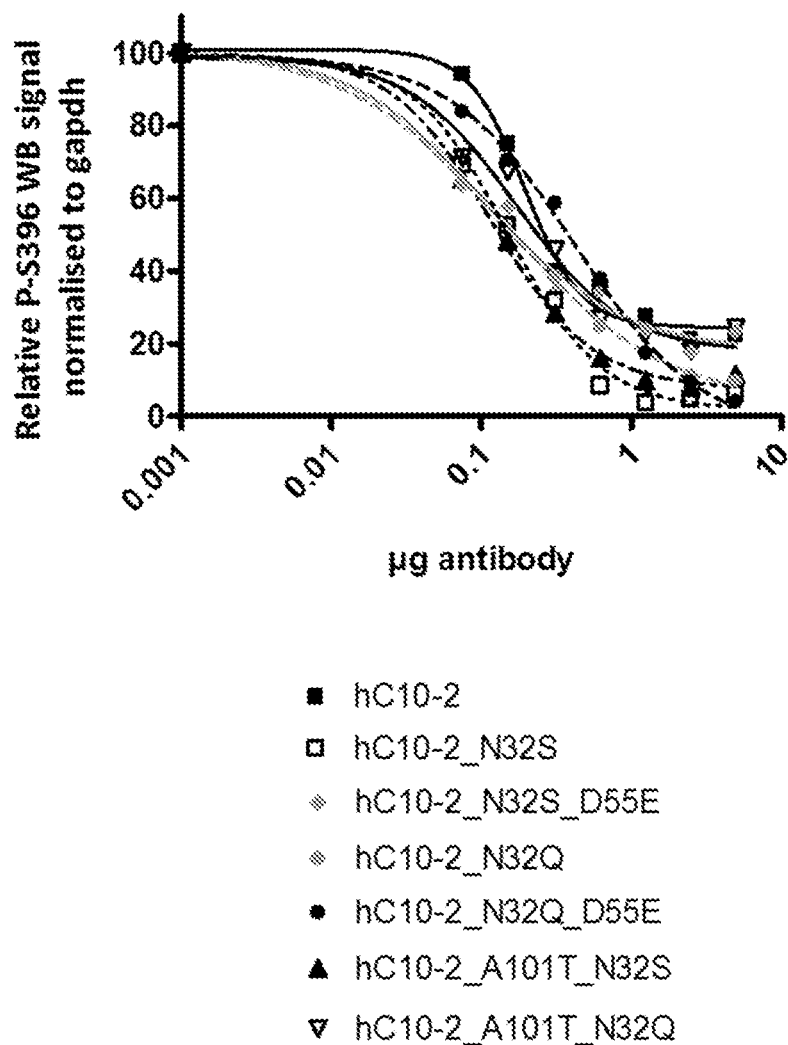

FIG. 16. Quantification of pS396 Tau western blot signal after immunodepletion AD brain extracts using different amounts of hC10-2 variants N32S, N32Q, N32S_A101T, N32Q_A101T, N32Q_D55E and N32S_D55E. As can be concluded from Example 8, the ability of the antibodies of the invention to remove tau phosphorylated at Serine 396 from AD brain homogenates was substantial. At less than 0.1 µg of antibody (data point at 75 ng), the variants resulted in a decrease in the pS396 signal by at least 28% (except for N32Q, D55E which was 16%) whereas the C10.2 resulted in a decrease in the pS396 signal of less than 6%.

Figure 17:
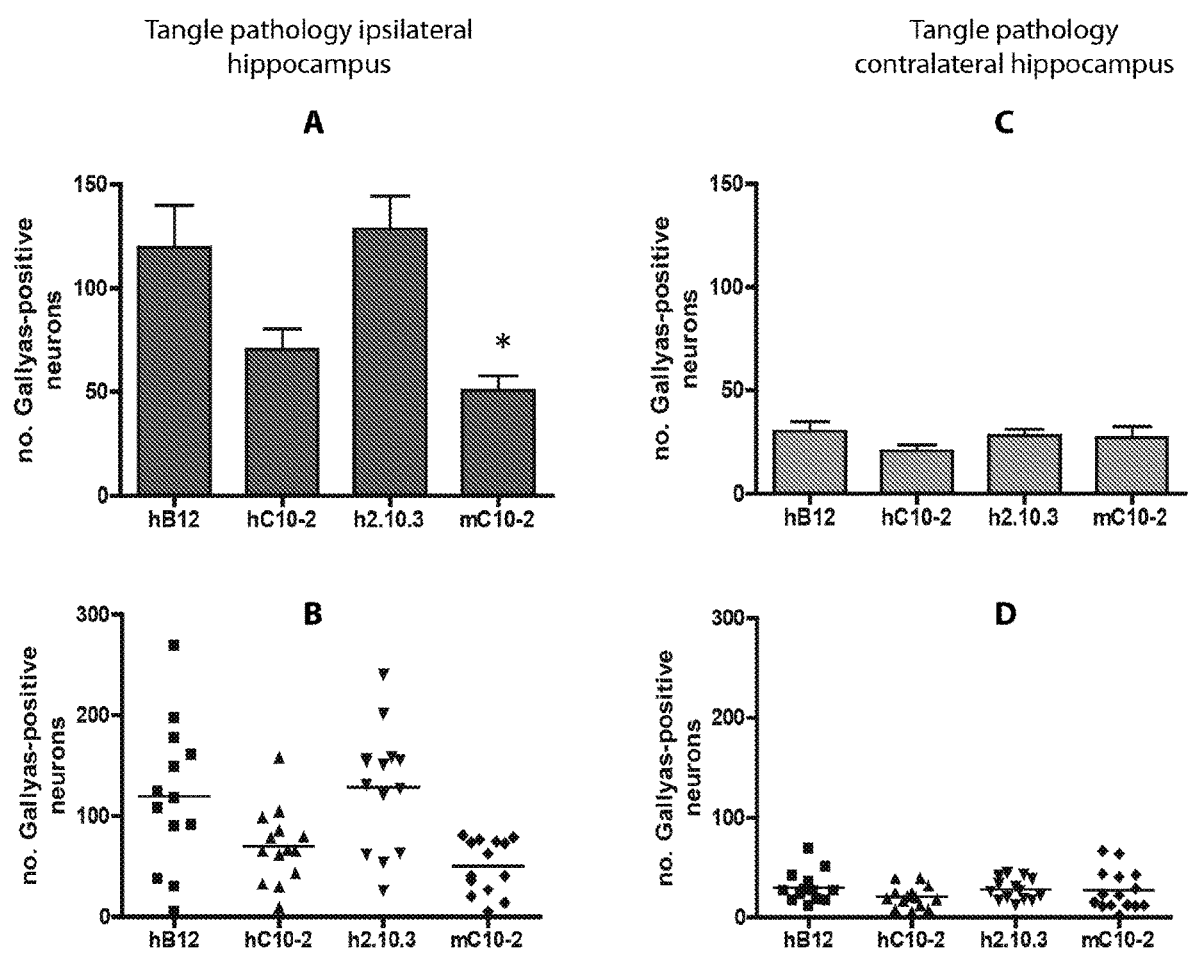

FIG. 17 (Panels A-D). Seeding of tau tangles the hippocampus, caused by injecting AD brain extracts. As performed in Example 8a, at a dose of 15 mg/kg, the mC10-2 treatment significantly reduced tangle pathology in the seeded hippocampus by 57% (P<0.05). There was a clear trend indicating hC10-2 also reduced pathology. By comparison, 2.10.3 failed to show an effect, at the same dose.

Figure 18:
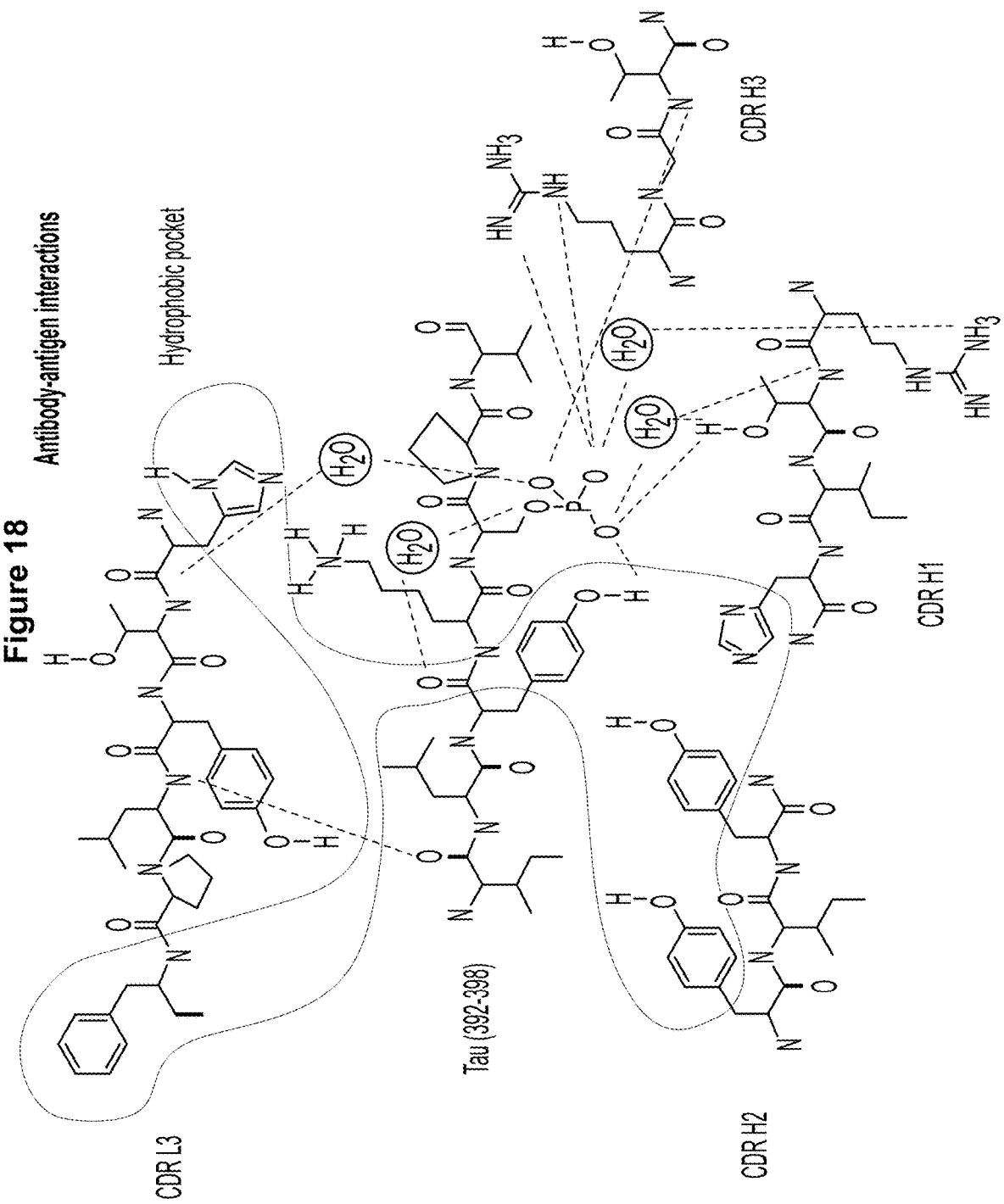

FIG. 18. Residue P-Ser396 and Tyr394 are at the center of the antigen binding site The structure of Ile(392)-Val(393)-Tyr(394)-Lys(395)-pSer(396)-Pro(397)-Val(398) is shown. The main interaction with the antibody of the invention involves the hydrophobic pocket, the pSer396 and Y394 of tau peptide. There is an extensive hydrogen bonding network formed and charge/polar interactions between the Y(394) sidechain and the backbone with phosphonate of pSer396. The HC CDR1 of the antibodies of invention comprise the palindromic 8-residue motif POLAR AA-HYRDROPHOBIC AA-POLAR AA-CHARGED AA-CHARGED AA-POLAR AA-HYRDROPHOBIC AA-POLAR AA (Thr-Phe-Thr-Asp-Arg-Thr-Ile-His). The charged residues interact via an extensive bonding network formed by hydrogen bonding, charge/charge, and charge/polar interactions between the antibody and the tau protein.

Figure 19:
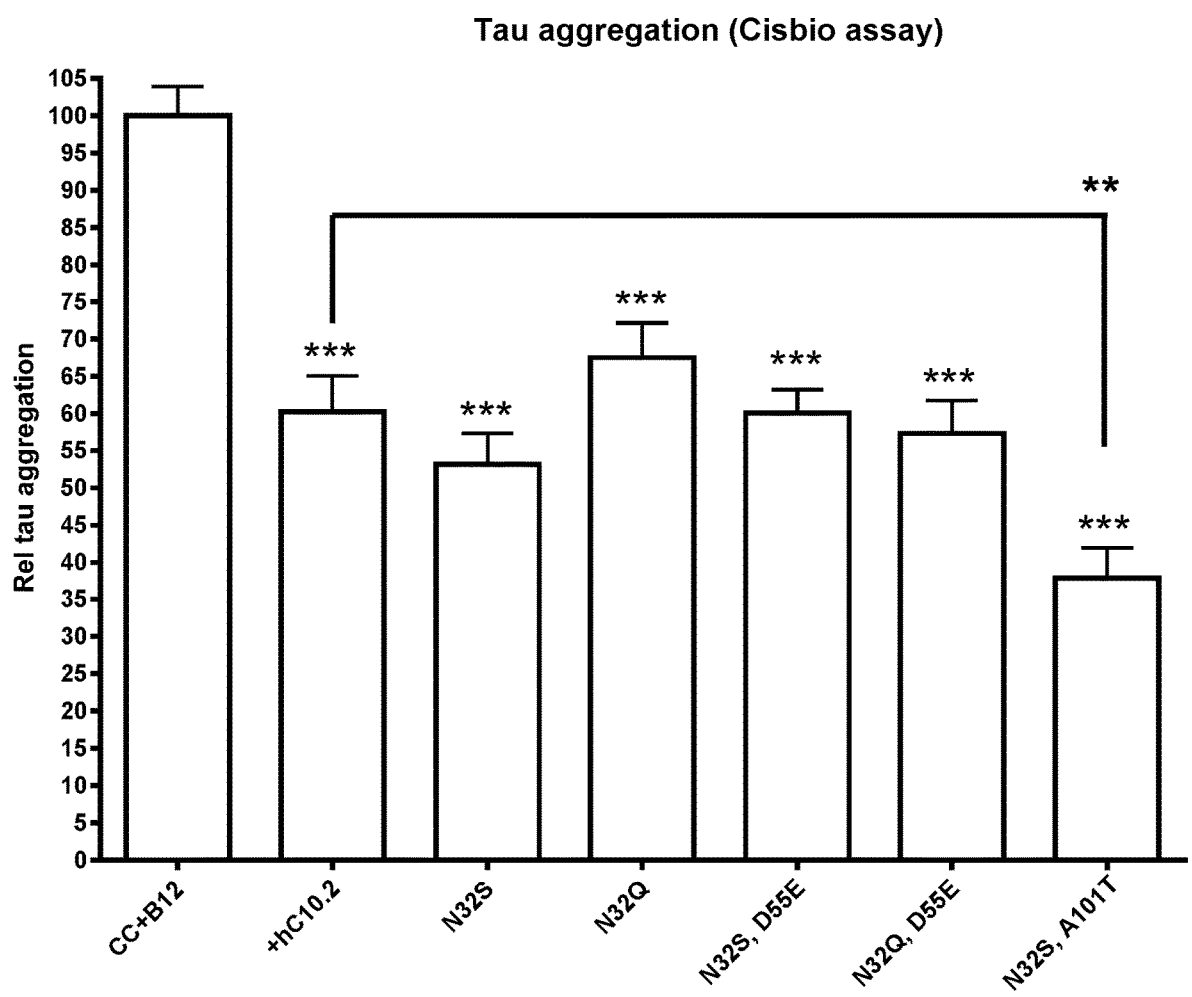

FIG. 19. Antibody efficacy in treatment paradigm

As performed in Example 8b, HEK293 cells expressing hTau-P301L were seeded with Tg4510 homogenates pre-incubated with indicated antibodies, trypsinized and re-seeded 24 hours post (antibodies re-added) and harvested 48 h post-seeding. Total cell homogenates were probed for aggregated tau using Cisbio tau aggregation. Data are the pooled data of 4 independent biological replicas+/−S.E.M., normalized to CC+B12 (tg4510).

P301L-htau expressing cells were seeded with 40 µg Tg4510 brain homogenate (total protein) pre-incubated o/n at 4° C. with antibodies (20 µg/ml≈133 nM) per 6-well. Seeding with CC+B12 gave a large seeding response. hC10.2 had an impact on aggregation approximately 40% All other antibodies showed an at least comparable effect to hC10.2. In particular, the N32S and N32S_A101T variants of hC10.2 showed stronger effects 45% and 62% reduction in aggregated tau. The N32S_A101T variant showed a significant stronger effect on aggregation compared to hC10.2. The Figure demonstrates that humanized C10.2 is effective at engaging tau induced seeding, but the addition of the N32S and in particular of the N32S and A101T double mutation increases the neutralizing activity of the mAb.

FIG. 20. Deamidation studies of the variants at stressed conditions

As performed in Example 8c, deamidation of Asn residues at position 32 or 34 of the VL chain was monitored by analyzing the tryptic peptide LC:T2 [VTMTCQASQDTSIXLNWFQQKPGK; SEQ ID NO:58] by LC-MS. X is either Asn, Gln or Ser in the respective variants indicated in FIG. 20. The MS analysis allows the calculation of relative content of deamidated to non deamidated peptide. In the WT, A101T and D55E variants extensive deamidation at the LC:T2 peptide is observed. It is also clear that changing Asn32 to either Gln or Ser completely prevents deamidation of the peptide at the other Asn34 residues. Also, we do not detect any deamidation of the Gln32 variants. Similar results were observed with variants of the Asn34.

Figure 21A:
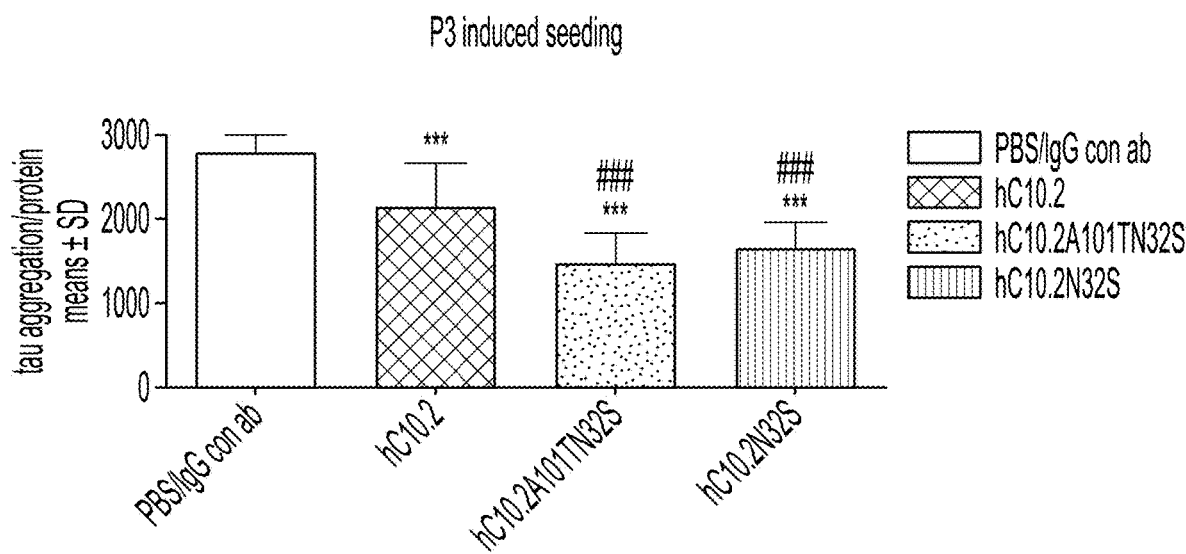
Figure 21B:
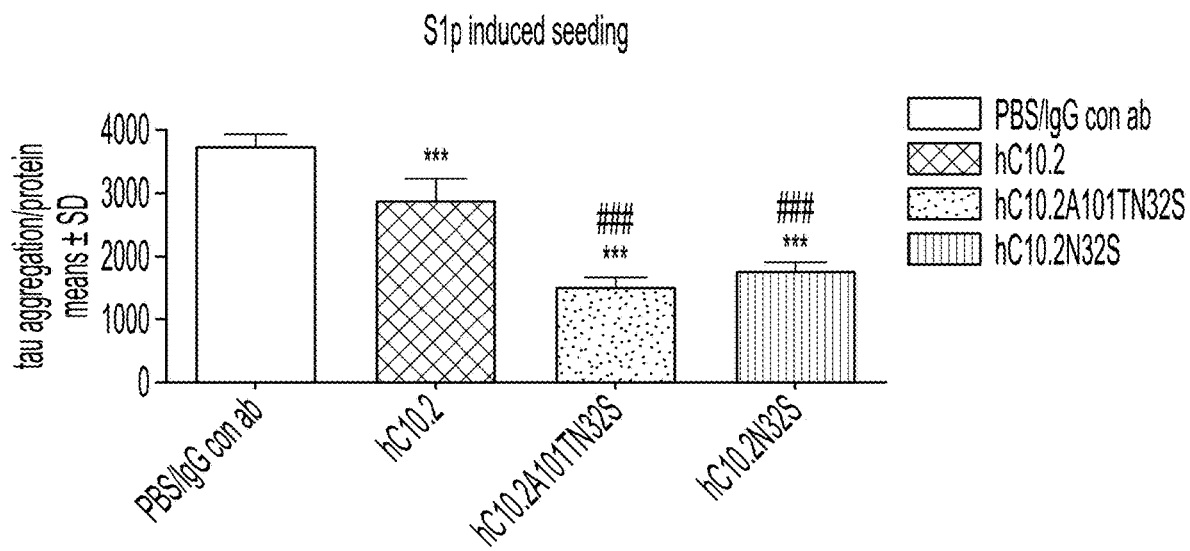

FIGS. 21A-21B. Reduction of tau seeding and aggregation in cortical neurons by tau antibodies Tau seeding and aggregation in cortical neuronal cultures from rTg4510 mouse embryos was induced by 0.2 ng pathological tau from P3 or S1p fractions from 40 weeks old rTg4510 mice and measured by the Cisbio tau aggregation assay. At 7 days in culture (DIV) neurons were treated with a mixture of P3 or S1p and 10 µg antibody or phosphate-buffered saline (PBS). Complete medium change was performed at DIV11 to remove residual P3 and S1p seeds and antibodies. Tau seeding was allowed for additional 4 days and neurons lysed at DIV15 to measure tau seeding and aggregation. PBS and human control IgG antibody (IgG con ab) did not affected tau seeding and aggregation. Tau seeding and aggregation was partially reversed by treatment with tau antibodies (hC10.2_A101T_N32S>hC10.2_N32S>hC10.2). Following reduction of tau seeding and aggregation was measured: 23% with hC10.2, 41-53% with hC10.2_N32S, and 48-60% with hC10.2_A101T_N32S. The bar graphs represent data from two independent experiments of tau aggregation normalized to neuronal protein as means±SD. One way ANOVA Newman-Keuls Multiple Comparison Test (PBS/IgG con ab vs hC10.2, hC10.2_N32S, hC10.2_A101T_N32S ***$p<0.001$; hC10.2 vs hC10.2_N32S, hC10.2_A101T_N32S ###$p<0.001$).

Figure 22:
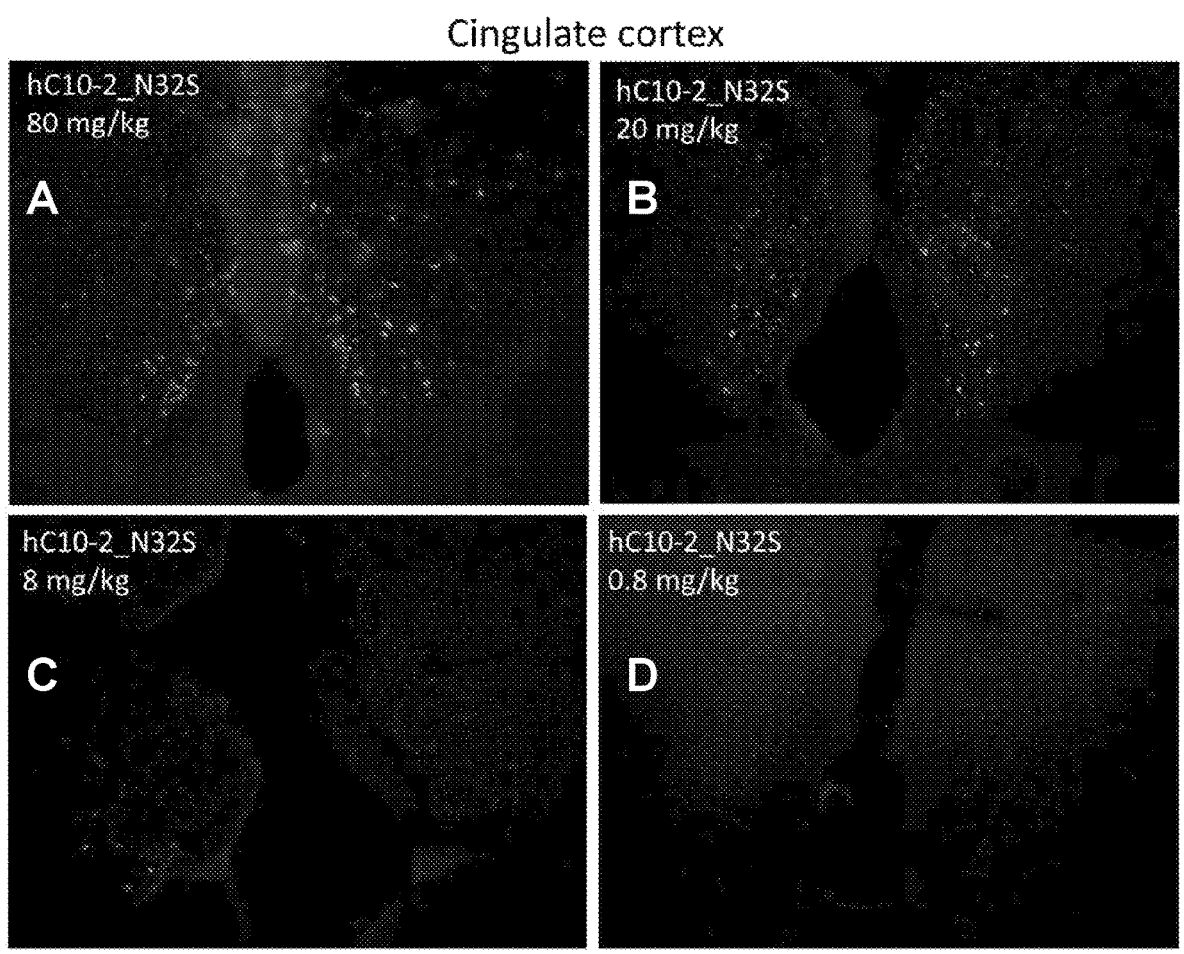

FIG. 22 (Panels A-D). Dose-dependent decoration of tau structures in rTg4510 mice following i.v. injection of hC10-2_N32S.

hC10-2_N32S specifically labels target structures in vivo in hippocampus and cortex in rTg4510 brains. Images from cingulate cortex are shown. Strongest signals at 20 and 80 mg/kg, weak signals at 8 mg/kg, no signal visible at 0.8 mg/kg.

Figure 23:
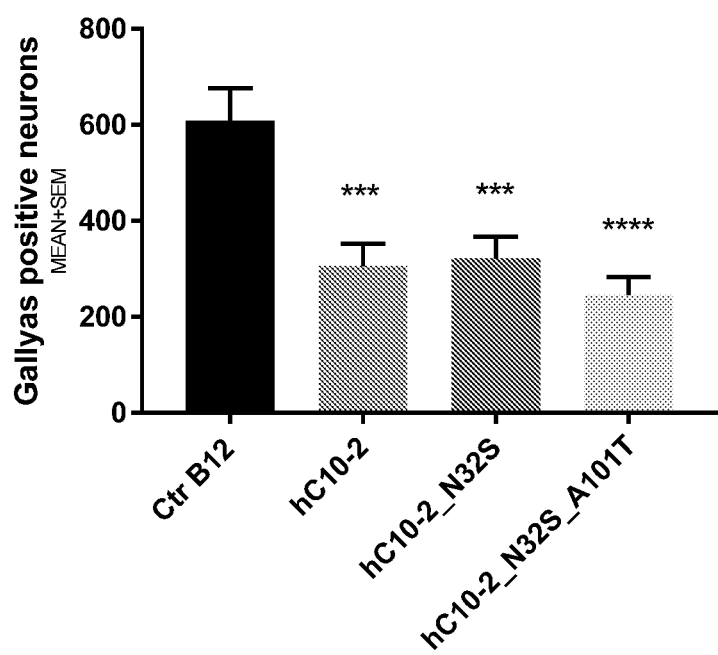

FIG. 23 Seeded tau pathology in hippocampus

The number of cells having Gallyas tangle staining in the seeded hippocampus was reduced by hC10-2 (50%), hC10-2_N32S (48%) and hC10-2_N32S_A101T (47%) treatment.

The quantification was made in every 6$^{th}$ sections covering the dorsal hippocampus, in total 8 sections were used per animal. The cell number reflects the sum of positive cells in all sub-regions of the hippocampus identified in the 8 sections. One way anova and Dunnett's multiple comparisons test was used to analyse the data.

SEQUENCES INCORPORATED BY REFERENCE

SEQ ID NO:1 Human tau (2N4R)
SEQ ID NO:2 tau residues 386-408 (pS396, pS404)
SEQ ID NO:3 C10-2 Light Chain CDR1
SEQ ID NO:4 C10-2 Light Chain CDR2
SEQ ID NO:5 C10-2 Light Chain CDR3
SEQ ID NO:6 C10-2 Heavy Chain CDR1
SEQ ID NO:7 C10-2 Heavy Chain CDR2
SEQ ID NO:8 C10-2 Heavy Chain CDR3
SEQ ID NO:9 Mouse C10-2 Light Chain
SEQ ID NO:10 Mouse C10-2 Heavy Chain
SEQ ID NO:11 humanized C10-2 Heavy Chain
SEQ ID NO:12 humanized C10-2 Light Chain
SEQ ID NO:13 humanized C10-2 Heavy Chain Variant D55E
SEQ ID NO:14 humanized C10-2 Heavy Chain Variant D55Q
SEQ ID NO:15 humanized C10-2 Heavy Chain Variant D55S
SEQ ID NO:16 humanized C10-2 Light Chain Variant N32S
SEQ ID NO:17 humanized C10-2 Light Chain Variant N32Q
SEQ ID NO:18 humanized C10-2 Light Chain Variant N34S
SEQ ID NO:19 humanized C10-2 Light Chain Variant N34Q
SEQ ID NO:20 humanized C10-2 Light Chain Variant N32S, N34S
SEQ ID NO:21 humanized C10-2 Light Chain Variant N32Q, N34S
SEQ ID NO:22 humanized C10-2 Light Chain Variant N32Q, N34Q
SEQ ID NO:23 humanized C10-2 Light Chain Variant N32S, N34Q
SEQ ID NO:24 humanized C10-2 Heavy Chain Variant A101T
SEQ ID NO:25 humanized C10-2 Heavy Chain Variant D55E, A101T
SEQ ID NO:26 humanized C10-2 Heavy Chain Variant D55Q, A101T
SEQ ID NO:27 humanized C10-2 Heavy Chain Variant D55S, A101T
SEQ ID NO:28 humanized C10-2 Heavy Chain CDR2 Variant D55E
SEQ ID NO:29 humanized C10-2 Heavy Chain CDR2 Variant D55Q
SEQ ID NO:30 humanized C10-2 Heavy Chain CDR2 Variant D55S
SEQ ID NO:31 humanized C10-2 Light Chain CDR1 Variant N32S
SEQ ID NO:32 humanized C10-2 Light Chain CDR1 Variant N32Q
SEQ ID NO:33 humanized C10-2 Light Chain CDR1 Variant N34S
SEQ ID NO:34 humanized C10-2 Light Chain CDR1 Variant N34Q SEQ ID NO:35 humanized C10-2 Light Chain CDR1 Variant N32S, N34S
SEQ ID NO:36 humanized C10-2 Light Chain CDR1 Variant N32Q, N34S
SEQ ID NO:37 humanized C10-2 Light Chain CDR1 Variant N32Q, N34Q
SEQ ID NO:38 humanized C10-2 Light Chain CDR1 Variant N32S, N34Q
SEQ ID NO:39 humanized C10-2 Heavy Chain CDR3 Variant A101T
SEQ ID NO:40 IMGT numbering humanized C10-2 Light Chain CDR1
SEQ ID NO:41 IMGT numbering humanized C10-2 Light Chain CDR2
SEQ ID NO:42 IMGT numbering humanized C10-2 Light Chain CDR3
SEQ ID NO:43 IMGT numbering humanized C10-2 Heavy Chain CDR1
SEQ ID NO:44 IMGT numbering humanized C10-2 Heavy Chain CDR2
SEQ ID NO:45 IMGT numbering humanized C10-2 Heavy Chain CDR3
SEQ ID NO:46 IMGT numbering humanized C10-2 Light Chain CDR1 Variant N32S
SEQ ID NO:47 IMGT numbering humanized C10-2 Light Chain CDR2 Variant N32S
SEQ ID NO:48 IMGT numbering humanized C10-2 Light Chain CDR3 Variant N32S
SEQ ID NO:49 IMGT numbering humanized C10-2 Heavy Chain CDR1 Variant A101T
SEQ ID NO:50 IMGT numbering humanized C10-2 Heavy Chain CDR2 Variant A101T
SEQ ID NO:51 IMGT numbering humanized C10-2 Heavy Chain CDR3 Variant A101T
SEQ ID NO:52 Chotia numbering humanized C10-2 Heavy Chain CDR1
SEQ ID NO:53 Chotia numbering humanized C10-2 Heavy Chain CDR2
SEQ ID NO:54 Chotia numbering humanized C10-2 Heavy Chain CDR3
SEQ ID NO:55 Chotia numbering humanized C10-2 Heavy Chain CDR1 Variant A101T
SEQ ID NO:56 Chotia numbering humanized C10-2 Heavy Chain CDR2 Variant A101T
SEQ ID NO:57 Chotia numbering humanized C10-2 Heavy Chain CDR3 Variant A101T
SEQ ID NO:58 5-residue motif of the HC CDR1
SEQ ID NO:59 8-residue motif of the HC CDR1
SEQ ID NO:60 first primer for the tTA activator transgene
SEQ ID NO:61 second primer for the tTA activator transgene
SEQ ID NO:62 first primer for the mutant tau responder transgene
SEQ ID NO:63 second primer for the mutant tau responder transgene

DETAILED DESCRIPTION OF THE INVENTION

As used herein, the term "tau" is synonymous with "the tau protein" and refers to any of the tau protein isoforms (identified in, for example, UniProt as P10636, 1-9). The amino acid numbering of tau that is used herein is given with respect to isoform 2 (SEQ ID NO:1) as shown below, with methionine (M) being amino acid residue 1:

SEQ ID NO: 1:
MAEPRQEFEV MEDHAGTYGL GDRKDQGGYT MHQDQEGDTD

AGLKESPLQT PTEDGSEEPG SETSDAKSTP TAEDVTAPLV

DEGAPGKQAA AQPHTEIPEG TTAEEAGIGD TPSLEDEAAG

HVTQARMVSK SKDGTGSDDK KAKGADGKTK IATPRGAAPP

GQKGQANATR IPAKTPPAPK TPPSSGEPPK SGDRSGYSSP

GSPGTPGSRS RTPSLPTPPT REPKKVAVVR TPPKSPSSAK

SRLQTAPVPM PDLKNVKSKI GSTENLKHQP GGGKVQIINK

KLDLSNVQSK CGSKDNIKHV PGGGSVQIVY KPVDLSKVTS

KCGSLGNIHH KPGGGQVEVK SEKLDFKDRV QSKIGSLDNI

THVPGGGNKK IETHKLTFRE NAKAKTDHGA EIVYKSPVVS

GDTSPRHLSN VSSTGSIDMV DSPQLATLAD EVSASLAKQG L

The present invention relates to antibodies and epitope-binding fragments thereof that are capable of specifically binding to tau, and in particular to human tau, and in one embodiment exhibit the ability to specifically bind to the phosphorylated S396 residue (pS396) of human tau. The antibodies and epitope-binding fragments thereof of the invention, are further characterized by being incapable or substantially incapable of specifically binding to the phosphorylated serine 404 (pS404) residue on human tau, for example under antibody limited or non-saturating conditions. Furthermore, phosphorylation at pS404 does not interfere with the specific binding to pS396 containing epitopes. As used herein, the notations "pS" and "$^{\{p\}}$S" denote the amino acid residue phosphoserine and the subsequent numbers identify the position of the residue relative to the sequence of SEQ ID NO:1. As used herein, an antibody is "substantially" incapable of binding to an epitope if relative to another epitope such binding is less than 20%, less than 10%, less than 5%, less than 2%, and more preferably, less than 1% of the binding observed with such other epitope.

The term "antibody" (Ab) in the context of the present invention refers to an immunoglobulin molecule or according to some embodiments of the invention, a fragment of an immunoglobulin molecule which has the ability to specifically bind to an epitope of a molecule ("antigen"). Naturally occurring antibodies typically comprise a tetramer which is usually composed of at least two heavy chains (HC) and at least two light chains (LC). Each heavy chain is comprised of a heavy chain variable domain (abbreviated herein as VH) and a heavy chain constant domain, usually comprised of three domains (CH1, CH2 and CH3). Human heavy chains can be of any isotype, including IgG (IgG1, IgG2, IgG3 and IgG4 subtypes). Each light chain is comprised of a light chain variable domain (abbreviated herein as VL) and a light chain constant domain (CL). Human light chains include kappa chains and lambda chains. The heavy and light chain variable domain is typically responsible for antigen recognition, while the heavy and light chain constant domain may mediate the binding of the immunoglobulin to host tissues or factors, including various cells of the immune system (e.g., effector cells) and the first component (C1q) of the classical complement system. The VH and VL domains can be further subdivided into domains of hypervariability, termed "complementarity determining regions," that are interspersed with domains of more conserved sequence, termed "framework regions" (FR). Each VH and VL is composed of three CDR Domains and four FR Domains arranged from amino-terminus to carboxy-terminus in the following order: FR1-CDR1-FR2-CDR2-FR3-CDR3-FR4. The variable domains of the heavy and light chains contain a binding domain that interacts with an antigen. Of particular relevance are antibodies and their epitope-binding fragments that have been "isolated" so as to exist in a physical milieu distinct from that in which it may occur in nature or that have been modified so as to differ from a naturally occurring antibody or their epitope-binding fragments in amino acid sequence.

The term "epitope" means an antigenic determinant capable of specific binding to an antibody. Epitopes usually consist of surface groupings of molecules such as amino acids or sugar side chains and usually have specific three dimensional structural characteristics, as well as specific charge characteristics. Conformational and linear epitopes are distinguished in that the binding to the former, but not the latter, is always lost in the presence of denaturing solvents. The epitope may comprise amino acid residues directly involved in the binding and other amino acid residues, which are not directly involved in the binding, such as amino acid residues which are effectively blocked by the specifically epitope-binding peptide (in other words, the amino acid residue is within the footprint of the specifically epitope-binding peptide).

As used herein, the term "epitope-binding fragment of an antibody" means a fragment, portion, region or domain of an antibody (regardless of how it is produced (e.g., via cleavage, recombinantly, synthetically, etc.) that is capable of specifically binding to an epitope. An epitope-binding fragment may contain any 1, 2, 3, 4, 5 or all 6 of the CDR Domains of such antibody and, although capable of specifically binding to such epitope, may exhibit a specificity, affinity or selectivity toward such epitope that differs from that of such antibody. Preferably, however, an epitope-binding fragment will contain all 6 of the CDR Domains of such antibody. An epitope-binding fragment of an antibody may be part of, or comprise, a single polypeptide chain (e.g., an scFv), or may be part of, or comprise, two or more polypeptide chains, each having an amino-terminus and a carboxyl terminus (e.g., a diabody, a Fab fragment, a Fab$_2$ fragment, etc.). Fragments of antibodies that exhibit epitope-binding ability can be obtained, for example, by protease cleavage of intact antibodies. More preferably, although the two domains of the Fv fragment, VL and VH, are naturally encoded by separate genes, or polynucleotides that encode such gene sequences (e.g., their encoding cDNA) can be joined, using recombinant methods, by a flexible linker that enables them to be made as a single protein chain in which the VL and VH regions associate to form monovalent epitope-binding molecules (known as single-chain Fv (scFv); see e.g., Bird et al., (1988) Science 242:423-426; and Huston et al. (1988) Proc. Natl. Acad. Sci. (U.S.A.) 85:5879-5883). Alternatively, by employing a flexible linker that is too short (e.g., less than about 9 residues) to enable the VL and VH domains of a single polypeptide chain to associate together, one can form a bispecific antibody, diabody, or similar molecule (in which two such polypeptide chains associate together to form a bivalent epitope-binding molecule) (see for instance PNAS USA 90(14), 6444-8 (1993) for a description of diabodies). Examples of epitope-binding fragments encompassed within the present invention include (i) a Fab' or Fab fragment, a monovalent fragment consisting of the VL, VH, CL and CH1 domains, or a monovalent antibody as described in WO2007059782; (ii) F(ab')2 fragments, bivalent fragments comprising two Fab fragments linked by a disulfide bridge at the hinge domain; (iii) an Fd fragment consisting essentially of the VH and CH1 domains; (iv) a Fv fragment consisting essentially of a VL and VH domains, (v) a dAb fragment (Ward et al., Nature 341, 544-546 (1989)), which consists essentially of a VH domain and also called domain antibodies (Holt et al; Trends Biotechnol. 2003 November; 2i(II):484-90); (vi) camelid or nanobodies (Revets et al; Expert Opin Biol Ther. 2005 January; 5 (1): 111-24) and (vii) an isolated complementarity determining region (CDR). Furthermore, although the two domains of the Fv fragment, VL and VH, are coded for by separate genes, they may be joined, using recombinant methods, by a synthetic linker that enables them to be made as a single protein chain in which the VL and VH domains pair to form monovalent molecules (known as single chain antibodies or single chain Fv (scFv), see for instance Bird et al., Science 242, 423-426 (1988) and Huston et al., PNAS USA 85, 5879-5883 (1988)). These and other useful antibody fragments in the context of the present invention are discussed further herein. It also should be understood that the term antibody, unless specified otherwise, also includes antibody-like polypeptides, such as chimeric antibodies and humanized antibodies, and antibody fragments retaining the ability to specifically bind to the antigen (epitope-binding fragments) provided by any known technique, such as enzymatic cleavage, peptide synthesis, and recombinant techniques. An antibody as generated can possess any isotype. As used herein, "isotype" refers to the immunoglobulin class (for instance IgG1, IgG2, IgG3 or IgG4) that is encoded by heavy chain constant domain genes. Such antibody fragments are obtained using conventional techniques known to those of skill in the art; suitable fragments capable of binding to a desired epitope may be readily screened for utility in the same manner as an intact antibody. In one embodiment, the Fc region of the antibodies of the invention comprise a mutation that modulates effector functions.

The term "bispecific antibody" refers to an antibody containing two independent epitope-binding fragments that each target independent targets. These targets can be epitopes present on different proteins or different epitopes present on the same target. Bispecific antibody molecules can be made using compensatory amino acid changes in the constant domains of the HCs of the parent monospecific bivalent antibody molecules. The resulting heterodimeric antibody contains one Fabs contributed from two different parent monospecific antibodies. Amino acid changes in the Fc domain leads to increased stability of the heterodimeric antibody with bispecificity that is stable over time. (Ridgway et al., Protein Engineering 9, 617-621 (1996), Gunasekaran et al., JBC 285, 19637-1(2010), Moore et al., MAbs 3:6 546-557 (2011), Strop et al., JMB 420, 204-219 (2012), Metz et al., Protein Engineering 25:10 571-580 (2012), Labrijn et al., PNAS 110:113, 5145-5150 (2013), Spreter Von Kreudenstein et al., MAbs 5:5 646-654 (2013)). Bispecific antibodies can also include molecules that are generated using ScFv fusions. Two monospecific scfv are then independently joined to Fc domains able to form stable heterodimers to generate a single bispecific molecule (Mabry et al., PEDS 23:3 115-127 (2010). Bispecific molecules have dual binding capabilities.

The terms "C10-2", "human C10-2", "hC10-2", "HC10-2", "hC10.2", "Humanized C10-2" and "humanized C10-2" as used herein and in the Figures are intended to be synonymous and are defined as Antibody C10-2. The term is intended to denote an antibody or an epitope-binding fragment thereof comprising, or consisting of, an antibody Light Chain Variable domain having:

(a) a Light Chain CDR1 having the amino acid sequence of SEQ ID NO:3;
(b) a Light Chain CDR2 having the amino acid sequence of SEQ ID NO:4; and
(c) a Light Chain CDR3 having the amino acid sequence of SEQ ID NO:5;
and an antibody Heavy Chain Variable domain having:
(d) a Heavy Chain CDR1 having the amino acid sequence of SEQ ID NO:6;
(e) a Heavy Chain CDR2 having the amino acid sequence of SEQ ID NO:7; and
(f) a Heavy Chain CDR3 having the amino acid sequence of SEQ ID NO:8.

Antibody C10-2 is a humanized antibody which may be defined as comprising the heavy chain of SEQ ID NO:11, the light chain of SEQ ID NO:12., or both. One embodiment of the invention is directed to an antibody or epitope-binding fragment thereof comprising of the heavy chain of SEQ ID NO:11 and the light chain of SEQ ID NO:12.

The term "mC10-2" as used herein and in the Figures is intended to mean mouse antibody C10-2 and is defined by SEQ ID. NO. 9 and 10. Mouse antibody C10.2 is used as a control antibody and is not part of the invention.

The terms "hC10-2_N32S" and "C10-2_N32S" as used herein and in the Figures are intended to be synonymous and are variants of Antibody C10-2 wherein the light chain has been mutated to at least comprise mutation of amino acid residue 32 from N to S and is defined as Antibody N32S. The terms "hC10-2_N32Q" and "C10-2_N32Q" as used herein and in the Figures are intended to be synonymous and are variants of Antibody C10-2 wherein the light chain has been mutated to at least comprise mutation of amino acid residue 32 from N to Q and is defined as Antibody N32Q.

The terms "hC10-2_N34S" and "C10-2_N34S" as used herein and in the Figures are intended to be synonymous and are variants of Antibody C10-2 wherein the light chain has been mutated to at least comprise mutation of amino acid residue 34 from N to S and is defined as Antibody N34S. The terms "hC10-2_N34Q" and "C10-2_N34Q" as used herein and in the Figures are intended to be synonymous and are variants of Antibody C10-2 wherein the light chain has been mutated to at least comprise mutation of amino acid residue 34 from N to Q and is defined as Antibody N34Q.

The terms "hC10-2_N32S_N34S" and "C10-2_N32S_N34S" as used herein and in the Figures are intended to be synonymous and are variants of Antibody C10-2 wherein the light chain has been mutated to at least comprise mutations of amino acid residues 32 and 34 from N to S and is defined as Antibody N32S, N34S. The terms "hC10-2_N32Q_N34S" and "C10-2_N32Q_N34S" as used herein and in the Figures are intended to be synonymous and are variants of Antibody C10-2 wherein the light chain has been mutated to at least comprise mutations of amino acid residues 32 and 34 from N to Q and to N to S, respectively and is defined as Antibody N32Q, N34S. The terms "hC10-2_N32Q_N34Q" and "C10-2_N32Q_N34Q" as used herein and in the Figures are intended to be synonymous and are variants of Antibody C10-2 wherein the light chain has been mutated to at least comprise mutations of amino acid residues 32 and 34 from N to Q and is defined as Antibody N32Q, N34Q. The terms "hC10-2_N32S_N34Q" and "C10-2_N32S_N34Q" as used herein and in the Figures are intended to be synonymous and are variants of Antibody C10-2 wherein the light chain has been mutated to at least comprise mutations of amino acid residues 32 and 34 from N to S and to N to Q, respectively and is defined as Antibody N32S, N34Q.

The terms "hC10-2_D55E" and "C10-2_D55E" as used herein and in the Figures are intended to be synonymous and are variants of Antibody C10-2 wherein the heavy chain has been mutated to at least comprise mutation of amino acid residue 55 from D to E and is defined as Antibody D55E. The term "hC10-2_D55Q", "C10-2_D55Q" as used herein and in the Figures are intended to be synonymous and are variants of Antibody C10-2 wherein the heavy chain has been mutated to at least comprise mutation of amino acid residue 55 from D to Q and is defined as Antibody D55Q. The term "hC10-2_D55S", "C10-2_D55S" as used herein and in the Figures are intended to be synonymous and are variants of Antibody C10-2 wherein the heavy chain has been mutated to at least comprise mutation of amino acid residue 55 from D to S and is defined as Antibody D55S.

The terms "hC10-2_A101T" and "C10-2_A101T" as used herein and in the Figures are intended to be synonymous and are variants of Antibody C10-2 wherein the heavy chain has been mutated to at least comprise mutation of amino acid residue 101 from A to T and is defined as Antibody A101T The term "hC10-2_N32S_A101T", "C10-2_N32S_A101T", hC10-2_A101T_N32S" and "C10-2_A101T_N32S as used herein and in in the Figures are intended to be synonymous and are variants of Antibody C10-2 wherein the heavy chain has been mutated to at least comprise mutation of amino acid residue 101 from A to T and wherein the light chain has been mutated to at least comprise mutation of amino acid residue 32 from N to S and is defined as Antibody N32S, A101T.

The term "hC10-2_N32Q_A101T", "C10-2_N32Q_A101T", hC10-2_A101T_N32Q" and "C10-2_A101T_N32Q as used herein and in in the Figures are intended to be synonymous and are variants of Antibody C10-2 wherein the heavy chain has been mutated to at least comprise mutation of amino acid residue 101 from A to T and wherein the light chain has been mutated to at least comprise mutation of amino acid residue 32 from N to Q and is defined as Antibody N32Q, A101T.

The terms "monoclonal antibody" or "monoclonal antibody composition" as used herein refer to a preparation of antibody molecules of single molecular composition. A conventional monoclonal antibody composition displays a single binding specificity and affinity for a particular epitope. In certain embodiments, a monoclonal antibody can be composed of more than one Fab domain thereby increasing the specificity to more than one target. The terms "monoclonal antibody" or "monoclonal antibody composition" are not intended to be limited by any particular method of production (e.g., recombinant, transgenic, hybridoma, etc.).

The antibodies of the present invention and epitope-binding fragments thereof will preferably be "humanised," particularly if employed for therapeutic purposes. The term "humanised" refer to a molecule, generally prepared using recombinant techniques, having an epitope-binding site derived from an immunoglobulin from a non-human species and a remaining immunoglobulin structure based upon the structure and/or sequence of a human immunoglobulin. The epitope-binding site may comprise either complete non-human antibody variable domains fused to human constant domains, or only the complementarity determining regions (CDRs), or parts hereof, of such variable domains grafted to appropriate human framework regions of human variable domains. The framework residues of such humanized molecules may be wild type (e.g., fully human) or they may be modified to contain one or more amino acid substitutions not found in the human antibody whose sequence has served as the basis for humanization. Humanisation lessens or eliminates the likelihood that a constant domain of the molecule will act as an immunogen in human individuals, but the possibility of an immune response to the foreign variable domain remains (LoBuglio, A. F. et al. (1989) "*Mouse/Human Chimeric Monoclonal Antibody In Man: Kinetics And Immune Response*," Proc. Natl. Acad. Sci. (U.S.A.) 86:4220-4224). Another approach focuses not only on providing human-derived constant domains, but modifying the variable domains as well so as to reshape them as closely as possible to human form. It is known that the variable domains of both heavy and light chains contain three complementarity-determining regions (CDRs) which vary in response to the antigens in question and determine binding capability, flanked by four framework regions (FRs) which are relatively conserved in a given species and which putatively provide scaffolding for the CDRs. When nonhuman antibodies are prepared with respect to a particular antigen, the variable domains can be "reshaped" or "humanized" by grafting CDRs derived from nonhuman antibody on the FRs present in the human antibody to be modified. Application of this approach to various antibodies has been reported by Sato, K. et al. (1993) Cancer Res 53:851-856. Riechmann, L. et al. (1988) "*Reshaping Human Antibodies for Therapy*", Nature 332:323-327; Verhoeyen, M. et al. (1988) "*Reshaping Human Antibodies: Grafting An Antilysozyme Activity*," Science 239:1534-1536; Kettleborough, C. A. et al. (1991) "*Humanization Of A Mouse Monoclonal Antibody By CDR-Grafting: The Importance Of Framework Residues On Loop Conformation*," Protein Engineering 4:773-3783; Maeda, H. et al. (1991) "*Construction Of Reshaped Human Antibodies With HIV-Neutralizing Activity*", Human Antibodies Hybridoma 2:124-134; Gorman, S. D. et al. (1991) "*Reshaping A Therapeutic CD4 Antibody*," Proc. Natl. Acad. Sci. (U.S.A.) 88:4181-4185; Tempest, P. R. et al. (1991) "*Reshaping A Human Monoclonal Antibody To Inhibit Human Respiratory Syncytial Virus Infection in vivo*", Bio/Technology 9:266-271; Co, M. S. et al. (1991) "*Humanized Antibodies For Antiviral Therapy*", Proc. Natl. Acad. Sci. (U.S.A.) 88:2869-2873; Carter, P. et al. (1992) "*Humanization Of An Anti-p185her2 Antibody For Human Cancer Therapy*," Proc. Natl. Acad. Sci. (U.S.A.) 89:4285-4289; and Co, M. S. et al. (1992) "*Chimeric And Humanized Antibodies With Specificity For The CD33 Antigen*," J. Immunol. 148:1149-1154. In some embodiments, humanised antibodies preserve all CDR sequences (for example, a humanized mouse antibody which contains all six CDRs from the mouse antibodies). In other embodiments, humanised antibodies have one or more CDRs (one, two, three, four, five, six) which are altered with respect to the original antibody, which are also termed one or more CDRs "derived from" one or more CDRs from the original antibody. The ability to humanise an antibody is well known (see, e.g., U.S. Pat. Nos. 5,225,539; 5,530,101; 5,585,089; 5,859,205; 6,407,213; 6,881,557).

The term "antibody "XX" is intended to denote an antibody or epitope-binding fragment thereof (for example antibody "C10-2"), comprising or consisting of: (a) the Light Chain and either the Heavy Chain, the Heavy Chain Variable Domain, or the Heavy Chain Variable Domain CDR1-3 as defined by its respective SEQ ID NO, or (b) the Light Chain Variable domain and either the Heavy Chain, the Heavy Chain Variable Domain, or the Heavy Chain Variable Domain CDR1-3 as defined by its respective SEQ ID NO, or (c) the Light Chain Variable domain CDR1-3, as defined by its respective SEQ ID NO, and either the Heavy Chain, the Heavy Chain Variable Domain, or the Heavy Chain Variable Domain CDR1-3 as defined by its respective SEQ ID NO. In certain embodiments, the antibody or epitope-binding fragment thereof are defined by their entire Heavy Chain Variable Domain comprising as defined by their SEQ ID NO and their Light Chain Variable Domain as defined by their SEQ ID NO.

Unless otherwise specified herein, numbering of amino acid residues in the Fc region or constant domain of an antibody is according to the EU numbering system, also called the EU index, as described in Kabat et al., Sequences of Proteins of Immunological Interest, 5th Ed. Public Health Service, National Institutes of Health, Bethesda, MD, 1991.

In some antibodies, only part of a CDR, namely the subset of CDR residues required for binding, termed the SDRs, are needed to retain binding in a humanized antibody. CDR residues not contacting the relevant epitope and not in the SDRs can be identified based on previous studies. For example, residues Tyr Ser Gln Lys Phe Gln, corresponding to residues 60-65 of the HC of SEQ ID NO. 11 are often not required from regions of Kabat CDRs (these are also found in HC CDR2 (SEQ. ID. NO. 7), lying outside Chothia hypervariable loops (see, Kabat et al. (1992) SEQUENCES OF PROTEINS OF IMMUNOLOGICAL INTEREST, National Institutes of Health Publication No. 91-3242; Chothia, C. et al. (1987) "*Canonical Structures For The Hypervariable Regions Of Immunoglobulins*," J. Mol. Biol. 196:901-917), by molecular modeling and/or empirically, or as described in Gonzales, N. R. et al. (2004) "*SDR Grafting Of A Murine Antibody Using Multiple Human Germline Templates To Minimize Its Immunogenicity*," Mol. Immunol. 41:863-872. In such humanized antibodies at positions in which one or more donor CDR residues is absent or in which an entire donor CDR is omitted, the amino acid occupying the position can be an amino acid occupying the corresponding position (by Kabat numbering) in the acceptor antibody sequence. The number of such substitutions of acceptor for donor amino acids in the CDRs to include reflects a balance of competing considerations. Such substitutions are potentially advantageous in decreasing the number of mouse amino acids in a humanized antibody and consequently decreasing potential immunogenicity. However, substitutions can also cause changes of affinity, and significant reductions in affinity are preferably avoided. Positions for substitution within CDRs and amino acids to substitute can also be selected empirically.

Antibodies are also characterized according to the IMGT numbering system, which is well defined in the field. The length (in number of amino acids, that is in number of occupied positions) is a crucial and original concept of IMGT-ONTOLOGY (imgt.org). The CDR-IMGT lengths characterize the IG and TR V-REGIONs of the germline genes and the V-DOMAINs of the rearranged genes, cDNAs and proteins.

Antibodies are may for example be characterized according to the Chothia Numbering Scheme bioinf.org.uk/abs/. The Chothia numbering scheme is identical to the Kabat scheme, but places the insertions in CDR-L1 and CDR-H1 at the structurally defined positions. The Chothia numbering scheme is based on the location of the structural loop regions. This means that topologically equivalent residues in these loops do get the same label (unlike the Kabat scheme).

The fact that a single amino acid alteration of a CDR residue can result in loss of functional binding (Rudikoff, S. etc. (1982) "*Single Amino Acid Substitution Altering Antigen-Binding Specificity*," Proc. Natl. Acad. Sci. (USA) 79(6):1979-1983) provides a means for systematically identifying alternative functional CDR sequences. In one preferred method for obtaining such variant CDRs, a polynucleotide encoding the CDR is mutagenized (for example via random mutagenesis or by a site-directed method (e.g., polymerase chain-mediated amplification with primers that encode the mutated locus)) to produce a CDR having a substituted amino acid residue. By comparing the identity of the relevant residue in the original (functional) CDR sequence to the identity of the substituted (non-functional) variant CDR sequence, the BLOSUM62.iij substitution score for that substitution can be identified. The BLOSUM system provides a matrix of amino acid substitutions created by analyzing a database of sequences for trusted alignments (Eddy, S. R. (2004) "*Where Did The BLOSUM62 Alignment Score Matrix Come From?*," Nature Biotech. 22(8):1035-1036; Henikoff, J. G. (1992) "Amino acid substitution matrices from protein blocks," Proc. Natl. Acad. Sci. (USA) 89:10915-10919; Karlin, S. et al. (1990) "*Methods For Assessing The Statistical Significance Of Molecular Sequence Features By Using General Scoring Schemes*," Proc. Natl. Acad. Sci. (USA) 87:2264-2268; Altschul, S. F. (1991) "*Amino Acid Substitution Matrices From An Information Theoretic Perspective*," J. Mol. Biol. 219, 555-565. Currently, the most advanced BLOSUM database is the BLOSUM62 database (BLOSUM62.iij). Table 1 presents the BLOSUM62.iij substitution scores (the higher the score the more conservative the substitution and thus the more likely the substitution will not affect function). If an epitope-binding fragment comprising the resultant CDR fails to bind to tau, for example, then the BLOSUM62.iij substitution score is deemed to be insufficiently conservative, and a new candidate substitution is selected and produced having a higher substitution score. Thus, for example, if the original residue was glutamate (E), and the non-functional substitute residue was histidine (H), then the BLOSUM62.iij substitution score will be 0, and more conservative changes (such as to aspartate, asparagine, glutamine, or lysine) are preferred.

TABLE 1

| | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | +4 | −1 | −2 | −2 | 0 | −1 | −1 | 0 | −2 | −1 | −1 | −1 | −1 | −2 | −1 | +1 | 0 | −3 | −2 | 0 |
| R | −1 | +5 | 0 | −2 | −3 | +1 | 0 | −2 | 0 | −3 | −2 | +2 | −1 | −3 | −2 | −1 | −1 | −3 | −2 | −3 |
| N | −2 | 0 | +6 | +1 | −3 | 0 | 0 | 0 | +1 | −3 | −3 | 0 | −2 | −3 | −2 | +1 | 0 | −4 | −2 | −3 |
| D | −2 | −2 | +1 | +6 | −3 | 0 | +2 | −1 | −1 | −3 | −4 | −1 | −3 | −3 | −1 | 0 | −1 | −4 | −3 | −3 |
| C | 0 | −3 | −3 | −3 | +9 | −3 | −4 | −3 | −3 | −1 | −1 | −3 | −1 | −2 | −3 | −1 | −1 | −2 | −2 | −1 |
| Q | −1 | +1 | 0 | 0 | −3 | +5 | +2 | −2 | 0 | −3 | −2 | +1 | 0 | −3 | −1 | 0 | −1 | −2 | −1 | −2 |
| E | −1 | 0 | 0 | +2 | −4 | +2 | +5 | −2 | 0 | −3 | −3 | +1 | −2 | −3 | −1 | 0 | −1 | −3 | −2 | −2 |
| G | 0 | −2 | 0 | −1 | −3 | −2 | −2 | +6 | −2 | −4 | −4 | −2 | −3 | −3 | −2 | 0 | −2 | −2 | −3 | −3 |
| H | −2 | 0 | +1 | −1 | −3 | 0 | 0 | −2 | +8 | −3 | −3 | −1 | −2 | −1 | −2 | −1 | −2 | −2 | +2 | −3 |
| I | −1 | −3 | −3 | −3 | −1 | −3 | −3 | −4 | −3 | +4 | +2 | −3 | +1 | 0 | −3 | −2 | −1 | −3 | −1 | +3 |
| L | −1 | −2 | −3 | −4 | −1 | −2 | −3 | −4 | −3 | +2 | +4 | −2 | +2 | 0 | −3 | −2 | −1 | −2 | −1 | +1 |
| K | −1 | +2 | 0 | −1 | −3 | +1 | +1 | −2 | −1 | −3 | −2 | +5 | −1 | −3 | −1 | 0 | −1 | −3 | −2 | −2 |
| M | −1 | −1 | −2 | −3 | −1 | 0 | −2 | −3 | −2 | +1 | +2 | −1 | +5 | 0 | −2 | −1 | −1 | −1 | −1 | +1 |
| F | −2 | −3 | −3 | −3 | −2 | −3 | −3 | −3 | −1 | 0 | 0 | −3 | 0 | +6 | −4 | −2 | −2 | +1 | +3 | −1 |
| P | −1 | −2 | −2 | −1 | −3 | −1 | −1 | −2 | −2 | −3 | −3 | −1 | −2 | −4 | +7 | −1 | −1 | −4 | −3 | −2 |
| S | +1 | −1 | +1 | 0 | −1 | 0 | 0 | 0 | −1 | −2 | −2 | 0 | −1 | −2 | −1 | +4 | +1 | −3 | −2 | −2 |
| T | 0 | −1 | 0 | −1 | −1 | −1 | −1 | −2 | −2 | −1 | −1 | −1 | −1 | −2 | −1 | +1 | +5 | −2 | −2 | 0 |
| W | −3 | −3 | −4 | −4 | −2 | −2 | −3 | −2 | −2 | −3 | −2 | −3 | −1 | +1 | −4 | −3 | −2 | +11 | +2 | −3 |
| Y | −2 | −2 | −2 | −3 | −2 | −1 | −2 | −3 | +2 | −1 | −1 | −2 | −1 | +3 | −3 | −2 | −2 | +2 | +7 | −1 |
| V | 0 | −3 | −3 | −3 | −1 | −2 | −2 | −3 | −3 | +3 | +1 | −2 | +1 | −1 | −2 | −2 | 0 | −3 | −1 | +4 |

The invention thus contemplates the use of random mutagenesis to identify improved CDRs. In the context of the present invention, conservative substitutions may be defined by substitutions within the classes of amino acids reflected in one or more of Tables 2, 3, or 4:

Amino Acid Residue Classes for Conservative Substitutions:

TABLE 2

| | |
|---|---|
| Acidic Residues | Asp (D) and Glu (E) |
| Basic Residues | Lys (K), Arg (R), and His (H) |
| Hydrophilic Uncharged Residues | Ser (S), Thr (T), Asn (N), and Gln (Q) |
| Aliphatic Uncharged Residues | Cly (G), Ala (A), Val (V), Leu (L), and Ile (I) |
| Non-polar Uncharged Residues | Cys (C), Met (M), and Pro (P) |
| Aromatic Residues | Phe (F), Tyr (Y), and Trp (W) |

Alternative Conservative Amino Acid Residue Substitution Classes:

TABLE 3

| | | | |
|---|---|---|---|
| 1 | A | S | T |
| 2 | D | E | |
| 3 | N | Q | |
| 4 | R | K | |
| 5 | I | L | M |
| 6 | F | Y | W |

Alternative Physical and Functional Classifications of Amino Acid Residues:

TABLE 4

| | |
|---|---|
| Alcohol Group-Containing Residues | S and T |
| Aliphatic Residues | I, L, V and M |
| Cycloalkenyl-Associated Residues | F, H, W and Y |
| Hydrophobic Residues | A, C, F, G, H, I, L, M, R, T, V, W and Y |
| Negatively Charged Residues | D and E |
| Polar Residues | C, D, E, H, K, N, Q, R, S and T |
| Positively Charged Residues | H, K and R |
| Small Residues | A, C, D, G, N, P, S, T and V |
| Very Small Residues | A, G and S |
| Residues Involved In Turn | A, C, D, E, G, H, K, N, Q, R, S, |

TABLE 4-continued

| | |
|---|---|
| Formation | P and T |
| Flexible Residues | Q, T, K, S, G, P, D, E and R |

More conservative substitutions groupings include: valine-leucine-isoleucine, phenylalanine-tyrosine, lysine-arginine, alanine-valine, and asparagine-glutamine.

Additional groups of amino acids may also be formulated using the principles described in, e.g., Creighton (1984) Proteins: Structure and Molecular Properties (2d Ed. 1993), W. H. Freeman and Company.

Phage display technology can alternatively be used to increase (or decrease) CDR affinity. This technology, referred to as affinity maturation, employs mutagenesis or "CDR walking" and re-selection uses the target antigen or an antigenic epitope-binding fragment thereof to identify antibodies having CDRs that bind with higher (or lower) affinity to the antigen when compared with the initial or parental antibody (See, e.g. Glaser et al. (1992) J. Immunology 149:3903). Mutagenizing entire codons rather than single nucleotides results in a semi-randomized repertoire of amino acid mutations. Libraries can be constructed consisting of a pool of variant clones each of which differs by a single amino acid alteration in a single CDR and which contain variants representing each possible amino acid substitution for each CDR residue. Mutants with increased (or decreased) binding affinity for the antigen can be screened by contacting the immobilized mutants with labeled antigen. Any screening method known in the art can be used to identify mutant antibodies with increased or decreased affinity to the antigen (e.g., ELISA) (See Wu et al. 1998, Proc. Natl. Acad. Sci. (U.S.A.) 95:6037; Yelton et al., 1995, J. Immunology 155:1994). CDR walking which randomizes the Light Chain may be used possible (see, Schier et al., 1996, J. Mol. Bio. 263:551).

Methods for accomplishing such affinity maturation are described for example in: Krause, J. C. et al. (2011) "*An Insertion Mutation That Distorts Antibody Binding Site Architecture Enhances Function Of A Human Antibody*," MBio. 2(1) pii: e00345-10. doi: 10.1128/mBio.00345-10; Kuan, C. T. et al. (2010) "*Affinity-Matured Anti-Glycoprotein NMB Recombinant Immunotoxins Targeting Malignant Gliomas And Melanomas*," Int. J. Cancer 10.1002/ijc.25645; Hackel, B. J. et al. (2010) "*Stability And CDR Composition Biases Enrich Binder Functionality Landscapes*," J. Mol. Biol. 401(1):84-96; Montgomery, D. L. et al. (2009) "*Affinity Maturation And Characterization Of A Human Monoclonal Antibody Against HIV-1 gp41*," MAbs 1(5):462-474; Gustchina, E. et al. (2009) "*Affinity Maturation By Targeted Diversification Of The CDR-H2 Loop Of A Monoclonal Fab Derived From A Synthetic Naïve Human Antibody Library And Directed Against The Internal Trimeric Coiled-Coil Of Gp41 Yields A Set Of Fabs With Improved HIV-1 Neutralization Potency And Breadth*," Virology 393(1):112-119; Finlay, W. J. et al. (2009) "*Affinity Maturation Of A Humanized Rat Antibody For Anti-RAGE Therapy: Comprehensive Mutagenesis Reveals A High Level Of Mutational Plasticity Both Inside And Outside The Complementarity-Determining Regions*," J. Mol. Biol. 388(3):541-558; Bostrom, J. et al. (2009) "*Improving Antibody Binding Affinity And Specificity For Therapeutic Development*," Methods Mol. Biol. 525: 353-376; Steidl, S. et al. (2008) "*In Vitro Affinity Maturation Of Human GM-CSF Antibodies By Targeted CDR-Diversification*," Mol. Immunol. 46(1):135-144; and Barderas, R. et al. (2008) "*Affinity Maturation Of Antibodies Assisted By In Silico Modeling*," Proc. Natl. Acad. Sci. (USA) 105(26): 9029-9034.

Thus, the sequence of CDR variants of encompassed antibodies or their epitope-binding fragments may differ from the sequence of the CDR of the parent antibody, C10-2 and C10.2 Variants, through substitutions; for instance substituted 4 amino acid residue, 3 amino acid residue, 2 amino acid residue or 1 of the amino acid residues. According to an embodiment of the invention it is furthermore envisaged that the amino acids in the CDR regions may be substituted with conservative substitutions, as defined in the 3 tables above. For example, the acidic residue Asp can be substituted with Glu without substantially affecting the binding characteristic of the antibody.

As used herein, an antibody or an epitope-binding fragment thereof is said to "specifically" bind a region of another molecule (i.e., an epitope) if it reacts or associates more frequently, more rapidly, with greater duration and/or with greater affinity or avidity with that epitope relative to alternative epitopes. It is also understood by reading this definition that, for example, an antibody or epitope-binding fragment thereof that specifically binds to a first target may not or may not specifically or preferentially bind to a second target. As used herein, the term "binding" in the context of the binding of an antibody to a predetermined antigen typically refers to binding with an affinity corresponding to a KD of about $10^{-7}$ M or less, such as about $10^{-8}$ M or less, such as about $10^{-9}$ M or less when determined by for instance surface plasmon resonance (SPR) technology in a BIAcore® 3000 instrument using the antigen as the ligand and the antibody as the analyte, and binds to the predetermined antigen with an affinity corresponding to a KD that is at least ten-fold lower, such as at least 100 fold lower, for instance at least 1,000 fold lower, such as at least 10,000 fold lower, for instance at least 100,000 fold lower than its affinity for binding to a non-specific antigen (e.g., BSA, casein) other than the predetermined antigen or a closely-related antigen. The amount with which the affinity is lower is dependent on the KD of the antibody, so that when the KD of the antibody is very low (that is, the antibody is highly specific), then the amount with which the affinity for the antigen is lower than the affinity for a non-specific antigen may be at least 10,000 fold.

The term "kd" (sec-1 or 1/s), as used herein, refers to the dissociation rate constant of a particular antibody-antigen interaction. Said value is also referred to as the koff value.

The term "ka" (M−1×sec-1 or 1/Msec), as used herein, refers to the association rate constant of a particular antibody-antigen interaction.

The term "KD" (M), as used herein, refers to the dissociation equilibrium constant of a particular antibody-antigen interaction and is obtained by dividing the kd by the ka.

The term "KA" (M−1 or 1/M), as used herein, refers to the association equilibrium constant of a particular antibody-antigen interaction and is obtained by dividing the ka by the kd.

In one embodiment, the invention relates to an anti-tau antibody, or epitope-binding fragment thereof, which exhibits one or more of the following properties:
(i) a substantial inability to bind to non-phosphorylated tau;
(ii) a substantial inability to bind to tau that is phosphorylated at S404 and not phosphorylated at S396;
(iii) the ability to bind to tau phosphorylated at S396;
(iv) the ability to bind to tau phosphorylated at both S396 and at S404;

(v) the ability to selectively discriminate between phosphorylated tau residues S396 and S404 such that it is substantially unable to bind the phosphorylated 404 residue (pS404);
(vi) the ability to bind hyper-phosphorylated tau from human Alzheimer's disease brains;
(vii) the ability to discriminate between pathological and non-pathological human tau protein; and/or
(viii) the capability, when used as described herein with immune-depleted rTg4510 extracts from transgenic mice, to specifically reduce the hyperphosphorylated tau 64 kDa and 70 kDa bands by at least 90%, while not reducing the 55 kDa tau band by more than 10%; or the capability, when used as described herein with extracts from human AD post-mortem brains to specifically reduce the S396 phosphorylated hyperphosphorylated tau bands by at least 90%, while not reducing the non-hyperphosphorylated tau bands by more than 10%.

A further embodiment of the invention relates to a method for obtaining high specificity, high affinity antibodies, wherein the method comprises the steps of:
(A) injecting an immunogen into a mammal, to thereby immunize said mammal;
(B) repeating said immunization of said mammal two or more times;
(C) screening a serum sample from said repeatedly immunized mammal for the presence of the desired high specificity, high affinity antibodies but substantially less capable of binding to other protein; and
(D) recovering said high specificity, high affinity antibodies.

The invention thus relates to a high specificity, high affinity antibody specific for pathogenic hyperphosphorylated tau comprising residue a phosphorylated S396. Such antibodies may be generated by adaptation of the above-indicated method for generating high specificity, high affinity antibodies by:
(A) injecting an immunogen into a mammal, said immunogen comprising the bi-phosphorylated peptide comprising 18-40, such as at 18-30, such as 20-30 amino consecutive acid residues comprising TDHGAEIVYK$^{\{p\}}$SPVVSGDT$^{\{p\}}$SPRHL (SEQ ID NO:2) covering residues 386-410 of 2N4R tau, to thereby immunize said mammal;
(B) repeating said immunization of said mammal two or more times;
(C) screening a serum sample from said repeatedly immunized mammal for the presence of high specificity, high affinity antibodies capable of binding pathogenic hyperphosphorylated tau comprising residue a phosphorylated S396, but substantially less capable of binding non-pathogenic tau; and
(D) recovering said high specificity, high affinity antibodies.

As used herein, a "substantial inability" to bind a tau molecule denotes more than a 20% difference, more than a 40% difference, more than a 60% difference, more than an 80% difference, more than a 100% difference, more than a 150% difference, more than a 2-fold difference, more than a 4-fold difference, more than a 5-fold difference, or more than a 10-fold difference in functionality, relative to the detectable binding mediated by a reference antibody.

The term "selective" and "immunoselective" when referring to the binding capabilities of an anti-tau antibody with respect to two epitopes is intended to denote that the observed binding under saturating conditions exhibits at least an 80% difference, at least a 95% difference, and most preferably a 100% difference (i.e., no detectable binding to one epitope). The term "selective" and "immunoselective" when referring to a tau antibody is further intended to mean the antibody binds hyper-phosphorylated tau from human Alzheimer's disease brains and is able to discriminate between pathological and non-pathological human tau protein.

The terms TBS-extractable (S1), high salt/sarkosyl-extractable (S3), and sarkosyl-insoluble (P3) fractions are fractions as obtained by the tau biochemical fractionation described herein.

The term "normal tau" refers to normal brain tau containing 2-3 moles of phosphate per mole of the protein.

The term "hyperphosphorylated tau" refers to a poly-phosphorylated species of tau consistent with poly-anionic species induced mobility shift in Western Blot or to a tau species which has more than five, six or seven Serine, Threonine or Tyrosine sites phosphorylated.

The term "tau having residue 396 phosphorylated" relates to hyperphosphorylated tau wherein the serine residue 396 is phosphorylated.

The term "transgenic non-human animal" refers to a non-human animal having a genome comprising one or more human heavy and/or light chain transgenes or trans-chromosomes (either integrated or non-integrated into the animal's natural genomic DNA) and which is capable of expressing fully human antibodies. For example, a transgenic mouse can have a human light chain transgene and either a human heavy chain transgene or human heavy chain trans-chromosome, such that the mouse produces human anti-tau antibody when immunized with tau antigen and/or cells expressing tau. The human heavy chain transgene may be integrated into the chromosomal DNA of the mouse, as is the case for transgenic mice, for instance HuMAb mice, such as HCo7 or HCo12 mice, or the human heavy chain transgene may be maintained extra-chromosomally, as is the case for trans-chromosomal KM mice as described in WO02/43478. Such transgenic and trans-chromosomal mice (collectively referred to herein as "transgenic mice") are capable of producing multiple isotypes of human monoclonal antibodies to a given antigen (such as IgG, IgA, IgM, IgD and/or IgE) by undergoing V-D-J recombination and isotype switching.

Transgenic, nonhuman animal can also be used for production of antibodies against a specific antigen by introducing genes encoding such specific antibody, for example by operatively linking the genes to a gene which is expressed in the milk of the animal.

The term "treatment" or "treating" as used herein means ameliorating, slowing, attenuating, or reversing the progress or severity of a disease or disorder, or ameliorating, slowing, attenuating, or reversing one or more symptoms or side effects of such disease or disorder. For purposes of this invention, "treatment" or "treating" further means an approach for obtaining beneficial or desired clinical results, where "beneficial or desired clinical results" include, without limitation, alleviation of a symptom, diminishment of the extent of a disorder or disease, stabilized (i.e., not worsening) disease or disorder state, delay or slowing of the progression a disease or disorder state, amelioration or palliation of a disease or disorder state, and remission of a disease or disorder, whether partial or total.

An "effective amount," when applied to an antibody or epitope-binding fragment thereof of the invention, refers to an amount sufficient, at dosages and for periods of time necessary, to achieve an intended biological effect or a desired therapeutic result including, without limitation, clinical results. The phrase "therapeutically effective amount," when applied to an antibody or an epitope-binding fragment thereof of the invention, is intended to denote an amount of the antibody, or epitope-binding fragment thereof, that is sufficient to ameliorate, palliate, stabilize, reverse, slow, attenuate or delay the progression of a disorder or disease state, or of a symptom of the disorder or disease. In an embodiment, the method of the present invention provides for administration of the antibody, or epitope-binding fragment thereof, in combinations with other compounds. In such instances, the "effective amount" is the amount of the combination sufficient to cause the intended biological effect.

A therapeutically effective amount of an anti-tau antibody or epitope-binding fragment thereof of the invention may vary according to factors such as the disease state, age, sex, and weight of the individual, and the ability of the anti-tau antibody, or epitope-binding fragment thereof, to elicit a desired response in the individual. A therapeutically effective amount is also one in which any toxic or detrimental effects of the antibody or antibody portion are outweighed by the therapeutically beneficial effects.

As indicated above, the present invention particularly relates to monoclonal antibodies, or epitope-binding fragments thereof, and to a completely new method for producing such molecules (and thus of such epitope-binding fragments thereof). This ability of the new method to isolate monoclonal antibodies is exemplified herein by its use to isolate monoclonal antibodies that are capable of specifically binding to the phosphorylated residue serine 396 (P-S396, pS396, $^{\{p\}}$S396) of human tau (SEQ ID NO:1). These antibodies are further characterized by their ability to discriminate between phosphorylated residues serine 396 and serine 404 (P-S404, pS404) such that they do not bind to tau protein with phosphorylated serine 404 unless the tau is also phosphorylated at residue 396.

The antibodies of the present invention, or epitope-binding fragment thereof, have been generated and isolated by use of a novel a method which favors the selection of pS396 specific antibodies. Furthermore, by applying this very strict antibody clone selection procedure, antibodies have been obtained that are not only highly specific towards S396, but also highly selective towards the phosphorylated pS396 epitope. These antibodies uniquely recognize tau from Alzheimer's disease brains. The screening procedure ensures the identification of antibodies which possess a functional and therapeutic utility.

Antibodies were raised against the bi-phosphorylated peptide: TDHGAEIVYK{p}SPVVSGDT{p}SPRHL (SEQ ID NO:2) covering residues 386-408 of 2N4R tau. Mice were immunized with the phospho-peptide. Once sufficient antibody titres had been obtained, the mice were sacrificed and hybridomas were generated. The hybridomas were screened using dot-blot and MSD ELISA with immobilized human pathological and non-pathological tau. The ability to discriminate between pathological and non-pathological human tau protein in dot-blot and Western blot was used for the selection of hybridomas. Sixteen clones were selected, of which four hybridoma clones were recovered that produced antibodies which exhibited extraordinary capabilities for binding to human pathological tau material.

Specific binding to pathological and non-pathological tau was also determined by isolation of tau from diseased and non-diseased human AD brains and immobilization of this material on MSD ELISA plates (Example 4).

A further aspect of the invention relates to monoclonal antibody or an epitope-binding fragment thereof elicited against the bi-phosphorylated peptide comprising at least 18, such as at least 20 amino consecutive acid residues within TDHGAEIVYK$^{\{p\}}$SPVVSGDT$^{\{p\}}$SPRHL (SEQ ID NO:2) covering residues 386-410 of 2N4R tau. In this aspect of the invention, the monoclonal antibody or an epitope-binding fragment thereof is typically elicited against the bi-phosphorylated peptide comprising 18-40, such as at 18-30, such as 20-30 amino consecutive acid residues comprising TDHGAEIVYK$^{\{p\}}$SPVVSGDT$^{\{p\}}$SPRHL (SEQ ID NO:2) covering residues 386-410 of 2N4R tau.

A further aspect of the invention is directed to the monoclonal antibody or an epitope-binding fragment thereof of the invention, having a specificity for phosphoTau (pTau) from AD-diseased patients over age-matched healthy controls, such that said monoclonal antibody or an epitope-binding fragment thereof has a specificity difference for phosphoTau (pTau) from AD-diseased patients over tau from age-healthy matched controls of more than 50-fold, such as more than 100-fold increase in specificity for AD disease material compared to healthy control material in an ELISA based assay detect phosphoTau (pTau) in brain homogenates from AD and from healthy control subjects, using a phospho- and multimer-specific Setup 1 ELISA or MSD as described herein.

A related aspect of the invention is directed to the monoclonal antibody or an epitope-binding fragment thereof of the invention, having a specificity for AD-diseased Tau such that said monoclonal antibody or an epitope-binding fragment thereof has a specificity difference for AD over age-healthy matched controls of more than 50-fold, such as more than 100-fold increase in specificity for AD disease material compared to healthy control material in an ELISA or MSD based assay detect phosphoTau (pTau) in brain homogenates from AD and from healthy control subjects, using a phospho- and multimer-specific Setup 1 ELISA.

Setup 1 ELISA or MSD method comprises the steps A) a capture of pathological human Tau antigens from AD brains using C10-2 coated plates; B) incubation of Tau antigens with increasing concentrations of pS396 specific antibodies; and C) detection of the residual free Tau antigen captured by immobilized C10.2 using sulfo-tagged anti human (total) Tau antibodies from MSD.

More specifically, step A comprises: coating of MSD plates (typically overnight at 4 degrees C.) with C10-2 antibody, typically 0.5 µg/ml (capture antibody) in coating buffer, blocking (typically 1 hour at room temperature) and washing, typically 3 times. Step B comprises: mixing of samples of P3 lysate (typically diluted 1:1000=2-4 µg/ml total protein) and/or S1(p) (typically diluted 1:300=20-40 ng/ml total protein) from AD (pooled from 3 patients) with graded concentrations of pS396 peptide epitope specific antibody and incubating (typically 1 hour at room temperature). The reactions are subsequently incubated for 2 hours on plates prepared in step A. Step C comprises detecting C10-2 captured Tau was using sulfo-tagged human tau antibody (typically 1:50) from MSD following manufacturer's instructions. Plates are analyzed on MSD SECTOR® S600. AD P3 and AD S1(p) are tested in a similar setup.

A further embodiment is directed to an antibody, or antigen-binding fragment thereof, capable of specifically binding to the phosphorylated serine residue 396 of human tau (SEQ ID NO:1), which has been produced or manufactured in a cell line such as a human cell line, a mammal non-human cell line, an insect, yeast or bacterial cell line.

The antibody, or antigen binding fragment thereof, capable of specifically binding to the phosphorylated residue 396 of human tau (SEQ ID NO:1), produced in a CHO cell line, HEK cell line, BHK-21 cell line, murine cell line (such as a myeloma cell line), fibrosarcoma cell line, PER.C6 cell line, HKB-11 cell line, CAP cell line and HuH-7 human cell line.

Specific affinities and binding properties of C10-2 and C10.2 Variants have been characterized using tau 386-410 (2R4N) peptides which are either phosphorylated or un-phosphorylated at position 396 or 404. Using the specific immunization and screening protocol outlined in this application will produce highly phosphor-serine-396 (pS396) specific antibodies.

In order to demonstrate that the antibodies are specific towards pathological tau, C10-2 antibodies have also been characterized by immune-histochemical analysis. The antibodies exhibit highly specific binding to neurofibrillary tangles in Alzheimer's disease brains (tau tangles) and in sections from Tg4510 tau transgenic mice expressing human (P301L) mutant tau. No binding is observed to tissue from human control brains and from non-transgenic mouse brains, demonstrating that the antibodies specifically bind human tau and in particular tau associated with Alzheimer's pathology.

Antibody C10-2

One aspect of the invention is directed to a monoclonal antibody, or epitope binding fragment thereof, comprising
(a) a Light Chain CDR1 having the amino acid sequence of SEQ ID NO:3;
(b) a Light Chain CDR2 having the amino acid sequence of SEQ ID NO:4;
(c) a Light Chain CDR3 having the amino acid sequence of SEQ ID NO:5;
(d) a Heavy Chain CDR1 having the amino acid sequence of SEQ ID NO:6;
(e) a Heavy Chain CDR2 having the amino acid sequence of SEQ ID NO:7; and
(f) a Heavy Chain CDR3 having the amino acid sequence of SEQ ID NO:8.

A further aspect of the invention is directed to a monoclonal antibody, or epitope binding fragment thereof, comprising
(a) a Light Chain comprising the amino acid sequence of SEQ ID NO:12; and
(b) a Heavy Chain comprising the amino acid sequence of SEQ ID NO:11.

Alternatively defined, using the IMGT definition, one aspect of the invention is directed to a monoclonal antibody, or epitope binding fragment thereof, comprising
(a) a Light Chain CDR1 having the amino acid sequence of SEQ ID NO:40;
(b) a Light Chain CDR2 having the amino acid sequence of SEQ ID NO:41;
(c) a Light Chain CDR3 having the amino acid sequence of SEQ ID NO:42;
(d) a Heavy Chain CDR1 having the amino acid sequence of SEQ ID NO:43;
(e) a Heavy Chain CDR2 having the amino acid sequence of SEQ ID NO:44; and
(f) a Heavy Chain CDR3 having the amino acid sequence of SEQ ID NO:45.

Alternatively defined, using the Chotia definition, one aspect of the invention is directed to a monoclonal antibody, or epitope binding fragment thereof, comprising
(a) a Light Chain CDR1 having the amino acid sequence of SEQ ID NO:3;
(b) a Light Chain CDR2 having the amino acid sequence of SEQ ID NO:4;
(c) a Light Chain CDR3 having the amino acid sequence of SEQ ID NO:5;
(d) a Heavy Chain CDR1 having the amino acid sequence of SEQ ID NO:52;
(e) a Heavy Chain CDR2 having the amino acid sequence of SEQ ID NO:53; and
(f) a Heavy Chain CDR3 having the amino acid sequence of SEQ ID NO:54.

The unique capability of the antibodies of the invention to recognize tau associated with disease pathology is demonstrated. The binding of pathological vs. non-pathological tau was compared. The comparison is to five published tau antibodies: hACI-2B6, IPN002, HJ8.5, 2.10.3, and 4E4. 2.10.3 antibody is a commercially available recombinant monoclonal antibody that specifically binds to Tau that is phosphorylated at serine 422 (pS422). HJ8.5 is a commercially available monoclonal antibody that recognizes only human tau at the N-terminal region (epitope at residues 25-30 aa). The antibody is of the IgG2b isotype. Anti-Tau Therapeutic Antibody NI-105-4E4 is a commercially available antibody. The table demonstrates that the isolated antibodies exhibit an exceptionally high degree of specificity and selectivity towards human pathological tau. This selectivity is superior to any of the comparator antibodies as shown in Table 5.

TABLE 5

| mAb Tested | AD/ctrl | TG/wt |
| --- | --- | --- |
| hACI-2B6 | 3 | 1 |
| IPN002 | 3 | 37 |
| HJ8.5 | 3 | 51 |
| 4E4 | no binding | 1 |
| 2.10.3 | 5 | 2 |
| Antibody C10-2 | >100 | 118 |

At saturation, Antibody C10-2 exhibits more than 100-fold selectivity towards P3 tau isolated from human AD brains.

To demonstrate that the selected antibodies have functional and therapeutic utility, antibodies were tested in in-vitro and in-cell tau-aggregation assays (Example 8). These assays are functional assays which demonstrate that the antibodies are able to interfere with the pathological aggregation process of tau. HEK293 cells are transiently transfected with human tau-P301L-FLAG (4RON). Subsequently the cells are exposed to tau extracts from human AD brains or from transgenic Tg4510 brains. This exposure to pathological tau promotes tau uptake into cells and intracellular aggregation. Both immuno-depletion of tau-preparations using Antibody C10-2, and direct treatment of cells with these antibodies is able to reduce the formation of tau aggregates dramatically.

Therapeutic utility of Antibody C10-2 has also been evaluated in the human tau/PS1 mouse. This mouse model is a more AD disease relevant animal model which only generates AD pathology late in life (12-18 month of age). However, the mice do exhibit tau hyper phosphorylation before the occurrence of solid tangle pathology. Mice were injected chronically for 13 weeks, twice weekly with 15 mg/kg dose. Antibody treated mice exhibit a dramatic reduction in phosphorylated tau, indicating that chronic treatment with C10-2 will reduce tangle pathology and thus subsequent neurodegeneration in vivo.

The antibodies of the invention specifically remove hyperphosphorylated tau from rTg4510 mouse brain extracts by immunodepletion methods. Moreover, the antibodies of the invention do not remove the normal tau from the homogenates, whereas the commercially available tau5 antibody does. In contrast to commercial antibodies which bind to tau proteins wherein phosphorylation at residue 404 or at both residues 404 and 396, the antibodies of the invention specifically remove the hyperphosphorylated tau by 95% that is phosphorylated on serine 396. Experiments (Example 12) demonstrate that the antibody of the invention, despite only removing a very small fraction of the total tau in the brain homogenate (8%), the antibodies do however specifically remove the hyperphosphorylated tau (by 90%). Accordingly, one aspect of the invention is directed to a monoclonal antibody, or an epitope-binding fragment thereof, capable of specifically binding to the pathogenic hyperphosphorylated tau. Furthermore, in experiments wherein hyperphosphorylated Tau was removed using an antibody of the invention, the seeding activity is abolished. By removing hyperphosphorylated tau from the homogenates, the homogenates no longer induce seeding of Tau pathology. It has been proposed that reduction of seeding reduces the development of tangle formation and the progression of tauopathies, including Alzheimer's disease. Accordingly, a further aspect of the invention is directed to an antibody of the invention for use in the reduction of the progression of AD or in the symptoms of AD.

Antibody D55E

One aspect of the invention relates to the variant antibody of Antibody C10-2, Antibody D55E. This aspect of the invention is directed to a monoclonal antibody, or epitope binding fragment thereof, comprising
  (a) a Light Chain CDR1 having the amino acid sequence of SEQ ID NO:3;
  (b) a Light Chain CDR2 having the amino acid sequence of SEQ ID NO:4;
  (c) a Light Chain CDR3 having the amino acid sequence of SEQ ID NO:5;
  (d) a Heavy Chain CDR1 having the amino acid sequence of SEQ ID NO:6;
  (e) a Heavy Chain CDR2 having the amino acid sequence of SEQ ID NO:28 and
  (f) a Heavy Chain CDR3 having the amino acid sequence of SEQ ID NO:8.

A further embodiment of the aspect of the invention directed to Antibody D55E relates to a monoclonal antibody, or epitope binding fragment thereof, comprising
  (a) a Light Chain comprising the amino acid sequence of SEQ ID NO:12:
  (b) a Heavy Chain comprising the amino acid sequence of SEQ ID NO:13.

Alternatively defined, a further embodiment of the aspect of the invention directed to Antibody D55E relates to a monoclonal antibody, or epitope binding fragment thereof, comprising at least one of
  (a) a Light Chain CDR1 having the amino acid sequence of SEQ ID NO:3;
  (b) a Light Chain CDR2 having the amino acid sequence of SEQ ID NO:4; and
  (c) a Light Chain CDR3 having the amino acid sequence of SEQ ID NO:5;
  and further comprising
  (d) a Heavy Chain CDR1 having the amino acid sequence of SEQ ID NO:6;
  (e) a Heavy Chain CDR2 having the amino acid sequence of SEQ ID NO:28 and
  (f) a Heavy Chain CDR3 having the amino acid sequence of SEQ ID NO:8.

Antibody D55Q

Another aspect of the invention relates to the variant antibody of Antibody C10-2, Antibody D55Q. This aspect of the invention is directed to a monoclonal antibody, or epitope binding fragment thereof, comprising
  (a) a Light Chain CDR1 having the amino acid sequence of SEQ ID NO:3;
  (b) a Light Chain CDR2 having the amino acid sequence of SEQ ID NO:4;
  (c) a Light Chain CDR3 having the amino acid sequence of SEQ ID NO:5;
  (d) a Heavy Chain CDR1 having the amino acid sequence of SEQ ID NO:6;
  (e) a Heavy Chain CDR2 having the amino acid sequence of SEQ ID NO:29; and
  (f) a Heavy Chain CDR3 having the amino acid sequence of SEQ ID NO:8.

A further embodiment of the aspect of the invention directed to Antibody D55Q relates to a monoclonal antibody, or epitope binding fragment thereof, comprising
  (a) a Light Chain comprising the amino acid sequence of SEQ ID NO:12; and
  (b) a Heavy Chain comprising the amino acid sequence of SEQ ID NO:14.

Alternatively defined, a further embodiment of the aspect of the invention directed to Antibody D55Q relates to a monoclonal antibody, or epitope binding fragment thereof, comprising at least one of
  (a) a Light Chain CDR1 having the amino acid sequence of SEQ ID NO:3;
  (b) a Light Chain CDR2 having the amino acid sequence of SEQ ID NO:4; and
  (c) a Light Chain CDR3 having the amino acid sequence of SEQ ID NO:5;
  and further comprising
  (d) a Heavy Chain CDR1 having the amino acid sequence of SEQ ID NO:6;
  (e) a Heavy Chain CDR2 having the amino acid sequence of SEQ ID NO:29; and
  (f) a Heavy Chain CDR3 having the amino acid sequence of SEQ ID NO:8.

Antibody D55S

Another aspect of the invention relates to the variant antibody of Antibody C10-2, Antibody D55S. This aspect of the invention is directed to a monoclonal antibody, or epitope binding fragment thereof, comprising
  (a) a Light Chain CDR1 having the amino acid sequence of SEQ ID NO:3;
  (b) a Light Chain CDR2 having the amino acid sequence of SEQ ID NO:4;
  (c) a Light Chain CDR3 having the amino acid sequence of SEQ ID NO:5;
  (d) a Heavy Chain CDR1 having the amino acid sequence of SEQ ID NO:6;
  (e) a Heavy Chain CDR2 having the amino acid sequence of SEQ ID NO:30; and
  (f) a Heavy Chain CDR3 having the amino acid sequence of SEQ ID NO:8.

A further embodiment of the aspect of the invention directed to Antibody D55S relates to a monoclonal antibody, or epitope binding fragment thereof, comprising
  (a) a Light Chain comprising the amino acid sequence of SEQ ID NO:12 and
  (b) a Heavy Chain comprising the amino acid sequence of SEQ ID NO:15.

Alternatively defined, a further embodiment of the aspect of the invention directed to Antibody D55S relates to a monoclonal antibody, or epitope binding fragment thereof, comprising at least one of
(a) a Light Chain CDR1 having the amino acid sequence of SEQ ID NO:3;
(b) a Light Chain CDR2 having the amino acid sequence of SEQ ID NO:4; and
(c) a Light Chain CDR3 having the amino acid sequence of SEQ ID NO:5;
and further comprising
(d) a Heavy Chain CDR1 having the amino acid sequence of SEQ ID NO:6;
(e) a Heavy Chain CDR2 having the amino acid sequence of SEQ ID NO:30; and
(f) a Heavy Chain CDR3 having the amino acid sequence of SEQ ID NO:8.

Studies using Antibody D55S, Antibody D55Q, Antibody D55E indicates that mutation of this residue results in an antibody with unaltered binding properties when comparing said antibodies prior to and subsequent to treatment with low pH for an extended period of time at room temperature, indicating that no isomerization is taken place at low pH or that the any isomerized protein has unaltered binding properties compared to pre-treatment.

Antibody N32S

Another aspect of the invention relates to the variant antibody of Antibody C10-2, Antibody N32S. This aspect of the invention is directed to a monoclonal antibody, or epitope binding fragment thereof, comprising
(a) a Light Chain CDR1 having the amino acid sequence of SEQ ID NO:31;
(b) a Light Chain CDR2 having the amino acid sequence of SEQ ID NO:4;
(c) a Light Chain CDR3 having the amino acid sequence of SEQ ID NO:5;
(d) a Heavy Chain CDR1 having the amino acid sequence of SEQ ID NO:6;
(e) a Heavy Chain CDR2 having the amino acid sequence of SEQ ID NO:7; and
(f) a Heavy Chain CDR3 having the amino acid sequence of SEQ ID NO:8.

A further embodiment of the aspect of the invention directed to Antibody N32S relates to a monoclonal antibody, or epitope binding fragment thereof, comprising
(a) a Light Chain comprising the amino acid sequence of SEQ ID NO:16; and
(b) a Heavy Chain comprising the amino acid sequence of SEQ ID NO:11.

Alternatively defined, a further embodiment of the aspect of the invention directed to Antibody N32S relates to a monoclonal antibody, or epitope binding fragment thereof, comprising
(a) a Light Chain CDR1 having the amino acid sequence of SEQ ID NO:31;
(b) a Light Chain CDR2 having the amino acid sequence of SEQ ID NO:4; and
(c) a Light Chain CDR3 having the amino acid sequence of SEQ ID NO:5;
and further comprising at least one of
(d) a Heavy Chain CDR1 having the amino acid sequence of SEQ ID NO:6;
(e) a Heavy Chain CDR2 having the amino acid sequence of SEQ ID NO:7; and
(f) a Heavy Chain CDR3 having the amino acid sequence of SEQ ID NO:8.

An alternative definition of Antibody N32S, using the IMGT definition, is a monoclonal antibody, or epitope binding fragment thereof, comprising
(a) a Light Chain CDR1 having the amino acid sequence of SEQ ID NO:46;
(b) a Light Chain CDR2 having the amino acid sequence of SEQ ID NO:47;
(c) a Light Chain CDR3 having the amino acid sequence of SEQ ID NO:48;
(d) a Heavy Chain CDR1 having the amino acid sequence of SEQ ID NO:43;
(e) a Heavy Chain CDR2 having the amino acid sequence of SEQ ID NO:44; and
(f) a Heavy Chain CDR3 having the amino acid sequence of SEQ ID NO:45.

A further alternative definition of Antibody N32S, using the Chotia definition, is a monoclonal antibody, or epitope binding fragment thereof, comprising
(a) a Light Chain CDR1 having the amino acid sequence of SEQ ID NO:31;
(b) a Light Chain CDR2 having the amino acid sequence of SEQ ID NO:4;
(c) a Light Chain CDR3 having the amino acid sequence of SEQ ID NO:5;
(d) a Heavy Chain CDR1 having the amino acid sequence of SEQ ID NO:52;
(e) a Heavy Chain CDR2 having the amino acid sequence of SEQ ID NO:53; and
(f) a Heavy Chain CDR3 having the amino acid sequence of SEQ ID NO:54.

Figure 1:
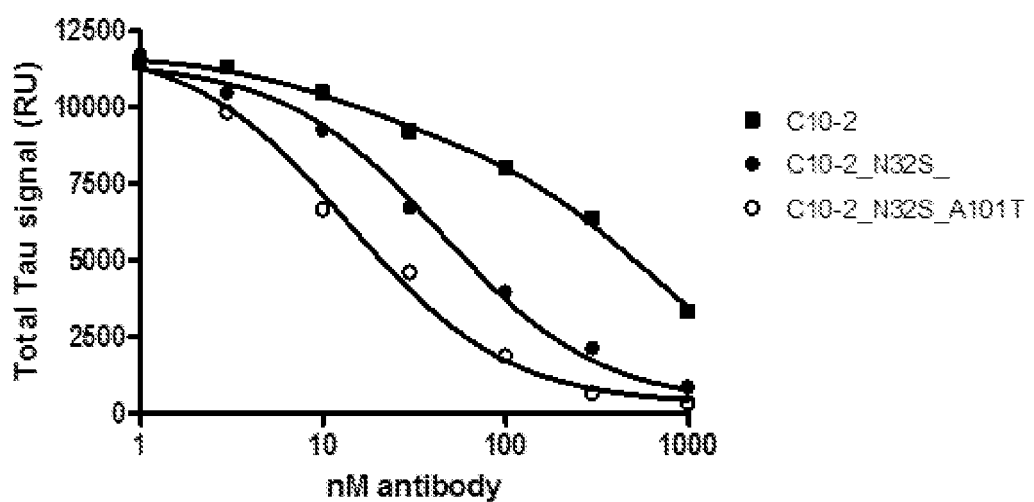
FIG. 1. Fluid Phase inhibition assay for AD-P3 capture using humanised C10-2 and variants (C10-2_N32S and C10-2_N32S_A101T). As described in Example 3A, concentration dependent inhibition of AD-P3 capture by P396-specific antibodies hC10-2 (squares), hC10-2_N32S (black circles) and hC10-2_N332_A101T (open circles) was investigated. AD-P3 fraction were incubated 60 min. at room temperature (r/t) with increasing concentrations of antibodies (0-1000 nM) prior to incubation with 200 ng/ml mouse C10-2 antibody immobilized on 96 well plates. Captured AD-P3 antigens were detected with sulfo tagged anti—total tau antibody (MSD).

As can be seen from FIG. 1, the IC50 of Antibody N32S (black circles) is reduced compared to Antibody C10-2: the IC50 of N32S was calculated to be 44 nM. This notable improvement over C10-2 was not anticipated. As supported by FIG. 1, one aspect of the invention is directed to an antibody that inhibits AD-P3 in the fluid phase inhibition assay described herein, such that the signal is reduced by 50% at a concentration of 100 nM or less of the antibody. In one embodiment, the antibody of the invention has an IC50 of from 0.1 nM to 100 nM, such as at a concentration of 50 nM or less, such as from 0.1 nM to 50 nM, based on fluid phase inhibition assay for AD-P3 capture.

The data generated using Antibody N32S indicates that mutation at position 32 of the Light Chain of Antibody C10-2, or of the LC CDR1 of Antibody C10-2 to serine results in increased apparent affinity (IC50) in peptide inhibition assays. Moreover, mutation at position 32 to serine or glutamine (Antibody N32S and Antibody N32Q) abolishes deamidation in both positions 32 and 34 as shown in FIG. 20. Potency, as determined in terms of in-vitro seeding and aggregation studies, is maintained in both N32S and N32Q variants.

The potential deamidation potential identified in C 10-2 at position which could lead to heterogeneity of protein batches. C 10-2 showed heterogenous binding to AD-P3 antigens with a minor fraction of high apparent affinity (2-5 nM) and a predominant binding with low apparent affinity (200-1000 nM) (FIG. 1). The heterogenous binding could reflect different subpopulations of deamidated and non-deamidated C 10-2. A variant was generated by substitution (N32S) which prevented deamidation. As shown improved binding by activity as indicated by overall reduced IC50 (higher apparent affinity) compared to C 10-2. An additional substitution A101T was introduced resulting in homogenous binding of high apparent affinity type. The improved binding activity in both the N32S and N32S-A101T suggest more stable and homogenous antibodies was achieved by mutations described above.

Antibody N32Q

Another aspect of the invention relates to the variant antibody of Antibody C10-2, Antibody N32Q. This aspect of the invention is directed to a monoclonal antibody, or epitope binding fragment thereof, comprising
  (a) a Light Chain CDR1 having the amino acid sequence of SEQ ID NO:32;
  (b) a Light Chain CDR2 having the amino acid sequence of SEQ ID NO:4;
  (c) a Light Chain CDR3 having the amino acid sequence of SEQ ID NO:5;
  (d) a Heavy Chain CDR1 having the amino acid sequence of SEQ ID NO:6;
  (e) a Heavy Chain CDR2 having the amino acid sequence of SEQ ID NO:7; and
  (f) a Heavy Chain CDR3 having the amino acid sequence of SEQ ID NO:8.

A further embodiment of the aspect of the invention directed to Antibody N32Q relates to a monoclonal antibody, or epitope binding fragment thereof, comprising
  (a) a Light Chain comprising the amino acid sequence of SEQ ID NO:17; and
  (b) a Heavy Chain comprising the amino acid sequence of SEQ ID NO:11.

Alternatively defined, a further embodiment of the aspect of the invention directed to Antibody N32Q relates to a monoclonal antibody, or epitope binding fragment thereof, comprising
  (a) a Light Chain CDR1 having the amino acid sequence of SEQ ID NO:32;
  (b) a Light Chain CDR2 having the amino acid sequence of SEQ ID NO:4; and
  (c) a Light Chain CDR3 having the amino acid sequence of SEQ ID NO:5;
  and further comprising at least one of
  (d) a Heavy Chain CDR1 having the amino acid sequence of SEQ ID NO:6;
  (e) a Heavy Chain CDR2 having the amino acid sequence of SEQ ID NO:7; and
  (f) a Heavy Chain CDR3 having the amino acid sequence of SEQ ID NO:8.

As stated, the data generated using Antibody N32S indicates that mutation at position 32 of the Light Chain of Antibody C10-2, or of the LC CDR1 of Antibody C10-2 to serine results in increased apparent affinity (IC50), whereas mutation to glutamine (Antibody N32Q) results in unaltered binding activity. However, mutation at position 32 to serine or glutamine (Antibody N32S and Antibody N32Q) abolishes deamidation in both positions 32 and 34 as shown in FIG. 20. Accordingly, there are advantages to both Antibody N32S and Antibody N32Q. Potency, as determined in terms of in-vitro seeding and aggregation studies, is maintained in both N32S and N32Q variants.

Antibody N34S

Another aspect of the invention relates to the variant antibody of Antibody C10-2, Antibody N34S. This aspect of the invention is directed to a monoclonal antibody, or epitope binding fragment thereof, comprising
  (a) a Light Chain CDR1 having the amino acid sequence of SEQ ID NO:33;
  (b) a Light Chain CDR2 having the amino acid sequence of SEQ ID NO:4;
  (c) a Light Chain CDR3 having the amino acid sequence of SEQ ID NO:5;
  (d) a Heavy Chain CDR1 having the amino acid sequence of SEQ ID NO:6;
  (e) a Heavy Chain CDR2 having the amino acid sequence of SEQ ID NO:7; and
  (f) a Heavy Chain CDR3 having the amino acid sequence of SEQ ID NO:8.

A further embodiment of the aspect of the invention directed to Antibody N34S relates to a monoclonal antibody, or epitope binding fragment thereof, comprising
  (a) a Light Chain comprising the amino acid sequence of SEQ ID NO:18; and
  (b) a Heavy Chain comprising the amino acid sequence of SEQ ID NO:11.

Alternatively defined, a further embodiment of the aspect of the invention directed to Antibody N34S relates to a monoclonal antibody, or epitope binding fragment thereof, comprising
  (a) a Light Chain CDR1 having the amino acid sequence of SEQ ID NO:33;
  (b) a Light Chain CDR2 having the amino acid sequence of SEQ ID NO:4; and
  (c) a Light Chain CDR3 having the amino acid sequence of SEQ ID NO:5;
  and further comprising at least one of
  (d) a Heavy Chain CDR1 having the amino acid sequence of SEQ ID NO:6;
  (e) a Heavy Chain CDR2 having the amino acid sequence of SEQ ID NO:7; and
  (f) a Heavy Chain CDR3 having the amino acid sequence of SEQ ID NO:8.

Antibody N34Q

Another aspect of the invention relates to the variant antibody of Antibody C10-2, Antibody N34Q. This aspect of the invention is directed to a monoclonal antibody, or epitope binding fragment thereof, comprising
  (a) a Light Chain CDR1 having the amino acid sequence of SEQ ID NO:34;
  (b) a Light Chain CDR2 having the amino acid sequence of SEQ ID NO:4;
  (c) a Light Chain CDR3 having the amino acid sequence of SEQ ID NO:5;
  (d) a Heavy Chain CDR1 having the amino acid sequence of SEQ ID NO:6;
  (e) a Heavy Chain CDR2 having the amino acid sequence of SEQ ID NO:7; and
  (f) a Heavy Chain CDR3 having the amino acid sequence of SEQ ID NO:8.

A further embodiment of the aspect of the invention directed to Antibody N34Q relates to a monoclonal antibody, or epitope binding fragment thereof, comprising
  (a) a Light Chain comprising the amino acid sequence of SEQ ID NO:19; and
  (b) a Heavy Chain comprising the amino acid sequence of SEQ ID NO:11.

Alternatively defined, a further embodiment of the aspect of the invention directed to Antibody N34Q relates to a monoclonal antibody, or epitope binding fragment thereof, comprising
  (a) a Light Chain CDR1 having the amino acid sequence of SEQ ID NO:34;
  (b) a Light Chain CDR2 having the amino acid sequence of SEQ ID NO:4; and
  (c) a Light Chain CDR3 having the amino acid sequence of SEQ ID NO:5;
  and further comprising at least one of
  (d) a Heavy Chain CDR1 having the amino acid sequence of SEQ ID NO:6;

(e) a Heavy Chain CDR2 having the amino acid sequence of SEQ ID NO:7; and
(f) a Heavy Chain CDR3 having the amino acid sequence of SEQ ID NO:8.

Antibody N32S, N34S

Another aspect of the invention relates to the variant antibody of Antibody C10-2, Antibody N32S, N34S. This aspect of the invention is directed to a monoclonal antibody, or epitope binding fragment thereof, comprising
(a) a Light Chain CDR1 having the amino acid sequence of SEQ ID NO:35;
(b) a Light Chain CDR2 having the amino acid sequence of SEQ ID NO:4;
(c) a Light Chain CDR3 having the amino acid sequence of SEQ ID NO:5;
(d) a Heavy Chain CDR1 having the amino acid sequence of SEQ ID NO:6;
(e) a Heavy Chain CDR2 having the amino acid sequence of SEQ ID NO:7; and
(f) a Heavy Chain CDR3 having the amino acid sequence of SEQ ID NO:8.

Alternatively defined, a further embodiment of the aspect of the invention directed to Antibody N32S, N34S relates to a monoclonal antibody, or epitope binding fragment thereof, comprising
(a) a Light Chain comprising the amino acid sequence of SEQ ID NO:20; and
(b) a Heavy Chain comprising the amino acid sequence of SEQ ID NO:11.

Alternatively defined, a further embodiment of the aspect of the invention directed to Antibody N32S, N34S relates to a monoclonal antibody, or epitope binding fragment thereof, comprising
(a) a Light Chain CDR1 having the amino acid sequence of SEQ ID NO:35;
(b) a Light Chain CDR2 having the amino acid sequence of SEQ ID NO:4; and
(c) a Light Chain CDR3 having the amino acid sequence of SEQ ID NO:5;
and further comprising at least one of
(d) a Heavy Chain CDR1 having the amino acid sequence of SEQ ID NO:6;
(e) a Heavy Chain CDR2 having the amino acid sequence of SEQ ID NO:7; and
(f) a Heavy Chain CDR3 having the amino acid sequence of SEQ ID NO:8.

Antibody N32Q, N34S

Another aspect of the invention relates to the variant antibody of Antibody C10-2, Antibody N32Q, N34S. This aspect of the invention is directed to a monoclonal antibody, or epitope binding fragment thereof, comprising
(a) a Light Chain CDR1 having the amino acid sequence of SEQ ID NO:36;
(b) a Light Chain CDR2 having the amino acid sequence of SEQ ID NO:4;
(c) a Light Chain CDR3 having the amino acid sequence of SEQ ID NO:5;
(d) a Heavy Chain CDR1 having the amino acid sequence of SEQ ID NO:6;
(e) a Heavy Chain CDR2 having the amino acid sequence of SEQ ID NO:7; and
(f) a Heavy Chain CDR3 having the amino acid sequence of SEQ ID NO:8.

Alternatively defined, a further embodiment of the aspect of the invention directed to Antibody N32Q, N34S relates to a monoclonal antibody, or epitope binding fragment thereof, comprising
(a) a Light Chain comprising the amino acid sequence of SEQ ID NO:21;
(b) a Heavy Chain comprising the amino acid sequence of SEQ ID NO:11.

Alternatively defined, a further embodiment of the aspect of the invention directed to Antibody N32Q, N34S relates to a monoclonal antibody, or epitope binding fragment thereof, comprising
(a) a Light Chain CDR1 having the amino acid sequence of SEQ ID NO:36;
(b) a Light Chain CDR2 having the amino acid sequence of SEQ ID NO:4; and
(c) a Light Chain CDR3 having the amino acid sequence of SEQ ID NO:5;
and further comprising at least one of
(d) a Heavy Chain CDR1 having the amino acid sequence of SEQ ID NO:6;
(e) a Heavy Chain CDR2 having the amino acid sequence of SEQ ID NO:7; and
(f) a Heavy Chain CDR3 having the amino acid sequence of SEQ ID NO:8.

Antibody N32Q, N34Q

Another aspect of the invention relates to the variant antibody of Antibody C10-2, Antibody N32Q, N34Q. This aspect of the invention is directed to a monoclonal antibody, or epitope binding fragment thereof, comprising
(a) a Light Chain CDR1 having the amino acid sequence of SEQ ID NO:37;
(b) a Light Chain CDR2 having the amino acid sequence of SEQ ID NO:4;
(c) a Light Chain CDR3 having the amino acid sequence of SEQ ID NO:5;
(d) a Heavy Chain CDR1 having the amino acid sequence of SEQ ID NO:6;
(e) a Heavy Chain CDR2 having the amino acid sequence of SEQ ID NO:7; and
(f) a Heavy Chain CDR3 having the amino acid sequence of SEQ ID NO:8;

Alternatively defined, a further embodiment of the aspect of the invention directed to Antibody N32Q, N34Q relates to a monoclonal antibody, or epitope binding fragment thereof, comprising
(a) a Light Chain comprising the amino acid sequence of SEQ ID NO:22; and
(b) a Heavy Chain comprising the amino acid sequence of SEQ ID NO:11.

Alternatively defined, a further embodiment of the aspect of the invention directed to Antibody N32Q, N34Q relates to a monoclonal antibody, or epitope binding fragment thereof, comprising
(a) a Light Chain CDR1 having the amino acid sequence of SEQ ID NO:37;
(b) a Light Chain CDR2 having the amino acid sequence of SEQ ID NO:4; and
(c) a Light Chain CDR3 having the amino acid sequence of SEQ ID NO:5;
and further comprising at least one of
(d) a Heavy Chain CDR1 having the amino acid sequence of SEQ ID NO:6;
(e) a Heavy Chain CDR2 having the amino acid sequence of SEQ ID NO:7; and
(f) a Heavy Chain CDR3 having the amino acid sequence of SEQ ID NO:8.

Antibody N32S, N34Q

Another aspect of the invention relates to the variant antibody of Antibody C10-2, Antibody N32S, N34Q. This aspect of the invention is directed to a monoclonal antibody, or epitope binding fragment thereof, comprising
- (a) a Light Chain CDR1 having the amino acid sequence of SEQ ID NO:38;
- (b) a Light Chain CDR2 having the amino acid sequence of SEQ ID NO:4;
- (c) a Light Chain CDR3 having the amino acid sequence of SEQ ID NO:5;
- (d) a Heavy Chain CDR1 having the amino acid sequence of SEQ ID NO:6;
- (e) a Heavy Chain CDR2 having the amino acid sequence of SEQ ID NO:7; and
- (f) a Heavy Chain CDR3 having the amino acid sequence of SEQ ID NO:8.

Alternatively defined, a further embodiment of the aspect of the invention directed to Antibody N32S, N34Q relates to a monoclonal antibody, or epitope binding fragment thereof, comprising
- (a) a Light Chain comprising the amino acid sequence of SEQ ID NO:23; and
- (b) a Heavy Chain comprising the amino acid sequence of SEQ ID NO:11.

Alternatively defined, a further embodiment of the aspect of the invention directed to Antibody N32S, N34Q relates to a monoclonal antibody, or epitope binding fragment thereof, comprising
- (a) a Light Chain CDR1 having the amino acid sequence of SEQ ID NO:38;
- (b) a Light Chain CDR2 having the amino acid sequence of SEQ ID NO:4; and
- (c) a Light Chain CDR3 having the amino acid sequence of SEQ ID NO:5;

and further comprising at least one of
- (d) a Heavy Chain CDR1 having the amino acid sequence of SEQ ID NO:6;
- (e) a Heavy Chain CDR2 having the amino acid sequence of SEQ ID NO:7; and
- (f) a Heavy Chain CDR3 having the amino acid sequence of SEQ ID NO:8.

Antibody A101T

Another aspect of the invention relates to the variant antibody of Antibody C10-2, Antibody A101T. This aspect of the invention is directed to a monoclonal antibody, or epitope binding fragment thereof, comprising
- (a) a Light Chain CDR1 having the amino acid sequence of SEQ ID NO:3;
- (b) a Light Chain CDR2 having the amino acid sequence of SEQ ID NO:4;
- (c) a Light Chain CDR3 having the amino acid sequence of SEQ ID NO:5;
- (d) a Heavy Chain CDR1 having the amino acid sequence of SEQ ID NO:6;
- (e) a Heavy Chain CDR2 having the amino acid sequence of SEQ ID NO:7; and
- (f) a Heavy Chain CDR3 having the amino acid sequence of SEQ ID NO:39.

Alternatively defined, a further embodiment of the aspect of the invention directed to Antibody A101T relates to a monoclonal antibody, or epitope binding fragment thereof, comprising
- (a) a Light Chain comprising the amino acid sequence of SEQ ID NO:12; and
- (b) a Heavy Chain comprising the amino acid sequence of SEQ ID NO:24.

Alternatively defined, a further embodiment of the aspect of the invention directed to Antibody A101T relates to a monoclonal antibody, or epitope binding fragment thereof, comprising at least one of
- (a) a Light Chain CDR1 having the amino acid sequence of SEQ ID NO:3;
- (b) a Light Chain CDR2 having the amino acid sequence of SEQ ID NO:4; and
- (c) a Light Chain CDR3 having the amino acid sequence of SEQ ID NO:5;

and further comprising
- (d) a Heavy Chain CDR1 having the amino acid sequence of SEQ ID NO:6;
- (e) a Heavy Chain CDR2 having the amino acid sequence of SEQ ID NO:7; and
- (f) a Heavy Chain CDR3 having the amino acid sequence of SEQ ID NO:39.

The data generated using Antibody A101T indicates that the mutation of Heavy Chain of Antibody C10-2 or of the Heavy Chain CR3 of Antibody C10-2 results in a two-fold increased peptide binding and a 10-20 fold increased binding to P3 material. Furthermore, variants comprising the A101T mutation have increased potency in in-vitro seeding assays.

Antibody N32S, A101T

Another aspect of the invention relates to the variant antibody of Antibody C10-2, Antibody N32S, A101T. This aspect of the invention is directed to a monoclonal antibody, or epitope binding fragment thereof, comprising
- (a) a Light Chain CDR1 having the amino acid sequence of SEQ ID NO:31;
- (b) a Light Chain CDR2 having the amino acid sequence of SEQ ID NO:4;
- (c) a Light Chain CDR3 having the amino acid sequence of SEQ ID NO:5;
- (d) a Heavy Chain CDR1 having the amino acid sequence of SEQ ID NO:6;
- (e) a Heavy Chain CDR2 having the amino acid sequence of SEQ ID NO:7; and
- (f) a Heavy Chain CDR3 having the amino acid sequence of SEQ ID NO:39.

Alternatively defined, a further embodiment of the aspect of the invention directed to Antibody N32S, A101T relates to a monoclonal antibody, or epitope binding fragment thereof, comprising
- (a) a Light Chain comprising the amino acid sequence of SEQ ID NO:16;
- (b) a Heavy Chain comprising the amino acid sequence of SEQ ID NO:24.

Alternatively defined, a further embodiment of the aspect of the invention directed to Antibody N32S, A101T relates to a monoclonal antibody, or epitope binding fragment thereof, comprising
- (a) a Light Chain CDR1 having the amino acid sequence of SEQ ID NO:31; and
- (f) a Heavy Chain CDR3 having the amino acid sequence of SEQ ID NO:39;

and further comprising at least one of
- (b) a Light Chain CDR2 having the amino acid sequence of SEQ ID NO:4; and
- (c) a Light Chain CDR3 having the amino acid sequence of SEQ ID NO:5;

and further comprising at least one of
- (d) a Heavy Chain CDR1 having the amino acid sequence of SEQ ID NO:6; and
- (e) a Heavy Chain CDR2 having the amino acid sequence of SEQ ID NO:7.

Using the IMGT definition, Antibody N32S, A101T is a monoclonal antibody, or epitope binding fragment thereof, comprising
- (a) a Light Chain CDR1 having the amino acid sequence of SEQ ID NO:46;
- (b) a Light Chain CDR2 having the amino acid sequence of SEQ ID NO:47;
- (c) a Light Chain CDR3 having the amino acid sequence of SEQ ID NO:48;
- (d) a Heavy Chain CDR1 having the amino acid sequence of SEQ ID NO:49;
- (e) a Heavy Chain CDR2 having the amino acid sequence of SEQ ID NO:50; and
- (f) a Heavy Chain CDR3 having the amino acid sequence of SEQ ID NO:51.

Using the Chotia definition, Antibody N32S, A101T is a monoclonal antibody, or epitope binding fragment thereof, comprising
- (a) a Light Chain CDR1 having the amino acid sequence of SEQ ID NO:31;
- (b) a Light Chain CDR2 having the amino acid sequence of SEQ ID NO:4;
- (c) a Light Chain CDR3 having the amino acid sequence of SEQ ID NO:5;
- (d) a Heavy Chain CDR1 having the amino acid sequence of SEQ ID NO:55;
- (e) a Heavy Chain CDR2 having the amino acid sequence of SEQ ID NO:56; and
- (f) a Heavy Chain CDR3 having the amino acid sequence of SEQ ID NO:57.

As can be seen from FIG. 1, the IC50 of Antibody N32S, A101T (white circles) is dramatically reduced compared to Antibody C10-2: the IC50 of N32S A101T was calculated to be 14 nM. This notable improvement over C10-2 was not anticipated. Based upon FIG. 1, one aspect of the invention is directed to an antibody that inhibits AD-P3 in the fluid phase inhibition assay described herein, such that the signal is reduced by 50% at a concentration of 100 nM or less of the antibody, such as from 10 nM to 100 nM of the antibody, such as at a concentration of 50 nM or less, such as from 10 nM to 50 nM of the antibody. As shown in FIG. 20, Antibody N32S, A101 is very stable against deamidation. As shown in FIG. 19, Antibody N32S, A101T showed a stronger reduction in aggregation.

Antibody N32Q, A101T

Another aspect of the invention relates to the variant antibody of Antibody C10-2, Antibody N32Q, A101T. This aspect of the invention is directed to a monoclonal antibody, or epitope binding fragment thereof, comprising
- (a) a Light Chain CDR1 having the amino acid sequence of SEQ ID NO:32;
- (b) a Light Chain CDR2 having the amino acid sequence of SEQ ID NO:4;
- (c) a Light Chain CDR3 having the amino acid sequence of SEQ ID NO:5;
- (d) a Heavy Chain CDR1 having the amino acid sequence of SEQ ID NO:6;
- (e) a Heavy Chain CDR2 having the amino acid sequence of SEQ ID NO:7; and
- (f) a Heavy Chain CDR3 having the amino acid sequence of SEQ ID NO:39.

Alternatively defined, a further embodiment of the aspect of the invention directed to Antibody N32Q, A101T relates to a monoclonal antibody, or epitope binding fragment thereof, comprising
- (a) a Light Chain comprising the amino acid sequence of SEQ ID NO:17; and
- (b) a Heavy Chain comprising the amino acid sequence of SEQ ID NO:24.

Alternatively defined, a further embodiment of the aspect of the invention directed to Antibody N32Q, A101T relates to a monoclonal antibody, or epitope binding fragment thereof, comprising
- (a) a Light Chain CDR1 having the amino acid sequence of SEQ ID NO:32; and
- (f) a Heavy Chain CDR3 having the amino acid sequence of SEQ ID NO:39;

and further comprising at least one of
- (b) a Light Chain CDR2 having the amino acid sequence of SEQ ID NO:4; and
- (c) a Light Chain CDR3 having the amino acid sequence of SEQ ID NO:5;

and further comprising at least one of
- (d) a Heavy Chain CDR1 having the amino acid sequence of SEQ ID NO:6; and
- (e) a Heavy Chain CDR2 having the amino acid sequence of SEQ ID NO:7.

Antibody N32S, D55E

Another aspect of the invention relates to the variant antibody of Antibody C10-2, Antibody N32S, D55E. This aspect of the invention is directed to a monoclonal antibody, or epitope binding fragment thereof, comprising
- (a) a Light Chain CDR1 having the amino acid sequence of SEQ ID NO:31;
- (b) a Light Chain CDR2 having the amino acid sequence of SEQ ID NO:4;
- (c) a Light Chain CDR3 having the amino acid sequence of SEQ ID NO:5;
- (d) a Heavy Chain CDR1 having the amino acid sequence of SEQ ID NO:6;
- (e) a Heavy Chain CDR2 having the amino acid sequence of SEQ ID NO:28; and
- (f) a Heavy Chain CDR3 having the amino acid sequence of SEQ ID NO:8.

Alternatively defined, a further embodiment of the aspect of the invention directed to Antibody N32S, D55E relates to a monoclonal antibody, or epitope binding fragment thereof, comprising
- (a) a Light Chain comprising the amino acid sequence of SEQ ID NO:16;
- (b) a Heavy Chain comprising the amino acid sequence of SEQ ID NO:13.

Alternatively defined, a further embodiment of the aspect of the invention directed to Antibody N32S, D55E relates to a monoclonal antibody, or epitope binding fragment thereof, comprising
- (a) a Light Chain CDR1 having the amino acid sequence of SEQ ID NO:31; and (e) a Heavy Chain CDR2 having the amino acid sequence of SEQ ID NO:28;

and further comprising at least one of
- (b) a Light Chain CDR2 having the amino acid sequence of SEQ ID NO:4; and
- (c) a Light Chain CDR3 having the amino acid sequence of SEQ ID NO:5;

and further comprising at least one of
- (d) a Heavy Chain CDR1 having the amino acid sequence of SEQ ID NO:6; and
- (f) a Heavy Chain CDR3 having the amino acid sequence of SEQ ID NO:8.

Antibody N32Q, D55E

Another aspect of the invention relates to the variant antibody of Antibody C10-2, Antibody N32Q, D55E. This aspect of the invention is directed to a monoclonal antibody, or epitope binding fragment thereof, comprising (a) a Light Chain CDR1 having the amino acid sequence of SEQ ID NO:32;
(b) a Light Chain CDR2 having the amino acid sequence of SEQ ID NO:4;
(c) a Light Chain CDR3 having the amino acid sequence of SEQ ID NO:5;
(d) a Heavy Chain CDR1 having the amino acid sequence of SEQ ID NO:6;
(e) a Heavy Chain CDR2 having the amino acid sequence of SEQ ID NO:28; and
(f) a Heavy Chain CDR3 having the amino acid sequence of SEQ ID NO:8.

Alternatively defined, a further embodiment of the aspect of the invention directed to Antibody N32Q, D55E relates to a monoclonal antibody, or epitope binding fragment thereof, comprising
(a) a Light Chain comprising the amino acid sequence of SEQ ID NO:17;
(b) a Heavy Chain comprising the amino acid sequence of SEQ ID NO:13.

Alternatively defined, a further embodiment of the aspect of the invention directed to Antibody N32Q, D55E relates to a monoclonal antibody, or epitope binding fragment thereof, comprising
(a) a Light Chain CDR1 having the amino acid sequence of SEQ ID NO:32; and (e) a Heavy Chain CDR2 having the amino acid sequence of SEQ ID NO:28;
and further comprising at least one of
(b) a Light Chain CDR2 having the amino acid sequence of SEQ ID NO:4; and
(c) a Light Chain CDR3 having the amino acid sequence of SEQ ID NO:5;
and further comprising at least one of
(d) a Heavy Chain CDR1 having the amino acid sequence of SEQ ID NO:6; and
(f) a Heavy Chain CDR3 having the amino acid sequence of SEQ ID NO:8.

Antibody N34S, A101T

Another aspect of the invention relates to the variant antibody of Antibody C10-2, Antibody N34S, A101T. This aspect of the invention is directed to a monoclonal antibody, or epitope binding fragment thereof, comprising
(a) a Light Chain CDR1 having the amino acid sequence of SEQ ID NO:33;
(b) a Light Chain CDR2 having the amino acid sequence of SEQ ID NO:4;
(c) a Light Chain CDR3 having the amino acid sequence of SEQ ID NO:5;
(d) a Heavy Chain CDR1 having the amino acid sequence of SEQ ID NO:6;
(e) a Heavy Chain CDR2 having the amino acid sequence of SEQ ID NO:7; and
(f) a Heavy Chain CDR3 having the amino acid sequence of SEQ ID NO:39.

Alternatively defined, a further embodiment of the aspect of the invention directed to Antibody N34S, A101T relates to a monoclonal antibody, or epitope binding fragment thereof, comprising
(a) a Light Chain comprising the amino acid sequence of SEQ ID NO:18; and
(b) a Heavy Chain comprising the amino acid sequence of SEQ ID NO:24.

Alternatively defined, a further embodiment of the aspect of the invention directed to Antibody N34S, A101T relates to a monoclonal antibody, or epitope binding fragment thereof, comprising
(a) a Light Chain CDR1 having the amino acid sequence of SEQ ID NO:33; and
(f) a Heavy Chain CDR3 having the amino acid sequence of SEQ ID NO:39;
and further comprising at least one of
(b) a Light Chain CDR2 having the amino acid sequence of SEQ ID NO:4; and
(c) a Light Chain CDR3 having the amino acid sequence of SEQ ID NO:5;
and further comprising at least one of
(d) a Heavy Chain CDR1 having the amino acid sequence of SEQ ID NO:6; and
(e) a Heavy Chain CDR2 having the amino acid sequence of SEQ ID NO:7.

Antibody N34Q, A101T

Another aspect of the invention relates to the variant antibody of Antibody C10-2, Antibody N34Q, A101T. This aspect of the invention is directed to a monoclonal antibody, or epitope binding fragment thereof, comprising
(a) a Light Chain CDR1 having the amino acid sequence of SEQ ID NO:34;
(b) a Light Chain CDR2 having the amino acid sequence of SEQ ID NO:4;
(c) a Light Chain CDR3 having the amino acid sequence of SEQ ID NO:5;
(d) a Heavy Chain CDR1 having the amino acid sequence of SEQ ID NO:6;
(e) a Heavy Chain CDR2 having the amino acid sequence of SEQ ID NO:7; and
(f) a Heavy Chain CDR3 having the amino acid sequence of SEQ ID NO:39.

Alternatively defined, a further embodiment of the aspect of the invention directed to Antibody N34Q, A101T relates to a monoclonal antibody, or epitope binding fragment thereof, comprising
(a) a Light Chain comprising the amino acid sequence of SEQ ID NO:19; and
(b) a Heavy Chain comprising the amino acid sequence of SEQ ID NO:24.

Alternatively defined, a further embodiment of the aspect of the invention directed to Antibody N34Q, A101T relates to a monoclonal antibody, or epitope binding fragment thereof, comprising
(a) a Light Chain CDR1 having the amino acid sequence of SEQ ID NO:34; and
(f) a Heavy Chain CDR3 having the amino acid sequence of SEQ ID NO:39;
and further comprising at least one of
(b) a Light Chain CDR2 having the amino acid sequence of SEQ ID NO:4; and
(c) a Light Chain CDR3 having the amino acid sequence of SEQ ID NO:5;
and further comprising at least one of
(d) a Heavy Chain CDR1 having the amino acid sequence of SEQ ID NO:6;
(e) a Heavy Chain CDR2 having the amino acid sequence of SEQ ID NO:7.

Antibody D55E, A101T

Another aspect of the invention relates to the variant antibody of Antibody C10-2, Antibody D55E, A101T. This aspect of the invention is directed to a monoclonal antibody, or epitope binding fragment thereof, comprising
(a) a Light Chain CDR1 having the amino acid sequence of SEQ ID NO:3;
(b) a Light Chain CDR2 having the amino acid sequence of SEQ ID NO:4;

(c) a Light Chain CDR3 having the amino acid sequence of SEQ ID NO:5;
(d) a Heavy Chain CDR1 having the amino acid sequence of SEQ ID NO:6;
(e) a Heavy Chain CDR2 having the amino acid sequence of SEQ ID NO:28; and
(f) a Heavy Chain CDR3 having the amino acid sequence of SEQ ID NO:39.

Alternatively defined, a further embodiment of the aspect of the invention directed to Antibody D55E, A101T relates to a monoclonal antibody, or epitope binding fragment thereof, comprising
(a) a Light Chain comprising the amino acid sequence of SEQ ID NO:12; and
(b) a Heavy Chain comprising the amino acid sequence of SEQ ID NO:25.

Alternatively defined, a further embodiment of the aspect of the invention directed to Antibody D55E, A101T relates to a monoclonal antibody, or epitope binding fragment thereof, comprising at least one of
(a) a Light Chain CDR1 having the amino acid sequence of SEQ ID NO:3;
(b) a Light Chain CDR2 having the amino acid sequence of SEQ ID NO:4; and
(c) a Light Chain CDR3 having the amino acid sequence of SEQ ID NO:5;
and further comprising
(d) a Heavy Chain CDR1 having the amino acid sequence of SEQ ID NO:6;
(e) a Heavy Chain CDR2 having the amino acid sequence of SEQ ID NO:28; and
(f) a Heavy Chain CDR3 having the amino acid sequence of SEQ ID NO:39.

Antibody D55Q, A101T

Another aspect of the invention relates to the variant antibody of Antibody C10-2, Antibody D55Q, A101T. This aspect of the invention is directed to a monoclonal antibody, or epitope binding fragment thereof, comprising
(a) a Light Chain CDR1 having the amino acid sequence of SEQ ID NO:3;
(b) a Light Chain CDR2 having the amino acid sequence of SEQ ID NO:4;
(c) a Light Chain CDR3 having the amino acid sequence of SEQ ID NO:5;
(d) a Heavy Chain CDR1 having the amino acid sequence of SEQ ID NO:6;
(e) a Heavy Chain CDR2 having the amino acid sequence of SEQ ID NO:29; and
(f) a Heavy Chain CDR3 having the amino acid sequence of SEQ ID NO:39.

Alternatively defined, a further embodiment of the aspect of the invention directed to Antibody D55Q, A101T relates to a monoclonal antibody, or epitope binding fragment thereof, comprising
(a) a Light Chain comprising the amino acid sequence of SEQ ID NO:12; and
(b) a Heavy Chain comprising the amino acid sequence of SEQ ID NO:26.

Alternatively defined, a further embodiment of the aspect of the invention directed to Antibody D55Q, A101T relates to a monoclonal antibody, or epitope binding fragment thereof, comprising at least one of
(a) a Light Chain CDR1 having the amino acid sequence of SEQ ID NO:3;
(b) a Light Chain CDR2 having the amino acid sequence of SEQ ID NO:4; and
(c) a Light Chain CDR3 having the amino acid sequence of SEQ ID NO:5;
and further comprising
(d) a Heavy Chain CDR1 having the amino acid sequence of SEQ ID NO:6;
(e) a Heavy Chain CDR2 having the amino acid sequence of SEQ ID NO:29; and
(f) a Heavy Chain CDR3 having the amino acid sequence of SEQ ID NO:39.

Antibody D55S, A101T

Another aspect of the invention relates to the variant antibody of Antibody C10-2, Antibody D55S, A101T. This aspect of the invention is directed to a monoclonal antibody, or epitope binding fragment thereof, comprising
(a) a Light Chain CDR1 having the amino acid sequence of SEQ ID NO:3;
(b) a Light Chain CDR2 having the amino acid sequence of SEQ ID NO:4;
(c) a Light Chain CDR3 having the amino acid sequence of SEQ ID NO:5;
(d) a Heavy Chain CDR1 having the amino acid sequence of SEQ ID NO:6;
(e) a Heavy Chain CDR2 having the amino acid sequence of SEQ ID NO:30; and
(f) a Heavy Chain CDR3 having the amino acid sequence of SEQ ID NO:39.

Alternatively defined, a further embodiment of the aspect of the invention directed to Antibody D55S, A101T relates to a monoclonal antibody, or epitope binding fragment thereof, comprising
(a) a Light Chain comprising the amino acid sequence of SEQ ID NO:12; and
(b) a Heavy Chain comprising the amino acid sequence of SEQ ID NO:27.

Alternatively defined, a further embodiment of the aspect of the invention directed to Antibody D55S, A101T relates to a monoclonal antibody, or epitope binding fragment thereof, comprising at least one of
(a) a Light Chain CDR1 having the amino acid sequence of SEQ ID NO:3;
(b) a Light Chain CDR2 having the amino acid sequence of SEQ ID NO:4; and
(c) a Light Chain CDR3 having the amino acid sequence of SEQ ID NO:5;
and further comprising
(d) a Heavy Chain CDR1 having the amino acid sequence of SEQ ID NO:6;
(e) a Heavy Chain CDR2 having the amino acid sequence of SEQ ID NO:30; and
(f) a Heavy Chain CDR3 having the amino acid sequence of SEQ ID NO:39.

Combinations of the Heavy Chains Variants and Light Chain Variants are anticipated, such as multiple variants within a Light Chain and/or multiple variants within a Heavy Chain are anticipated, a combination of a singular variant within a Light Chain with a singular or multiple variant within a Heavy Chain, combinations of multiple variants within a Light Chain with multiple variants within a Heavy Chain. The antibody of the invention preferably comprises a Light Chain selected from the group consisting of SEQ ID NO:12 (Light Chain C10-2); SEQ ID NO:16 (Light Chain Variant N32S); SEQ ID NO:17 (Light Chain Variant N32Q); SEQ ID NO:18 (Light Chain Variant N34S); SEQ ID NO:19 Light Chain Variant N34Q); SEQ ID NO:20 (Light Chain Variant N32S, N34S); SEQ ID NO:21 (Light Chain Variant N32Q, N34S); SEQ ID NO:22 (Light Chain Variant N32Q, N34Q); and SEQ ID NO:23 (Light Chain Variant N32S, N34Q); and a Heavy Chain selected from the group consisting of SEQ ID NO:11 (Heavy Chain C10-2); SEQ ID NO:13 (Heavy Chain Variant D55E); SEQ ID NO:14 (Heavy Chain Variant D55Q); SEQ ID NO:15 (Heavy Chain Variant D55S); SEQ ID NO:24 (Heavy Chain Variant A101T); SEQ ID NO:25 (Heavy Chain Variant D55E, A101T); SEQ ID NO:26 (Heavy Chain Variant D55Q, A101T), and SEQ ID NO:27 (Heavy Chain Variant D55S, A101T).

In one embodiment, when the Light Chain is SEQ ID NO:12, the Heavy Chain is selected from the group consisting of SEQ ID NO:13 (Heavy Chain Variant D55E); SEQ ID NO:14 (Heavy Chain Variant D55Q); SEQ ID NO:15 (Heavy Chain Variant D55S); SEQ ID NO:24 (Heavy Chain Variant A101T); SEQ ID NO:25 (Heavy Chain Variant D55E, A101T); SEQ ID NO:26 (Heavy Chain Variant D55Q, A101T), and SEQ ID NO:27 (Heavy Chain Variant D55S, A101T). In an alternative embodiment, when the Heavy Chain is SEQ ID NO:11, the Light Chain is selected from the group consisting of SEQ ID NO:16 (Light Chain Variant N32S); SEQ ID NO:17 (Light Chain Variant N32Q); SEQ ID NO:18 (Light Chain Variant N34S); SEQ ID NO:19 Light Chain Variant N34Q); SEQ ID NO:20 (Light Chain Variant N32S, N34S); SEQ ID NO:21 (Light Chain Variant N32Q, N34S); SEQ ID NO:22 (Light Chain Variant N32Q, N34Q); and SEQ ID NO:23 (Light Chain Variant N32S, N34Q).

The monoclonal antibody, or epitope-binding fragment thereof, suitably comprises
(a) a Light Chain CDR1 comprising the amino acid sequence selected from the group consisting of SEQ ID NO:3, SEQ ID NO:31; SEQ ID NO:32; SEQ ID NO:33; SEQ ID NO:34; SEQ ID NO:35; SEQ ID NO:36; SEQ ID NO:37; and SEQ ID NO:38; (b) a Light Chain CDR2 comprising the amino acid sequence of SEQ ID NO:4; (c) a Light Chain CDR3 comprising the amino acid sequence of SEQ ID NO:5; (d) a Heavy Chain CDR1 comprising the amino acid sequence of SEQ ID NO:6; (e) a Heavy Chain CDR2 comprising the amino acid sequence selected from the group consisting of SEQ ID NO:7; SEQ ID NO:28; SEQ ID NO:29; and SEQ ID NO:30; and (f) a Heavy Chain CDR3 comprising the amino acid sequence selected from the group consisting of SEQ ID NO:8, and SEQ ID NO:39.

Interesting embodiments of combinations of variants include wherein the antibodies are selected from the group consisting of Antibody N32S, A101T; Antibody N32Q, A101T; Antibody N32S, D55E; and Antibody N32Q, D55E, preferably Antibody N32S, A101T. As can be seen from the Examples, Antibody N32S and Antibody N32S, A101T are preferred embodiment.

Altogether, the Examples show that the antibodies of the invention, including C10-2, bind efficiently to AD-P3 antigens coated MSD plates. In comparison, commercial antibodies such as PHF-13, have low binding activity. Furthermore PHF-13 demonstrated substantial higher degree of non-specific binding in comparison to the antibodies of the invention. C10-2 fluid phase inhibition of Ptau antigen capture in C10-2 coated plate is effective (IC50=10-20 nM) whereas PHF-13 is ineffective (IC50=500-1000 nM).

One aspect of the invention is directed to an antibody comprising
(a) a Light Chain CDR1 having the amino acid sequence of SEQ ID NO:3;
(b) a Light Chain CDR2 having the amino acid sequence of SEQ ID NO:4;
(c) a Light Chain CDR3 having the amino acid sequence of SEQ ID NO:5; and
(d) a Heavy Chain selected from the group consisting of SEQ ID NO:11, SEQ ID NO:13, SEQ ID NO:14, SEQ ID NO:15, SEQ ID NO:24, SEQ ID NO:25, SEQ ID NO:26, and SEQ ID NO:27.

One aspect of the invention is directed to an antibody comprising
(a) a Heavy Chain CDR1 having the amino acid sequence of SEQ ID NO:6;
(b) a Heavy Chain CDR2 having the amino acid sequence of SEQ ID NO:7;
(c) a Heavy Chain CDR3 having the amino acid sequence of SEQ ID NO:8; and
(d) a Light Chain selected from the group consisting of SEQ ID NO:16, SEQ ID NO:17, SEQ ID NO:18, SEQ ID NO:19, SEQ ID NO:20, SEQ ID NO:21, SEQ ID NO:22, and SEQ ID NO:23.

The monoclonal antibody, or epitope-binding fragment thereof, of the invention, typically inhibits AD-P3 in the fluid phase inhibition assay such that the signal is reduced by 50% at a concentration of 100 nM or less of the antibody, such as from 10 nM to 100 nM of the antibody, such as at a concentration of 50 nM or less, such as from 10 nM to 50 nM of the antibody. The monoclonal antibody, or epitope-binding fragment thereof, of the invention, typically, according to Western Blot signal of pS396 tau after immunodepletion studies on Alzheimers diseased brain extracts, is capable of removing at least 15% tau phosphorylated at serine 396 from AD brain homogenates at about 75 ng of antibody.

The antibody or epitope-binding fragment thereof is preferably a human or humanized antibody.

The antibodies and epitope-binding fragment thereof mentioned above may, according to one embodiment, further comprise a variant of such light and/or heavy chain CDR1, CDR2 or CDR3 (with no more than 4 amino acid differences, or no more than 3 amino acid differences, or no more than 2 amino acid differences, or no more than 1 amino acid difference.

As can be seen from FIG. 18, HC CDR1, HC CDR2, HC CDR3 and LC CDR3 are, in at least one embodiment, important, for the binding to the 392-398 region of Tau. In one embodiment of the invention, the antibody of the invention, or epitope-binding fragment thereof comprises: In one aspect of the invention, the invention is directed to an antibody or epitope-binding fragments thereof, that forms a hydrophobic pocket formed by L3:H3, L3:F8*, H1:H13, H2:Y1, H2:Y3 with Y394 of the tau peptide. In an embodiment, the invention is directed to an antibody that competes with an antibody further described herein for forming a hydrogen bonding network between solvated $^{\{p\}}$S396 and L3:T4, H1:R10, H1:T11, H3:R1, H3:T3; (*) L3:F8 is the C-terminal flanking framework residue of CDR L3 (see FIG. 11).

As can be seen from the x-ray crystal structure, the antibody of the invention binds with two levels of selectivity. The first level of selectivity is selectivity for hyperphosphorylated pathological, tau and the second level of selectivity is selectivity for a phosphorylated serine residue wherein the phosphate of said phosphorylated serine is hydrogen bonded to the side chain of a tyrosine residue separated by one residues from said phosphorylated serine. Accordingly, an interesting aspect of the invention is directed to a monoclonal antibody, or epitope-binding fragment thereof, selective for an amino acid motif of hyperphosphorylated tau whose motif comprises of a phosphorylated serine residue and tyrosine residue spaced by a single residue. Typically, the amino acid motif has the sequence:

Y-X-S(phosphorylated)-P- wherein Y is tyrosine, X is a naturally occurring amino acid, P is proline and S(phosphorylated) is serine with a phosphorylated hydroxyl side chain.

Similarly, an interesting aspect of the invention is directed to an antibody or epitope-binding fragment thereof which binds to phosphorylated tau, preferably hyperphosphorylated tau, wherein said antibody or epitope-binding fragment thereof is selective for the amino acid residue motif IA, wherein R is a side chain of a naturally occurring amino acid.

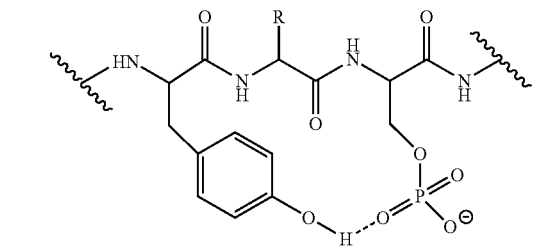

IA

Without being bound to a particular theory, it is believed that the antibody of the invention is selective for amino acid motif IA when said motif is in a conformation adopted by pathological tau. Accordingly, the amino acid motif IA is typically the sequence selectively recognized by the antibody of the invention. Accordingly, an interesting aspect of the invention is directed to an antibody or epitope-binding fragment thereof which binds to phosphorylated tau, preferably hyperphosphorylated tau, wherein said antibody or epitope-binding fragment thereof is selective for the amino acid residue motif IA, wherein R is a side chain of a naturally occurring amino acid.

In a typical embodiment of this aspect of the invention, the invention is directed to an antibody or epitope-binding fragment thereof which binds to phosphorylated tau, preferably hyperphosphorylated tau, wherein said antibody or epitope-binding fragment thereof is selective for the amino acid residue motif IB, wherein R is a side chain of a naturally occurring amino acid such as, but not limited to IC or ID.

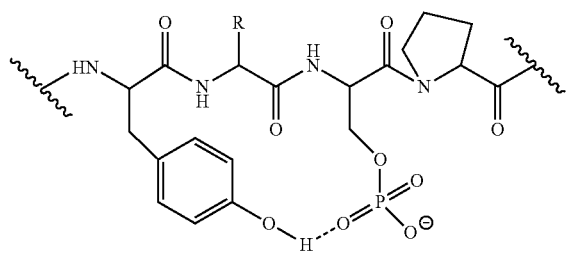

IB

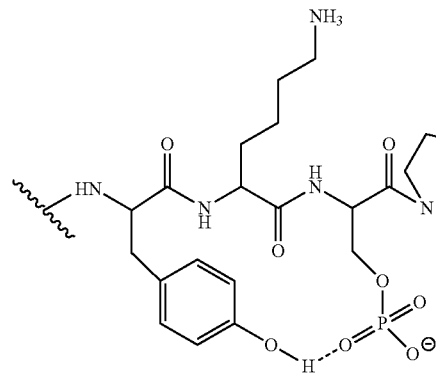

IC

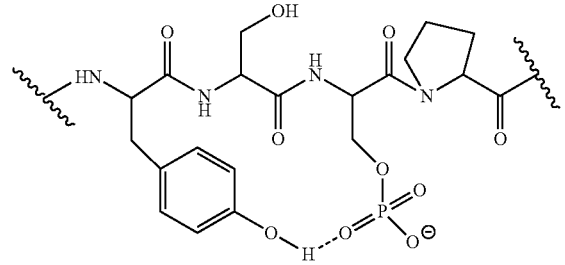

ID

One aspect of the invention, the HC CDR1 region of the antibody of the invention, Asp Arg Thr Ile His (SEQ. ID. NO. 7) interacts with the motifs IA-ID of hyperphosphorylated tau.

As can be seen from FIG. 18, in this aspect of the invention, the presence of two consecutive charged residues, namely aspartic acid and arginine, in the HC CDR1 play a role in hydrogen bonding with the motif within the targeted tau epitope wherein the antibody is selective for an amino acid motif of hyperphosphorylated tau whose motif comprises of a phosphorylated serine residue and tyrosine residue spaced by a single residue. Accordingly, one aspect of the invention is directed to an antibody or epitope-binding fragment thereof which binds to phosphorylated tau, preferably hyperphosphorylated tau, wherein said antibody or epitope-binding fragment thereof is selective for the amino acid residue motif IA-ID wherein the antibody comprises a HC CDR1 region comprises two consecutive charged amino acid residues, such as aspartic acid and arginine. In a further alternative of this aspect of the invention, the antibody or epitope-binding fragment thereof of invention binds to hyperphosphorylated tau, wherein said antibody or epitope-binding fragment thereof is selective an epitope comprising Serine 396 and Tyrosine 394, wherein a P04 group forms a covalent bond with one of said Serine 396 and Tyrosine 394 and a hydrogen bond with the other of Serine 396 and Tyrosine 394 wherein the antibody comprises a HC CDR1 regions comprising two consecutive charged residues, such as aspartic acid and arginine. The charged amino acid residues of the HC CDR1 region may be selected from the group consisting of arginine, lysine, aspartic acid and glutamic acid wherein at least one of said residues is aspartic acid or arginine, preferably wherein one charged residue is arginine and the other is aspartic acid.

In a further embodiment of this aspect of the invention, one or both of the two consecutive charged amino acid residues are flanked by a polar amino acid residue, preferably selected from threonine and tyrosine. Furthermore, one or both of the one or both of the two consecutive charged amino acid residues are flanked by a 3-amino acid residue motif of polar residue-hydrophobic residue-polar residue.

In one embodiment, HC CDR1 comprises the 5-residue motif POLAR AA-HYRDROPHOBIC AA-POLAR AA-CHARGED AA-CHARGED AA, wherein at least one of said residues is aspartic acid or arginine, preferably wherein one charged residue is arginine and the other is aspartic acid. Preferably, the 5-residue motif has the motif POLAR AA-HYRDROPHOBIC AA-POLAR AA-Asp-Arg. More preferably, the 5-residue motif of the HC CDR1 has the sequence TFTDR (SEQ ID NO:58).

It is interesting to note that the HC CDR1 of the antibody of the invention comprises the motif POLAR-HYRDROPHOBIC-POLAR-CHARGED on both sides of the two consecutive charged amino acid residues involved in hydrogen bonding with the phosphate group involved in the electrostatic interaction between S396 and Y394. Accordingly, in the preferred embodiment, the HC CDR1 of invention comprises the palindromic 8-residue motif POLAR AA-HYRDROPHOBIC AA-POLAR AA-CHARGED AA-CHARGED AA-POLAR AA-HYRDROPHOBIC AA-POLAR AA. Preferably, the 8-residue motif of HC CDR1 comprises the motif TFTDR (SEQ ID NO:58)—POLAR AA-HYRDROPHOBIC AA-POLAR AA. More preferably, the 8-residue motif of HC CDR1 comprises the motif TFTDRTIH (SEQ ID NO:59).

In one embodiment, the antibody recognizes an epitope within residue 392-398 of hyperphopshorylated tau comprising Serine 396 and Tyrosine 394 wherein Serine 396 is phosphorylated and wherein the antibody comprises a HC CDR1 region comprising two consecutive charged amino acid residues. In a preferred embodiment, the antibody recognizes an epitope within residue 392-398 of hyperphopshorylated tau comprising Serine 396 and Tyrosine 394 wherein Serine 396 is phosphorylated and wherein the antibody comprise a HC CDR1 region comprises the 5-residue motif POLAR AA-HYRDROPHOBIC AA-POLAR AA-CHARGED AA-CHARGED AA. In a more preferred embodiment, the antibody recognizes an epitope within residue 392-398 of hyperphopshorylated tau comprising Serine 396 and Tyrosine 394 wherein Serine 396 is phosphorylated and wherein the antibody comprises a HC CDR1 region comprising the motif POLAR AA-HYRDROPHOBIC AA-POLAR AA-CHARGED AA-CHARGED AA-POLAR AA-HYRDROPHOBIC AA-POLAR AA.

In a further preferred embodiment, the antibody comprises a HC CDR1 region as defined herein and a HC CDR3 region comprising a 6-residue motif comprising at least two charged residues.

The present invention also provides a method of reducing tau tangle formation in a patient, comprising administering to the patient in need of such treatment, a therapeutically effective amount of an antibody of the invention, or epitope-binding fragments thereof.

One aspect of the invention is directed to a method of treating a taupathy using an antibody of the invention, or epitope-binding fragments thereof. Typically, the taupathy is selected from the group consisting of Alzheimer's disease, Argyrophilic Grain Disease (AGD), Psychosis, particularly Psychosis due to AD or Psychosis in patients with AD, psychiatric symptoms of patients with Lewy body dementia, Progressive Supranuclear Palsy (PSP), Frontotemporal dementia (FTD or variants thereof), TBI (traumatic brain injury, acute or chronic), Corticobasal Degeneration (CBD), Picks Disease, Primary age-related tauopathy (PART), Neurofibrillary tangle-predominant senile dementia, Dementia pugilistica, Chronic traumatic encephalopathy, stroke, stroke recovery, neurodegeneration in relation to Parkinson's disease, Parkinsonism linked to chromosome, Lytico-Bodig disease (Parkinson-dementia complex of Guam), Ganglioglioma and gangliocytoma, Meningioangiomatosis, Postencephalitic parkinsonism, Subacute sclerosing panencephalitis, Huntington's disease, lead encephalopathy, tuberous sclerosis, Hallervorden-Spatz disease and lipofuscinosis. More typically, the taupathy is selected from the group consisting of Alzheimer's disease, Argyrophilic Grain Disease (AGD), Psychosis, particularly Psychosis due to AD or Psychosis in patients with AD, psychiatric symptoms of patients with Lewy body dementia, Progressive Supranuclear Palsy (PSP), Frontotemporal dementia (FTD or variants thereof), TBI (traumatic brain injury, acute or chronic), Corticobasal Degeneration (CBD), and Picks Disease. In particular, the tauopathies may be selected from Alzheimer's disease, Argyrophilic Grain Disease (AGD), Psychosis due to AD or Psychosis in patients with AD, and psychiatric symptoms of patients with Lewy body dementia.

Accordingly, a further aspect of the invention is directed to an antibody of the invention or epitope-binding fragments thereof, for use in the treatment of a taupathy. Typically, the taupathy is selected from the group consisting of Alzheimer's disease, Argyrophilic Grain Disease (AGD), Psychosis, particularly Psychosis due to AD or Psychosis in patients with AD, psychiatric symptoms of patients with Lewy body dementia, Progressive Supranuclear Palsy (PSP), Frontotemporal dementia (FTD or variants thereof), TBI (traumatic brain injury, acute or chronic), Corticobasal Degeneration (CBD), Picks Disease, Primary age-related tauopathy (PART), Neurofibrillary tangle-predominant senile dementia, Dementia pugilistica, Chronic traumatic encephalopathy, stroke, stroke recovery, neurodegeneration in relation to Parkinson's disease, Parkinsonism linked to chromosome, Lytico-Bodig disease (Parkinson-dementia complex of Guam), Ganglioglioma and gangliocytoma, Meningioangiomatosis, Postencephalitic parkinsonism, Subacute sclerosing panencephalitis, Huntington's disease, lead encephalopathy, tuberous sclerosis, Hallervorden-Spatz disease and lipofuscinosis. More typically, the taupathy is selected from the group consisting of Alzheimer's disease, Argyrophilic Grain Disease (AGD), Psychosis, particularly Psychosis due to AD or Psychosis in patients with AD, apathy due to AD or apathy in patients with AD, psychiatric symptoms of patients with Lewy body dementia, Progressive Supranuclear Palsy (PSP), Frontotemporal dementia (FTD or variants thereof), TBI (traumatic brain injury, acute or chronic), Corticobasal Degeneration (CBD), and Picks Disease. In particular, the tauopathies may be selected from Alzheimer's disease, Argyrophilic Grain Disease (AGD), Psychosis due to AD or Psychosis in patients with AD, apathy due to AD or apathy in patients with AD, and psychiatric symptoms of patients with Lewy body dementia.

One aspect of the invention is directed to a therapy comprising the administration of i) a Tau antibody and ii) a compound selected from the group consisting of
 a) a BACE inhibitor;
 b) a compound useful in active or passive Tau immunotherapy;
 c) a compound useful in active or passive As peptide immunotherapy;
 d) an NMDA receptor antagonists;
 e) a further Tau protein aggregation inhibitor;
 e) an acetylcholine esterase inhibitor;
 f) an antiepileptic;
 g) an anti-inflammatory drug; and
 h) an SSRI.

A further aspect of the invention is directed to a composition comprising i) a Tau antibody and ii) a compound selected from the group consisting of
  a) a BACE inhibitor;
  b) a compound useful in active or passive Tau immunotherapy;
  c) a compound useful in active or passive As peptide immunotherapy;
  d) an NMDA receptor antagonists;
  e) a further Tau protein aggregation inhibitor;
  e) an acetylcholine esterase inhibitor;
  f) an antiepileptic;
  g) an anti-inflammatory drug; and
  h) an SSRI.

A further aspect of the invention is directed to a kit comprising i) a composition comprising a Tau antibody and ii) a composition a compound selected from the group consisting of
  a) a BACE inhibitor;
  b) a compound useful in active or passive Tau immunotherapy;
  c) a compound useful in active or passive As peptide immunotherapy;
  d) an NMDA receptor antagonists;
  e) a further Tau protein aggregation inhibitor;
  f) an acetylcholine esterase inhibitor;
  g) an antiepileptic;
  h) an anti-inflammatory drug; and
  i) an antidepressant.

a) Tau Antibody Combined with a BACE 1 Inhibitor

In the therapy, composition or kit of the invention, a tau antibody may be combined with a BACE 1 inhibitor. The BACE1 inhibitor may be a small molecule BACE I inhibitor such as LY2886721, MK-8931, AZD3293, or E2609.

In a further embodiment, the BACE 1 inhibitor is of the formula I

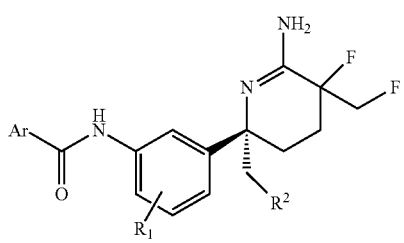

[I]

wherein Ar is selected from the group consisting of phenyl, pyridyl, pyrimidyl, pyrazinyl, imidazolyl, pyrazolyl, thiazolyl, oxazolyl, isoxazolyl, and wherein Ar is optionally substituted with one or more substituents selected from halogen, CN, C1-C6 alkyl, C2-C6 alkenyl, C2-C6 alkynyl, C1-C6 fluoroalkyl or C1-C6 alkoxy; and R1 is one or more hydrogen, halogen, C1-C3 fluoroalkyl or C1-C3 alkyl; and R2 presents hydrogen or fluoro.

Exemplary compounds of Formula I include

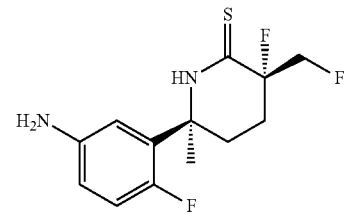 [SMILES: C[C@@]1(c2cc(N)ccc2F)CC[C@](F)(CF)C(=S)N1]

(3S,6S)-6-(5-amino-2-fluorophenyl)-3-fluoro-3-(fluoromethyl)-6-methylpiperidine-2-thione

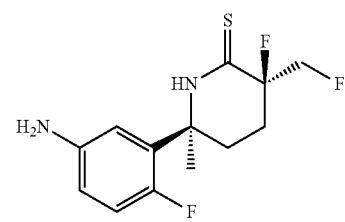 [SMILES: C[C@@]1(c2cc(N)ccc2F)CC[C@@](F)(CF)C(=S)N1]

(3R,6S)-6-(5-amino-2-fluorophenyl)-3-fluoro-3-(fluoromethyl)-6-methylpiperidine-2-thione

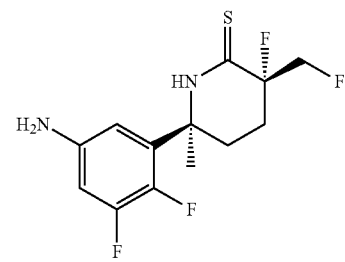 [SMILES: C[C@@]1(c2cc(N)cc(F)c2F)CC[C@](F)(CF)C(=S)N1]

(3S,6S)-6-(5-amino-2,3-difluorophenyl)-3-fluoro-3-(fluoromethyl)-6-methylpiperidine-2-thione

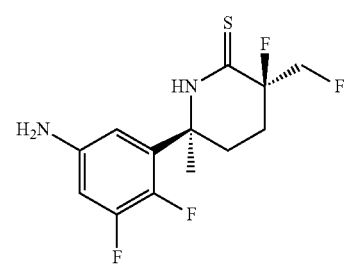 [SMILES: C[C@@]1(c2cc(N)cc(F)c2F)CC[C@@](F)(CF)C(=S)N1]

(3R,6S)-6-(5-amino-2,3-difluorophenyl)-3-fluoro-3-(fluoromethyl)-6-methylpiperidine-2-thione

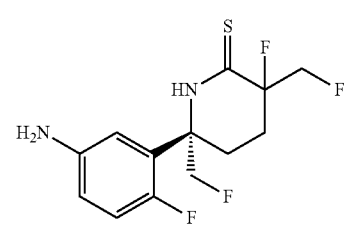 [SMILES: Nc1ccc(F)c([C@]2(CF)CCC(F)(CF)C(=S)N2)c1]

(6S)-6-(5-amino-2-fluorophenyl)-3-fluoro-3,6-bis(fluoromethyl)piperidine-2-thione.

Furthermore, a suitable BACE 1 inhibitor may be of Formula II

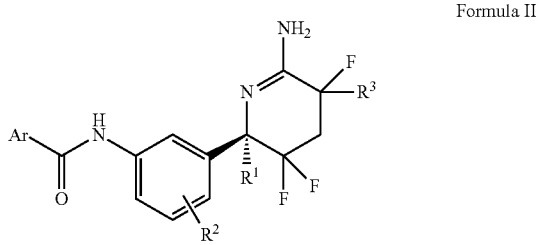

Formula II wherein Ar is selected from the group consisting of phenyl, pyridyl, pyrimidyl, pyrazinyl, imidazolyl, pyrazolyl, 1,2,4-triazolyl, thiophenyl, thiazolyl, oxazolyl, isoxazolyl, 1,3,4-thiadiazolyl, isothiazolyl, 1,3,4-oxadiazolyl, 1,2,4-oxadiazolyl, furazanyl and 1,2,4-thiadiazolyl and where the Ar is optionally substituted with one or more halogen, CN, $C_1$-$C_6$ alkyl, $C_2$-$C_6$ alkenyl, $C_2$-$C_6$ alkynyl, $C_1$-$C_6$ fluoroalkyl or $C_1$-$C_6$ alkoxy; $R^1$ is $C_1$-$C_3$ alkyl or $C_1$-$C_3$ fluoroalkyl; $R^2$ is hydrogen, halogen, $C_1$-$C_3$ fluoroalkyl or $C_1$-$C_3$ alkyl; and $R^3$ is $C_1$-$C_3$ alkyl.

Exemplary compounds of the BACE 1 inhibitor of Formula II include the compounds selected from the group consisting of: N-(3-((2R,5S)-6-amino-3,3,5-trifluoro-2,5-dimethyl-2,3,4,5-tetrahydropyridin-2-yl)-4 fluorophenyl)-5-fluoropicolinamide; N-(3-((2R,5S)-6-amino-3,3,5-trifluoro-2,5-dimethyl-2,3,4,5-tetrahydropyridin-2-yl)-4fluorophenyl)-5-methoxypyrazine-2-carboxamide; N-(3-((2R,5S)-6-amino-3,3,5-trifluoro-2,5-dimethyl-2,3,4,5-tetrahydropyridin-2-yl)-4-fluorophenyl)-5-methoxypicolinamide; N-(3-((2R,5S)-6-amino-3,3,5-trifluoro-2,5-dimethyl-2,3,4,5-tetrahydropyridin-2-yl)-4fluorophenyl)-5-cyano-3-methylpicolinamide; and N-(3-((2R,5R)-6-amino-3,3,5-trifluoro-2,5-dimethyl-2,3,4,5-tetrahydropyridin-2-yl)-4 fluorophenyl)-5-(difluoromethyl)pyrazine-2-carboxamide.

Other BACE inhibitors may be selected from the below formula

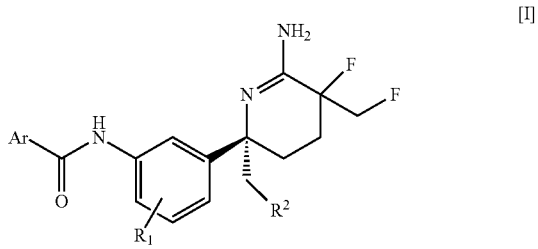

[I]

wherein Ar is selected from the group consisting of phenyl, pyridyl, pyrimidyl, pyrazinyl, imidazolyl, pyrazolyl, thiazolyl, oxazolyl, isoxazolyl, and wherein Ar is optionally substituted with one or more substituents selected from halogen, CN, $C_1$-$C_6$ alkyl, $C_2$-$C_6$ alkenyl, $C_2$-$C_6$ alkynyl, $C_1$-$C_6$ fluoroalkyl or $C_1$-$C_6$ alkoxy; and $R^1$ is one or more hydrogen, halogen, $C_1$-$C_3$ fluoroalkyl or $C_1$-$C_3$ alkyl;

$R^2$ presents hydrogen or fluoro;

or a pharmaceutically acceptable salt thereof.

For example, compounds such as
N-(3-((2S,5S)-6-amino-5-fluoro-5-(fluoromethyl)-2-methyl-2,3,4,5-tetrahydropyridin-2-yl)-4-fluorophenyl)-5-methoxypicolinamide;
N-(3-((2S,5S)-6-amino-5-fluoro-5-(fluoromethyl)-2-methyl-2,3,4,5-tetrahydropyridin-2-yl)-4-fluorophenyl)-5-(methoxy-d3)picolinamide;
N-(3-((2S,5S)-6-amino-5-fluoro-5-(fluoromethyl)-2-methyl-2,3,4,5-tetrahydropyridin-2-yl)-4-fluorophenyl)-5-cyano-3-methylpicolinamide;
N-(3-((2S,5S)-6-amino-5-fluoro-5-(fluoromethyl)-2-methyl-2,3,4,5-tetrahydropyridin-2-yl)-4-fluorophenyl)-5-chloropicolinamide;
N-(3-((2S,5S)-6-amino-5-fluoro-5-(fluoromethyl)-2-methyl-2,3,4,5-tetrahydropyridin-2-yl)-4-fluorophenyl)-5-methoxypyrazine-2-carboxamide;
N-(3-((2S,5S)-6-amino-5-fluoro-5-(fluoromethyl)-2-methyl-2,3,4,5-tetrahydropyridin-2-yl)-4-fluorophenyl)-2-methyloxazole-4-carboxamide;
N-(3-((2S,5S)-6-amino-5-fluoro-5-(fluoromethyl)-2-methyl-2,3,4,5-tetrahydropyridin-2-yl)-4-fluorophenyl)-4-bromo-1-methyl-1H-imidazole-2-carboxamide;
N-(3-((2S,5S)-6-amino-5-fluoro-5-(fluoromethyl)-2-methyl-2,3,4,5-tetrahydropyridin-2-yl)-4-fluorophenyl)-4-methylthiazole-2-carboxamide;
N-(3-((2S,5S)-6-amino-5-fluoro-5-(fluoromethyl)-2-methyl-2,3,4,5-tetrahydropyridin-2-yl)-4-fluorophenyl)-2-(difluoromethyl)oxazole-4-carboxamide;
N-(3-((2S,5S)-6-amino-5-fluoro-5-(fluoromethyl)-2-methyl-2,3,4,5-tetrahydropyridin-2-yl)-4-fluorophenyl)-1-(difluoromethyl)-1H-pyrazole-3-carboxamide;
N-(3-((2S,5S)-6-amino-5-fluoro-5-(fluoromethyl)-2-methyl-2,3,4,5-tetrahydropyridin-2-yl)-4-fluorophenyl)-5-(difluoromethyl)pyrazine-2-carboxamide;
N-(3-((2S,5S)-6-amino-5-fluoro-5-(fluoromethyl)-2-methyl-2,3,4,5-tetrahydropyridin-2-yl)-4-fluorophenyl)-4-chlorobenzamide;
N-(3-((2S,5S)-6-amino-5-fluoro-5-(fluoromethyl)-2-methyl-2,3,4,5-tetrahydropyridin-2-yl)-4-fluorophenyl)-5-fluoropicolinamide;
N-(3-((2S,5R)-6-amino-5-fluoro-5-(fluoromethyl)-2-methyl-2,3,4,5-tetrahydropyridin-2-yl)-4-fluorophenyl)-5-methoxypicolinamide;
N-[3-[(2S,5S)-6-amino-5-fluoro-5-(fluoromethyl)-2-methyl-3,4-dihydropyridin-2-yl]-4,5-difluoro-phenyl]-5-fluoro-pyridine-2-carboxamide;
N-[3-[(2S,5S)-6-amino-5-fluoro-5-(fluoromethyl)-2-methyl-3,4-dihydropyridin-2-yl]-4,5-difluoro-phenyl]-5-methoxy-pyridine-2-carboxamide;
N-[3-[(2S,5S)-6-amino-5-fluoro-5-(fluoromethyl)-2-methyl-3,4-dihydropyridin-2-yl]-4,5-difluoro-phenyl]-5-methoxy-pyrazine-2-carboxamide;
N-[3-[(2S,5R)-6-amino-5-fluoro-5-(fluoromethyl)-2-methyl-3,4-dihydropyridin-2-yl]-4,5-difluoro-phenyl]-5-fluoro-pyridine-2-carboxamide;
N-[3-[(2S,5R)-6-amino-5-fluoro-5-(fluoromethyl)-2-methyl-3,4-dihydropyridin-2-yl]-4,5-difluoro-phenyl]-5-methoxy-pyridine-2-carboxamide;
N-[3-[(2S,5R)-6-amino-5-fluoro-5-(fluoromethyl)-2-methyl-3,4-dihydropyridin-2-yl]-4,5-difluoro-phenyl]-5-methoxy-pyrazine-2-carboxamide;
N-[3-[(2S,5S)-6-amino-5-fluoro-2,5-bis(fluoromethyl)-3,4-dihydropyridin-2-yl]-4-fluoro-phenyl]-5-fluoro-pyridine-2-carboxamide;
N-[3-[(2S,5S)-6-amino-5-fluoro-2,5-bis(fluoromethyl)-3,4-dihydropyridin-2-yl]-4-fluoro-phenyl]-5-methoxy-pyridine-2-carboxamide;

N-[3-[(2S,5S)-6-amino-5-fluoro-2,5-bis(fluoromethyl)-3,4-dihydropyridin-2-yl]-4-fluoro-phenyl]-5-methoxy-pyrazine-2-carboxamide;

N-[3-[(2S,5R)-6-amino-5-fluoro-2,5-bis(fluoromethyl)-3,4-dihydropyridin-2-yl]-4-fluoro-phenyl]-5-fluoro-pyridine-2-carboxamide;

N-[3-[(2S,5R)-6-amino-5-fluoro-2,5-bis(fluoromethyl)-3,4-dihydropyridin-2-yl]-4-fluoro-phenyl]-5-methoxy-pyridine-2-carboxamide and N-[3-[(2S,5R)-6-amino-5-fluoro-2,5-bis(fluoromethyl)-3,4-dihydropyridin-2-yl]-4-fluoro-phenyl]-5-methoxy-pyrazine-2-carboxamide;

or a pharmaceutically acceptable salt of said compounds.

Other BACE inhibitors may be of the below formula

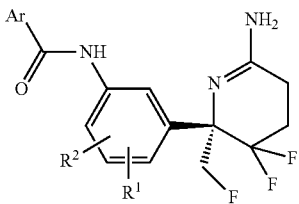

Formula I wherein Ar is selected from the group consisting of phenyl, pyridyl, pyrimidyl, pyrazinyl, imidazolyl, pyrazolyl, oxazolyl, thiazolyl and isoxazolyl, and where the Ar is optionally substituted with one or more halogen, CN, $C_1$-$C_6$ alkyl, $C_2$-$C_6$ alkenyl, $C_2$-$C_6$ alkynyl, $C_1$-$C_6$ fluoroalkyl or $C_1$-$C_6$ alkoxy; and R1 and R2 independently are hydrogen, halogen, $C_1$-$C_3$ fluoroalkyl or $C_1$-$C_3$ alkyl;

or a pharmaceutically acceptable salt thereof.

For example, compounds such as (S)-N-(3-(6-amino-3,3-difluoro-2-(fluoromethyl)-2,3,4,5-tetrahydropyridin-2-yl)-4-fluorophenyl)-5-chloropicolinamide (S)-N-(3-(6-amino-3,3-difluoro-2-(fluoromethyl)-2,3,4,5-tetrahydropyridin-2-yl)-4-fluorophenyl)-5-fluoropicolinamide (S)-N-(3-(6-amino-3,3-difluoro-2-(fluoromethyl)-2,3,4,5-tetrahydropyridin-2-yl)-4-fluorophenyl)-5-methoxypyrazine-2-carboxamide (S)-N-(3-(6-amino-3,3-difluoro-2-(fluoromethyl)-2,3,4,5-tetrahydropyridin-2-yl)-4-fluorophenyl)-1-(difluoromethyl)-1H-pyrazole-3-carboxamide (S)-N-(3-(6-amino-3,3-difluoro-2-(fluoromethyl)-2,3,4,5-tetrahydropyridin-2-yl)-4-fluorophenyl)-2-(difluoromethyl)oxazole-4-carboxamide (S)-N-(3-(6-amino-3,3-difluoro-2-(fluoromethyl)-2,3,4,5-tetrahydropyridin-2-yl)-4-fluorophenyl)-5-cyanopicolinamide (S)-N-(3-(6-amino-3,3-difluoro-2-(fluoromethyl)-2,3,4,5-tetrahydropyridin-2-yl)-4-fluorophenyl)-2-methyloxazole-4-carboxamide (S)-N-(3-(6-amino-3,3-difluoro-2-(fluoromethyl)-2,3,4,5-tetrahydropyridin-2-yl)-4-fluorophenyl)-5-methoxypyrimidine-2-carboxamide (S)-N-(3-(6-amino-3,3-difluoro-2-(fluoromethyl)-2,3,4,5-tetrahydropyridin-2-yl)-4-fluorophenyl)-5-(difluoromethyl)pyrazine-2-carboxamide (S)-N-(3-(6-amino-3,3-difluoro-2-(fluoromethyl)-2,3,4,5-tetrahydropyridin-2-yl)-4,5-difluorophenyl)-2-methyloxazole-4-carboxamide (S)-N-(3-(6-amino-3,3-difluoro-2-(fluoromethyl)-2,3,4,5-tetrahydropyridin-2-yl)-4,5-difluorophenyl)-5-methoxypyrazine-2-carboxamide (S)-N-(3-(6-amino-3,3-difluoro-2-(fluoromethyl)-2,3,4,5-tetrahydropyridin-2-yl)-4,5-difluorophenyl)-5-fluoropicolinamide (S)-N-(3-(6-amino-3,3-difluoro-2-(fluoromethyl)-2,3,4,5-tetrahydropyridin-2-yl)-4,5-difluorophenyl)-5-chloropicolinamide (S)-N-(3-(6-amino-3,3-difluoro-2-(fluoromethyl)-2,3,4,5-tetrahydropyridin-2-yl)-4,5-difluorophenyl)-5-cyanopicolinamide (S)-N-(3-(6-amino-3,3-difluoro-2-(fluoromethyl)-2,3,4,5-tetrahydropyridin-2-yl)-4,5-difluorophenyl)-5-methoxypicolinamide (S)-N-(3-(6-amino-3,3-difluoro-2-(fluoromethyl)-2,3,4,5-tetrahydropyridin-2-yl)-4,5-difluorophenyl)-5-(methoxy-d3)picolinamide (S)-N-(3-(6-amino-3,3-difluoro-2-(fluoromethyl)-2,3,4,5-tetrahydropyridin-2-yl)-4,5-difluorophenyl)-5-cyano-3-methylpicolinamide (S)-N-(3-(6-amino-3,3-difluoro-2-(fluoromethyl)-2,3,4,5-tetrahydropyridin-2-yl)-4-fluorophenyl)-5-(methoxy-d3)picolinamide(S)-N-(3-(6-amino-3,3-difluoro-2-(fluoromethyl)-2,3,4,5-tetrahydropyridin-2-yl)-4-fluorophenyl)-5-bromopicolinamide (S)-N-(3-(6-amino-3,3-difluoro-2-(fluoromethyl)-2,3,4,5-tetrahydropyridin-2-yl)-4-fluorophenyl)-5-bromopicolinamide or a pharmaceutically acceptable salt of said compounds.

Other BACE compounds may be from the below formula

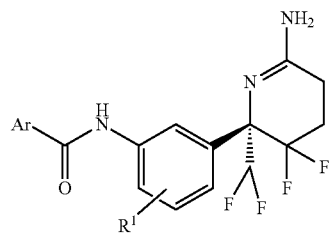

Formula I wherein Ar is selected from the group consisting of phenyl, pyridyl, pyrimidyl, pyrazinyl, imidazolyl, pyrazolyl, thiazolyl, oxazolyl, isoxazolyl, and where the Ar is optionally substituted with one or more substituent selected from halogen, CN, C1-C6 alkyl, C2-C6 alkenyl, C2-C6 alkynyl, C1-C6 fluoroalkyl or C1-C6 alkoxy; and R1 is hydrogen, halogen, C1-C3 fluoroalkyl or C1-C3 alkyl;

or a pharmaceutically acceptable salt thereof.

The compounds may be (S)-N-(3-(6-amino-2-(difluoromethyl)-3,3-difluoro-2,3,4,5-tetrahydropyridin-2-yl)-4-fluorophenyl)-5-chloropicolinamide, (S)-N-(3-(6-amino-2-(difluoromethyl)-3,3-difluoro-2,3,4,5-tetrahydropyridin-2-yl)-4-fluorophenyl)-5-fluoropicolinamide, (S)-N-(3-(6-amino-2-(difluoromethyl)-3,3-difluoro-2,3,4,5-tetrahydropyridin-2-yl)-4-fluorophenyl)-5-methoxypyrazine-2-carboxamide, (S)-N-(3-(6-amino-2-(difluoromethyl)-3,3-difluoro-2,3,4,5-tetrahydropyridin-2-yl)-4-fluorophenyl)-2-methyloxazole-4-carboxamide, (S)-N-(3-(6-amino-2-(difluoromethyl)-3,3-difluoro-2,3,4,5-tetrahydropyridin-2-yl)-4-fluorophenyl)-5-methoxypicolinamide,
(S)-N-(3-(6-amino-2-(difluoromethyl)-3,3-difluoro-2,3,4,5-tetrahydropyridin-2-yl)-4-fluorophenyl)-5-(difluoromethyl)pyrazine-2-carboxamide,
(S)-N-(3-(6-amino-2-(difluoromethyl)-3,3-difluoro-2,3,4,5-tetrahydropyridin-2-yl)-4-fluorophenyl)-5-cyanopicolinamide,
(S)-N-(3-(6-amino-2-(difluoromethyl)-3,3-difluoro-2,3,4,5-tetrahydropyridin-2-yl)-4-fluorophenyl)-4-methylthiazole-2-carboxamide,
(S)-N-(3-(6-amino-2-(difluoromethyl)-3,3-difluoro-2,3,4,5-tetrahydropyridin-2-yl)-4-fluorophenyl)-5-methoxypyrimidine-2-carboxamide,
(S)-N-(3-(6-amino-2-(difluoromethyl)-3,3-difluoro-2,3,4,5-tetrahydropyridin-2-yl)-4-fluorophenyl)-5-methoxy-3-methylpyrazine-2-carboxamide,
(S)-N-(3-(6-amino-2-(difluoromethyl)-3,3-difluoro-2,3,4,5-tetrahydropyridin-2-yl)-4-fluorophenyl)-5-cyano-3-methylpicolinamide,
(S)-N-(3-(6-amino-2-(difluoromethyl)-3,3-difluoro-2,3,4,5-tetrahydropyridin-2-yl)-4-fluorophenyl)-5-bromopicolinamide,
(S)-N-(3-(6-amino-2-(difluoromethyl)-3,3-difluoro-2,3,4,5-tetrahydropyridin-2-yl)-4-fluorophenyl)-5-(methoxy-d3)picolinamide and
(S)-N-(3-(6-amino-2-(difluoromethyl)-3,3-difluoro-2,3,4,5-tetrahydropyridin-2-yl)-4-fluorophenyl)-5-(methoxy-d3)pyrazine-2-carboxamide;
or a pharmaceutically acceptable salt of said compounds. Other BACE inhibitors may be of the below formula

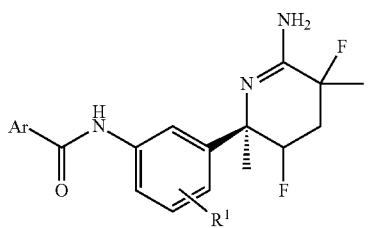

wherein Ar is selected from the group consisting of phenyl, pyridyl, pyrimidyl, pyrazinyl, imidazolyl, pyrazolyl, thiazolyl, oxazolyl, isoxazolyl, and where the Ar is optionally substituted with one or more substituent selected from halogen, CN, C1-C6 alkyl, C2-C6 alkenyl, C2-C6 alkynyl, C1-C6 fluoroalkyl or C1-C6 alkoxy; and
R1 is one or more hydrogen, halogen, C1-C3 fluoroalkyl or C1-C3 alkyl;
or a pharmaceutically acceptable salt thereof.
The compound may be
N-(3-((2R,3S,5S)-6-amino-3,5-difluoro-2,5-dimethyl-2,3,4,5-tetrahydropyridin-2-yl)-4-fluoro-phenyl)-5-fluoropicolinamide,
N-(3-((2R,3S,5S)-6-amino-3,5-difluoro-2,5-dimethyl-2,3,4,5-tetrahydropyridin-2-yl)-4-fluoro-phenyl)-5-methoxypyrazine-2-carboxamide,
N-(3-((2R,3S,5S)-6-amino-3,5-difluoro-2,5-dimethyl-2,3,4,5-tetrahydropyridin-2-yl)-4-fluoro-phenyl)-5-methoxypicolinamide,
N-(3-((2R,3S,5R)-6-amino-3,5-difluoro-2,5-dimethyl-2,3,4,5-tetrahydropyridin-2-yl)-4-fluoro-phenyl)-5-fluoropicolinamide,
N-(3-((2R,3S,5R)-6-amino-3,5-difluoro-2,5-dimethyl-2,3,4,5-tetrahydropyridin-2-yl)-4-fluoro-phenyl)-5-methoxypyrazine-2-carboxamide,
N-(3-((2R,3S,5R)-6-amino-3,5-difluoro-2,5-dimethyl-2,3,4,5-tetrahydropyridin-2-yl)-4-fluoro-phenyl)-2-methyloxazole-4-carboxamide,
N-(3-((2R,3S,5R)-6-amino-3,5-difluoro-2,5-dimethyl-2,3,4,5-tetrahydropyridin-2-yl)-4-fluoro-phenyl)-5-methoxypicolinamide,
N-(3-((2R,3S,5R)-6-amino-3,5-difluoro-2,5-dimethyl-2,3,4,5-tetrahydropyridin-2-yl)-4-fluorophenyl)-5-(methoxy-d3)picolinamide,
N-(3-((2R,3S,5R)-6-amino-3,5-difluoro-2,5-dimethyl-2,3,4,5-tetrahydropyridin-2-yl)-4-fluorophenyl)-5-chloropicolinamide,
N-(3-((2R,3S,5R)-6-amino-3,5-difluoro-2,5-dimethyl-2,3,4,5-tetrahydropyridin-2-yl)-4-fluorophenyl)-1-methyl-1H-imidazole-2-carboxamide,
N-(3-((2R,3S,5R)-6-amino-3,5-difluoro-2,5-dimethyl-2,3,4,5-tetrahydropyridin-2-yl)-4-fluorophenyl)-5-(trifluoromethyl)pyrazine-2-carboxamide,
N-(3-((2R,3S,5R)-6-amino-3,5-difluoro-2,5-dimethyl-2,3,4,5-tetrahydropyridin-2-yl)-4-fluorophenyl)-4-methylthiazole-2-carboxamide,
N-(3-((2R,3S,5R)-6-amino-3,5-difluoro-2,5-dimethyl-2,3,4,5-tetrahydropyridin-2-yl)-4-fluorophenyl)-2-(difluoromethyl)oxazole-4-carboxamide,
N-(3-((2R,3S,5R)-6-amino-3,5-difluoro-2,5-dimethyl-2,3,4,5-tetrahydropyridin-2-yl)-4-fluorophenyl)-1-(difluoromethyl)-1H-pyrazole-3-carboxamide,
N-(3-((2R,3S,5R)-6-amino-3,5-difluoro-2,5-dimethyl-2,3,4,5-tetrahydropyridin-2-yl)-4-fluorophenyl)-5-(difluoromethyl)pyrazine-2-carboxamide,
N-(3-((2R,3S,5R)-6-amino-3,5-difluoro-2,5-dimethyl-2,3,4,5-tetrahydropyridin-2-yl)-4-fluorophenyl)-4-chlorobenzamide,
N-(3-((2R,3S,5R)-6-amino-3,5-difluoro-2,5-dimethyl-2,3,4,5-tetrahydropyridin-2-yl)-4-fluorophenyl)-5-cyanopicolinamide,
N-(3-((2R,3S,5R)-6-amino-3,5-difluoro-2,5-dimethyl-2,3,4,5-tetrahydropyridin-2-yl)-4,5-difluorophenyl)-5-(methoxy-d3)picolinamide,
N-(3-((2R,3S,5S)-6-amino-3,5-difluoro-2,5-dimethyl-2,3,4,5-tetrahydropyridin-2-yl)-4-fluorophenyl)-5-(methoxy-d3)picolinamide,
N-(3-((2R,3S,5S)-6-amino-3,5-difluoro-2,5-dimethyl-2,3,4,5-tetrahydropyridin-2-yl)-4-fluorophenyl)-5-(methoxy-d3)pyrazine-2-carboxamide,
N-(3-((2R,3S,5S)-6-amino-3,5-difluoro-2,5-dimethyl-2,3,4,5-tetrahydropyridin-2-yl)-4-fluorophenyl)-5-cyano-3-methylpicolinamide,
N-(3-((2R,3S,5S)-6-amino-3,5-difluoro-2,5-dimethyl-2,3,4,5-tetrahydropyridin-2-yl)-4,5-difluorophenyl)-5-(methoxy-d3)picolinamide,
N-(3-((2R,3R,5S)-6-amino-3,5-difluoro-2,5-dimethyl-2,3,4,5-tetrahydropyridin-2-yl)-4-fluorophenyl)-5-(methoxy-d3)picolinamide,
N-(3-((2R,3S,5S)-6-amino-3,5-difluoro-2,5-dimethyl-2,3,4,5-tetrahydropyridin-2-yl)-4-fluorophenyl)-5-bromopicolinamide
or a pharmaceutically acceptable salt of said compounds.
b) Tau Antibody Combined with a N3PGLU ABETA Antibody
In the therapy, composition or kit of the invention, a tau antibody may be combined with a N3PGLU ABETA antibody.

c) Tau Antibody Combined with a Compound Useful in Active or Passive as Peptide Immunotherapy In the therapy, composition or kit of the invention, a tau antibody may be combined with a compound useful in active or passive As peptide immunotherapy d) Tau Antibody Combined with an NMDA Receptor Antagonist In the therapy, composition or kit of the invention, a tau antibody may be combined with an NMDA receptor antagonists. The NMDA receptor antagonist may be selected from the group consisting of, Memantine, Namenda, Namzaric (memantine/donepezil), and generic forms thereof. The NMDA receptor antagonist may be selected from an antipsychotic. Presynaptic neurons prohibit excessive glutamate release via negative feedback mechanisms, but such mechanisms are compromised under conditions of cellular stress, such as AD. Excess glutamate in the synaptic cleft causes postsynaptic calcium channels to be continually opened, leading to increased intracellular calcium levels within neurons, causing severe neuronal damage and/or death. By antagonizing the NMDA receptor under conditions of excessive calcium inflow, antipsychotic reduce the excessive influx of calcium into neurons, decreasing cellular damage and improving normal neuronal signaling and thus cognitive function.

e) Tau Antibody Combined with a Further Tau Protein Aggregation Inhibitor;

In the therapy, composition or kit of the invention, a tau antibody may be combined with a Tau protein aggregation inhibitor.

f) Tau Antibody Combined with an Acetylcholine Esterase Inhibitor

In the therapy, composition or kit of the invention, a tau antibody may be combined with an acetylcholine esterase inhibitor (AChEI). AChEIs are often used as a first-line treatment for cognitive symptoms in mild to moderate AD. AChEIs are also used broadly to treat moderate to severe AD, including donepezil which is approved for this subpopulation. AChEIs alleviate the cholinergic deficit observed in AD patients, and improve a patient's ability to perform daily activities. In one embodiment, the invention comprises a therapy comprising a tau antibody as define herein, and an acetylcholine esterase inhibitor In one embodiment, the AChEI is selected from the group consisting of Donepezil, Galantamine and Rivastigmine. The AChEI may be an oral tablet, a jelly, a syrup, or the form of oral solution formulation. The AChEI may be also be a patch for transdermal administration.

g) Tau Antibody Combined with an Antiepileptic;

In the therapy, composition or kit of the invention, a tau antibody may be combined with an antiepileptic.

h) Tau Antibody Combined with an Anti-Inflammatory Drug;

In the therapy, composition or kit of the invention, a tau antibody may be combined with an anti-inflammatory drug.

i) Tau Antibody Combined with an Antidepressant

In the therapy, composition or kit of the invention, a tau antibody may be combined with an antidepressant.

Depression is a common early comorbid symptom of AD dementia. Tricyclic antidepressants were once the preferred treatment for depressive symptoms in AD, but SSRIs have largely replaced these agents. In one embodiment, Escitalopram is the antidepressant since it is frequently prescribed for AD because of its favorable sideeffect profile and minimal drug interactions. In a further embodiment, citalopram or sertraline is the antidepressant as they are also frequently used. In a further embodiment, vortioxetine is the antidepressant since it is related to improvement in cognitive performance and imaging evidence of neural efficacy in patients suffering from MDD. The antidepressant may be selected from the group consisting of Escitalopram, Sertraline, Citalopram, Paroxetine, Fluoxetine, Venlafaxine, Trazodone, Mirtazapine, Vortioxetine and generic forms thereof.

A further aspect of the invention is directed to an antibody of the invention or epitope-binding fragments thereof, in a composition together with a pharmaceutically acceptable carrier, diluent, adjuvant and/or stabilizer. The antibodies of the invention, or epitope-binding fragments thereof, may be used in therapy for the treatment of a taupathy. Typically, the taupathy is selected from the group consisting of Alzheimer's disease, Argyrophilic Grain Disease (AGD), Psychosis, particularly Psychosis due to AD or Psychosis in patients with AD, apathy due to AD or apathy in patients with AD, psychiatric symptoms of patients with Lewy body dementia, Progressive Supranuclear Palsy (PSP), Frontotemporal dementia (FTD or variants thereof), TBI (traumatic brain injury, acute or chronic), Corticobasal Degeneration (CBD), Picks Disease, Primary age-related tauopathy (PART), Neurofibrillary tangle-predominant senile dementia, Dementia pugilistica, Chronic traumatic encephalopathy, stroke, stroke recovery, neurodegeneration in relation to Parkinson's disease, Parkinsonism linked to chromosome, Lytico-Bodig disease (Parkinson-dementia complex of Guam), Ganglioglioma and gangliocytoma, Meningioangiomatosis, Postencephalitic parkinsonism, Subacute sclerosing panencephalitis, Huntington's disease, lead encephalopathy, tuberous sclerosis, Hallervorden-Spatz disease and lipofuscinosis. More typically, the taupathy is selected from the group consisting of Alzheimer's disease, Argyrophilic Grain Disease (AGD), Psychosis, particularly Psychosis due to AD or Psychosis in patients with AD, apathy due to AD or apathy in patients with AD, psychiatric symptoms of patients with Lewy body dementia, Progressive Supranuclear Palsy (PSP), Frontotemporal dementia (FTD or variants thereof), TBI (traumatic brain injury, acute or chronic), Corticobasal Degeneration (CBD), and Picks Disease. In particular, the tauopathies may be selected from Alzheimer's disease, Argyrophilic Grain Disease (AGD), Psychosis due to AD or Psychosis in patients with AD, apathy due to AD or apathy in patients with AD, and psychiatric symptoms of patients with Lewy body dementia.

The treatment envisioned by the present invention may be chronic and the patient may be treated at least 2 weeks, such as at least for 1 month, 6, months, 1 year or more.

The antibodies of the present invention may, for example, be monoclonal antibodies produced by the hybridoma method first described by Kohler et al., Nature 256, 495 (1975), or may be monoclonal antibodies produced by recombinant DNA or other methods, or more preferably may be produced by the novel method disclosed. Monoclonal antibodies may also be isolated from antibody phage display libraries using the techniques described in, for example, Clackson et al., Nature 352, 624-628 (1991) and Marks et al., J. Mol. Biol. 222, 581-597 (1991). Monoclonal antibodies may be obtained from any suitable source. Thus, for example, monoclonal antibodies may be obtained from hybridomas prepared from murine splenic B lymphocyte cells obtained from mice immunized with an antigen of interest, for instance, in the form of cells expressing the antigen on the surface, or a nucleic acid encoding an antigen of interest. Monoclonal antibodies may also be obtained from hybridomas derived from antibody-expressing cells of immunized humans or from non-human mammals such as rats, rabbits, dogs, sheep, goats, primates, etc.

In one embodiment, the antibody of the invention is a human antibody. Human monoclonal antibodies directed against tau may be generated using transgenic or transchromosomal mice carrying parts of the human immune system rather than the mouse system. Such transgenic and transchromosomic mice include mice referred to herein as HuMAb (Human monoclonal antibody) mice and KM mice, respectively, and are collectively referred to herein as "transgenic mice".

The HuMAb mouse contains a human immunoglobulin gene mini-locus that encodes un-rearranged human heavy variable and constant (p and Y) and light variable and constant (K) chain immunoglobulin sequences, together with targeted mutations that inactivate the endogenous p and K chain loci (Lonberg, N. et al., Nature 368, 856-859 (1994)). Accordingly, the mice exhibit reduced expression of mouse IgM or K and in response to immunization, the introduced human heavy and light chain transgenes, undergo class switching and somatic mutation to generate high affinity human IgG, κ monoclonal antibodies (Lonberg, N. et al. (1994), supra; reviewed in Lonberg, N., Handbook of Experimental Pharmacology 113, 49-101 (1994), Lonberg, N. and Huszar, D., Intern. Rev. Immunol. Vol. 13 65-93 (1995) and Harding, F. and Lonberg, N., Ann. N. Y. Acad. Sci 764 536-546 (1995)). The preparation of HuMAb mice is described in detail in Taylor, L. et al., Nucleic Acids Research 20, 6287-6295 (1992), Chen, J. et al., International Immunology 5, 647-656 (1993), Tuaillon et al., J. Immunol. 152, 2912-2920 (1994), Taylor, L. et al., International Immunology 6, 579-591 (1994), Fishwild, D. et al., Nature Biotechnology 14, 845-851 (1996). See also U.S. Pat. Nos. 5,545,806, 5,569,825, 5,625,126, 5,633,425, 5,789,650, 5,877,397, 5,661,016, 5,814,318, 5,874,299, 5,770,429, 5,545,807, WO 98/24884, WO 94/25585, WO 93/1227, WO 92/22645, WO 92/03918 and WO 01/09187.

The HCo7, HCo12, HCo17 and HCo20 mice have a JKD disruption in their endogenous light chain (kappa) genes (as described in Chen et al., EMBO J. 12, 811-820 (1993)), a CMD disruption in their endogenous heavy chain genes (as described in Example 1 of WO 01/14424), and a KCo5 human kappa light chain transgene (as described in Fishwild et al., Nature Biotechnology 14, 845-851 (1996)). Additionally, the HCo7 mice have a HCo7 human heavy chain transgene (as described in U.S. Pat. No. 5,770,429), the HCo12 mice have a HCo12 human heavy chain transgene (as described in Example 2 of WO 01/14424), the HCo17 mice have a HCo17 human heavy chain transgene (as described in Example 2 of WO 01/09187) and the HCo20 mice have a HCo20 human heavy chain transgene. The resulting mice express human immunoglobulin heavy and kappa light chain transgenes in a background homozygous for disruption of the endogenous mouse heavy and kappa light chain loci.

In the KM mouse strain, the endogenous mouse kappa light chain gene has been homozygously disrupted as described in Chen et al., EMBO J. 12, 811-820 (1993) and the endogenous mouse heavy chain gene has been homozygously disrupted as described in Example 1 of WO 01/09187. This mouse strain carries a human kappa light chain transgene, KCo5, as described in Fishwild et al., Nature Biotechnology 14, 845-851 (1996). This mouse strain also carries a human heavy chain transchromosome composed of chromosome 14 fragment hCF (SC20) as described in WO 02/43478. HCo12-Balb/c, HCo17-Balb/c and HCo20-Balb/c mice can be generated by crossing HCo12, HCo17 and HCo20 to KCo5[J/K](Balb) as described in WO 09/097006.

The rTg4510 mouse is a known tauopathy model providing temporal and spatial control over mutant tau transgene expression. In the KM mouse strain, the endogenous mouse kappa light chain gene has been homozygously disrupted as described in Chen et al., EMBO J. 12, 811-820 (1993) and the endogenous mouse heavy chain gene has been homozygously disrupted as described in Example 1 of WO 01/09187. This mouse strain carries a human kappa light chain transgene, KCo5, as described in Fishwild et al., Nature Biotechnology 14, 845-851 (1996). This mouse strain also carries a human heavy chain trans-chromosome composed of chromosome 14 epitope-binding fragment hCF (SC20) as described in WO 02/43478.

Splenocytes from these transgenic mice may be used to generate hybridomas that secrete human monoclonal antibodies according to well-known techniques. Human monoclonal or polyclonal antibodies of the present invention, or antibodies, of the present invention originating from other species may also be generated transgenically through the generation of another non-human mammal or plant that is transgenic for the immunoglobulin heavy and light chain sequences of interest and production of the antibody in a recoverable form therefrom. In connection with the transgenic production in mammals, antibodies may be produced in, and recovered from, the milk of goats, cows, or other mammals (see for instance U.S. Pat. Nos. 5,827,690; 5,756,687; 5,750,172 and 5,741,957).

The antibody of the invention may be of any isotype. The choice of isotype typically will be guided by the desired effector functions, such as ADCC induction. Exemplary isotypes are IgG1, IgG2, IgG3, and IgG4. Either of the human light chain constant domains, kappa or lambda, may be used. If desired, the class of an anti-tau antibody of the present invention may be switched by known methods. For example, an antibody of the present invention that was originally IgM may be class switched to an IgG antibody of the present invention. Further, class switching techniques may be used to convert one IgG subclass to another, for instance from IgG1 to IgG2. Thus, the effector function of the antibodies of the present invention may be changed by isotype switching to, e.g., an IgG1, IgG2, IgG3, IgG4, IgD, IgA, IgE, or IgM antibody for various therapeutic uses. In one embodiment an antibody of the present invention is an IgG1 antibody, for instance an IgG1, κ. An antibody is said to be of a particular isotype if its amino acid sequence is most homologous to that isotype, relative to other isotypes.

In one embodiment, the antibody of the invention is a full-length antibody, preferably an IgG antibody, in particular an IgG1, κ; antibody. In another embodiment, the antibody of the invention is an antibody epitope-binding fragment or a single-chain antibody.

Antibodies and epitope-binding fragments thereof may e.g. be obtained by epitope-binding fragmentation using conventional techniques, and epitope-binding fragments screened for utility in the same manner as described herein for whole antibodies. For example, F(ab')$_2$ epitope-binding fragments may be generated by treating antibody with pepsin. The resulting F(ab')$_2$ epitope-binding fragment may be treated to reduce disulfide bridges to produce Fab' epitope-binding fragments. Fab epitope-binding fragments may be obtained by treating an IgG antibody with papain; Fab' epitope-binding fragments may be obtained with pepsin digestion of IgG antibody. An F(ab') epitope-binding fragment may also be produced by binding Fab'-described below via a thioether bond or a disulfide bond. A Fab' epitope-binding fragment is an antibody epitope-binding fragment obtained by cutting a disulfide bond of the hinge domain of the F(ab')$_2$. A Fab'-epitope-binding fragment may be obtained by treating an F(ab')2 epitope-binding fragment with a reducing agent, such as dithiothreitol. Antibody epitope-binding fragment may also be generated by expression of nucleic acids encoding such epitope-binding fragments in recombinant cells (see for instance Evans et al., J. Immunol. Meth. 184, 123-38 (1995)). For example, a chimeric gene encoding a portion of an F(ab')2 epitope-binding fragment could include DNA sequences encoding the CH1 domain and hinge domain of the H chain, followed by a translational stop codon to yield such a truncated antibody epitope-binding fragment molecule.

In one embodiment, the anti-tau antibody is a monovalent antibody, preferably a monovalent antibody as described in WO2007059782 (which is incorporated herein by reference in its entirety) having a deletion of the hinge region. Accordingly, in one embodiment, the antibody is a monovalent antibody, wherein said anti-tau antibody is constructed by a method comprising: i) providing a nucleic acid construct encoding the light chain of said monovalent antibody, said construct comprising a nucleotide sequence encoding the VL region of a selected antigen specific anti-tau antibody and a nucleotide sequence encoding the constant CL region of an Ig, wherein said nucleotide sequence encoding the VL region of a selected antigen specific antibody and said nucleotide sequence encoding the CL region of an Ig are operably linked together, and wherein, in case of an IgG1 subtype, the nucleotide sequence encoding the CL region has been modified such that the CL region does not contain any amino acids capable of forming disulfide bonds or covalent bonds with other peptides comprising an identical amino acid sequence of the CL region in the presence of polyclonal human IgG or when administered to an animal or human being; ii) providing a nucleic acid construct encoding the heavy chain of said monovalent antibody, said construct comprising a nucleotide sequence encoding the VH region of a selected antigen specific antibody and a nucleotide sequence encoding a constant CH region of a human Ig, wherein the nucleotide sequence encoding the CH region has been modified such that the region corresponding to the hinge region and, as required by the Ig subtype, other regions of the CH region, such as the CH3 region, does not comprise any amino acid residues which participate in the formation of disulphide bonds or covalent or stable non-covalent inter-heavy chain bonds with other peptides comprising an identical amino acid sequence of the CH region of the human Ig in the presence of polyclonal human IgG or when administered to an animal human being, wherein said nucleotide sequence encoding the VH region of a selected antigen specific antibody and said nucleotide sequence encoding the CH region of said Ig are operably linked together; iii) providing a cell expression system for producing said monovalent antibody; iv) producing said monovalent antibody by co-expressing the nucleic acid constructs of (i) and (ii) in cells of the cell expression system of (iii).

Similarly, in one embodiment, the anti-tau antibody of the invention is a monovalent antibody, which comprises:
(i) a variable domain of an antibody of the invention as described herein or an epitope-binding part of the said domain, and
(ii) a CH domain of an immunoglobulin or a domain thereof comprising the CH2 and CH3 domains, wherein the CH domain or domain thereof has been modified such that the domain corresponding to the hinge domain and, if the immunoglobulin is not an IgG4 subtype, other domains of the CH domain, such as the CH3 domain, do not comprise any amino acid residues, which are capable of forming disulfide bonds with an identical CH domain or other covalent or stable non-covalent inter-heavy chain bonds with an identical CH domain in the presence of polyclonal human IgG.

In a further embodiment, the heavy chain of the monovalent antibody of the invention has been modified such that the entire hinge region has been deleted.

In another further embodiment, the sequence of the monovalent antibody has been modified so that it does not comprise any acceptor sites for N-linked glycosylation.

The invention also includes "Bispecific Antibodies," wherein an anti-tau binding region (e.g., a tau-binding region of an anti-tau monoclonal antibody) is part of a bivalent or polyvalent bispecific scaffold that targets more than one epitope, (for example a second epitope could comprise an epitope of an active transport receptor, such that the Bispecific Antibody would exhibit improved transcytosis across a biological barrier, such as the Blood Brain Barrier). Thus, in another further embodiment, the monovalent Fab of an anti-tau antibody may be joined to an additional Fab or scfv that targets a different protein to generate a bispecific antibody. A bispecific antibody can have a dual function, for example a therapeutic function imparted by an anti-tau binding domain and a transport function that can bind to a receptor molecule to enhance transfer cross a biological barrier, such as the blood brain barrier.

Antibodies and epitope-binding fragments thereof of the invention, also include single chain antibodies. Single chain antibodies are peptides in which the heavy and light chain Fv domains are connected. In one embodiment, the present invention provides a single-chain Fv (scFv) wherein the heavy and light chains in the Fv of an anti-tau antibody of the present invention are joined with a flexible peptide linker (typically of about 10, 12, 15 or more amino acid residues) in a single peptide chain. Methods of producing such antibodies are described in for instance U.S. Pat. No. 4,946,778, Pluckthun in The Pharmacology of Monoclonal Antibodies, vol. 113, Rosenburg and Moore eds. Springer-Verlag, New York, pp. 269-315 (1994), Bird et al., Science 242, 423-426 (1988), Huston et al., PNAS USA 85, 5879-5883 (1988) and McCafferty et al., Nature 348, 552-554 (1990). The single chain antibody may be monovalent, if only a single VH and VL are used, bivalent, if two VH and VL are used, or polyvalent, if more than two VH and VL are used.

The antibodies and epitope-binding fragments thereof described herein may be modified by inclusion of any suitable number of modified amino acids and/or associations with such conjugated substituents. Suitability in this context is generally determined by the ability to at least substantially retain the tau selectivity and/or the tau specificity associated with the non-derivatized parent anti-tau antibody. The inclusion of one or more modified amino acids may be advantageous in, for example, increasing polypeptide serum half-life, reducing polypeptide antigenicity, or increasing polypeptide storage stability. Amino acid(s) are modified, for example, co-translationally or post-translationally during recombinant production (e.g., N-linked glycosylation at N-X-S/T motifs during expression in mammalian cells) or modified by synthetic means. Non-limiting examples of a modified amino acid include a glycosylated amino acid, a sulfated amino acid, a prenylated (e.g., farnesylated, geranyl-geranylated) amino acid, an acetylated amino acid, an acylated amino acid, a PEGylated amino acid, a biotinylated amino acid, a carboxylated amino acid, a phosphorylated amino acid, and the like. References adequate to guide one of skill in the modification of amino acids are replete throughout the literature. Example protocols are found in Walker (1998) Protein Protocols On CD-Rom, Humana Press, Totowa, NJ. The modified amino acid may, for instance, be selected from a glycosylated amino acid, a PEGylated amino acid, a farnesylated amino acid, an acetylated amino acid, a biotinylated amino acid, an amino acid conjugated to a lipid moiety, or an amino acid conjugated to an organic derivatizing agent.

The antibodies and epitope-binding fragments thereof of the invention, may also be chemically modified by covalent conjugation to a polymer to for instance increase their circulating half-life. Exemplary polymers, and methods to attach them to peptides, are illustrated in for instance U.S. Pat. Nos. 4,766,106; 4,179,337; 4,495,285 and 4,609,546. Additional illustrative polymers include polyoxyethylated polyols and polyethylene glycol (PEG) (e.g., a PEG with a molecular weight of between about 1,000 and about 40,000, such as between about 2,000 and about 20,000, e.g., about 3,000-12,000 g/mol).

The antibodies and epitope-binding fragments thereof of the present invention may further be used in a diagnostic method or as a diagnostic imaging ligand.

In one embodiment, antibodies and epitope-binding fragments thereof of the invention comprising one or more radiolabeled amino acids are provided. A radiolabeled anti-tau antibody may be used for both diagnostic and therapeutic purposes (conjugation to radiolabeled molecules is another possible feature). Non-limiting examples of such labels include, but are not limited to bismuth ($^{213}$Bi), carbon ($^{11}$C, $^{13}$C, $^{14}$C), chromium ($^{51}$Cr), cobalt ($^{57}$Co, $^{60}$Co), copper ($^{64}$Cu), dysprosium ($^{165}$Dy), erbium ($^{169}$Er), fluorine ($^{18}$F), gadolinium ($^{153}$Gd, $^{159}$Gd), gallium ($^{68}$Ga, $^{67}$Ga), germanium ($^{68}$Ge), gold ($^{198}$Au), holmium ($^{166}$Ho), hydrogen ($^{3}$H), indium ($^{111}$In, $^{112}$In, $^{113}$In, $^{115}$In), iodine ($^{121}$I, $^{123}$I, $^{125}$I, $^{131}$I), iridium ($^{192}$Ir), iron ($^{59}$Fe), krypton ($^{81m}$Kr), lanthanium ($^{11}$La), lutelium ($^{177}$Lu), manganese ($^{54}$Mn), molybdenum ($^{99}$Mo), nitrogen ($^{13}$N, $^{15}$N), oxygen ($^{15}$O), palladium ($^{103}$Pd), phosphorus ($^{32}$P), potassium ($^{42}$K), praseodymium ($^{142}$Pr), promethium ($^{149}$Pm), rhenium ($^{186}$Re, $^{188}$Re), rhodium ($^{105}$Rh), rubidium ($^{81}$Rb, $^{82}$Rb), ruthenium ($^{82}$Ru, $^{97}$Ru), samarium ($^{153}$Sm), scandium ($^{47}$Sc), selenium ($^{75}$Se), sodium ($^{24}$Na), strontium ($^{85}$Sr, $^{89}$Sr, $^{92}$Sr), sulfur ($^{35}$S), technetium ($^{99}$Tc), thallium ($^{201}$Tl), tin ($^{113}$Sn, $^{117}$Sn), xenon ($^{133}$Xe), ytterbium ($^{169}$Yb, $^{175}$Yb, $^{177}$Yb), yttrium ($^{90}$Y), zinc ($^{65}$Zn) and zirconium ($^{89}$Zr). Zirconium ($^{89}$Zr) is particularly interesting. Methods for preparing radiolabeled amino acids and related peptide derivatives are known in the art (see for instance Junghans et al., in Cancer Chemotherapy and Biotherapy 655-686 (2nd edition, Chafner and Longo, eds., Lippincott Raven (1996)) and U.S. Pat. Nos. 4,681,581; 4,735,210; 5,101,827; 5,102,990 (U.S. Pat. No. RE35,500), 5,648,471 and 5,697,902. For example, a radioisotope may be conjugated by a chloramine T method (Lindegren, S. et al. (1998) "*Chloramine-T In High-Specific-Activity Radioiodination Of Antibodies Using N-Succinimidyl-3-(Trimethylstannyl)Benzoate As An Intermediate*," Nucl. Med. Biol. 25(7):659-665; Kurth, M. et al. (1993) "*Site-Specific Conjugation Of A Radioiodinated Phenethylamine Derivative To A Monoclonal Antibody Results In Increased Radioactivity Localization In Tumor*," J. Med. Chem. 36(9):1255-1261; Rea, D. W. et al. (1990) "Site-specifically radioiodinated antibody for targeting tumors," Cancer Res. 50(3 Suppl):857s-861s).

The invention also provides anti-tau antibodies and epitope-binding fragments thereof that are detectably labeled using a fluorescent label (such as a rare earth chelate (e.g., a europium chelate)), a fluorescein-type label (e.g., fluorescein, fluorescein isothiocyanate, 5-carboxyfluorescein, 6-carboxy fluorescein, dichlorotriazinylamine fluorescein), a rhodamine-type label (e.g., ALEXA FLUOR® 568 (Invitrogen), TAMRA® or dansyl chloride), VIVOTAG 680 XL FLUOROCHROME™ (Perkin Elmer), phycoerythrin; umbelliferone, Lissamine; a cyanine; a phycoerythrin, Texas Red, BODIPY FL-SE® (Invitrogen) or an analogue thereof, all of which are suitable for optical detection. Chemiluminescent labels may be employed (e.g., luminol, luciferase, luciferin, and aequorin). Such diagnosis and detection can also be accomplished by coupling the diagnostic molecule of the present invention to detectable substances including, but not limited to, various enzymes, enzymes including, but not limited to, horseradish peroxidase, alkaline phosphatase, beta-galactosidase, or acetylcholinesterase, or to prosthetic group complexes such as, but not limited to, streptavidin/biotin and avidin/biotin.

Chemiluminescent labels may be employed (e.g., luminol, luciferase, luciferin, and aequorin). Such diagnosis and detection can also be accomplished by coupling the diagnostic molecule of the present invention to detectable substances including, but not limited to, various enzymes, enzymes including, but not limited to, horseradish peroxidase, alkaline phosphatase, beta-galactosidase, or acetylcholinesterase, or to prosthetic group complexes such as, but not limited to, streptavidin/biotin and avidin/biotin. Paramagnetic labels can also be employed, and are preferably detected using Positron Emission Tomography (PET) or Single-Photon Emission Computed Tomography (SPECT). Such paramagnetic labels include, but are not limited to compounds containing paramagnetic ions of Aluminum (Al), Barium (Ba), Calcium (Ca), Cerium (Ce), Dysprosium (Dy), Erbium (Er), Europium (Eu), Gandolinium (Gd), Holmium (Ho), Iridium (Ir), Lithium (Li), Magnesium (Mg), Manganese (Mn), Molybdenum (M), Neodymium (Nd), Osmium (Os), Oxygen (O), Palladium (Pd), Platinum (Pt), Rhodium (Rh), Ruthenium (Ru), Samarium (Sm), Sodium (Na), Strontium (Sr), Terbium (Tb), Thulium (Tm), Tin (Sn), Titanium (Ti), Tungsten (W), and Zirconium (Zi), and particularly, $Co^{+2}$, $CR^{+2}$, $Cr^{+3}$, $Cu^{+2}$, $Fe^{+2}$, $Fe^{+3}$, $Ga^{+3}$, $Mn^{+3}$, $Ni^{+2}$, $Ti^{+3}$, $V^{+3}$, and $V^{+4}$, positron emitting metals using various positron emission tomographies, and non-radioactive paramagnetic metal ions.

Thus in one embodiment the anti-tau antibody or tau-binding fragment thereof of the invention may be labelled with a fluorescent label, a chemiluminescent label, a paramagnetic label, a radioisotopic label or an enzyme label. The labelled antibody of fragment may be used in detecting or measuring the presence or amount of said tau in the brain of a subject. This method may comprise the detection or measurement of in vivo imaging of anti-tau antibody or tau-binding fragment bound to said tau and may comprises ex vivo imaging of said anti-tau antibody or tau-binding fragment bound to such tau.

In a further aspect, the invention relates to an expression vector encoding one or more polypeptide chains of an antibody of the invention or a tau-binding fragment thereof. Such expression vectors may be used for recombinant production of antibodies or epitope-binding fragments thereof of the invention.

An expression vector in the context of the present invention may be any suitable DNA or RNA vector, including chromosomal, non-chromosomal, and synthetic nucleic acid vectors (a nucleic acid sequence comprising a suitable set of expression control elements). Examples of such vectors include derivatives of SV40, bacterial plasmids, phage DNA, baculovirus, yeast plasmids, vectors derived from combinations of plasmids and phage DNA, and viral nucleic acid (RNA or DNA) vectors. In one embodiment, an anti-tau antibody-encoding nucleic acid is comprised in a naked DNA or RNA vector, including, for example, a linear expression element (as described in, for instance, Sykes and Johnston, Nat Biotech 12, 355-59 (1997)), a compacted nucleic acid vector (as described in for instance U.S. Pat. No. 6,077,835 and/or WO 00/70087), a plasmid vector such as pBR322, pUC 19/18, or pUC 118/119, a "midge" minimally-sized nucleic acid vector (as described in, for instance, Schakowski et al., Mol Ther 3, 793-800 (2001)), or as a precipitated nucleic acid vector construct, such as a CaPO$_4$-precipitated construct (as described in, for instance, WO 00/46147, Benvenisty and Reshef, PNAS USA 83, 9551-55 (1986), Wigler et al., Cell 14, 725 (1978), and Coraro and Pearson, Somatic Cell Genetics 2, 603 (1981)). Such nucleic acid vectors and the usage thereof are well known in the art (see for instance U.S. Pat. Nos. 5,589,466 and 5,973,972).

In one embodiment, the vector is suitable for expression of anti-tau antibodies or epitope-binding fragments thereof of the invention in a bacterial cell. Examples of such vectors include expression vectors such as BlueScript (Stratagene), pIN vectors (Van Heeke & Schuster, J. Biol. Chem. 264, 5503-5509 (1989), pET vectors (Novagen, Madison, WI), and the like.

An expression vector may also or alternatively be a vector suitable for expression in a yeast system. Any vector suitable for expression in a yeast system may be employed. Suitable vectors include, for example, vectors comprising constitutive or inducible promoters such as alpha factor, alcohol oxidase and PGH (reviewed in: F. Ausubel et al., ed. Current Protocols in Molecular Biology, Greene Publishing and Wiley InterScience New York (1987), Grant et al., Methods in Enzymol 153, 516-544 (1987), Mattanovich, D. et al. Methods Mol. Biol. 824, 329-358 (2012), Celik, E. et al. Biotechnol. Adv. 30(5), 1108-1118 (2012), Li, P. et al. Appl. Biochem. Biotechnol. 142(2), 105-124 (2007), Böer, E. et al. Appl. Microbiol. Biotechnol. 77(3), 513-523 (2007), van der Vaart, J. M. Methods Mol. Biol. 178, 359-366 (2002), and Holliger, P. Methods Mol. Biol. 178, 349-357 (2002)).

In an expression vector of the invention, anti-tau antibody-encoding nucleic acids may comprise or be associated with any suitable promoter, enhancer, and other expression-facilitating elements. Examples of such elements include strong expression promoters (e.g., human CMV IE promoter/enhancer as well as RSV, SV40, SL3-3, MMTV, and HIV LTR promoters), effective poly (A) termination sequences, an origin of replication for plasmid product in *E. coli*, an antibiotic resistance gene as selectable marker, and/or a convenient cloning site (e.g., a polylinker). Nucleic acids may also comprise an inducible promoter as opposed to a constitutive promoter such as CMV IE (the skilled artisan will recognize that such terms are actually descriptors of a degree of gene expression under certain conditions).

In an even further aspect, the invention relates to a recombinant eukaryotic or prokaryotic host cell, such as a transfectoma, which produces an antibody or epitope-binding fragment thereof of the invention as defined herein or a bispecific molecule of the invention as defined herein. Examples of host cells include yeast, bacteria, and mammalian cells, such as CHO or HEK cells. For example, in one embodiment, the present invention provides a cell comprising a nucleic acid stably integrated into the cellular genome that comprises a sequence coding for expression of an anti-tau antibody of the present invention or an epitope-binding fragment thereof. In another embodiment, the present invention provides a cell comprising a non-integrated nucleic acid, such as a plasmid, cosmid, phagemid, or linear expression element, which comprises a sequence coding for expression of an anti-tau antibody or epitope-binding fragment thereof of the invention.

In a further aspect, the invention relates to a method for producing an anti-tau antibody of the invention, said method comprising the steps of a) culturing a hybridoma or a host cell of the invention as described herein above, and b) purifying the antibody of the invention from the culture media.

In one embodiment, the invention relates to a preparation that, as such term is used herein, comprises an anti-tau antibody as defined herein, and that is substantially free of naturally-arising antibodies that are either not capable of binding to tau or that do not materially alter the anti-tau functionality of the preparation. Thus, such a preparation does not encompass naturally-arising serum, or a purified derivative of such serum, that comprises a mixture of an anti-tau antibody and another antibody that does not alter the functionality of the anti-tau antibody of the preparation, wherein such functionality is:
  (i) a substantial inability to bind to non-phosphorylated tau;
  (ii) a substantial inability to bind to tau that is phosphorylated at S404 and not phosphorylated at S396;
  (iii) the ability to bind to tau phosphorylated at S396;
  (iv) the ability to bind to tau phosphorylated at both S396 and at S404;
  (v) the ability to selectively discriminate between phosphorylated tau residues S396 and S404 such that it is substantially unable to bind the phosphorylated 404 residue;
  (vi) the ability to bind hyper-phosphorylated tau from human Alzheimer's disease brains;
  (vii) the ability to discriminate between pathological and non-pathological human tau protein; and/or
  (viii) the capability, when used as described herein with immune-depleted rTg4510 extracts from transgenic mice, to specifically reduce the hyperphosphorylated tau 64 kDa and 70 kDa bands by at least 90%, while not reducing the 55 kDa tau band by more than 10% or the capability, when used as described herein with extracts from human AD post-mortem brains, to specifically reduce the S396 phosphorylated hyperphosphorylated tau bands by at least 90%, while not reducing the non-hyperphosphorylated tau bands by more than 10%.

The invention particularly relates to preparations of such an anti-tau antibody having a structural change in its amino acid sequence (in any of its CDRs, variable domains, framework residues and/or constant domains) relative to the structure of a naturally-occurring anti-tau antibody, wherein said structural change causes the anti-tau antibody to exhibit a markedly altered functionality (i.e., more than a 20% difference, more than a 40% difference, more than a 60% difference, more than an 80% difference, more than a 100% difference, more than a 150% difference, more than a 2-fold difference, more than a 4-fold difference, more than a 5-fold difference, or more than a 10-fold difference in functionality) relative to the functionality exhibited by said naturally-occurring anti-tau antibody; wherein such functionality is:
  (i) a substantial inability to bind to non-phosphorylated tau;
  (ii) a substantial inability to bind to tau that is phosphorylated at S404 and not phosphorylated at S396;

(iii) the ability to bind to tau phosphorylated at S396;
(iv) the ability to bind to tau phosphorylated at both S396 and at S404;
(v) the ability to selectively discriminate between phosphorylated tau residues S396 and S404 such that it is substantially unable to bind the phosphorylated 404 residue;
(vi) the ability to bind hyper-phosphorylated tau from human Alzheimer's disease brains;
(vii) the ability to discriminate between pathological and non-pathological human tau protein; and/or
(viii) the capability, when used as described herein with immune-depleted rTg4510 extracts from transgenic mice, to specifically reduce the hyperphosphorylated tau 64 kDa and 70 kDa bands by at least 90%, while not reducing the 55 kDa tau band by more than 10%; or the capability, when used as described herein with extracts from human AD post-mortem brains to specifically reduce the S396 phosphorylated hyperphosphorylated tau bands by at least 90%, while not reducing the non-hyperphosphorylated tau bands by more than 10%.

The term "substantially free" of naturally-arising antibodies refers to the complete absence of such naturally-arising antibodies in such preparations, or of the inclusion of a concentration of such naturally-arising antibodies in such preparations that does not materially affect the tau-binding properties of the preparations. An antibody is said to be "isolated" if it has no naturally-arising counterpart or has been separated or purified from components which naturally accompany it.

The term "naturally-arising antibodies," as it relates to such preparations, refers to antibodies (including naturally-arising autoantibodies) elicited within living humans or other animals, as a natural consequence to the functioning of their immune systems.

Thus, the preparations of the present invention do not exclude, and indeed explicitly encompass, such preparations that contain an anti-tau antibody and a deliberately added additional antibody capable of binding to an epitope that is not possessed by tau. Such preparations particularly include embodiments thereof wherein the preparation exhibits enhanced efficacy in treating Alzheimer's disease (AD), Argyrophilic Grain Disease (AGD), Progressive Supranuclear Palsy (PSP), and Corticobasal Degeneration (CBD). Furthermore, the present invention is directed to preparations that contain an anti-tau antibody antibodies, or epitope-binding fragments thereof, intended for use in the treatment of Psychosis, particularly Psychosis due to AD or Psychosis in patients with AD, apathy due to AD or apathy in patients with AD, and psychiatric symptoms of patients with Lewy body dementia. Furthermore, the preparations of the present invention contain an anti-tau antibody antibodies, or epitope-binding fragments thereof, that may be used in the treatment of stroke, stroke recovery, neurodegeneration in relation to Parkinson's disease.

In an even further aspect, the invention relates to a pharmaceutical composition comprising:
(i) a tau antibody, or epitope-binding fragment thereof, both as defined herein, or a preparation, as such term is defined herein, that comprises such an anti-tau antibody or epitope-binding fragment thereof; and
(ii) a pharmaceutically-acceptable carrier.

The pharmaceutical compositions may be formulated with pharmaceutically acceptable carriers or diluents as well as any other known adjuvants and excipients in accordance with conventional techniques such as those disclosed in Remington: The Science and Practice of Pharmacy, 22nd Edition, Gennaro, Ed., Mack Publishing Co., Easton, P A, 2013.

The pharmaceutically acceptable carriers or diluents as well as any other known adjuvants and excipients should be suitable for the chosen compound of the present invention and the chosen mode of administration. Suitability for carriers and other components of pharmaceutical compositions is determined based on the lack of significant negative impact on the desired biological properties of the chosen compound or pharmaceutical composition of the present invention (e.g., less than a substantial impact (10% or less relative inhibition, 5% or less relative inhibition, etc.)) on epitope binding.

A pharmaceutical composition of the present invention may also include diluents, fillers, salts, buffers, detergents (e.g., a nonionic detergent, such as Tween-20 or Tween-80), stabilizers (e.g., sugars or protein-free amino acids), preservatives, tissue fixatives, solubilizers, and/or other materials suitable for inclusion in a pharmaceutical composition. The diluent is selected to not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, or non-toxic, nontherapeutic, non-immunogenic stabilizers and the like. The compositions may also include large, slowly metabolized macromolecules, such as proteins, polysaccharides like chitosan, polylactic acids, polyglycolic acids and copolymers (e.g., latex functionalized sepharose, agarose, cellulose, and the like), polymeric amino acids, amino acid copolymers, and lipid aggregates (e.g., oil droplets or liposomes).

The actual dosage levels of the active ingredients in the pharmaceutical compositions of the present invention may be varied so as to obtain an amount of the active ingredient which is effective to achieve the desired therapeutic response for a particular patient, composition, and mode of administration. The selected dosage level will depend upon a variety of pharmacokinetic factors including the activity of the particular compositions of the present invention employed, or the amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The pharmaceutical composition may be administered by any suitable route and mode, including: parenteral, topical, oral or intranasal means for prophylactic and/or therapeutic treatment. In one embodiment, a pharmaceutical composition of the present invention is administered parenterally. The phrases "parenteral administration" and "administered parenterally" as used herein means modes of administration other than enteral and topical administration, usually by injection, and include epidermal, intravenous, intramuscular, intraarterial, intrathecal, intracapsular, intraorbital, intracardiac, intradermal, intraperitoneal, intratendinous, transtracheal, subcutaneous, subcuticular, intraarticular, subcapsular, subarachnoid, intraspinal, intracranial, intrathoracic, epidural and intrasternal injection and infusion.

Additional suitable routes of administering a compound of the present invention in vivo and in vitro are well known in the art and may be selected by those of ordinary skill in the art.

In one embodiment that pharmaceutical composition is administered by intravenous or subcutaneous injection or infusion.

Pharmaceutically acceptable carriers include any and all suitable solvents, dispersion media, coatings, antibacterial and antifungal agents, isotonicity agents, antioxidants and absorption delaying agents, and the like that are physiologically compatible with a compound of the present invention.

Examples of suitable aqueous and nonaqueous carriers which may be employed in the pharmaceutical compositions of the present invention include water, saline, phosphate buffered saline, ethanol, dextrose, polyols (such as glycerol, propylene glycol, polyethylene glycol, and the like), and suitable mixtures thereof, vegetable oils, such as olive oil, corn oil, peanut oil, cottonseed oil, and sesame oil, carboxymethyl cellulose colloidal solutions, tragacanth gum and injectable organic esters, such as ethyl oleate, and/or various buffers. Other carriers are well known in the pharmaceutical arts.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the present invention is contemplated.

Proper fluidity may be maintained, for example, by the use of coating materials, such as lecithin, by the maintenance of the required particle size in the case of dispersions, and by the use of surfactants.

Pharmaceutical compositions of the present invention may also comprise pharmaceutically acceptable antioxidants for instance (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Pharmaceutical compositions of the present invention may also comprise isotonicity agents, such as sugars, polyalcohols, such as mannitol, sorbitol, glycerol or sodium chloride in the compositions.

The pharmaceutical compositions of the present invention may also contain one or more adjuvants appropriate for the chosen route of administration such as preservatives, wetting agents, emulsifying agents, dispersing agents, preservatives or buffers, which may enhance the shelf life or effectiveness of the pharmaceutical composition. The compounds of the present invention may be prepared with carriers that will protect the compound against rapid release, such as a controlled release formulation, including implants, transdermal patches, and microencapsulated delivery systems. Such carriers may include gelatin, glyceryl monostearate, glyceryl distearate, biodegradable, biocompatible polymers such as ethylene vinyl acetate, polyanhydrides, polyglycolic acid, collagen, polyorthoesters, and polylactic acid alone or with a wax, or other materials well known in the art. Methods for the preparation of such formulations are generally known to those skilled in the art. See, e.g., Sustained and Controlled Release Drug Delivery Systems, J. R. Robinson, ed., Marcel Dekker, Inc., New York, 1978.

In one embodiment, the compounds of the present invention may be formulated to ensure proper distribution in vivo.

Pharmaceutically acceptable carriers for parenteral administration include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the present invention is contemplated. Supplementary active compounds may also be incorporated into the compositions.

Pharmaceutical compositions for injection must typically be sterile and stable under the conditions of manufacture and storage. The composition may be formulated as a solution, micro-emulsion, liposome, or other ordered structure suitable to high drug concentration. The carrier may be an aqueous or non-aqueous solvent or dispersion medium containing for instance water, ethanol, polyols (such as glycerol, propylene glycol, polyethylene glycol, and the like), and suitable mixtures thereof, vegetable oils, such as olive oil, and injectable organic esters, such as ethyl oleate. The proper fluidity may be maintained, for example, by the use of a coating such as lecithin, by the maintenance of the required particle size in the case of dispersion and by the use of surfactants. In many cases, it will be preferable to include isotonic agents, for example, sugars, polyalcohols such as glycerol, mannitol, sorbitol, or sodium chloride in the composition. Prolonged absorption of the injectable compositions may be brought about by including in the composition an agent that delays antibody absorption, for example, monostearate salts and gelatin. Sterile injectable solutions may be prepared by incorporating the active compound in the required amount in an appropriate solvent with one or a combination of ingredients e.g. as enumerated above, as required, followed by sterilization microfiltration. Generally, dispersions are prepared by incorporating the active compound into a sterile vehicle that contains a basic dispersion medium and the required other ingredients e.g. from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

Sterile injectable solutions may be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

Dosage regimens in the above methods of treatment and uses described herein are adjusted to provide the optimum desired response (e.g., a therapeutic response). For example, a single bolus may be administered, several divided doses may be administered over time or the dose may be proportionally reduced or increased as indicated by the exigencies of the therapeutic situation. Parenteral compositions may be formulated in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the present invention are dictated by and directly dependent on (a) the unique characteristics of the active compound and the particular therapeutic effect to be achieved, and (b) the limitations inherent in the art of compounding such an active compound for the treatment of sensitivity in individuals.

The effective dosages and the dosage regimens for the antibodies or epitope-binding fragments thereof of the invention depend on the disease or condition to be treated and may be determined by persons skilled in the art. On any given day that a dosage is given, the dosage may range from about 0.0001 to about 100 mg/kg, and more usually from about 0.01 to about 5 mg/kg, of the host body weight. For example, dosages can be 1 mg/kg body weight or 10 mg/kg body weight or within the range of 1-10 mg/kg body weight. Exemplary dosages thus include: from about 0.1 to about 10 mg/kg/body weight, from about 0.1 to about 5 mg/kg/body weight, from about 0.1 to about 2 mg/kg/body weight, from about 0.1 to about 1 mg/kg/body weight, for instance about 0.15 mg/kg/body weight, about 0.2 mg/kg/body weight, about 0.5 mg/kg/body weight, about 1 mg/kg/body weight, about 1.5 mg/kg/body weight, about 2 mg/kg/body weight, about 5 mg/kg/body weight, or about 10 mg/kg/body weight.

A physician having ordinary skill in the art may readily determine and prescribe the effective amount of the pharmaceutical composition required. For example, the physician could start doses of an antibody or epitope-binding fragment thereof of the invention employed in the pharmaceutical composition at levels lower than that required in order to achieve the desired therapeutic effect and gradually increase the dosage until the desired effect is achieved. In general, a suitable daily dose of a composition of the present invention will be that amount of the compound which is the lowest dose effective to produce a therapeutic effect. Such an effective dose will generally depend upon the factors described above. Administration may e.g. be intravenous, intramuscular, intraperitoneal, or subcutaneous. If desired, the effective daily dose of a pharmaceutical composition may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical composition as described above.

The labeled antibodies or epitope-binding fragments thereof of the invention can be used for diagnostic purposes to detect, diagnose, or monitor diseases or disorders. The invention provides for the detection or diagnosis of a neurodegenerative or cognitive disease or disorder, including but not limited to Alzheimer's disease, Argyrophilic Grain Disease (AGD), Progressive Supranuclear Palsy (PSP), and Corticobasal Degeneration (CBD), comprising: (a) assaying the existence of pyroglutamated As fragments in cells or tissue samples of a subject using one or more antibodies that specifically bind to tau; and (b) comparing the level of the antigen with a control level, e.g. levels in normal tissue samples, whereby an increase in the assayed level of antigen compared to the control level of antigen is indicative of the disease or disorder, or indicative of the severity of the disease or disorder.

The antibodies or epitope-binding fragments thereof of the invention can be used to assay tau or fragments of tau in a biological sample using immunohistochemical methods well-known in the art. Other antibody-based methods useful for detecting protein include immunoassays such as the enzyme linked immunoassay (ELISA) and the radioimmunoassay assay (RIA) and mesoscale discovery platform based assays (MSD). Suitable antibody labels may be used in such kits and methods, and labels known in the art include enzyme labels, such as alkaline phosphatase and glucose oxidase; radioisotope labels, such as iodine ($^{125}$I, $^{131}$I), carbon ($^{14}$C), sulfur ($^{35}$S), tritium ($^{3}$H), indium ($^{121}$In), and technetium ($^{99m}$Tc); and luminescent labels, such as luminol and luciferase; and fluorescent labels, such as fluorescein and rhodamine.

The presence of labeled anti-tau antibodies or their tau-binding fragments may be detected in vivo for diagnostic purposes. In one embodiment, diagnosis comprises: a) administering to a subject an effective amount of such labeled molecule; b) waiting for a time interval following administration to allow the labeled molecule to concentrate at sites (if any) of As deposition and to allow for unbound labeled molecule to be cleared to background level; c) determining a background level; and d) detecting the labeled molecule in the subject, such that detection of labeled molecule above the background level is indicative that the subject has the disease or disorder, or is indicative of the severity of the disease or disorder. In accordance with such embodiment, the molecule is labeled with an imaging moiety suitable for detection using a particular imaging system known to those skilled in the art. Background levels may be determined by various methods known in the art, including comparing the amount of labeled antibody detected to a standard value previously determined for a particular imaging system. Methods and systems that may be used in the diagnostic methods of the invention include, but are not limited to, computed tomography (CT), whole body scan such as positron emission tomography (PET), magnetic resonance imaging (MRI), and sonography.

In a further aspect, the invention provides a monoclonal antibody, or an epitope-binding fragment thereof, as defined herein for use in therapy.

In a further aspect, the invention provides a monoclonal antibody, or an epitope-binding fragment thereof, as defined herein for use in treating, diagnosing or imaging of tauopathies.

In a further aspect, the invention provides a monoclonal antibody, or an epitope-binding fragment thereof, as defined herein for use in treating Alzheimer's disease, Argyrophilic Grain Disease (AGD), Progressive Supranuclear Palsy (PSP), and Corticobasal Degeneration (CBD).

In a further aspect, the invention provides a monoclonal antibody, or an epitope-binding fragment thereof, as defined herein for use in the manufacture of a medicament for treating, diagnosing or imaging tauopathies.

Preferably, the medicament is for treating Alzheimer's disease (AD), Argyrophilic Grain Disease (AGD), Progressive Supranuclear Palsy (PSP), and Corticobasal Degeneration (CBD) most preferably Alzheimer's disease (AD). The medicament is also preferably for the treatment of Psychosis, particularly Psychosis due to AD or Psychosis in patients with AD, apathy due to AD or apathy in patients with AD, and psychiatric symptoms of patients with Lewy body dementia.

In a further aspect, the invention provides a method of treating, diagnosing or imaging Alzheimer's disease or other tauopathies in a subject, said method comprising administering the medicament monoclonal antibody or epitope-binding fragment thereof as defined herein, to said subject in an effective amount.

In a preferred embodiment, the treatment is chronic, preferably for at least 2 weeks, such as at least for 1 month, 6, months, 1 year or more.

In a further aspect, the invention provides a kit comprising the antibody, or fragment thereof, as defined herein for use in therapy.

LIST OF EMBODIMENTS

The present invention particularly concerns the following embodiments:
1. A monoclonal antibody, or an epitope-binding fragment thereof, capable of specifically binding to the phosphorylated residue 396 of human tau (SEQ ID NO:1) such that the antibody or an epitope-binding fragment thereof does not substantially bind to SEQ ID NO:1 phosphorylated at residue 404 when residue 396 is not phosphorylated.
2. The monoclonal antibody, or epitope-binding fragment thereof, according to embodiment 1, which inhibits AD-P3 in the fluid phase inhibition assay such that the monoclonal antibody, or epitope-binding fragment thereof has an IC50 of 100 nM or less, such as from 0.1 nM to 100 nM, such as at a concentration of 50 nM or less, such as from 0.1 nM to 50 nM.
3. The monoclonal antibody, or epitope-binding fragment thereof, according to any one embodiments 1 or 2, wherein according to Western Blot signal of pS396 Tau after immunodepletion studies on Alzheimers diseased brain extracts capable of removing at least 15% Tau phosphorylated at serine 396 from Alzheimer brain homogenates at about 75 ng of antibody.
4. A monoclonal antibody, or epitope-binding fragment thereof, comprising
    (a) a Light Chain CDR1 comprising the amino acid sequence selected from the group consisting of SEQ ID NO:3, SEQ ID NO:31; SEQ ID NO:32; SEQ ID NO:33; SEQ ID NO:34; SEQ ID NO:35; SEQ ID NO:36; SEQ ID NO:37; SEQ ID NO:38; SEQ ID NO:40; and SEQ ID NO:46;
    (b) a Light Chain CDR2 comprising the amino acid sequence of SEQ ID NO:4; SEQ ID NO:41; and SEQ ID NO:47;
    (c) a Light Chain CDR3 comprising the amino acid sequence of SEQ ID NO:5; SEQ ID NO:42; and SEQ ID NO:48;
    (d) a Heavy Chain CDR1 comprising the amino acid sequence of SEQ ID NO:6; SEQ ID NO:43; SEQ ID NO:49; SEQ ID NO:52; and SEQ ID NO:55;
    (e) a Heavy Chain CDR2 comprising the amino acid sequence selected from the group consisting of SEQ ID NO:7; SEQ ID NO:28; SEQ ID NO:29; SEQ ID NO:30; SEQ ID NO:44; SEQ ID NO:50; SEQ ID NO:53; and SEQ ID NO:56; and
    (f) a Heavy Chain CDR3 comprising the amino acid sequence selected from the group consisting of SEQ ID NO:8, SEQ ID NO:39; SEQ ID NO:45; SEQ ID NO:51; SEQ ID NO:54; and SEQ ID NO:57.
5. A monoclonal antibody, or an epitope-binding fragment thereof, comprising
    (a) a Light Chain selected from the group consisting of SEQ ID NO:12; SEQ ID NO:16; SEQ ID NO:17; SEQ ID NO:18; SEQ ID NO:19; SEQ ID NO:20; SEQ ID NO:21; SEQ ID NO:22 and SEQ ID NO:23; and
    (b) a Heavy Chain selected from the group consisting of SEQ ID NO:11; SEQ ID NO:13; SEQ ID NO:14; SEQ ID NO:15; SEQ ID NO:24; SEQ ID NO:25; SEQ ID NO:26; and SEQ ID NO:27.
6. The monoclonal antibody, or an epitope-binding fragment thereof, according to embodiment 1 or 5, wherein
    (a) the Light Chain is SEQ ID NO:12; and
    (b) the Heavy Chain is selected from the group consisting of SEQ ID NO:13, SEQ ID NO:14, SEQ ID NO:15, SEQ ID NO:24, SEQ ID NO:25, SEQ ID NO:26 and SEQ ID NO:27.
7. The monoclonal antibody, or an epitope-binding fragment thereof, according to embodiment 1 or 5, wherein
    (a) the Light Chain is selected from the group consisting of SEQ ID NO:16; SEQ ID NO:17; SEQ ID NO:18; SEQ ID NO:19; SEQ ID NO:20; SEQ ID NO:21; SEQ ID NO:22 and SEQ ID NO:23; and
    (b) the Heavy Chain is SEQ ID NO:11.
8. The monoclonal antibody, or epitope binding fragment thereof, according to embodiment 1 or 4, comprising
    (a) a Light Chain CDR1 having the amino acid sequence of SEQ ID NO:3;
    (b) a Light Chain CDR2 having the amino acid sequence of SEQ ID NO:4;
    (c) a Light Chain CDR3 having the amino acid sequence of SEQ ID NO:5;
    (d) a Heavy Chain CDR1 having the amino acid sequence of SEQ ID NO:6;
    (e) a Heavy Chain CDR2 having the amino acid sequence of SEQ ID NO:28 and
    (f) a Heavy Chain CDR3 having the amino acid sequence of SEQ ID NO:8.
9. The monoclonal antibody, or epitope binding fragment thereof, according to embodiment 1 or 5, comprising
    (a) a Light Chain comprising the amino acid sequence of SEQ ID NO:12;
    (b) a Heavy Chain comprising the amino acid sequence of SEQ ID NO:13.
10. The monoclonal antibody, or epitope binding fragment thereof, according to embodiment 1 or 4, comprising at least one of
    (a) a Light Chain CDR1 having the amino acid sequence of SEQ ID NO:3;
    (b) a Light Chain CDR2 having the amino acid sequence of SEQ ID NO:4; and
    (c) a Light Chain CDR3 having the amino acid sequence of SEQ ID NO:5;
    and further comprising
    (d) a Heavy Chain CDR1 having the amino acid sequence of SEQ ID NO:6;
    (e) a Heavy Chain CDR2 having the amino acid sequence of SEQ ID NO:28 and
    (f) a Heavy Chain CDR3 having the amino acid sequence of SEQ ID NO:8.
11. The monoclonal antibody, or epitope binding fragment thereof, according to embodiment 1 or 4, comprising
    (a) a Light Chain CDR1 having the amino acid sequence of SEQ ID NO:3;
    (b) a Light Chain CDR2 having the amino acid sequence of SEQ ID NO:4;
    (c) a Light Chain CDR3 having the amino acid sequence of SEQ ID NO:5;
    (d) a Heavy Chain CDR1 having the amino acid sequence of SEQ ID NO:6;
    (e) a Heavy Chain CDR2 having the amino acid sequence of SEQ ID NO:29; and
    (f) a Heavy Chain CDR3 having the amino acid sequence of SEQ ID NO:8.

12. The monoclonal antibody, or epitope binding fragment thereof, according to embodiment 1 or 5, comprising
    (a) a Light Chain comprising the amino acid sequence of SEQ ID NO:12; and
    (b) a Heavy Chain comprising the amino acid sequence of SEQ ID NO:14.
13. The monoclonal antibody, or epitope binding fragment thereof, according to embodiment 1 or 4, comprising at least one of
    (a) a Light Chain CDR1 having the amino acid sequence of SEQ ID NO:3;
    (b) a Light Chain CDR2 having the amino acid sequence of SEQ ID NO:4; and
    (c) a Light Chain CDR3 having the amino acid sequence of SEQ ID NO:5;
    and further comprising
    (d) a Heavy Chain CDR1 having the amino acid sequence of SEQ ID NO:6;
    (e) a Heavy Chain CDR2 having the amino acid sequence of SEQ ID NO:29; and
    (f) a Heavy Chain CDR3 having the amino acid sequence of SEQ ID NO:8.
14. The monoclonal antibody, or epitope binding fragment thereof, according to embodiment 1 or 4, comprising
    (a) a Light Chain CDR1 having the amino acid sequence of SEQ ID NO:3;
    (b) a Light Chain CDR2 having the amino acid sequence of SEQ ID NO:4;
    (c) a Light Chain CDR3 having the amino acid sequence of SEQ ID NO:5;
    (d) a Heavy Chain CDR1 having the amino acid sequence of SEQ ID NO:6;
    (e) a Heavy Chain CDR2 having the amino acid sequence of SEQ ID NO:30; and
    (f) a Heavy Chain CDR3 having the amino acid sequence of SEQ ID NO:8.
15. The monoclonal antibody, or epitope binding fragment thereof, according embodiment 1 or 5, comprising
    (a) a Light Chain comprising the amino acid sequence of SEQ ID NO:12; and
    (b) a Heavy Chain comprising the amino acid sequence of SEQ ID NO:15.
16. The monoclonal antibody, or epitope binding fragment thereof, according to embodiment 1 or 4, comprising at least one of
    (a) a Light Chain CDR1 having the amino acid sequence of SEQ ID NO:3;
    (b) a Light Chain CDR2 having the amino acid sequence of SEQ ID NO:4; and
    (c) a Light Chain CDR3 having the amino acid sequence of SEQ ID NO:5;
    and further comprising
    (d) a Heavy Chain CDR1 having the amino acid sequence of SEQ ID NO:6;
    (e) a Heavy Chain CDR2 having the amino acid sequence of SEQ ID NO:30; and
    (f) a Heavy Chain CDR3 having the amino acid sequence of SEQ ID NO:8.
17. The monoclonal antibody, or epitope binding fragment thereof, according to embodiment 1 or 4, comprising
    (a) a Light Chain CDR1 having the amino acid sequence of SEQ ID NO:31;
    (b) a Light Chain CDR2 having the amino acid sequence of SEQ ID NO:4;
    (c) a Light Chain CDR3 having the amino acid sequence of SEQ ID NO:5;
    (d) a Heavy Chain CDR1 having the amino acid sequence of SEQ ID NO:6;
    (e) a Heavy Chain CDR2 having the amino acid sequence of SEQ ID NO:7; and
    (f) a Heavy Chain CDR3 having the amino acid sequence of SEQ ID NO:8.
18. The monoclonal antibody, or epitope binding fragment thereof, according to embodiment 1 or 5, comprising
    (a) a Light Chain comprising the amino acid sequence of SEQ ID NO:16; and
    (b) a Heavy Chain comprising the amino acid sequence of SEQ ID NO:11.
19. The monoclonal antibody, or epitope binding fragment thereof, according to embodiment 1 or 4, comprising
    (a) a Light Chain CDR1 having the amino acid sequence of SEQ ID NO:31;
    (b) a Light Chain CDR2 having the amino acid sequence of SEQ ID NO:4; and
    (c) a Light Chain CDR3 having the amino acid sequence of SEQ ID NO:5;
    and further comprising at least one of
    (d) a Heavy Chain CDR1 having the amino acid sequence of SEQ ID NO:6;
    (e) a Heavy Chain CDR2 having the amino acid sequence of SEQ ID NO:7; and
    (f) a Heavy Chain CDR3 having the amino acid sequence of SEQ ID NO:8.
20. The monoclonal antibody, or epitope binding fragment thereof, according to embodiment 1 or 4, comprising
    (a) a Light Chain CDR1 having the amino acid sequence of SEQ ID NO:32;
    (b) a Light Chain CDR2 having the amino acid sequence of SEQ ID NO:4;
    (c) a Light Chain CDR3 having the amino acid sequence of SEQ ID NO:5;
    (d) a Heavy Chain CDR1 having the amino acid sequence of SEQ ID NO:6;
    (e) a Heavy Chain CDR2 having the amino acid sequence of SEQ ID NO:7; and
    (f) a Heavy Chain CDR3 having the amino acid sequence of SEQ ID NO:8.
21. The monoclonal antibody, or epitope binding fragment thereof, according to embodiment 1 or 5, comprising
    (a) a Light Chain comprising the amino acid sequence of SEQ ID NO:17; and
    (b) a Heavy Chain comprising the amino acid sequence of SEQ ID NO:11.
22. The monoclonal antibody, or epitope binding fragment thereof, according to embodiment 1 or 4, comprising
    (a) a Light Chain CDR1 having the amino acid sequence of SEQ ID NO:32;
    (b) a Light Chain CDR2 having the amino acid sequence of SEQ ID NO:4; and
    (c) a Light Chain CDR3 having the amino acid sequence of SEQ ID NO:5;
    and further comprising at least one of
    (d) a Heavy Chain CDR1 having the amino acid sequence of SEQ ID NO:6;
    (e) a Heavy Chain CDR2 having the amino acid sequence of SEQ ID NO:7; and (f) a Heavy Chain CDR3 having the amino acid sequence of SEQ ID NO:8;

23. The monoclonal antibody, or epitope binding fragment thereof, according to embodiment 1 or 4, comprising
   (a) a Light Chain CDR1 having the amino acid sequence of SEQ ID NO:33;
   (b) a Light Chain CDR2 having the amino acid sequence of SEQ ID NO:4;
   (c) a Light Chain CDR3 having the amino acid sequence of SEQ ID NO:5;
   (d) a Heavy Chain CDR1 having the amino acid sequence of SEQ ID NO:6;
   (e) a Heavy Chain CDR2 having the amino acid sequence of SEQ ID NO:7; and
   (f) a Heavy Chain CDR3 having the amino acid sequence of SEQ ID NO:8.

24. The monoclonal antibody, or epitope binding fragment thereof, according to embodiment 1 or 5, comprising
   (a) a Light Chain comprising the amino acid sequence of SEQ ID NO:18; and
   (b) a Heavy Chain comprising the amino acid sequence of SEQ ID NO:11.

25. The monoclonal antibody, or epitope binding fragment thereof, according to embodiment 1 or 4, comprising
   (a) a Light Chain CDR1 having the amino acid sequence of SEQ ID NO:33;
   (b) a Light Chain CDR2 having the amino acid sequence of SEQ ID NO:4; and
   (c) a Light Chain CDR3 having the amino acid sequence of SEQ ID NO:5;
   and further comprising at least one of
   (d) a Heavy Chain CDR1 having the amino acid sequence of SEQ ID NO:6;
   (e) a Heavy Chain CDR2 having the amino acid sequence of SEQ ID NO:7; and
   (f) a Heavy Chain CDR3 having the amino acid sequence of SEQ ID NO:8;

26. The monoclonal antibody, or epitope binding fragment thereof, according to embodiment 1 or 4, comprising
   (a) a Light Chain CDR1 having the amino acid sequence of SEQ ID NO:34;
   (b) a Light Chain CDR2 having the amino acid sequence of SEQ ID NO:4;
   (c) a Light Chain CDR3 having the amino acid sequence of SEQ ID NO:5;
   (d) a Heavy Chain CDR1 having the amino acid sequence of SEQ ID NO:6;
   (e) a Heavy Chain CDR2 having the amino acid sequence of SEQ ID NO:7; and
   (f) a Heavy Chain CDR3 having the amino acid sequence of SEQ ID NO:8.

27. The monoclonal antibody, or epitope binding fragment thereof, according to embodiment 1 or 5, comprising
   (a) a Light Chain comprising the amino acid sequence of SEQ ID NO:19; and
   (b) a Heavy Chain comprising the amino acid sequence of SEQ ID NO:11.

28. The monoclonal antibody, or epitope binding fragment thereof, according to embodiment 1 or 4, comprising
   (a) a Light Chain CDR1 having the amino acid sequence of SEQ ID NO:34;
   (b) a Light Chain CDR2 having the amino acid sequence of SEQ ID NO:4; and
   (c) a Light Chain CDR3 having the amino acid sequence of SEQ ID NO:5;
   and further comprising at least one of
   (d) a Heavy Chain CDR1 having the amino acid sequence of SEQ ID NO:6;
   (e) a Heavy Chain CDR2 having the amino acid sequence of SEQ ID NO:7; and
   (f) a Heavy Chain CDR3 having the amino acid sequence of SEQ ID NO:8.

29. The monoclonal antibody, or epitope binding fragment thereof, according to embodiment 1 or 4, comprising
   (a) a Light Chain CDR1 having the amino acid sequence of SEQ ID NO:35;
   (b) a Light Chain CDR2 having the amino acid sequence of SEQ ID NO:4;
   (c) a Light Chain CDR3 having the amino acid sequence of SEQ ID NO:5;
   (d) a Heavy Chain CDR1 having the amino acid sequence of SEQ ID NO:6;
   (e) a Heavy Chain CDR2 having the amino acid sequence of SEQ ID NO:7; and
   (f) a Heavy Chain CDR3 having the amino acid sequence of SEQ ID NO:8.

30. The monoclonal antibody, or epitope binding fragment thereof, according to embodiment 1 or 5, comprising
   (a) a Light Chain comprising the amino acid sequence of SEQ ID NO:20; and
   (b) a Heavy Chain comprising the amino acid sequence of SEQ ID NO:11.

31. The monoclonal antibody, or epitope binding fragment thereof, according to embodiment 1 or 4, comprising
   (a) a Light Chain CDR1 having the amino acid sequence of SEQ ID NO:35;
   (b) a Light Chain CDR2 having the amino acid sequence of SEQ ID NO:4; and
   (c) a Light Chain CDR3 having the amino acid sequence of SEQ ID NO:5;
   and further comprising at least one of
   (d) a Heavy Chain CDR1 having the amino acid sequence of SEQ ID NO:6;
   (e) a Heavy Chain CDR2 having the amino acid sequence of SEQ ID NO:7; and
   (f) a Heavy Chain CDR3 having the amino acid sequence of SEQ ID NO:8.

32. The monoclonal antibody, or epitope binding fragment thereof, according to embodiment 1 or 4, comprising
   (a) a Light Chain CDR1 having the amino acid sequence of SEQ ID NO:36;
   (b) a Light Chain CDR2 having the amino acid sequence of SEQ ID NO:4;
   (c) a Light Chain CDR3 having the amino acid sequence of SEQ ID NO:5;
   (d) a Heavy Chain CDR1 having the amino acid sequence of SEQ ID NO:6;
   (e) a Heavy Chain CDR2 having the amino acid sequence of SEQ ID NO:7; and
   (f) a Heavy Chain CDR3 having the amino acid sequence of SEQ ID NO:8.

33. The monoclonal antibody, or epitope binding fragment thereof, according to embodiment 1 or 5, comprising (a) a Light Chain comprising the amino acid sequence of SEQ ID NO:21;
(b) a Heavy Chain comprising the amino acid sequence of SEQ ID NO:11.

34. The monoclonal antibody, or epitope binding fragment thereof, according to embodiment 1 or 4, comprising
(a) a Light Chain CDR1 having the amino acid sequence of SEQ ID NO:36;
(b) a Light Chain CDR2 having the amino acid sequence of SEQ ID NO:4; and
(c) a Light Chain CDR3 having the amino acid sequence of SEQ ID NO:5;
and further comprising at least one of
(d) a Heavy Chain CDR1 having the amino acid sequence of SEQ ID NO:6;
(e) a Heavy Chain CDR2 having the amino acid sequence of SEQ ID NO:7; and
(f) a Heavy Chain CDR3 having the amino acid sequence of SEQ ID NO:8.

35. The monoclonal antibody, or epitope binding fragment thereof, according to embodiment 1 or 4, comprising
(a) a Light Chain CDR1 having the amino acid sequence of SEQ ID NO:37;
(b) a Light Chain CDR2 having the amino acid sequence of SEQ ID NO:4;
(c) a Light Chain CDR3 having the amino acid sequence of SEQ ID NO:5;
(d) a Heavy Chain CDR1 having the amino acid sequence of SEQ ID NO:6;
(e) a Heavy Chain CDR2 having the amino acid sequence of SEQ ID NO:7; and
(f) a Heavy Chain CDR3 having the amino acid sequence of SEQ ID NO:8.

36. The monoclonal antibody, or epitope binding fragment thereof, according to embodiment 1 or 5, comprising
(a) a Light Chain comprising the amino acid sequence of SEQ ID NO:22; and
(b) a Heavy Chain comprising the amino acid sequence of SEQ ID NO:11.

37. The monoclonal antibody, or epitope binding fragment thereof, according to embodiment 1 or 4, comprising
(a) a Light Chain CDR1 having the amino acid sequence of SEQ ID NO:37;
(b) a Light Chain CDR2 having the amino acid sequence of SEQ ID NO:4; and
(c) a Light Chain CDR3 having the amino acid sequence of SEQ ID NO:5;
and further comprising at least one of
(d) a Heavy Chain CDR1 having the amino acid sequence of SEQ ID NO:6;
(e) a Heavy Chain CDR2 having the amino acid sequence of SEQ ID NO:7; and
(f) a Heavy Chain CDR3 having the amino acid sequence of SEQ ID NO:8.

38. The monoclonal antibody, or epitope binding fragment thereof, according to embodiment 1 or 4, comprising
(a) a Light Chain CDR1 having the amino acid sequence of SEQ ID NO:38;
(b) a Light Chain CDR2 having the amino acid sequence of SEQ ID NO:4;
(c) a Light Chain CDR3 having the amino acid sequence of SEQ ID NO:5;
(d) a Heavy Chain CDR1 having the amino acid sequence of SEQ ID NO:6;
(e) a Heavy Chain CDR2 having the amino acid sequence of SEQ ID NO:7; and
(f) a Heavy Chain CDR3 having the amino acid sequence of SEQ ID NO:8.

39. The monoclonal antibody, or epitope binding fragment thereof, according to embodiment 1 or 5, comprising
(a) a Light Chain comprising the amino acid sequence of SEQ ID NO:23; and
(b) a Heavy Chain comprising the amino acid sequence of SEQ ID NO:11.

40. The monoclonal antibody, or epitope binding fragment thereof, according to embodiment 4, comprising
(a) a Light Chain CDR1 having the amino acid sequence of SEQ ID NO:38;
(b) a Light Chain CDR2 having the amino acid sequence of SEQ ID NO:4; and
(c) a Light Chain CDR3 having the amino acid sequence of SEQ ID NO:5;
and further comprising at least one of
(d) a Heavy Chain CDR1 having the amino acid sequence of SEQ ID NO:6;
(e) a Heavy Chain CDR2 having the amino acid sequence of SEQ ID NO:7; and
(f) a Heavy Chain CDR3 having the amino acid sequence of SEQ ID NO:8.

41. The monoclonal antibody, or epitope binding fragment thereof, according to embodiment 1 or 4, comprising
(a) a Light Chain CDR1 having the amino acid sequence of SEQ ID NO:3;
(b) a Light Chain CDR2 having the amino acid sequence of SEQ ID NO:4;
(c) a Light Chain CDR3 having the amino acid sequence of SEQ ID NO:5;
(d) a Heavy Chain CDR1 having the amino acid sequence of SEQ ID NO:6;
(e) a Heavy Chain CDR2 having the amino acid sequence of SEQ ID NO:7; and
(f) a Heavy Chain CDR3 having the amino acid sequence of SEQ ID NO:39.

42. The monoclonal antibody, or epitope binding fragment thereof, according to embodiment 1 or 5, comprising
(a) a Light Chain comprising the amino acid sequence of SEQ ID NO:12; and
(b) a Heavy Chain comprising the amino acid sequence of SEQ ID NO:24.

43. The monoclonal antibody, or epitope binding fragment thereof, according to embodiment 1 or 4, comprising at least one of
(a) a Light Chain CDR1 having the amino acid sequence of SEQ ID NO:3;
(b) a Light Chain CDR2 having the amino acid sequence of SEQ ID NO:4; and
(c) a Light Chain CDR3 having the amino acid sequence of SEQ ID NO:5;
and further comprising
(d) a Heavy Chain CDR1 having the amino acid sequence of SEQ ID NO:6;
(e) a Heavy Chain CDR2 having the amino acid sequence of SEQ ID NO:7; and
(f) a Heavy Chain CDR3 having the amino acid sequence of SEQ ID NO:39.

44. The monoclonal antibody, or epitope binding fragment thereof, according to embodiment 1 or 4, comprising
    (a) a Light Chain CDR1 having the amino acid sequence of SEQ ID NO:31;
    (b) a Light Chain CDR2 having the amino acid sequence of SEQ ID NO:4;
    (c) a Light Chain CDR3 having the amino acid sequence of SEQ ID NO:5;
    (d) a Heavy Chain CDR1 having the amino acid sequence of SEQ ID NO:6;
    (e) a Heavy Chain CDR2 having the amino acid sequence of SEQ ID NO:7; and
    (f) a Heavy Chain CDR3 having the amino acid sequence of SEQ ID NO:39.

45. The monoclonal antibody, or epitope binding fragment thereof, according to embodiment 1 or 5, comprising
    (a) a Light Chain comprising the amino acid sequence of SEQ ID NO:16;
    (b) a Heavy Chain comprising the amino acid sequence of SEQ ID NO:24.

46. The monoclonal antibody, or epitope binding fragment thereof, according to embodiment 1 or 4, comprising
    (a) a Light Chain CDR1 having the amino acid sequence of SEQ ID NO:31; and
    (f) a Heavy Chain CDR3 having the amino acid sequence of SEQ ID NO:39;
    and further comprising at least one of
    (b) a Light Chain CDR2 having the amino acid sequence of SEQ ID NO:4; and
    (c) a Light Chain CDR3 having the amino acid sequence of SEQ ID NO:5;
    and further comprising at least one of
    (d) a Heavy Chain CDR1 having the amino acid sequence of SEQ ID NO:6; and
    (e) a Heavy Chain CDR2 having the amino acid sequence of SEQ ID NO:7.

47. The monoclonal antibody, or epitope binding fragment thereof, according to embodiment 1 or 4, comprising
    (a) a Light Chain CDR1 having the amino acid sequence of SEQ ID NO:32;
    (b) a Light Chain CDR2 having the amino acid sequence of SEQ ID NO:4;
    (c) a Light Chain CDR3 having the amino acid sequence of SEQ ID NO:5;
    (d) a Heavy Chain CDR1 having the amino acid sequence of SEQ ID NO:6;
    (e) a Heavy Chain CDR2 having the amino acid sequence of SEQ ID NO:7; and
    (f) a Heavy Chain CDR3 having the amino acid sequence of SEQ ID NO:39.

48. The monoclonal antibody, or epitope binding fragment thereof, according to embodiment 1 or 5, comprising
    (a) a Light Chain comprising the amino acid sequence of SEQ ID NO:17; and
    (b) a Heavy Chain comprising the amino acid sequence of SEQ ID NO:24.

49. The monoclonal antibody, or epitope binding fragment thereof, according to embodiment 1 or 4, comprising
    (a) a Light Chain CDR1 having the amino acid sequence of SEQ ID NO:32; and
    (f) a Heavy Chain CDR3 having the amino acid sequence of SEQ ID NO:39;
    and further comprising at least one of
    (b) a Light Chain CDR2 having the amino acid sequence of SEQ ID NO:4; and
    (c) a Light Chain CDR3 having the amino acid sequence of SEQ ID NO:5;
    and further comprising at least one of
    (d) a Heavy Chain CDR1 having the amino acid sequence of SEQ ID NO:6; and
    (e) a Heavy Chain CDR2 having the amino acid sequence of SEQ ID NO:7.

50. The monoclonal antibody, or epitope binding fragment thereof, according to embodiment 1 or 4, comprising
    (a) a Light Chain CDR1 having the amino acid sequence of SEQ ID NO:31;
    (b) a Light Chain CDR2 having the amino acid sequence of SEQ ID NO:4;
    (c) a Light Chain CDR3 having the amino acid sequence of SEQ ID NO:5;
    (d) a Heavy Chain CDR1 having the amino acid sequence of SEQ ID NO:6;
    (e) a Heavy Chain CDR2 having the amino acid sequence of SEQ ID NO:28; and
    (f) a Heavy Chain CDR3 having the amino acid sequence of SEQ ID NO:8.

51. The monoclonal antibody, or epitope binding fragment thereof, according to embodiment 1 or 5, comprising
    (a) a Light Chain comprising the amino acid sequence of SEQ ID NO:16;
    (b) a Heavy Chain comprising the amino acid sequence of SEQ ID NO:13.

52. The monoclonal antibody, or epitope binding fragment thereof, according to embodiment 1 or 4, comprising
    (a) a Light Chain CDR1 having the amino acid sequence of SEQ ID NO:31; and
    (e) a Heavy Chain CDR2 having the amino acid sequence of SEQ ID NO:28;
    and further comprising at least one of
    (b) a Light Chain CDR2 having the amino acid sequence of SEQ ID NO:4; and
    (c) a Light Chain CDR3 having the amino acid sequence of SEQ ID NO:5;
    and further comprising at least one of
    (d) a Heavy Chain CDR1 having the amino acid sequence of SEQ ID NO:6; and
    (f) a Heavy Chain CDR3 having the amino acid sequence of SEQ ID NO:8.

53. The monoclonal antibody, or epitope binding fragment thereof, according to embodiment 1 or 4, comprising
    (a) a Light Chain CDR1 having the amino acid sequence of SEQ ID NO:32;
    (b) a Light Chain CDR2 having the amino acid sequence of SEQ ID NO:4;
    (c) a Light Chain CDR3 having the amino acid sequence of SEQ ID NO:5;
    (d) a Heavy Chain CDR1 having the amino acid sequence of SEQ ID NO:6;
    (e) a Heavy Chain CDR2 having the amino acid sequence of SEQ ID NO:28; and
    (f) a Heavy Chain CDR3 having the amino acid sequence of SEQ ID NO:8.

54. The monoclonal antibody, or epitope binding fragment thereof, according to embodiment 1 or 5, comprising
   (a) a Light Chain comprising the amino acid sequence of SEQ ID NO:17;
   (b) a Heavy Chain comprising the amino acid sequence of SEQ ID NO:13.
55. The monoclonal antibody, or epitope binding fragment thereof, according to embodiment 1 or 4, comprising
   (a) a Light Chain CDR1 having the amino acid sequence of SEQ ID NO:32; and
   (e) a Heavy Chain CDR2 having the amino acid sequence of SEQ ID NO:28;
   and further comprising at least one of
   (b) a Light Chain CDR2 having the amino acid sequence of SEQ ID NO:4; and
   (c) a Light Chain CDR3 having the amino acid sequence of SEQ ID NO:5;
   and further comprising at least one of
   (d) a Heavy Chain CDR1 having the amino acid sequence of SEQ ID NO:6; and
   (f) a Heavy Chain CDR3 having the amino acid sequence of SEQ ID NO:8.
56. The monoclonal antibody, or epitope binding fragment thereof, according to embodiment 1 or 4, comprising
   (a) a Light Chain CDR1 having the amino acid sequence of SEQ ID NO:33;
   (b) a Light Chain CDR2 having the amino acid sequence of SEQ ID NO:4;
   (c) a Light Chain CDR3 having the amino acid sequence of SEQ ID NO:5;
   (d) a Heavy Chain CDR1 having the amino acid sequence of SEQ ID NO:6;
   (e) a Heavy Chain CDR2 having the amino acid sequence of SEQ ID NO:7; and
   (f) a Heavy Chain CDR3 having the amino acid sequence of SEQ ID NO:39.
57. The monoclonal antibody, or epitope binding fragment thereof, according to embodiment 1 or 5, comprising
   (a) a Light Chain comprising the amino acid sequence of SEQ ID NO:18; and
   (b) a Heavy Chain comprising the amino acid sequence of SEQ ID NO:24.
58. The monoclonal antibody, or epitope binding fragment thereof, according to embodiment 1 or 4, comprising
   (a) a Light Chain CDR1 having the amino acid sequence of SEQ ID NO:33; and
   (f) a Heavy Chain CDR3 having the amino acid sequence of SEQ ID NO:39;
   and further comprising at least one of
   (b) a Light Chain CDR2 having the amino acid sequence of SEQ ID NO:4; and
   (c) a Light Chain CDR3 having the amino acid sequence of SEQ ID NO:5;
   and further comprising at least one of
   (d) a Heavy Chain CDR1 having the amino acid sequence of SEQ ID NO:6; and
   (e) a Heavy Chain CDR2 having the amino acid sequence of SEQ ID NO:7.
59. The monoclonal antibody, or epitope binding fragment thereof, according to embodiment 1 or 4, comprising
   (a) a Light Chain CDR1 having the amino acid sequence of SEQ ID NO:34;
   (b) a Light Chain CDR2 having the amino acid sequence of SEQ ID NO:4;
   (c) a Light Chain CDR3 having the amino acid sequence of SEQ ID NO:5;
   (d) a Heavy Chain CDR1 having the amino acid sequence of SEQ ID NO:6;
   (e) a Heavy Chain CDR2 having the amino acid sequence of SEQ ID NO:7; and
   (f) a Heavy Chain CDR3 having the amino acid sequence of SEQ ID NO:39.
60. The monoclonal antibody, or epitope binding fragment thereof, according to embodiment 1 or 5, comprising
   (a) a Light Chain comprising the amino acid sequence of SEQ ID NO:19; and
   (b) a Heavy Chain comprising the amino acid sequence of SEQ ID NO:24.
61. The monoclonal antibody, or epitope binding fragment thereof, according to embodiment 1 or 4, comprising
   (a) a Light Chain CDR1 having the amino acid sequence of SEQ ID NO:34; and
   (f) a Heavy Chain CDR3 having the amino acid sequence of SEQ ID NO:39;
   and further comprising at least one of
   (b) a Light Chain CDR2 having the amino acid sequence of SEQ ID NO:4; and
   (c) a Light Chain CDR3 having the amino acid sequence of SEQ ID NO:5;
   and further comprising at least one of
   (d) a Heavy Chain CDR1 having the amino acid sequence of SEQ ID NO:6;
   (e) a Heavy Chain CDR2 having the amino acid sequence of SEQ ID NO:7.
62. The monoclonal antibody, or epitope binding fragment thereof, according to embodiment 1 or 4, comprising
   (a) a Light Chain CDR1 having the amino acid sequence of SEQ ID NO:3;
   (b) a Light Chain CDR2 having the amino acid sequence of SEQ ID NO:4;
   (c) a Light Chain CDR3 having the amino acid sequence of SEQ ID NO:5;
   (d) a Heavy Chain CDR1 having the amino acid sequence of SEQ ID NO:6;
   (e) a Heavy Chain CDR2 having the amino acid sequence of SEQ ID NO:28; and
   (f) a Heavy Chain CDR3 having the amino acid sequence of SEQ ID NO:39.
63. The monoclonal antibody, or epitope binding fragment thereof, according to embodiment 1 or 5, comprising
   (a) a Light Chain comprising the amino acid sequence of SEQ ID NO:12; and
   (b) a Heavy Chain comprising the amino acid sequence of SEQ ID NO:25.
64. The monoclonal antibody, or epitope binding fragment thereof, according to embodiment 1 or 4, comprising
   (a) a Light Chain CDR1 having the amino acid sequence of SEQ ID NO:3;
   (b) a Light Chain CDR2 having the amino acid sequence of SEQ ID NO:4; and
   (c) a Light Chain CDR3 having the amino acid sequence of SEQ ID NO:5;

and further comprising
(d) a Heavy Chain CDR1 having the amino acid sequence of SEQ ID NO:6;
(e) a Heavy Chain CDR2 having the amino acid sequence of SEQ ID NO:28; and
(f) a Heavy Chain CDR3 having the amino acid sequence of SEQ ID NO:39.

65. The monoclonal antibody, or epitope binding fragment thereof, according to embodiment 1 or 4, comprising
(a) a Light Chain CDR1 having the amino acid sequence of SEQ ID NO:3;
(b) a Light Chain CDR2 having the amino acid sequence of SEQ ID NO:4;
(c) a Light Chain CDR3 having the amino acid sequence of SEQ ID NO:5;
(d) a Heavy Chain CDR1 having the amino acid sequence of SEQ ID NO:6;
(e) a Heavy Chain CDR2 having the amino acid sequence of SEQ ID NO:29; and
(f) a Heavy Chain CDR3 having the amino acid sequence of SEQ ID NO:39.

66. The monoclonal antibody, or epitope binding fragment thereof, according to embodiment 1 or 5, comprising
(a) a Light Chain comprising the amino acid sequence of SEQ ID NO:12; and
(b) a Heavy Chain comprising the amino acid sequence of SEQ ID NO:26.

67. The monoclonal antibody, or epitope binding fragment thereof, according to embodiment 1 or 4, comprising
(a) a Light Chain CDR1 having the amino acid sequence of SEQ ID NO:3;
(b) a Light Chain CDR2 having the amino acid sequence of SEQ ID NO:4; and
(c) a Light Chain CDR3 having the amino acid sequence of SEQ ID NO:5;
and further comprising
(d) a Heavy Chain CDR1 having the amino acid sequence of SEQ ID NO:6;
(e) a Heavy Chain CDR2 having the amino acid sequence of SEQ ID NO:29; and
(f) a Heavy Chain CDR3 having the amino acid sequence of SEQ ID NO:39.

68. The monoclonal antibody, or epitope binding fragment thereof, according to embodiment 1 or 4, comprising
(a) a Light Chain CDR1 having the amino acid sequence of SEQ ID NO:3;
(b) a Light Chain CDR2 having the amino acid sequence of SEQ ID NO:4;
(c) a Light Chain CDR3 having the amino acid sequence of SEQ ID NO:5;
(d) a Heavy Chain CDR1 having the amino acid sequence of SEQ ID NO:6;
(e) a Heavy Chain CDR2 having the amino acid sequence of SEQ ID NO:30; and
(f) a Heavy Chain CDR3 having the amino acid sequence of SEQ ID NO:39.

69. The monoclonal antibody, or epitope binding fragment thereof, according to embodiment 1 or 5, comprising
(a) a Light Chain comprising the amino acid sequence of SEQ ID NO:12; and
(b) a Heavy Chain comprising the amino acid sequence of SEQ ID NO:27.

70. The monoclonal antibody, or epitope binding fragment thereof, according to embodiment 1 or 4, comprising
(a) a Light Chain CDR1 having the amino acid sequence of SEQ ID NO:3;
(b) a Light Chain CDR2 having the amino acid sequence of SEQ ID NO:4; and
(c) a Light Chain CDR3 having the amino acid sequence of SEQ ID NO:5;
and further comprising
(d) a Heavy Chain CDR1 having the amino acid sequence of SEQ ID NO:6;
(e) a Heavy Chain CDR2 having the amino acid sequence of SEQ ID NO:30; and
(f) a Heavy Chain CDR3 having the amino acid sequence of SEQ ID NO:39.

71. The monoclonal antibody, or epitope-binding fragment thereof, according to any one of embodiments 1 to 5, selective for an amino acid motif of hyperphosphorylated tau whose motif comprises of a phosphorylated serine residue and tyrosine residue spaced by a single residue.

72. The monoclonal antibody or epitope-binding fragment thereof according to embodiment 71, wherein the amino acid motif has the sequence:

-Y-X-S(phosphorylated)-P- wherein Y is tyrosine, X is a naturally occurring amino acid, P is proline and S(phosphorylated) is serine with a phosphorylated hydroxyl side chain.

73. The monoclonal antibody or epitope-binding fragment thereof according to any one of the preceding embodiments comprising an Fc region.

74. The monoclonal antibody or epitope-binding fragment thereof according to any one of the preceding embodiments further comprising a moiety for increasing the in vivo half-life of the agent.

75. The monoclonal antibody or an epitope-binding fragment thereof according to any one of the preceding embodiments, that specifically binds to human tau comprising a phosphorylated residue 396 according to the test criteria: i) the antibody does not substantially bind to non-phosphorylated tau; ii) the antibody does not substantially bind to tau phosphorylated at 404 when 396 is not phosphorylated; iii) the antibody does bind to tau phosphorylated at 396; and iv) the antibody does bind to tau when both 396 and 404 are phosphorylated.

76. The monoclonal antibody or an epitope-binding fragment thereof according to any one of the preceding embodiments, elicited against the bi-phosphorylated peptide comprising at least 18 consecutive amino acid residues, such as at least 20 consecutive amino acid residues within TDHGAEIVYK$^{\{p\}}$SPVVSGDT$^{\{p\}}$SPRHL (SEQ ID NO:2) covering residues 386-408 of 2N4R tau.

77. The monoclonal antibody or an epitope-binding fragment thereof according to embodiment 76, elicited against the bi-phosphorylated peptide comprising 18-40, such as at 18-30, such as 20-30 amino consecutive acid residues comprising TDHGAEIVYK$^{\{p\}}$SPVVSGDT$^{\{p\}}$SPRHL (SEQ ID NO:2) covering residues 386-410 of 2N4R tau.

78. The monoclonal antibody or an epitope-binding fragment thereof according to any of embodiments 1 to 70, having a specificity for phosphoTau (pTau) from AD-diseased patients over age-matched healthy controls, such that said monoclonal antibody or an epitope-binding fragment thereof has a specificity difference for phosphoTau (pTau) from AD-diseased patients over tau from age-healthy matched controls of more than 50-fold, such as more than 100-fold increase in specificity for AD disease material compared to healthy control material in an ELISA based assay detect phosphoTau (pTau) in brain homogenates from AD and from healthy control subjects, using a phospho- and multimer-specific Setup 1 ELISA.

79. The monoclonal antibody or an epitope-binding fragment thereof according to embodiment 78, having a specificity for AD-diseased Tau such that said monoclonal antibody or an epitope-binding fragment thereof has a specificity difference for AD over age-healthy matched controls of more than 50-fold, such as more than 100-fold increase in specificity for AD disease material compared to healthy control material in an ELISA based assay detect phosphoTau (pTau) in brain homogenates from AD and from healthy control subjects, using a phospho- and multimer-specific Setup 1 ELISA.

80. The monoclonal antibody or an epitope-binding fragment thereof according to any of embodiments 1 to 70, elicited against the bi-phosphorylated peptide: TDHGAEIVYK$^{\{p\}}$SPVVSGDT$^{\{p\}}$SPRHL (SEQ ID NO:2) covering residues 386-410 of 2N4R tau, or an epitope-binding fragment thereof, capable of specifically binding to the phosphorylated residue 396 of human tau.

81. An antibody, or epitope-binding fragment thereof, as defined according to any of embodiments 1 to 70, which has been produced or manufactured in a cell line such as a human cell line, a mammal non-human cell line, an insect, yeast or bacterial cell line, or by a recombinant technology.

82. The antibody, or epitope-binding fragment thereof, according to embodiment 81 produced in a CHO cell line, HEK cell line, BHK-21 cell line, murine cell line (such as a myeloma cell line), fibrosarcoma cell line, PER.C6 cell line, HKB-11 cell line, CAP cell line and HuH-7 human cell line.

83. The monoclonal antibody or an epitope-binding fragment thereof according to any of embodiments 1 to 70, wherein said monoclonal antibody is expressed by a hybridoma that was isolated by screening hybridomas with human pathological and non-pathological tau to isolate clones that both i) were specific towards the phospho-epitopes S396 and ii) specifically recognize hyper-phosphorylated tau from human Alzheimer's disease brains, wherein said antibodies or epitope binding fragments thereof are able to discriminate between pathological and non-pathological human tau protein.

84. The monoclonal antibody or epitope-binding fragment thereof according to any of embodiments 1 to 70, wherein the antibody or epitope-binding fragment thereof further comprises a detectable moiety.

85. The monoclonal antibody or epitope-binding fragment thereof according to embodiment 84 wherein the detectable moiety is a fluorescent label, a chemiluminescent label, a paramagnetic label, a radioisotopic label or an enzyme label.

86. A preparation comprising the antibody or epitope-binding fragment thereof define in any of embodiments 1 to 70, wherein said preparation is substantially free of naturally-arising antibodies that are either not capable of binding to tau or that do not materially alter an anti-tau functionality of the preparation, wherein said functionality is selected from the group consisting of:
  (i) a substantial inability to bind to non-phosphorylated tau;
  (ii) a substantial inability to bind to tau that is phosphorylated at S404 and not phosphorylated at S396;
  (iii) the ability to bind to tau phosphorylated at S396;
  (iv) the ability to bind tau phosphorylated at both S396 and at S404;
  (v) the ability to selectively discriminate between phosphorylated tau residues S396 and S404 such that it is substantially unable to bind the phosphorylated 404 residue or such that it preferentially binds to S396;
  (vi) the ability to bind hyper-phosphorylated tau from human Alzheimer's disease brains;
  (vii) the ability to discriminate between pathological and non-pathological human tau protein; and/or
  (viii) the capability, when used as described in the Examples with immune-depleted rTg4510 extracts from transgenic mice, to specifically reduce the hyperphosphorylated tau 64 kDa and 70 kDa bands by at least 90%, while not reducing the 55 kDa tau band by more than 10%.

87. A preparation comprising the antibody or epitope-binding fragment thereof defined by embodiments 1 to 70, wherein said antibody or said epitope-binding fragment thereof possesses a structural change in its amino acid sequence, relative to the structure of a naturally-occurring anti-tau antibody, wherein said structural change causes said antibody or said fragment to exhibit an altered functionality relative to the functionality exhibited by said naturally-occurring anti-tau antibody, wherein said functionality is selected from the group consisting of:
  (i) a substantial inability to bind to non-phosphorylated tau;
  (ii) a substantial inability to bind to tau that is phosphorylated at S404 and not phosphorylated at S396;
  (iii) the ability to bind to tau phosphorylated at S396;
  (iv) the ability to bind to tau phosphorylated at both S396 and at S404;
  (v) the ability to selectively discriminate between phosphorylated tau residues S396 and S404 such that it is substantially unable to bind the phosphorylated 404 residue or such that it preferentially binds to S396;
  (vi) the ability to bind hyper-phosphorylated tau from human Alzheimer's disease brains;
  (vii) the ability to discriminate between pathological and non-pathological human tau protein; and/or
  (viii) the capability, when used as described herein with immune-depleted rTg4510 extracts from transgenic mice, to specifically reduce the hyperphosphorylated tau 64 kDa and 70 kDa bands by at least 90%, while not reducing the 55 kDa tau band by more than 10%.

88. A pharmaceutical composition comprising the monoclonal antibody or epitope-binding fragment thereof defined in any of embodiments 1 to 70, or the preparation according to any of embodiments 86 to 87, and a pharmaceutical acceptable carrier.

89. A nucleic acid encoding a monoclonal antibody or epitope-binding fragment thereof according to any one of embodiments 1 to 70, or encoding a constituent chain thereof.

90. The monoclonal antibody, or epitope-binding fragment thereof, defined in any one of embodiments 1 to 70, or the preparation according to any one of embodiments 86 to 87, or the pharmaceutical composition of embodiment 88, for use in therapy.
91. The monoclonal antibody, or epitope-binding fragment thereof, according to any one of embodiments 1 to 70, or the preparation according to any one of embodiments 86 to 87, or the pharmaceutical composition of embodiment 88, for use in treating, diagnosing or imaging a tauopathy.
92. The monoclonal antibody, or epitope-binding fragment thereof, according to any one of embodiments 1 to 70, or the preparation according to any one of embodiments 86 to 87, or the pharmaceutical composition of embodiment 88, for use in treating a tauopathy selected from the group consisting of Alzheimer's disease, Argyrophilic Grain Disease (AGD), Psychosis, particularly Psychosis due to AD or Psychosis in patients with AD, apathy due to AD or apathy in patients with AD, psychiatric symptoms of patients with Lewy body dementia, Progressive Supranuclear Palsy (PSP), Frontotemporal dementia (FTD or variants thereof), TBI (traumatic brain injury, acute or chronic), Corticobasal Degeneration (CBD), Picks Disease, Primary age-related tauopathy (PART), Neurofibrillary tangle-predominant senile dementia, Dementia pugilistica, Chronic traumatic encephalopathy, stroke, stroke recovery, neurodegeneration in relation to Parkinson's disease, Parkinsonism linked to chromosome, Lytico-Bodig disease (Parkinson-dementia complex of Guam), Ganglioglioma and gangliocytoma, Meningioangiomatosis, Postencephalitic parkinsonism, Subacute sclerosing panencephalitis, Huntington's disease, lead encephalopathy, tuberous sclerosis, Hallervorden-Spatz disease and lipofuscinosis.
93. The monoclonal antibody, or epitope-binding fragment thereof, according to any one of embodiments 1 to 70, for use in the treatment of Alzheimer's disease.
94. The monoclonal antibody, or epitope-binding fragment thereof, according to any one of embodiments 1 to 70, or the preparation according to any one of embodiments 86 to 87, or the pharmaceutical composition of embodiment 88, for use in the manufacturing of a medicament for treating, diagnosing or imaging tauopathies.
95. The monoclonal antibody, or epitope-binding fragment thereof, according to any one of embodiments 1 to 70, or the preparation according to any one of embodiments 86 to 87, or the pharmaceutical composition of embodiment 88, for use as a medicament for treating a disease selected from the group consisting of Alzheimer's disease, Argyrophilic Grain Disease (AGD), Psychosis, particularly Psychosis due to AD or Psychosis in patients with AD, apathy due to AD or apathy in patients with AD, psychiatric symptoms of patients with Lewy body dementia, Progressive Supranuclear Palsy (PSP), Frontotemporal dementia (FTD or variants thereof), TBI (traumatic brain injury, acute or chronic), Corticobasal Degeneration (CBD), Picks Disease, Primary age-related tauopathy (PART), Neurofibrillary tangle-predominant senile dementia, Dementia pugilistica, Chronic traumatic encephalopathy, stroke, stroke recovery, neurodegeneration in relation to Parkinson's disease, Parkinsonism linked to chromosome, Lytico-Bodig disease (Parkinson-dementia complex of Guam), Ganglioglioma and gangliocytoma, Meningioangiomatosis, Postencephalitic parkinsonism, Subacute sclerosing panencephalitis, Huntington's disease, lead encephalopathy, tuberous sclerosis, Hallervorden-Spatz disease and lipofuscinosis.
96. A method of treating, diagnosing or imaging Alzheimer's disease or other tauopathies in a subject, said method comprising administering a therapeutically effective amount of the monoclonal antibody, or epitope-binding fragment thereof, according to any one of embodiments 1 to 70, the preparation according to any one of embodiments 86 to 87, or the pharmaceutical composition of embodiment 88 to said subject.
97. The method according to embodiment 96 wherein the treatment is chronic.
98. The method according to embodiment 97, wherein the chronic treatment is for at least 2 weeks, such as at least for 1 month, at least for 6 months, or at least for 1 year.
99. The method according to any one of embodiments 96 to 98 wherein the subject is human.
100. A kit comprising the antibody, or fragment thereof, according to any one of embodiments 1-70, the preparation according to any one of embodiments 86 to 87, or the pharmaceutical composition of embodiment 88 for use in therapy.
101. The monoclonal antibody, or epitope-binding fragment thereof, of embodiments 1 to 70, or a preparation or pharmaceutical composition comprising said antibody or fragment, for use in detecting or measuring the presence or amount of said tau in the brain of a subject.
102. The monoclonal antibody, or epitope-binding fragment thereof, preparation or pharmaceutical composition of embodiment 88, wherein said detection or measurement comprises in vivo imaging of said anti-tau antibody bound to said tau.
103. The monoclonal antibody, or epitope-binding fragment thereof, preparation or pharmaceutical composition of embodiment 99 to 100, wherein said detection or measurement comprises ex vivo imaging of said anti-tau antibody or said fragment thereof, bound to said tau.
104. A method of removing at least 90% of hyperphosphorylated Tau from a tangle said tangle comprising hyperphosphorylated Tau said method comprising contacting hyperphosphorylated Tau with a monoclonal antibody, or epitope-binding fragment thereof, said antibody or epitope-binding fragment thereof, being selective for Tau having residue 396 phosphorylated and as defined in any one of embodiments 1 to 70.
105. A method of delaying the progression of Alzheimer's Disease in a patient, said method comprising reducing or attenuating the accumulation of pathological tau protein in said patient by administering a monoclonal antibody, or epitope-binding fragment thereof, said antibody or epitope-binding fragment thereof, being selective for Tau having residue 396 phosphorylated and as defined in any one of embodiments 1 to 70.
106. A pharmaceutical composition comprising i) a Tau antibody according to embodiment 1-70 and in particular embodiments 17, 18, 44 or 45 and ii) a compound selected from the group consisting of
   a) a BACE inhibitor;
   b) a compound useful in active or passive Tau immunotherapy;
   c) a compound useful in active or passive As peptide immunotherapy;
   d) an NMDA receptor antagonists;
   e) a further a Tau protein aggregation inhibitor;
   e) an acetylcholine esterase inhibitor;
   f) an antiepileptic;

g) an anti-inflammatory drug; and
h) an SSRI; and
iii) one or more pharmaceutically acceptable excipients.
107. A method of treating Alzheimer's Disease, reducing of the progression of AD or reducing the symptoms of AD, comprising a therapy comprising the administration of
i) a Tau antibody according to embodiment 1-70 and in particular embodiments 17, 18, 44 or 45 and ii) a compound selected from the group consisting of
a) a BACE inhibitor;
b) a compound useful in active or passive Tau immunotherapy;
c) a compound useful in active or passive As peptide immunotherapy;
d) an NMDA receptor antagonists;
e) a further a Tau protein aggregation inhibitor;
e) an acetylcholine esterase inhibitor;
f) an antiepileptic;
g) an anti-inflammatory drug; and
h) an SSRI.
108. A kit comprising i) a composition comprising a Tau antibody according to embodiment 1-70 and in particular embodiments 17, 18, 44 or 45 and ii) a composition a compound selected from the group consisting of
a) a BACE inhibitor;
b) a compound useful in active or passive Tau immunotherapy;
c) a compound useful in active or passive As peptide immunotherapy;
d) an NMDA receptor antagonists;
e) a further Tau protein aggregation inhibitor;
f) an acetylcholine esterase inhibitor;
g) an antiepileptic;
h) an anti-inflammatory drug; and
i) an antidepressant.
109. A composition according to claim 106, a method according to claim 107, a kit according to claim 108 wherein said BACE1 inhibitor is a small molecule BACE I inhibitor selected from the group consisting of LY2886721, MK-8931, AZD3293, or E2609.
110. A composition according to claim 106, a method according to claim 107, a kit according to claim 108 wherein said BACE1 inhibitor is of the formula I

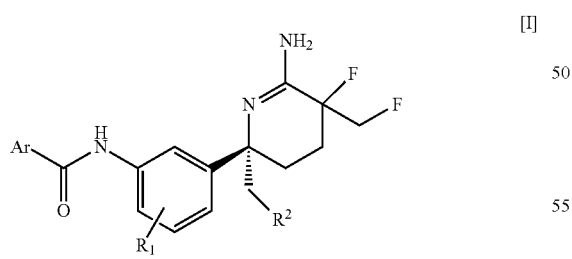

[I]

wherein Ar is selected from the group consisting of phenyl, pyridyl, pyrimidyl, pyrazinyl, imidazolyl, pyrazolyl, thiazolyl, oxazolyl, isoxazolyl, and wherein Ar is optionally substituted with one or more substituents selected from halogen, CN, C1-C6 alkyl, C2-C6 alkenyl, C2-C6 alkynyl, C1-C6 fluoroalkyl or C1-C6 alkoxy; and R1 is one or more hydrogen, halogen, C1-C3 fluoroalkyl or C1-C3 alkyl; and R2 presents hydrogen or fluoro.

111. A composition, method according or a kit according to claim 110, wherein the compound of Formula I is selected from the group consisting of

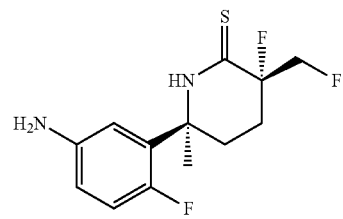 [SMILES: C[C@@]1(c2cc(N)ccc2F)CC[C@](F)(CF)C(=S)N1]

(3S,6S)-6-(5-amino-2-fluorophenyl)-3-fluoro-3-(fluoromethyl)-6-methylpiperidine-2-thione

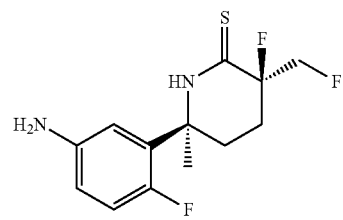 [SMILES: C[C@@]1(c2cc(N)ccc2F)CC[C@@](F)(CF)C(=S)N1]

(3R,6S)-6-(5-amino-2-fluorophenyl)-3-fluoro-3-(fluoromethyl)-6-methylpiperidine-2-thione

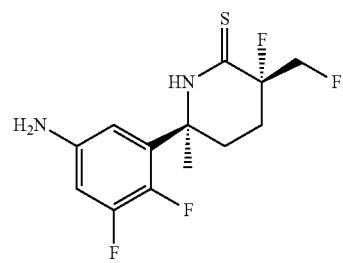 [SMILES: C[C@@]1(c2cc(N)cc(F)c2F)CC[C@](F)(CF)C(=S)N1]

(3S,6S)-6-(5-amino-2,3-difluorophenyl)-3-fluoro-3-(fluoromethyl)-6-methylpiperidine-2-thione

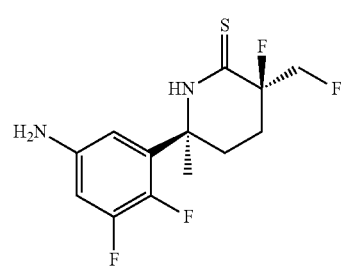 [SMILES: C[C@@]1(c2cc(N)cc(F)c2F)CC[C@@](F)(CF)C(=S)N1]

(3R,6S)-6-(5-amino-2,3-difluorophenyl)-3-fluoro-3-(fluoromethyl)-6-methylpiperidine-2-thione

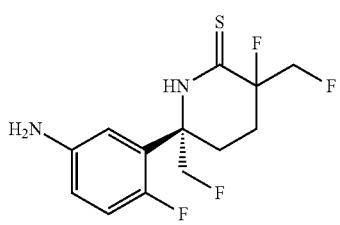 [SMILES: Nc1ccc(F)c([C@]2(CF)CCC(F)(CF)C(=S)N2)c1]

(6S)-6-(5-amino-2-fluorophenyl)-3-fluoro-3,6-bis(fluoromethyl)piperidine-2-thione 112. A composition according to claim 106, a method according to claim 107, a kit according to claim 108 wherein said BACE1 inhibitor is of the Formula II

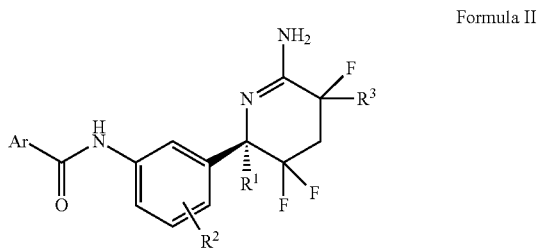

Formula II wherein Ar is selected from the group consisting of phenyl, pyridyl, pyrimidyl, pyrazinyl, imidazolyl, pyrazolyl, 1,2,4-triazolyl, thiophenyl, thiazolyl, oxazolyl, isoxazolyl, 1,3,4-thiadiazolyl, isothiazolyl, 1,3,4-oxadiazolyl, 1,2,4-oxadiazolyl, furazanyl and 1,2,4-thiadiazolyl and where the Ar is optionally substituted with one or more halogen, CN, C1-C6 alkyl, C2-C6 alkenyl, C2-C6 alkynyl, C1-C6 fluoroalkyl or C1-C6 alkoxy; R1 is C1-C3 alkyl or C1-C3 fluoroalkyl; R2 is hydrogen, halogen, C1-C3 fluoroalkyl or C1-C3 alkyl; and R3 is C1-C3 alkyl.

113. A composition according to claim 106, a method according to claim 107, a kit according to claim 108 wherein said BACE1 inhibitor selected from the group consisting of: N-(3-((2R,5S)-6-amino-3,3,5-trifluoro-2,5-dimethyl-2,3,4,5-tetrahydropyridin-2-yl)-4 fluorophenyl)-5-fluoropicolinamide; N-(3-((2R,5S)-6-amino-3,3,5-trifluoro-2,5-dimethyl-2,3,4,5-tetrahydropyridin-2-yl)-4fluorophenyl)-5-methoxypyrazine-2-carboxamide; N-(3-((2R,5S)-6-amino-3,3,5-trifluoro-2,5-dimethyl-2,3,4,5-tetrahydropyridin-2-yl)-4-fluorophenyl)-5-methoxypicolinamide; N-(3-((2R,5S)-6-amino-3,3,5-trifluoro-2,5-dimethyl-2,3,4,5-tetrahydropyridin-2-yl)-4fluorophenyl)-5-cyano-3-methylpicolinamide; and N-(3-((2R,5R)-6-amino-3,3,5-trifluoro-2,5-dimethyl-2,3,4,5-tetrahydropyridin-2-yl)-4 fluorophenyl)-5-(difluoromethyl)pyrazine-2-carboxamide.

114. A composition according to claim 106, a method according to claim 107, a kit according to claim 108 wherein said NMDA receptor antagonist is selected from the group consisting of, Memantine, Namenda, Namzaric (memantine/donepezil), and generic forms thereof.

115. A composition according to claim 106, a method according to claim 107, a kit according to claim 108 wherein said acetylcholine esterase inhibitor is selected from the group consisting of Donepezil, Galantamine and Rivastigmine.

116. A composition according to claim 106, a method according to claim 107, a kit according to claim 108 wherein said antidepressant is selected from the group consisting of Escitalopram, Sertraline, Citalopram, Paroxetine, Fluoxetine, Venlafaxine, Trazodone, Mirtazapine, Vortioxetine and generic forms thereof.

117. A composition according to claim 106, a method according to claim 107, a kit according to claim 108 for use in treating a tauopathy selected from the group consisting of Alzheimer's disease, Argyrophilic Grain Disease (AGD), Psychosis, particularly Psychosis due to AD or Psychosis in patients with AD, psychiatric symptoms of patients with Lewy body dementia, Progressive Supranuclear Palsy (PSP), Frontotemporal dementia (FTD or variants thereof), TBI (traumatic brain injury, acute or chronic), Corticobasal Degeneration (CBD), Picks Disease, Primary age-related tauopathy (PART), Neurofibrillary tangle-predominant senile dementia, Dementia pugilistica, Chronic traumatic encephalopathy, stroke, stroke recovery, neurodegeneration in relation to Parkinson's disease, Parkinsonism linked to chromosome, Lytico-Bodig disease (Parkinson-dementia complex of Guam), Ganglioglioma and gangliocytoma, Meningioangiomatosis, Postencephalitic parkinsonism, Subacute sclerosing panencephalitis, Huntington's disease, lead encephalopathy, tuberous sclerosis, Hallervorden-Spatz disease and lipofuscinosis.

118. A composition according to claim 106, a method according to claim 107, a kit according to claim 108 for use in the manufacturing of a medicament for treating, diagnosing or imaging tauopathies.

119. A composition according to claim 106, a method according to claim 107, a kit according to claim 108 for treating Alzheimer's disease, Argyrophilic Grain Disease (AGD), Progressive Supranuclear Palsy (PSP), Corticobasal Degeneration (CBD), Psychosis due to AD or Psychosis in patients with AD, and psychiatric symptoms of patients with Lewy body dementia.

EXAMPLES

Example 1: Immunization of Mice with Tau Phospho-Peptides 396/404

C56/BL6 and FVB mice were immunised with 10 µg P30 conjugated phosphorylated tau peptide 386-408 (pS396/pS404) (SEQ ID NO:2) formulated in TiterMax adjuvant.

Mice (C56/BL6 and FVB strains, female and male. 2- to 3-month-old mice were immunized with peptide epitope P30 conjugated phosphorylated tau 386-408.

Immunogenic P30 conjugated phosphorylated tau 386-408 (pS396/pS404) peptide was formulated in TiterMax (400 µg/ml peptide mixed 1:1 vol:vol) following the TiterMax/vendor protocol and mice were injected subcutaneously with 20 µg peptide (100 µl) of antigen. Control mice were injected with adjuvant only. All peptide-immunised mice were boosted with 0.5 µg peptide/Titermax (10 µg/ml peptide formulated as described above and injected) at monthly intervals. The mice were finally boosted with P30 conjugated phosphorylated tau 386-408 (pS396/pS404) without Titermax 3 days prior to harvest of splenocyte followed by fusion of splenocytes with SP-2 cells. Generated primary hybridomas were selected for re-cloning cycles after exhibiting positive binding to phosphorylated tau 386-408 (pS396/pS404) as detected by ELISA, and exhibiting preferential binding activity to S1 and P3 antigens from AD and TG4510 brain lysate (described below in Example 2B). Such binding was compared with the binding activity of such antibodies to brain lysate from controls, using dot blots and brain lysate coated ELISA or MSD plates.

Example 2A: Hybridoma Generation

The mice were boosted with P30 conjugated phosphorylated tau 386-408 (pS396/pS404) without Titermax 3 days prior to harvest from spleens from responding mice followed by fusion of splenocytes with SP-2 cells. Hybridomas were selected for re-cloning cycles after positive binding to phosphorylated tau 386-408 (pS396/pS404) detected by ELISA, and preferential binding activity to S1 and P3 antigens from AD and TG4510 brain lysate in comparison to brain lysate from controls using dot blots and brain lysate coated ELISA or MSD plates.

Example 2B: Western Blot and Dot-Blot Analysis of Specific Antibodies

Tau Biochemical Fractionation

Brain tissues from humans or rTg4510 mice overexpressing the human tau mutation P301L were homogenized in 10 volumes of Tris-buffered saline containing protease and phosphatase inhibitors as follows: 50 mM Tris/HCl (pH 7.4); 274 mM NaCl; 5 mM KCl; 1% protease inhibitor mixture (Roche); 1% phosphatase inhibitor cocktail I & II (Sigma); and 1 mM phenylmethylsulfonyl fluoride (PMSF; Sigma). The homogenates were centrifuged at 27,000×g for 20 min at 4° C. to obtain supernatant (S1) and pellet fractions. Pellets were re-homogenized in 5 volumes of high salt/sucrose buffer (0.8 M NaCl, 10% sucrose, 10 mM Tris/HCl, [pH 7.4], 1 mM EGTA, 1 mM PMSF) and centrifuged as above. The supernatants were collected and incubated with sarkosyl (1% final concentration; Sigma) for one hour at 37° C., followed by centrifugation at 150,000×g for one hour at 4° C. to obtain sarkosyl-insoluble pellets, referred to as P3 fraction herein. The P3 pellet was resuspended in TE buffer (10 mM Tris/HCl [pH 8.0], 1 mM EDTA) to a volume equivalent to half of the original volume used for the brain homogenates.

Western and Dot Blots

Fractionated tissue extracts S1 and P3 were dissolved in SDS-sample buffer containing 0.1 M DTT. The heat-treated samples (95° C. for 10 min) were separated by gel electrophoresis on 4-12% Bis-Tris SDS-PAGE gels (Invitrogen) and transferred onto PVDF membranes (BioRad Laboratories, Hercules, CA). Dot blot samples were spotted directly onto nitrocellulose membranes (Amersham, Pittsburgh, PA) at known concentrations across samples. Both Western and dot blot membranes were blocked in 5% non-fat dry milk in TBS-Tween (0.5%) pH 7.4, followed by incubation in 1 µg/ml of C10-2 overnight at 4° C. Membranes were washed and incubated with peroxidase-conjugated anti-mouse IgG (1:5000; Jackson ImmunoResearch, West Grove, PA). Bound antibodies were detected using an enhanced chemiluminescence system (ECL PLUS kit; PerkinElmer). Quantitation and visual analysis of Western and dot blot immunoreactivity was performed with a computer-linked LAS-4000 BioImaging Analyzer System (Fujifilm, Tokyo, Japan) and Multi Gauge v3.1 software (Fujifilm). Protein loading was adjusted by the volume of original fractions and can be converted to original tissue wet weight.

Example 3. Fluid Phase Inhibition Assay for AD-P3 Capture

Example 3A Purpose: To quantify inhibition of human C10-2 and mutated variants of binding to pS396 tau antigens in AD-P3 brain material to murine C10.2. MSD plates coated with mouse C10-2 prior to incubation with AD-P3 or AD-P3 preincubated with C10.2 variants of interest. The degree of inhibition is depicted as IC50 values reflecting apparent affinity of fluid phase antibody binding to antigens. IC50 values were obtained by fitting to one or two-site binding model using Graph Pad Prism software. A negative control antibody (mouse C10-1) reactive with P (404) Tau was added for comparison.

Method: MSD plates were coated with capture antibody (750 ng/ml murine C10-2 in carbonated buffer pH 8.5) overnight at room temperature followed by blocking (30 min. in PBS, 3% BSA, 0.1% NP40) and 5 times wash (PBS, 0.1% BSA, 0.1% NP40). Graded concentration (0-1000 nM) of antibodies was incubated 60 min. with AD-P3 material at room temperature and subsequently incubated 1 hour at room temperature in MSD plates coated with mouse C10-2 as described above. Plates were washed 5 times in (PBS, 0.1% BSA, 0-0.1% NP40) and anti-human total Tau (MSD sulfo tagged 1:50) was added to detect captured tau which reflect non-inhibited free tau antigens.

Results: Data showed dose dependent inhibition of tau capture using human C10-2 and variants (FIG. 1). The variants C10-2_N32S and C10-2_N32S:A101T inhibits stronger (IC50=44 and 14 nM respectively, fitted to one site binding models) whereas C10-2 showed heterogeneous inhibition reflected by best fit to two-site binding model (IC50 14 nM/630 nM). The low affinity binding (IC50=630) was predominant since high affinity antibody binding (IC50=14 nM) comprised less than 25% of the total binding. Results are shown in FIG. 1.

Example 3B Purpose: To quantify inhibition of human C10-2 and mutated variant binding to pS396 tau 386-408 peptides in fluid phase inhibition assay. The degree of inhibition is depicted as IC50 values reflecting apparent affinity of antibody binding. IC50 values were obtained by fitting to one or two-site binding model using Graph Pad Prism software. A negative control antibody (mouse C10-1) reactive with P (404) Tau was added for comparison.

Method: MSD plates were coated with pS396 Tau 386-408 peptide in carbonate buffer pH 9.5, overnight at room temperature followed by blocking (30 minutes in PBS, 3% BSA, 0.1% NP40) and 5 times wash (PBS, 0.1% BSA, 0.1% NP40). Graded concentration (0-1000 nM) of pS396 tau 386-408 was incubated 60 min. with 1 ng/ml antibody at room temperature and subsequently incubated 1 hour at room temperature in MSD plates coated with pS396 Tau 386-408 as described above. Plates were washed 5 times in (PBS, 0.1% BSA, 0.1% NP40) and anti-human total Tau (MSD sulfo tagged 1:50) was added to detect bound antibody which reflect non-inhibited free antibody. Results are shown in FIG. 2.

Example 4. Immunohistochemical Profiling of Antibodies

Tissues

Mouse: Mouse brain tissues were collected from 8 months old rTg4510 mice. These transgenic mice express human mutated Tau (P301L 0N4R) under a tet-off responsive element in CamK2 positive neurons and show a pronounced tau hyperphosphorylation and tangle formation from 6 months of age and onwards. Non-transgenic littermates served as controls. Mouse brains were fixed by immersion in 4% paraformaldehyde and embedded in paraffin. Human: Formalin-fixed paraffin-embedded human brain samples of frontal cortex were acquired from Tissue Solutions (Glasgow, UK). Tissues from 3 donors with diagnosed end stage Alzheimer's disease (AD; Braak stage V-VI) were compared to an age-matched non-demented control donor.

Immunohistochemistry:

Four m thick sections of mouse and human tissues were cut on a microtome, deparaffinized and subjected to antigen retrieval by microwaving the sections in 10 mM Citrate buffer, pH 6, for 10 minutes. Endogenous peroxidase was blocked with 1% hydrogen peroxide followed by 5% normal swine serum in PBS, 1% BSA, 0.3% Triton X-100 (PBS-BT). Sections were incubated overnight at 4 degrees C. with hC10-2, hC10-2_N32S and hC10-2_N32S_A101T antibodies diluted in PBS-BT at the range of concentrations indicated in FIG. 1. The sections were washed in PBS, 0.25% BSA, 0.1% Triton X-100, before being incubated with a biotinylated secondary swine anti-human antibody (#B1140; Sigma-Aldrich) at 1:200 for 1 hour. Following additional washing, StreptAvidin-Biotin Complex kit (Vector Laboratories, Burlingame, CA) was applied and finally, immunoreactivity was visualized with 0.05% diaminobenzidine. The sections were counterstained with hematoxylin to reveal the location of nuclei.

Results hC10-2, hC10-2_N32S and hC10-2_N32S_A101T labelled structures consistent with pathological tau in 3 AD brains (i.e. tangles, neuropil threads, dystrophic neurites). The intensity of immunoreactivity was concentration dependent. No apparent labelling of e.g. glia cells or vessels was detected. No immunoreactivity was detected in sections from a control brain. Likewise, all 3 antibodies gave rise to the expected pattern for phosphorylated tau in both hippocampus and cortex of rTg4510 brains. In brain sections from non-transgenic mice no immunoreactivity was detected.

Example 5. Decoration of Tau Structures in rTg4510 Mice Following i.v. Injection Method Ten months old rTg4510 mice. These transgenic mice express human mutated Tau (P301L 0N4R) under a tet-off responsive element in CamK2 positive neurons and show a pronounced tau hyperphosphorylation and tangle formation from 6 months of age and onwards. In addition, neurodegeneration is present at 10 months of age in rTg4510 mice in regions with strong pathology. Single transgenic tTA littermates served as controls. The mice received a single injection via the tail vein with either hC10-2, hC10-2_N32S or hC10-2_N32S_A101T antibodies at a concentration of 80 mg/kg. A volume of 150 µL was injected per mouse. Three days after injection, the mice were perfused for 2 min. with PBS followed by 10 min perfusion with 4% paraformaldehyde. The brains were cryoprotected in 30% sucrose and cut into 40 microns free floating cryosections. The sections were incubated with 5% normal swine serum in PBS/1% BSA/ 0.3% Triton X-100 for 20 min, washed in PBS and finally incubated with AlexaFluor488-conjugated secondary anti-human IgG at 1:200 (#709-545-149; Jackson ImmunoResearch Laboratories, West Grove, USA). Hoechst was used for nuclear staining. The sections were washed in PBS, mounted and examined by fluorescent microscopy.

Results

I.v. injection of hC10-2, hC10-2_N32S and hC10-2_N32S_A101T resulted in in vivo binding to target structures in hippocampus and cortex in aged rTg4510 mouse brains (FIGS. 4-7). The number of positive structures observed varied between individual rTg4510 animals. In tTA control mice, no specific fluorescent signals were detected after injection of any of the three antibodies (FIG. 4-7). Serving as a negative control, injection of a control human IgG did not result in signals in rTg4510 mice. The positive signals in rTg4510 brains did not readily appear as intracellular staining and may represent extracellular tau material released during the process of neurodegeneration. Collectively, these data suggest that hC10-2, hC10-2_N32S and hC10-2_N32S_A101T antibodies are able to penetrate into the brain parenchyma and specifically decorate targets in rTg4510 mice in vivo.

Example 6. Characterization of Tau Immunoreactivity in Alzheimer's Disease Brains Tissues:

Paraffin-embedded human brain samples of frontal cortex were acquired from Tissue Solutions (Glasgow, UK). Tissues from donors with diagnosed end stage Alzheimer's disease (AD; Braak stage V-VI) were included.

Immunohistochemistry

Four µm thick sections of human tissues were cut on a microtome, deparaffinized and subjected to antigen retrieval by microwaving the sections in 10 mM Citrate buffer, pH 6, for 10 minutes. Sections were incubated with 5% normal swine serum in PBS, 1% BSA, 0.3% Triton X-100 (PBS-BT) followed by overnight incubation at 4° C. with hC10-2 or hC10-2_N32S_A101T antibodies diluted in PBS-BT. The sections were washed in PBS, 0.25% BSA, 0.1% Triton X-100. Immunoreactivity was visualized by AlexaFluor488-conjugated secondary anti-human IgG (1:200; #709-545-149, Jackson ImmunoResearch Laboratories, West Grove, USA). For double immunofluorescence, sections were co-incubated with AT8 (1:500; #MN1020, ThermoFisher, Waltham USA) or E1 total human tau antibody, custom made rabbit antibody raised against N-terminal tau 19-33 (Crowe et al, 1991). AT8 and E1 immunoreactivities were visualized with anti-mouse AlexaFluor568 (1:400; #A10037, ThermoFisher) and anti-rabbit AlexaFluor568 (1:400; #A10042, ThermoFisher), respectively. The sections were analyzed by fluorescent microscopy.

Results

In AD sections double stained for N-terminal total tau and pS396 tau a population of tangle-bearing neurons were labelled by both E1 as well as either hC10-2 and hC10-2_N32S_A101T antibodies (FIG. 7). A number of tau tangles were only labelled by either hC10-2 and hC10-2_N32S_A101T antibodies (FIG. 7, arrows). Extracellular tau (ghost tangles) has previously been shown not to be stained by N-terminal tau antibodies (e.g. Bondareff et al, 1990; Braak et al, 1994; Flores-Rodrigues et al, 2015). Thus, tau species labelled by hC10-2 or hC10-2_N32S_A101T antibodies alone likely represent extracellular ghost tangles.

Western Blots and Immunoprecipitation

Experimental Procedure and Experimental Description

Transgenic rTg4510 mice were used: a human tau cDNA with the P301L mutation (4RON TauP301L) was placed downstream of a tetracycline-operon-responder (TRE) construct. To activate the transgene, the responder has to be co-expressed with an activator construct, consisting of the tetracycline conditional gene expression system (tTA). The tTA activator system was placed downstream of the CaMKIIα promoter thus restricting the expression of TRE mainly to forebrain structures. The tau transgene responder was expressed in the FVB/N (Taconic) mouse strain, and the tTA activator system was maintained on 129S6 (Taconic) mouse strain. Their F1 progeny carried responder and activator transgenes (rTg4510) along with non-transgenic (non-tg) and single-transgenic littermate mice. Only F1 mice were used for the experiments. All mice were bred at Taconic, Denmark and genotyped by the analysis of tail DNA using the primer pair's 5'-GATTAACAGCGCATTAGAGCTG-3' (SEQ ID NO:60) & 5'-GCATATGATCAATTCAAGGCC-GATAAG-3' (SEQ ID NO:61) for the tTA activator transgene and 5'-TGAACCAGGATGGCTGAGCC-3' (SEQ ID NO:62) & 5'-TTGTCATCGCTTCCAGTCCCCG-3' (SEQ ID NO:63) for the mutant tau responder transgene. Mice were group-housed and received water and food (Brogaarden, Denmark) ad libitum as well as enrichment materials. The light/dark cycle was 12 h; room temperature was 21±2° C. and a relative humidity of 55%±5%. Experiments were performed in accordance with Danish legislation on experimental animals (license no. 2014-15-0201-00339).

Mice were euthanized by cervical dislocation in order to preserve the metabolic environment of the brain and to prevent artefacts that could alter the biochemical profiles of tau. Mouse brains were bisected sagittal down the midline to yield two hemispheres. The cerebral cortex and hippocampus of the right hemisphere of each animal were quickly frozen on dry ice and stored at −80° C. until use. Frozen human cortices from Alzheimer's disease (AD) patients and aged healthy control (HC) donors were purchased from Tissue Solution (Glasgow, UK). Human brain specimens had similar postmortem processing time <6 h, and were characterized for amyloid and tau pathology and selected AD specimens classified as Braak stage V-VI.

To immunoprecipitate tau protein from brain lysates a Crosslink Immunoprecipitation kit (Thermo Fisher Pierce 26147) was used according to manufacturer's instructions. Briefly, the antibody was bound to Protein A/G plus agarose followed by crosslinking of the bound antibody with DSS (disuccinimidyl suberate). Brain homogenate was prepared in Tris buffer (25 mM Tris/HCl pH 7.6, 150 mM NaCl, 1 mM EDTA, 1 mM EGTA, and complete protease and phosphatase inhibitor mix) and pre-cleared overnight at 4° C. with control agarose resin. Pre-cleared lysate was incubated with antibody-crosslinked resin overnight at 4° C. followed by antigen elution with 50 µl elution buffer (pH 2.8) and immediately centrifuged into collection tubes containing 5 µl M Tris, pH 9.5. Immunoprecipitated tau was dissolved in SDS-sample buffer containing dithiothreitol (DTT, 100 mM), heat-treated (95° C. for 10 min) and subjected to Western blotting as described below.

Human tau concentrations were measured in brain homogenates and pre-cleared lysates by ELISA for total human tau according to the manufacturer's instructions (Invitrogen).

Tissues were homogenized in 10 volumes of Tris-buffered saline (TBS) containing protease and phosphatase inhibitors as follows: 50 mM Tris/HCl (pH 7.4); 274 mM NaCl; 5 mM KCl; 1% protease inhibitor mixture (Roche); 1% phosphatase inhibitor cocktail I & II (Sigma); and 1 mM phenylmethylsulfonyl fluoride (PMSF). The homogenates were centrifuged at 27,000×g for 20 min. at 4° C. to obtain supernatant (S1) and pellet fractions. Pellets were re-homogenized in 5 volumes of high salt/sucrose buffer (0.8 M NaCl, 10% sucrose, 10 mM Tris/HCl, [pH 7.4], 1 mM EGTA, 1 mM PMSF) and centrifuged as above. The supernatants were collected and incubated with sarkosyl (1% final concentration; Sigma) for one hour at 37° C., followed by centrifugation at 150,000×g for one hour at 4° C. to obtain salt and sarkosyl-extractable (S3) and sarkosyl-insoluble (P3) fractions. The P3 pellet was resuspended in TE buffer (10 mM Tris/HCl [pH 8.0], 1 mM EDTA) to a volume equivalent to half of the original volume used for the brain homogenates. To enrich S1 fractions for hyperphosphorylated tau species a portion of the S1 fraction was separated by further centrifugation at 150,000×g for 20 min. to supernatant (S1 s) and precipitate (S1p) fractions. The S1p pellet was re-suspended in TBS buffer to a volume equivalent to one fifth of the original S1 volume used. Fractionated tissue extracts S1, S1p and P3 were dissolved in SDS-sample buffer containing DTT (100 mM). The heat-treated samples (95° C. for 10 min.) were separated by gel electrophoresis on 4-12% Bis-Tris SDS-PAGE gels (Invitrogen) and transferred onto PVDF membranes (BioRad Laboratories, Hercules, CA). After blocking with a blocking solution containing 5% nonfat milk and 0.1% Triton-X100 in TBS, the membranes were incubated with 1 µg/ml hC10.2, hC10-2_N32S, hC10-2_N32S_A101T or rabbit anti-pS396 tau (Invitrogen). Membranes were washed, and incubated with peroxidase-conjugated anti-human IgG or anti-rabbit antibodies (1:5000; Jackson ImmunoResearch, West Grove, PA). Bound antibodies were detected using an enhanced chemiluminescence system (ECL PLUS kit; Perkin Elmer). Quantitation and visual analysis of Western blot immunoreactivity was performed with a computer-linked LAS-4000 BioImaging Analyzer System (Fujifilm, Tokyo, Japan) and Multi Gauge v3.1 software (Fujifilm). To detect tau protein, approximately 2 µg S1 from mouse was loaded, 20 µg S1 from human brains and equal volumes of the different fractions (S1, S1p, and P3) to SDS PAGE.

Detection of Pathological Tau by Western Blot

Forebrain homogenates pooled from three 32 weeks old rTg4510 mice and non-transgenic (non-tg) control littermates and pooled cortical specimen from four AD and four healthy control (HC) donors were isolated into a soluble (S1), a TBS-soluble pellet (S1p) and a sarkosyl-insoluble fraction (P3). hC10.2, hC10-2_N32S, hC10-2_N32S_A101T were used at 1 µg/ml on western blot and detected pathological tau from rTg4510 mice and AD. We observed detection of 55 and 64 kDa tau in S1 and 64 and 70 kDa tau in P3 and S1p fractions from 32 weeks old rTg4510 mice. Additionally, three truncated tau bands <50 kDa were observed in the P3 fraction. No signal was detected in S1p and P3 from non-tg control littermates not expressing human transgene tau. A weak signal around 50 kDa was detected in S1 fraction from non-tg mice, most likely representing endogenous murine tau phosphorylated at S396 residue (FIG. 8A-8C). It is summarized that hC10.2, hC10-2_N32S, hC10-2_N32S_A101T detected pS396 tau, and both normal phosphorylated 55 kDa and hyperphosphorylated 64 kDa tau species in rTg4510 mice. The strongest signal was observed with hC10-2_N32S_A101T.

In S1, S1p and P3 fractions from AD donors hC10.2, hC10-2_N32S, hC10-2_N32S_A101T detected the typical AD tau smear and the pathological four tau band pattern (54, 64, 69 and 74 kDa tau). As expected, sarkosyl-insoluble hyperphosphorylated tau species isolated from P3 fraction were most pronounced, followed by soluble hyperphosphorylated tau species enriched in the S1p fraction. No signal was detected in P3 fractions from healthy control (HC). In S1 and S1p fractions from HC a weak signal around 55 kDa was detected, likely representing normal phosphorylated tau at S396 residue (FIG. 8A-8C). It is summarized that hC10.2, hC10-2_N32S, hC10-2_N32S_A101T detected the typical tau smear characteristic for AD and the pathological four tau band patterns representing hyperphosphorylated tau. Strongest signal was observed with hC10-2_N32S_A101T.

Immunoprecipitation of Pathological Tau

To determine the ability of hC10.2, hC10-2_N32S, hC10-2_N32S_A101T to bind tau under non-denaturing conditions, a tau immunoprecipitation (IP) protocol was established where tau antibodies are covalently cross-linked onto protein A/G resin and thereby gives IPs free from antibody contaminations. For tau analysis by SDS-PAGE the presence of the heavy chains of the antibody used for IP can obtrude signals since both proteins are detected around 50 kDa. The efficacy of hC10.2, hC10-2_N32S, hC10-2_N32S_A101T to pull down pathological tau from human brain was investigated. As antigen, 500 µg pre-cleared lysate from brain homogenates was used from four pooled AD and HC donors containing 0.1 µg and 0.15 µg human tau (determined by human tau ELISA), respectively. hC10.2, hC10-2_N32S, hC10-2_N32S_A101T (10 µg) pulled down 54, 64, 69 and 74 kDa tau species (the four pathological tau bands) and AD smear from pre-cleared AD homogenates (antigen/ab 1:100 ratio) visualized by a polyclonal rabbit anti-pS396 tau antibody (FIG. 9). Comparing the intensity of the tau bands from AD brains pulled down with hC10.2, hC10-2_N32S, hC10-2_N32S_A101T to control human IgG antibody and to HC brain, it can be summarized that hC10.2, hC10-2_N32S, hC10-2_N32S_A101T immunoprecipitated hyperphosphorylated tau at the pS396 site exclusively from AD brains and were effective at an antigen/antibody ratio of 1:100.

Cell and Aggregation Assay

HEK293 cells were transiently transfected with human tau-P301L-FLAG in 6-well plates 24 hours after plating, followed 24 hours later by incubation with brain homogenate for 24 h, followed by splitting and re-plating cells and harvesting after an additional 24 hours. Cells were lysed and sonicated in PBS, supplemented with 1% triton X, Phos-stop and complete phosphatase and protease inhibitors (Roche) buffer and ultracentrifugated at 100,000×g for 30 min. The pellet was resuspended in SDS, sonicated and ultracentrifugated for 30 min. at 100,000×g. Supernatants were analyzed by western blotting. Cells expressing human tau-P301L showed insoluble (SDS fraction, E1/FLAG detection), hyperphosphorylated (pS396 detection) tau upon seeding with total brain homogenates from rTg4510 tau transgenic mice.

Cells treated with control brain homogenate from tTA mice showed an absence of aggregated hyperphosphorylated human tau. Additionally, total cell lysates of HEK293 cells were analyzed using the tau aggregation assay from Cisbio. This assay is based on time-resolved fluorescence using the same antibody for both donor (Tb3+ conjugated) and acceptor (d2 conjugated) Ab in FRET. A 10 µl sample was mixed with 10 µl antibody mix and incubated for 20 hours. The plate was read on the Pherastar plate reader to assess time-resolved fluorescence (FRET signal measured/integrated after switching of the excitation light). The assay measures aggregated tau both in human autopsy material, rTg4510 mice and in seeded HEK cells with high specificity and sensitivity. Results are shown in FIG. 10.

Example 7. Immunodepletion of Tau

Alzheimer brain extracts were made from frozen post mortem prefrontal cortex in 10× volume sterile cold PBS. The tissue was homogenized using a knife homogenizer followed by sonication, 5×0.9 second pulses at output 2 (Branson sonifier). The homogenate was then centrifuged at 3000 g for 5 minutes at 4 C. The supernatants were aliquoted, snap frozen and stored at −80 degrees C. until use.

25 µg antibody (humanized C10-2 variants and 2.10.3, mouse AT8, Thermo Scientific mn 1020) were immobilized to 125 µl of Magnetic dynabead suspension (Immunoprecipitation Kit Dynabeads Protein G Novex, Cat no 10007D). After thorough washing the coated beads were mixed with variable amounts of non-coated, washed beads. Starting from 100% Ab coated beads, corresponding to 5 µg antibody, down to 100% non-coated beads. The total amount of beads was the same in all samples. The beads were mixed with 20 µl AD extract and incubated at room temperature for 10 min. The magnetic beads were separated from the extract and the extracts were aliquoted, snap frozen and kept at −80 degrees C. until use.

Analysis of Depletion Using Western Blot

Samples were boiled in 1×SDS loading buffer and 100 mM DTT. A volume corresponding to 3 µl of extracts were loaded on a 4-12% Bis-Tris NuPAGE Gel (LifeTech Novex). After electrophoresis, the proteins were blotted over to an Immobilon-FL PVDF membrane (0.45 µm, IPFL10100, Millipore). The membrane was blocked with SEA blocking buffer (Prod #37527, Thermo). Tau and P-tau levels were assessed in the samples using Tau5 (Tau5 is a commercially available anti-tau antibody whose epitope is described as being in the middle of Tau amino acids 210-241. It is a mouse monoclonal to Tau. Abcam ab80579, 1:2000) mouse C10-2 (1 µg/ml), P-S199/202 (Invitrogen 44768 G, 1:1000), P-S422 (Abcam ab79415, 1:750), human IPN (1 µg/ml). Gapdh and actin were used as loading controls (Abcam ab9484, 1:2000, Sigma A5441, 1:20000). Secondary fluorophore conjugated IgG antibodies was used (IRDye 8000W Goat anti-Human, IRDye 8000W, Goat anti-rabbit, IRDye 680 Goat anti-mouse, LI-COR biosciences) and the signal was quantified using Odyssey CLx and Image studio software (LI-COR biosciences). Quantification of individual bands as well as signal in whole lanes was done and from this sigmoidal dose-response curves were plotted and when possible max effect and EC50 values were estimated.

Results 2.10.3 and C10-2 antibodies both remove a small fraction of tau from the Alzheimer's disease brain preparation. This demonstrates selectivity for a subset of tau within the total tau protein content. 2.10.3, designed to have specificity for pS422 tau removes up to 24% of the total tau amount, while C10-2 removes up to 15% of the total tau (see FIG. 11). This may be interpreted that the pS396 subset is a smaller subset of tau, all other factors being equal. Alternatively, the data may interpreted that the C10-2 antibodies are more selective for pS396 than the 2.10.3 antibody is selective for pS422.

2.10.3 and C10-2 both remove more than 90% of the tau phosphorylated at Serine 422, although the amount of antibody required to remove 50% of the pS422 tau differ, for 2.10.3, 0.42 µg antibody and for C10-2, 0.27 µg was needed for the same effect (see FIG. 12). In one embodiment of the invention, the antibody is specific for an epitope within 386-404 wherein serine residue 396 of human tau is phosphorylated and wherein 80% of pS422 tau is removed (in immunodepletion studies by Western blot analysis) using less than 1 µg of the antibody.

C10-2 efficiently removes tau which is phosphorylated at serine 396 (Max effect: 88% and half of the effect is reached by using 0.30 µg antibody). 2.10.3 removes a smaller fraction of tau being phosphorylated at the serine 396 (Max effect: 60% and half of that effect is reached when using 0.63 µg antibody) (see FIG. 13). This indicates that all Tau being phosphorylated at serine 422, also is phosphorylated at serine 396, but that there is a portion of hyperphosphorylated tau being phosphorylated at serine 396 where the phosphorylated serine at position 422 is not present. In one embodiment of the invention, the antibody is specific for an epitope within 386-404 wherein residue 396 of human tau is phosphorylated and wherein 80% of pS396 tau is removed (in immunodepletion studies by Western blot analysis) using less than 1 µg of the antibody A large portion of the tau, being removed by C10-2, is also phosphorylated at Serine 199/202, since 69% of the tau having that phosphorylation is affected by the immunodepletion (50% of the effect when using 0.34 µg antibody). The 2.10.3 immunodepletion does not give a sigmoidal dose response on the pS199/202 tau, although a drop in signal is seen with increasing amount of antibody (max 52% reduction when using the max amount of antibody (5 µg) (see FIG. 14). In one embodiment of the invention, the antibody is specific for an epitope within 386-404 wherein Serine residue 396 of human tau is phosphorylated and wherein 80% of P-S199/202 tau is removed (in immunodepletion studies by Western blot analysis) using less than 1 µg of the antibody.

These results indicate that the C10-2 antibody targeting the phosphorylated serine 396 binds a larger pool of the hyperphosphorylated tau then the 2.10.3 antibody targeting the phosphorylated serine at the 422 position.

In investigating individual bands on western blot after immunodepletion a 25 kDa band was identified as phosphorylated at Serine 396. This fragment was immunodepleted by C10-2, but 2.10.3 and AT8 did not deplete this fragment (see FIG. 15). Thus, C10-2 has a unique feature removing this truncated form of tau from Alzheimers diseased brain extracts.

Example 8. Comparing C10-2 Variants

All C10-2 variants had the same efficiency in the immunodepletion assay (see FIG. 16). These results demonstrate that the introduced mutations has not changed the functional binding to Alzheimer brain specific Tau.

8a. Antibody Treatment in Seeded rTg4510 Mice

Transgenic mice expressing human mutated Tau (P301L 0N4R) under a tet-off responsive element in CamK2 positive neurons (rTg4510) was used. This model normally starts developing Tau pathology at 3 months of age, but by feeding the mothers with doxycycline during pregnancy and for the first 3 weeks of the pup's life, the pathology develops at a later stage (starting after 6 months of age). The doxycycline pre-treated mice were chronically treated with mC10-2, hC10-2, 2.10.3 or control antibody, 15 mg/kg/week starting at 2 months of age. At 2.5 months, Alzheimer brain extract was infused into the hippocampus. Mice were 20 anesthetized by isoflouran inhalation fixed in a stereotactic frame. The scull was exposed and adjusted until bregma and lambda was in level. A hole was drilled in the scull 2 mm lateral (right) and 2.4 mm posterior of the bregma. A 10 µl syringe beveled tip (SGE) was used to inject the seeding material 1.4 mm ventral to the brain surface at the at the above mentioned co-ordinates. 2 µl of the extracts, described in Examples 7, was slowly infused at the site (1 µl/minute) and the syringe was left for 5 minutes before removing it. The wound was closed by stiches and mice were heated while waking up. The mice were housed for 3 months and then sacrificed and perfusion fixed with 4%. The mice were treated with antibody until sacrifice, 3 months after seeding.

Immunohistochemistry

Fixed brains were cut into 35 µm coronal sections at NSA 30 and every 6th section was stained for tau tangles (Gallyas silver stain). Positively stained neurons (soma) were counted in ipsi and contralateral sides of hippocampi of all brains. All sub-regions of hippocampus were included. Eight sections were counted per brain. Results reflect the sum of positive neurons from the 8 sections.

Statistical analysis: The variance is significantly different when comparing the groups. Thus the non-parametric, Kruskal-Wallis test and Dunn's multiple comparison test was used.

Results:

The extracts caused seeding of tangle pathology in the ipsilateral hippocampus. The mC10-2 treatment significantly reduced tangle pathology in the seeded hippocampus by 57% (P<0.05). There was a clear trend indicating hC10-2 reduced pathology. 2.10.3 failed to show an effect (see FIG. 17).

Example 8b. The Anti-Seeding Effects of the C10.2 Variants

Study Objective

Transcellular propagation of tau aggregates has been suggested to contribute to the pathological development and topological spread of Alzheimer's disease within the CNS. In vitro seeding models were established whereby cellular human tau expressed in HEK293 cells is seeded with extracellularly applied pathological tau aggregates. The purpose of this study was to evaluate and compare the therapeutic effect of the monoclonal human C10.2 and variants upon seeding in a treatment paradigm. Seeding is intended to mean the introduction of an amount of hyperphosphorylated tau (seed) that initiates hyperphosphorylation/misfolding of cellularly expressed tau.

Background Establishing Relevance of the Study

Depositions of extracellar plaques of Aβ and intra-neuronal paired helical filaments of tau are hallmarks of Alzheimer's disease. The intra-neuronal inclusions of tau are primarily made up of detergent insoluble, hyperphosphorylated, amyloid forms of tau and are in AD patients deposited in a spacio-temporal pattern suggestive of spreading of aggregates within the CNS. Tau aggregates have experimentally been shown to propagate from cells to cells both in vivo and in vitro in a prion-like mechanism. This presence of extra-cellular spreading impacting disease propagation opens up for immunotherapy with CNS penetrant antibodies.

Application of tau aggregates/seeds have been shown to lead to aggregation of cellular tau in vitro (Frost et al., 2009, Guo and Lee 2011, Yanamandra et al., 2013). We have established an in vitro seeding model, whereby crude brain homogenates from Tg4510 mice (containing aggregated human tau) is used to seed human 0N4R tau with a P301L mutation transiently expressed in HEK293 cells. Importantly, no residual tau aggregates (seeds) can be detected in seeded pcDNA control cells, so all readouts are detecting the conversion of cellular tau and do not detect any signal from the exogenous seeding material. Anti-seeding effects of different variants of hC10.2 were determined in this assay.

Variants
  Antibody C10-2 (hC10.2)
  Antibody N32S (hC10.2 N32S)
  Antibody N32Q (hC10.2 N32Q)
  Antibody N32S, D55E (hC10.2 N32S D55E)
  Antibody N32Q, D55E (hC10.2 N32Q D55E)
  Antibody N32S, A101T (hC10.2 N32S A101T)

Reference Item(s)
 Control hIgG1 (B12)
Test System/Animals
 HEK293 cells transiently transfected with hTau-P301L (0N4R).
Experimental Design
 Seeding material: Tg4510 homogenates (and controls) from 12 month old mice were homogenized as 10% homogenates in TBS without inhibitors by bead homogenization and sonicated. Homogenates were spun at 21000×g for 15 min. and the soluble fraction was used for seeding.
 HEK293 Seeding assay: In this assay 600,000 HEK293 cells are plated per well in a 6-well plate on day 0. On day 1, cells are transfected with 4 µg plasmid DNA using 10 µl lipofectamine2000 according to manufacturer's protocol. Medium is changed after 4 h. On day 2 cells are seeded with crude brain homogenate from 12 month old Tg4510 or tTa mice. Homogenates containing 40 µg total protein (approximately 65 ng total human tau for the tg4510 homogenates) are applied to the medium of each well. For antibody treatment experiments homogenates are pre-incubated with or without antibodies o/n at 4 degrees. 6 h post-seeding medium is changed to low serum medium to reduce cell proliferation and the antibodies are re-applied.
 On day 3 (24 h post-seeding), cells are trypsinized for 3 minutes to degrade extra-cellular seeds and re-plated at; 800,000 cells per well in 6-well plates for fractionation experiments, 20,000 cells per 96-well for the Cisbio tau aggregation assay and at 10,000 cells per 96-well for antibody uptake evaluation by high-content imaging. Antibodies are re-applied to each well.
 Cellular fractionation: 48 h post-seeding, cells for fractionation are harvested by scraping in cold PBS, pelleted and lyzed in TBS with 1% triton-X with phosphatase and protease inhibitors and sonicated. After ultracentrifugation (100,000×g for 30 min. at 4° C.) the pellet is resuspended in 1% SDS, sonicated and ultra-centrifuged once again. The Triton-X and SDS-soluble fractions are analysed by western blotting for total tau (E1) and phosphorylation of tau on S396 (D1.2). D1.2 signal is quantified by immunofluorescence on the Odyssey imagingmachine.
 Cisbio tau aggregation assay: 48 h post-seeding, cells for the Cisbio aggregation assay is washed in ice-cold PBS and frozen dry. Cells are lyzed in 1% triton-X with phosphatase/protease inhibitors and benzonase (an RNase and DNase) and incubated on an orbital shaker, at 650 RPM for 40 min. at 4 degrees C. Total cell lysate is analysed for tau aggregates by the Cisbio tau aggregation assay, an assay based on using the same antibody coupled to a donor and an acceptor for FRET measurements using homogenous time resolved fluorescence (HTRF®, Cisbio). Monomeric tau can only bind either the acceptor or the donor antibody, as they are competing for the same binding epitope=no FRET. In contrast oligomeric tau can bind both the donor and the acceptor=FRET signal. Total protein is determined for all samples by BCA and the signal-to-noise ratio of the sample is normalized to protein and plotted as relative tau aggregation using 8 technical replicates.
 Antibody uptake: 48 h post-seeding, plates for antibody uptake was fixed in 4% paraformaldehyde and 4% sucrose and stained with an anti-human secondary antibody. Antibody uptake was confirmed using Cellomics.
Data Analysis/Statistics
 Data are presented as the pooled data of four independent biological replicas performed and analysed over two different weeks+/−S.E.M. Data are analysed using a One-way ANOVA with a Tukey's multiple comparison test, *P<0.05, P<0.01, *P<0.001.
Results
 hC10.2 had a reductive impact on seeding and insoluble hyperphosphorylated tau by approximately 40% compared to the control. All other antibodies showed a similar or superior effect to hC10.2. In particular, the N32S and N32S_A101T variants of hC10.2 showed stronger effects 45% and 62% reduction in aggregated tau. The N32S_A101T variant showed a significant stronger effect on aggregation compared to hC10.2.

Example 8C: Stability Studies on hC10.2 and Variants of the Invention

Study Objective
 This study was performed to evaluate the basic stability issues with the antibodies of the invention, focusing on stressed conditions to reveal any potential differences in the variants.
Study Design
 All samples were initially prepared into identical starting conditions (buffer, concentration and aggregate level). This would eliminate differences in initial properties that potentially could influence subsequent development of the sample behaviour. A control was kept at −80° C. and analyzed in parallel with the stressed samples (40° C.). The samples were removed from 40° C. at different time point and analyzed simultaneously at the end by SEC-uplc, peptide mapping by Liquid chromatography-mass spectrometry (LCMS) and differential scanning fluorimetry (DSF).
Variants
 Antibody C10-2 (hC10.2)
 Antibody N32S (hC10.2 N32S)
 Antibody N32Q (hC10.2 N32Q)
 Antibody N32S, D55E (hC10.2 N32S D55E)
 Antibody N32Q, D55E (hC10.2 N32Q D55E)
 Antibody N32S, A101 (hC10.2 N32S A101T)
 Antibody A101T (hC10.2 A101T)
 Antibody D55E (hC10.2 D55E)
 Antibody N32Q, A101T (hC10.2 N32Q A101T)
Reference Item
 Antibody samples stored at −80° C. for the duration of the study were used for reference.
Background Information
 Stability aspects of a monoclonal antibody are important for both aspects of manufacturing, final storage and formulation of drug substance. In this study, we have stressed the antibodies by freeze-thaw cycles, high temperature and low pH in order to reveal if obvious problems is apparent in any of the candidates.

Materials and Methods

For deamidation studies, samples are vialed in 1 ml samples and incubated at 40° C. At predefined time points a sample is moved to −80° C. and stored until analysis.
Deamidation Studies
 Deamidation of Asn residues are studied at the peptide level in order to get detailed information on the actual residues in question. The mAb is therefore digested with porcine trypsin after reduction and alkylation (iodoacetic acid) using standard protocols. Peptides were separated on a CSHT130 C18 1.7 µm column and introduced to a XEVO QTOF (Waters) MS instrument operating in MSe mode. Identical parameters were used throughout the series. Peptide maps from all time points were analyzed in BiopharmaLynx and quantified with the following limitations: Only positively identified deamidated peptides are included, no in source fragments are included. The % deamidation of each identified peptide is monitored over time.

SEC Method Outline

Aggregation was determined by SEC chromatography on an ACQUITY UPLC® BEH200 SEC 1.7 µm 4.6×150 mm column in an Acquity UPLC with TUV detector (waters). Samples of 20 µl adjusted to 100 µg/ml (diluted in running buffer: Gibco PBS—Invitrogen #14190-094+0.1 M NaCl) were applied to the column at 0.4 ml/min and separated over 6 min. by isocratic elution.

Data are analyzed by MassLynx and AUC is used to quantify levels of aggregation.

Low pH Experiment hC10.2 was applied to a protein G column and eluted at pH 2.8 using standard conditions. Sample was kept at pH 2.8 and aliquots removed at time 0, 15, 30, 60, 120 and 180 min. and neutralized before desalted into PBS. Samples were analyzed for binding affinity, aggregation and deamidation.

Characterization of hC10.2 at Stressed Conditions: Deamidation at 40° C. and 28 Days Deamidation of Asn is observed at several minor and three major sites covered by peptides LC:T2, HC:T36 and HC:T25. In these deamidation increase over time, ending at 75%, 38% and 28% respectively. In contrast to peptide HC:T36 and T25, the Asn residues (LC N32 and N34) in the LC:T2 peptide was not expected, based on the in silico analysis (sequence motif), to be prone to deamidation, but surprisingly in the actual experiment they clearly differentiate from the other Asn residues in the hC10.2. Increased deamidation of this peptide correlates with a reduction in binding activity against the double phosphorylated peptide and suggests a mechanistic relationship between deamidation and IC50. This observation also suggests that changing the Asn residues 32 and/or 34 in hC10.2 LC could reduce the deamidation at these sites.

In the analysis of the variants, it is clear that simply modifying the Asn32 to either Ser or Gln completely prevents the deamidation reaction on the Asn34 (FIG. 20). Also we do not detect any deamidation of Gln32 in variants with this mutation.

Deamidation at Low pH

In this study, we analyzed hC10.2 in the same way as described above for the 40° C. stability study. Only in this case a mix of trypsin and Lys-C was used (Promega product) to optimize cleavage at Lysine residues. No additional sites or degree of deamidation were observed and again the most prominent peptides were LC-T2, HC-T25 and HC-T36. In addition no change in IC50 was observed in low pH treated samples.

SEC Analysis

Level of aggregation was below 3% in all preparations and no change in degree of aggregation was observed over 28 days at 40° C.

Example 9

Isolation of Tau Seeds from rTg4510 Mice

The rTg4510 mice are double transgenic co-expressing the 4RON tau with P301L mutation in the human MAPT gene downstream of a tetracycline-operon-responder (TRE) and an activator construct, consisting of the tetracycline conditional gene expression system (tTA). The P301L mutation is a dominant mutation leading to frontotemporal dementia with Parkinsonism linked to chromosome 17 (FTDP-17). In rTg4510 mice, expression of P301L hTau induces tau pathology including pre-tangle and neurofibrillary tangle (NFT) formation, neuronal loss and behavioural abnormalities in an age-dependent manner. NFTs are intraneuronal tau aggregates made of paired helical filaments (PHF), twisted ribbons, or straight filaments, are detergent-insoluble and contain predominantly hyperphosphorylated tau. Hyperphosphorylation means that tau is phosphorylated at more sites than tau from adult healthy brain and that for a given site a higher than normal percentage of tau molecules is phosphorylated (>8 phospho mole/tau mole). The anatomical distribution of NFTs is the post-mortem histopathological hallmark that correlates with cognitive decline in Alzheimer's disease (AD) and to memory loss in normal aging and mild cognitive impairment. The distribution pattern of NFT in the brain of AD patients is highly hierarchical and has been divided into six stages. The gradual invasion of the brain by NFT changes has also been confirmed biochemically and has been classified into ten stages according to the affected region. Biochemical characterization of the different tau species from AD brains was originally based on a fractionation protocol using 1% sarkosyl for isolation of insoluble tau. Based on this method, the sarkosyl-insoluble hyperphosphorylated tau species isolated in the sarkosyl-insoluble pellet (P3) fraction are defined as PHF-tau and regarded as the biochemical NFT equivalent. The buffer soluble hyperphosphorylated tau species isolated in the soluble fraction (S1) are defined as non-fibril oligomer tau species and regarded as the biochemical pre-tangle tau equivalent. In the rTg4510 mice, normal monomer phosphorylated and non-phosphorylated human 4RON transgenic tau is present in the soluble fraction (S1) and visualized as 55 kDa tau species on SDS page. Hyperphosphorylated 4RON tau with P301L mutation is displayed as mobility shifted tau of 64 kDa and 70 kDa in the soluble (S1), and exclusively in the Tris-buffered saline (TBS)-soluble precipitate (S1p) and the sarkosyl-insoluble pellet (P3) fraction. The sarkosyl-insoluble 64 kDa and 70 kDa tau species isolated in P3 are tau fibrils (PHF-tau) and the biochemical NFT equivalent. The buffer soluble 64 kDa and 70 kDa tau species in S1 and enriched in the TBS-soluble precipitate fraction (S1p) are oligomeric tau and the biochemical pre-tangle tau equivalent. The 70 kDa tau species are specific for the P301L mutant and also found in FTDP-17 patients' brains. Brain tissue from 40 weeks old rTg4510 mice was homogenized in 10 volumes of TBS containing 50 mM Tris/HCl (pH 7.4), 274 mM NaCl, and 5 mM KCl. The homogenates were centrifuged at 27,000×g for 20 min at 4° C. to obtain supernatant (S1) and pellet (P1) fractions. TBS-extractable S1 fraction was separated by centrifugation at 150,000×g for one hour at 4° C. into supernatant (S1s) and precipitate (S1p) fractions. The S1p pellet was re-suspended in 10 mM Tris/HCl [pH 8.0] to a volume equivalent to a fifth of the original S1 volume. The P1 pellet was re-homogenized in 5 volumes of high salt/sucrose buffer (0.8 M NaCl, 10% sucrose, 10 mM Tris/HCl, [pH 7.4]) and centrifuged at 27,000×g for 20 min at 4° C. The supernatants were collected and incubated with sarkosyl (1% final concentration; Sigma) for one hour at 37° C., followed by centrifugation at 150,000×g for one hour at 4° C. to obtain sarkosyl-insoluble pellets, referred to as P3 fraction. The P3 pellet was resuspended in 10 mM Tris/HCl [pH 8.0] to a volume equivalent to half of the original volume used for the brain homogenates. Pathological tau from rTg4510 mouse brain characterized as hyperphosphorylated tau of 64 and 70 kDa on SDS-page was exclusively present in the S1p and P3 fractions as TBS soluble oligomer and sarkosyl-insoluble fibril tau, respectively. The S1s fractions contain normal non- and phosphorylated tau displayed as 55 kDa tau on SDS-page. Pathological tau, soluble oligomeric and insoluble fibril isolated in S1p and P3 fractions respectively, was employed as hyperphosphorylated tau seeds to recruit endogenous monomeric human tau into inclusions of aggregated tau and to induce tau seeding in primary cortical cultures isolated from rTg4510 mice.

Seeding Assay in Primary Neuronal Culture Isolated from rTg4510 Mice

Murine cortical neurons (CTX) were isolated from day E14-16 rTg4510 mouse embryos. Single transgenic tTA activator mice were time-mated with single transgenic mutant tau responder mice. Pregnant females were euthanized at 14-16 days post conception and embryos were genotyped with brain DNA using the primer pair's 5'-GATTAACAGCGCATTAGAGCTG-3' (SEQ ID NO:60) and 5'-GCATATGATCAATTCAAGGCCGATAAG-3' (SEQ ID NO:61) for the tTA activator transgene and 5'-TGAACCAG-GATGGCTGAGCC-3' (SEQ ID NO:62) and 5'-TTGT-CATCGCTTCCAGTCCCCG-3' (SEQ ID NO:63) for the mutant tau responder transgene while isolated embryonic cortices were kept in Hibernate E without calcium chloride (BrainBits LLC) at 4° C. Cortices from rTg4510 mouse embryos were selected and dissociated neurons plated on 100 μg/ml poly-L-lysine coated dishes at a density of 0.13×106 cells/cm2 (420,000 cells/ml, 100 μl/well, 96-well plate) and cultured in glia conditioned Neurobasal medium supplemented with 2% B-27 supplement with antioxidants, 0.5 mM L-glutamine, 100 U/ml penicillin, 0.1 mg/ml streptomycin (all solutions from Gibco-BRL Invitrogen). Glia conditioned Neurobasal medium was generated by confluent and non-proliferating primary murine astrocyte cultures after 24 h incubation. Neurons were fed at 4 days in vitro (DIV) by replacing half of the medium with fresh glia conditioned Neurobasal medium and thereafter feeding was performed every seventh day. At DIV4 after feeding neuronal culture was treated with 1 μM cytosine arabinoside to halt proliferating cells. The proportion of glia cells in the cultures was less than 10%, as assessed by an antibody against glia-fibrillary-acidic protein (GFAP) at DIV15. CTX from rTg4510 mice express endogenous murine tau and transgenic human tau 4R0N. CTX from rTg4510 mice contain only normal human monomeric non- and phosphorylated tau displayed as 55 kDa tau bands on SDS-page; no hyperphosphorylated tau species (64 and 70 kDa) are present in naïve CTX from rTg4510 mice. At DIV7 tau seeding was induced by incubating CTX with pathological tau seeds, either soluble oligomeric or insoluble fibril hyperphosphorylated tau isolated in S1p and P3 fractions respectively. A complete medium change was introduced at DIV11 to prevent continuous uptake of pathological tau seeds and tau seeding in the CTX was measured at DIV15. Tau seeding was characterized by recruitment of monomeric soluble human tau into inclusions of aggregated and hyperphosphorylated tau displayed as mobility shifted tau bands at higher molecular weight of 64, 70 and 140 kDa on SDS page. Both hyperphosphorylated tau seeds, soluble oligomeric or insoluble fibril from S1p and P3 fractions, respectively, induced tau seeding equally in the CTX. To investigate the effect of tau antibodies on tau seeding, CTX were treated with a mixture of 0.1 μl P3 or 0.2 μl S1p fractions (containing 0.2 ng total human tau) isolated from 40 weeks old rTg4510 mice and 10 μg antibody (hC10.2, hC10.2_N32S, hC10.2_A101T_N32S, human IgG control) or phosphate-buffered saline (PBS). The tau seed-antibody mixture was pre-incubated for 2 h at 4° C. before addition to CTX. At DIV11 a complete medium change to fresh glia conditioned Neurobasal medium was performed. At DIV15 neurons were lysed in ice-cold triton lysis buffer (1% triton X-100 in 50 mM Tris, 150 mM NaCl (pH 7.6) with 1% protease inhibitor mixture (Roche), 1% phosphatase inhibitor cocktail I & II (Sigma), and 0.2% Benzonase (Sigma) under shaking at 200 rpm for 45 min at 4° C. and lysates were used in the Cisbio in vitro aggregation assay and the protein content was determined by bicinchoninic acid (BCA) assay according to manufactures' instructions. The tau aggregation assay from Cisbio is based on time-resolved fluorescence using the same antibody for both the donor (Tb3+ conjugated) and acceptor (d2 conjugated) antibody in fluorescence resonance energy transfer (FRET) and performed according to manufactures' instructions. Briefly, 9 μl sample was mixed with 9 μl antibody mix and incubated for 20 h. The plate was read on a Pherastar plate reader to assess time-resolved fluorescence (FRET signal measured/integrated after switching of the excitation light). The assay measures tau aggregation, both tau oligomers and fibrils, in brain material from rTg4510 mice and in neuronal lysates from tau seeded CTX isolated from rTg4510 embryos with a high specificity and sensitivity. Results can be seen in FIGS. 21A-21B. Incubation of P3 or S1p seeds with human IgG control antibody led to similar tau aggregation signal from seeded CTX as incubation of P3 or S1p seeds with PBS. Signals from PBS and human IgG control antibody were averaged and set as 100% tau aggregation. The tau antibodies hC10.2, hC10.2N32S and hC10.2A101T-N32S reduced significantly tau aggregation signals both from P3 and S1p induced tau seeding at DIV15. Results from 2 individual experiments were summarized. The hC10.2 antibody reduced P3 and S1p induced tau seeding by 23%. Variants hC10.2N32S and hC10.2A101T-N32S reduced P3 and S1p induced tau seeding by 41-53% and 48-60%, respectively. Variants hC10.2N32S and hC10.2A101T-N32S were superior compared to hC10.2 in decreasing tau seeding in CTX from rTg4510 induced by hyperphosphorylated tau seeds from S1p or P3 consisting of oligomer or fibril tau, respectively.

Example 10

Dose-Dependent Decoration of Tau Structures in rTg4510 Mice Following i.v. Injection of hC10-2_N32S_A101T Method:

Twelve months old rTg4510 mice. These transgenic mice express human mutated Tau (P301L 0N4R) under a tet-off responsive element in CamK2 positive neurons and show a pronounced tau hyperphosphorylation and tangle formation from 6 months of age and onwards. In addition, neurodegeneration is present at 12 months of age in rTg4510 mice in regions with strong pathology. The mice received a single i.v. injection via the tail vein with hC10-2_N32S antibodies at doses 80 mg/kg, 20 mg/kg, 8 mg/kg and 0.8 mg/kg. A volume of 100 microL was injected per mouse. Three days after injection, the mice were perfused for 2 min with PBS followed by 10 min perfusion with 4% paraformaldehyde. The brains were cryoprotected in 30% sucrose and cut into 40 microns free floating cryosections. The sections were incubated with 5% normal swine serum in PBS/1% BSA/0.3% Triton X-100 for 20 min, washed in PBS and finally incubated with AlexaFluor488-conjugated secondary anti-human IgG at 1:200 (#709-545-149; Jackson ImmunoResearch Laboratories, West Grove, USA). The sections were washed in PBS, mounted and examined by fluorescent microscopy.

Results:

I.v. injection of hC10-2_N32S resulted in in vivo binding to target structures mainly in hippocampus and cortex in aged rTg4510 mouse brains (FIG. 1). The number of positive structures observed varied between individual rTg4510 animals. The positive signals in rTg4510 brains did not readily appear as intracellular staining and may represent extracellular tau material released during the process of neurodegeneration. By semiquantitative scoring, the highest signals (fluorescence intensity and number of positive structures) were detected in all mice dosed at 20 and 80 mg/kg (Table 6). Labelled structures were present at 8 mg/kg in 3 out of 4 mice, but to a clearly lower level than at 20 and 80 mg/kg. Intravenous injection of 0.8 mg/kg did not result in signals above background with the applied method of visualization. Collectively, these data suggest that hC10-2_N32S antibodies in a dose-dependent manner are able to penetrate into the brain parenchyma and specifically decorate targets in rTg4510 mice in vivo. FIG. 22 (Panels A-D).

TABLE 6

| Aged Tg4510 n = | hC10-2_N32S i.v. injection | Fluorscent signal | Intensity (relative to 80 mg/kg) |
|---|---|---|---|
| 3 | 80 mg/kg | + in 3/3 | +++ |
| 4 | 20 mg/kg | + in 4/4 | ++-+++ |
| 4 | 8 mg/kg | + in 3/4 | + |
| 4 | 0.8 mg/kg | + in 4/4 | 0 |

Fluorescence-labelled tau structures detected in brain sections following i.v. injection of hC10-2_N32S. Semiquantitative scoring: +++ strong; ++ moderate; + weak; 0 not detected.

Example 11 Seed Tau Pathology in Tau

Seed Preparation

Frozen cortical tissue samples from AD donors were obtained from Tissue Solutions (Glasgow, UK). The brain tissue was weighed and homogenised using a knife homogeniser in sterile cold PBS (10 times volume of brain sample). The homogenate was then sonicated by 5×0.9 sec pulses on a Branson sonifier set at output 2. The homogenate was centrifuged at 3000 g for 5 min at 4° C. and the supernatant was aliquoted, snap frozen on dry ice and stored at −80° C. until use.

Animals Used in Study

Transgenic mice expressing human mutated tau (P301L 0N4R) under a tetracycline-controlled transactivator element in CamKII-positive neurones (rtg4510) were used. This model normally begins to develop tau pathology at 3-4 months of age. By feeding the mothers with doxycycline during pregnancy and for the first 3 weeks of the pup's life, the pathology develops at a later stage (after 6 months of age). The doxycycline pre-treated mice used in the studies were 2.5 months old at the time of seeding.

Antibody Treatment

Antibodies were prepared in a concentration of 1.5 mg/ml in sterile PBS and made into aliquots with enough antibody for one dosing time-point. The aliquots were stored at 4° C. until used. From 2 months of age until sacrifice at 5,5 months of age the mice received a weekly IP dose of antibody (15 mg/kg equal to 10 ml/kg). Antibodies used: Control human B12-IgGI, hC10-2, hC10-2_N32S and hC10-2_N32S_A101T.

Stereotactic Injection

Just after receiving the $3^{rd}$ antibody dose, mice were anesthetized by isoflourane inhalation and fixed in a stereotactic frame. The skull was exposed and positioning adjusted until bregma and lambda were level. A hole was drilled in the skull 2 mm lateral (right) and 2.4 mm posterior to bregma. A 10 µl syringe with a 26 gauche, bevelled tip (SGE) was used to inject the seeding material 1.4 mm ventral to the brain surface.

Two µl of material was slowly infused at the site (0.5 µl/min) and the syringe was left thereafter for an additional 5 min before retraction. The wound was closed and sealed with sutures and mice were thermically supported during recovery from anesthesia. Mice were then housed for 3 months before being perfusion-fixed with 4% paraformaldehyde.

Histology

Fixed brains were processed at Neuroscience Associates (Knoxville, TN) using MultiBrain® technology. Up to 25 mouse brains were embedded together per block and freeze-sectioned at 35 µm in the coronal plane through the entire brain. Every $6^{th}$ section was stained with the Gallyas silver stain to reveal neurofibrillary tangles. The sections were mounted, coverslipped and Gallyas silver-positive neurones (soma) were counted in the injected side of the hippocampi of all brains. All sub-regions of the hippocampus were included. Eight sections were counted per brain. Results reflect the sum of positive neurones from the 8 sections.

Result hC10-2, hC10-2_N32S and hC10-2_N32S_A101T all significantly reduced seeding of Tau tangles in the injected hippocampus (One way andova and Turkey's multiple comparisons test). hC10-2: 50%, hC10-2_N32S: 47% and hC10-2_N32S_A101T: 60% in comparison to control treated mice. FIG. 23.

What is claimed is:

1. A monoclonal antibody, or an epitope-binding fragment thereof, comprising:
   (a) a Light Chain CDR1 comprising an amino acid sequence selected from the group consisting of SEQ ID NO:3, SEQ ID NO:31; SEQ ID NO:32; SEQ ID NO:33; SEQ ID NO:34; SEQ ID NO:35; SEQ ID NO:36; SEQ ID NO:37; SEQ ID NO:38; SEQ ID NO:40; and SEQ ID NO:46;
   (b) a Light Chain CDR2 comprising the amino acid sequence of SEQ ID NO:4; SEQ ID NO:41; and SEQ ID NO:47;
   (c) a Light Chain CDR3 comprising the amino acid sequence of SEQ ID NO:5; SEQ ID NO:42; and SEQ ID NO:48;
   (d) a Heavy Chain CDR1 comprising the amino acid sequence of SEQ ID NO:6; SEQ ID NO:43; SEQ ID NO:49; SEQ ID NO:52; and SEQ ID NO:55;
   (e) a Heavy Chain CDR2 comprising an amino acid sequence selected from the group consisting of SEQ ID NO:7; SEQ ID NO:28; SEQ ID NO:29; SEQ ID NO:30; SEQ ID NO:44; SEQ ID NO:50; SEQ ID NO:53; and SEQ ID NO:56; and
   (f) a Heavy Chain CDR3 comprising an amino acid sequence selected from the group consisting of SEQ ID NO:8, SEQ ID NO:39; SEQ ID NO:45; SEQ ID NO:51; SEQ ID NO:54; and SEQ ID NO:57.

2. The monoclonal antibody, or epitope-binding fragment thereof, according to claim 1, wherein:
   (a) the Light Chain is SEQ ID NO:12; and
   (b) the Heavy Chain is selected from the group consisting of SEQ ID NO:13, SEQ ID NO:14, SEQ ID NO:15, SEQ ID NO:24, SEQ ID NO:25, SEQ ID NO:26 and SEQ ID NO:27.

3. The monoclonal antibody, or epitope-binding fragment thereof, according to claim 1, wherein:
   (a) the Light Chain is selected from the group consisting of SEQ ID NO:16; SEQ ID NO:17; SEQ ID NO:18; SEQ ID NO:19; SEQ ID NO:20; SEQ ID NO:21; SEQ ID NO:22 and SEQ ID NO:23; and
   (b) the Heavy Chain is SEQ ID NO:11.

4. The monoclonal antibody, or epitope binding fragment thereof, according to claim 1,
   comprising:
   (a) a Light Chain CDR1 having the amino acid sequence of SEQ ID NO:32;
   (b) a Light Chain CDR2 having the amino acid sequence of SEQ ID NO:4;
   (c) a Light Chain CDR3 having the amino acid sequence of SEQ ID NO:5;
   (d) a Heavy Chain CDR1 having the amino acid sequence of SEQ ID NO:6;

(e) a Heavy Chain CDR2 having the amino acid sequence of SEQ ID NO:7; and
(f) a Heavy Chain CDR3 having the amino acid sequence of SEQ ID NO:8.

5. The monoclonal antibody, or epitope binding fragment thereof, according to claim 4, comprising:
    (a) a Light Chain comprising the amino acid sequence of SEQ ID NO:17; and
    (b) a Heavy Chain comprising the amino acid sequence of SEQ ID NO:11.

6. The monoclonal antibody, or epitope binding fragment thereof, according to claim 1, comprising:
    (a) a Light Chain CDR1 having the amino acid sequence of SEQ ID NO:33;
    (b) a Light Chain CDR2 having the amino acid sequence of SEQ ID NO:4;
    (c) a Light Chain CDR3 having the amino acid sequence of SEQ ID NO:5;
    (d) a Heavy Chain CDR1 having the amino acid sequence of SEQ ID NO:6;
    (e) a Heavy Chain CDR2 having the amino acid sequence of SEQ ID NO:7; and
    (f) a Heavy Chain CDR3 having the amino acid sequence of SEQ ID NO:8.

7. The monoclonal antibody, or epitope binding fragment thereof, according to claim 6, comprising:
    (a) a Light Chain comprising the amino acid sequence of SEQ ID NO:18; and
    (b) a Heavy Chain comprising the amino acid sequence of SEQ ID NO:11.

8. The monoclonal antibody, or epitope binding fragment thereof, according to claim 1, comprising:
    (a) a Light Chain CDR1 having the amino acid sequence of SEQ ID NO:34;
    (b) a Light Chain CDR2 having the amino acid sequence of SEQ ID NO:4;
    (c) a Light Chain CDR3 having the amino acid sequence of SEQ ID NO:5;
    (d) a Heavy Chain CDR1 having the amino acid sequence of SEQ ID NO:6;
    (e) a Heavy Chain CDR2 having the amino acid sequence of SEQ ID NO:7; and
    (f) a Heavy Chain CDR3 having the amino acid sequence of SEQ ID NO:8.

9. The monoclonal antibody, or epitope binding fragment thereof, according to claim 8, comprising:
    (a) a Light Chain comprising the amino acid sequence of SEQ ID NO:19; and
    (b) a Heavy Chain comprising the amino acid sequence of SEQ ID NO:11.

10. A monoclonal antibody, or an epitope-binding fragment thereof, comprising:
    (a) a Light Chain selected from the group consisting of SEQ ID NO:12; SEQ ID NO:16; SEQ ID NO:17; SEQ ID NO:18; SEQ ID NO:19; SEQ ID NO:20; SEQ ID NO:21; SEQ ID NO:22 and SEQ ID NO:23; and
    (b) a Heavy Chain selected from the group consisting of SEQ ID NO:11; SEQ ID NO:13; SEQ ID NO:14; SEQ ID NO:15; SEQ ID NO:24; SEQ ID NO:25; SEQ ID NO:26; and SEQ ID NO:27.

11. A pharmaceutical composition comprising the monoclonal antibody, or epitope binding fragment thereof, according to claim 1 and a pharmaceutical acceptable carrier.

12. A method for the treatment of a tauopathy, which comprises administering a therapeutically effective amount of the monoclonal antibody, or epitope-binding fragment thereof, according to claim 1 to a subject in need thereof, wherein said tauopathy is selected from the group consisting of Alzheimer's disease, Argyrophilic Grain Disease (AGD), Psychosis, Psychosis due to AD or Psychosis in patients with AD, apathy due to AD or apathy in patients with AD, psychiatric symptoms of patients with Lewy body dementia, Progressive Supranuclear Palsy (PSP), Frontotemporal dementia (FTD or variants thereof), TBI (traumatic brain injury, acute or chronic), Corticobasal Degeneration (CBD), Picks Disease, Primary age-related tauopathy (PART), Neurofibrillary tangle-predominant senile dementia, Dementia pugilistica, Chronic traumatic encephalopathy, stroke, neurodegeneration in relation to Parkinson's disease, Parkinsonism linked to chromosome, Lytico-Bodig disease (Parkinson-dementia complex of Guam), Ganglioglioma and gangliocytoma, Meningioangiomatosis, Postencephalitic parkinsonism, Subacute sclerosing panencephalitis, Huntington's disease, lead encephalopathy, tuberous sclerosis, Hallervorden-Spatz disease and lipofuscinosis.

13. The method according to claim 12, wherein the treatment is chronic.

14. A method for the treatment of Alzheimer's disease which comprises administering a therapeutically effective amount of the monoclonal antibody, or epitope-binding fragment thereof, according to claim 1 to a subject in need thereof.

15. A method of diagnosing or imaging Alzheimer's disease or other tauopathies in a subject, said method comprising administering to said subject a detectably labelled monoclonal antibody, or epitope-binding fragment thereof, according to claim 1.

* * * * *